(12) United States Patent
Warrass et al.

(10) Patent No.: US 8,461,121 B2
(45) Date of Patent: *Jun. 11, 2013

(54) MACROLIDE SYNTHESIS PROCESS AND SOLID-STATE FORMS

(75) Inventors: Ralf Warrass, Schwabenheim (DE); Fritz Blatter, Basel (CH); Timo Rager, Basel (CH)

(73) Assignee: Intervet International B.V., Boxmeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/401,991

(22) Filed: Feb. 22, 2012

(65) Prior Publication Data

US 2012/0208779 A1 Aug. 16, 2012

Related U.S. Application Data

(63) Continuation of application No. 11/828,404, filed on Jul. 26, 2007, now Pat. No. 8,227,429.

(60) Provisional application No. 60/834,067, filed on Jul. 28, 2006.

(30) Foreign Application Priority Data

Jul. 31, 2006 (EP) .................................. 06118159

(51) Int. Cl.
*A61K 31/70* (2006.01)
*C07H 17/08* (2006.01)

(52) U.S. Cl.
USPC ............................................. 514/30; 536/7.1

(58) Field of Classification Search
USPC ......................................................... 536/7.1
See application file for complete search history.

(56) References Cited

U.S. PATENT DOCUMENTS

| | | | |
|---|---|---|---|
| 3,459,853 A | 8/1969 | Gorman et al. |
| 4,196,280 A | 4/1980 | Umezawa et al. |
| 4,438,109 A | 3/1984 | Umezawa et al. |
| 4,454,314 A | 6/1984 | Nagel |
| 4,468,511 A | 8/1984 | Kirst et al. |
| 4,579,940 A | 4/1986 | Fujiwara et al. |
| 4,629,786 A | 12/1986 | Debono et al. |
| 4,820,694 A | 4/1989 | Debono et al. |
| 4,820,695 A | 4/1989 | Debono et al. |
| 4,920,103 A | 4/1990 | Kirst et al. |
| 4,921,947 A | 5/1990 | Tao et al. |
| 5,140,014 A | 8/1992 | Maring et al. |
| 5,541,303 A | 7/1996 | Takeuchi et al. |
| 5,545,624 A | 8/1996 | Hecker et al. |
| 5,677,287 A | 10/1997 | Jaynes |
| 5,716,939 A | 2/1998 | Lundy et al. |
| 5,760,011 A | 6/1998 | Jaynes et al. |
| 6,034,070 A | 3/2000 | Armbruster |
| 6,462,026 B1 | 10/2002 | Or et al. |
| 6,469,067 B1 | 10/2002 | Bouvier et al. |
| 6,506,885 B1 | 1/2003 | Beier |
| 6,514,946 B1 | 2/2003 | Miyake et al. |
| 6,576,615 B2 | 6/2003 | Phan et al. |
| 6,664,240 B2 | 12/2003 | Phan et al. |
| 6,710,034 B2 | 3/2004 | Phan et al. |
| 6,753,415 B2 | 6/2004 | Phan et al. |
| 2003/0096764 A1 | 5/2003 | Phan et al. |
| 2004/0235760 A1 | 11/2004 | Phan et al. |
| 2005/0020823 A1 | 1/2005 | Phan et al. |
| 2010/0173892 A1 | 7/2010 | Almena-Perea et al. |

FOREIGN PATENT DOCUMENTS

| | | |
|---|---|---|
| EP | 0070170 B1 | 1/1983 |
| EP | 0132895 A1 | 2/1985 |
| EP | 0103465 B1 | 9/1986 |
| EP | 0124216 B1 | 10/1988 |
| EP | 0287082 B1 | 10/1988 |
| EP | 0376114 A2 | 7/1990 |
| EP | 0240264 B1 | 8/1991 |
| GB | 2135670 A | 9/1984 |
| GB | 2171991 A | 9/1986 |
| JP | 59044398 A | 3/1984 |
| JP | 59167598 A | 9/1984 |
| WO | 9402496 A1 | 2/1994 |
| WO | 9502594 A1 | 1/1995 |
| WO | 9609312 A1 | 3/1996 |
| WO | 9944619 A1 | 9/1999 |
| WO | 0116148 A1 | 3/2001 |
| WO | 03027250 A2 | 4/2003 |
| WO | 03039558 A1 | 5/2003 |
| WO | 03043642 A1 | 5/2003 |
| WO | 03089446 A2 | 10/2003 |
| WO | 03089447 A1 | 10/2003 |
| WO | 2009013351 A2 | 1/2009 |

OTHER PUBLICATIONS

Search report from parent European priority patent application, EP06118159.0. The report is dated Jan. 31, 2007.
H.A. Kirst, et al., "Synthesis, antimicrobial evaluation and structure-activity relationships within 23-modified derivatives of 5-O-Mycaminosyltylonolide," The Journal of Antibiotics, vol. XL, No. 6, pp. 823-842 (Jun. 1987).
Manuel Debono, et al, "Synthesis and antimicrobial evaluation of 20-deoxo-20-(3,5-dimethylpiperidin-1-yl) desmycosin (timicosin, EL-870) and related cyclic amino derivatives," The Journal of Antibiotics, vol. XLII, No. 8 (Aug. 1989).
Lawrence C. Creemer, et al., "Facile synthesis of tilmicosin and tylosin related haptens for use as protein conjugates," The Journal of Antibiotics, Vo. 56, No. 5 (May 2003).

(Continued)

Primary Examiner — Elli Peselev

(57) ABSTRACT

Described are methods for making macrolides, and, in particular, a method for making optionally substituted 20,23-dipiperidinyl-5-O-mycaminosyl-tylonolide and derivatives thereof, as well as uses of macrolides to make medicaments, methods of treatment using macrolides, and methods for making intermediates that, inter alia, may be used to make macrolides. Also described are solvated and non-solvated crystalline forms of 20,23-dipiperidinyl-5-O-mycaminosyl-tylonolide, as well as methods for making such crystalline forms, medicaments comprising (or derived from) such crystalline forms, methods for making medicaments comprising (or derived from) such crystalline forms, methods of treatment using such crystalline forms, and kits comprising such crystalline forms.

13 Claims, 40 Drawing Sheets

OTHER PUBLICATIONS

Andrew G. Fishman, et al., "Novel semisynthetic oxo and alkyl macrolide antibacterials and related derivatives," J. Chem. Soc. Perkin Trans I, 7, 1189-1209 (1987).

Kazuo Tsuzuki, et al., "Synthesis and antimicrobial activities of 9-O-acyl derivatives of tylosin and demycarsyltylosin," J. Antibiotics, 39(12), 1784-87 (1986).

Shuichi Sakamoto, et al., "Synthesis of 23-deoxy-23-N-ethyl-23-(2-fluoro-, 2,2-difluoro-, and 2,2,2-trifluoroethyl) amino derivatives of mycaminosyl tylonolide and 4'deoxymycaminosyl tylonolide," J. Antibiotics, 37(12), pp. 1628-1634 (1984).

Akihiro Tanaka, et al., "Synthesis of recyclized macrolide antibiotics and related derivatives and mycaminosyltylonide," Bull. Chem. Soc. Japan, 54(12), 3837-45 (1981).

Jensen et al., Influence of Temperature on Water and Aqueous Glucose Absorption Spectra in the Near- and Mid-Infrared Regions at Physiologically Relevant Temperatures, Applied Spectroscopy, 2003, pp. 28-36, vol. 57, No. 1.

Vergote et al., Near-infrared FT-Raman spectroscopy as a rapid analytical tool for the determination of diltiazem hydrochloride in tablets, European Journal of Pharmaceutical Sciences, 2002, pp. 63-67, vol. 16.

Stavroula et al., Univariate and Multivariate Calibration for the Quantitative Determination of Methyl-parthion in Pesticide Formulations by FT-Raman Spectroscopy, Applied Spectroscopy, 2000, pp. 747-752, vol. 54, No. 5.

Ellis et al., Metabolic fingerprinting in disease diagnosis: biomedical applications of infrared and Raman spectroscopy, Analyst, 2006, pp. 875-885, vol. 131.

Physicochemical Principles of Pharmacy, Fourth edition, Eds. Florence and Attwood, 2006, pp. 13-23, Pharmaceutical Press, Grayslake, IL, USA.

U.S. Appl. No. 12/804,847, filed Jul. 30, 2010, Inventor: Blatter et al., Title: Macrolide Synthesis Process and Solid-State Forms.

U.S. Appl. No. 11/828,404, filed Jul. 26, 2007, Inventor: Blatter et al., Title: Macrolide Synthesis Process and Solid-State Forms.

MACROLIDE SYNTHESIS PROCESS AND SOLID-STATE FORMS

CROSS-REFERENCE TO RELATED PATENT APPLICATION(S)

This application is a continuation of U.S. patent application Ser. No. 11/828,404, filed Jul. 26, 2007, now U.S. Pat. No. 8,227,429 issued Jul. 24, 2012, which claims priority to U.S. Provisional Patent Application Ser. No. 60/834,067, filed Jul. 28, 2006, and European Patent Application No. 06118159.0, filed Jul. 31, 2006, the entire disclosure of each of which is hereby incorporated herein by this reference.

TECHNICAL FIELD

Described are methods for making macrolides, and, in particular, a method for making optionally substituted 20,23-dipiperidinyl-5-O-mycaminosyl-tylonolide and derivatives thereof, as well as methods of treatment using such macrolides, uses of such macrolides to make medicaments, and methods for making intermediates that, inter alia, may be used to make macrolides. Also described are solvated and non-solvated crystalline forms of 20,23-dipiperidinyl-5-O-mycaminosyl-tylonolide, as well as methods for making such crystalline forms, medicaments comprising (or derived from) such crystalline forms, methods for making medicaments comprising (or derived from) such crystalline forms, methods of treatment using such crystalline forms, and kits comprising such crystalline forms.

BACKGROUND

Macrolides have long been known to be effective for treating infectious diseases in humans, livestock, poultry, and other animals. Early macrolides included 16-membered macrolides such as, e.g., tylosin A:

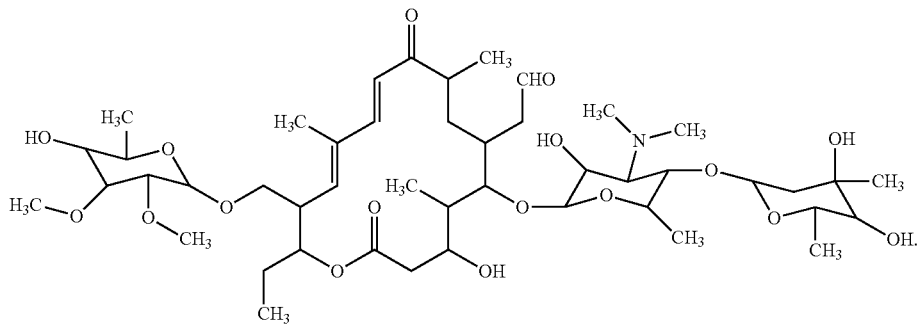 [SMILES: CCC1OC(=O)CC(O)C(C)C(OC2OC(C)C(OC3CC(C)(O)C(O)C(C)O3)C(N(C)C)C2O)C(CC=O)CC(C)C(=O)/C=C/C(C)=C/C1COC1OC(C)C(O)C(OC)C1OC]

See, e.g., U.S. Pat. No. 4,920,103 (col. 5, lines 12-38). See also, U.S. Pat. No. 4,820,695 (col. 7, lines 1-32) and EP 0103465B1 (page 5, line 3). Over the years, various tylosin derivatives have been developed with the goal of enhancing antibacterial activity and selectivity.

Tylosin derivatives include, e.g., compounds discussed in U.S. Pat. No. 6,514,946 that correspond in structure to Formula (I):

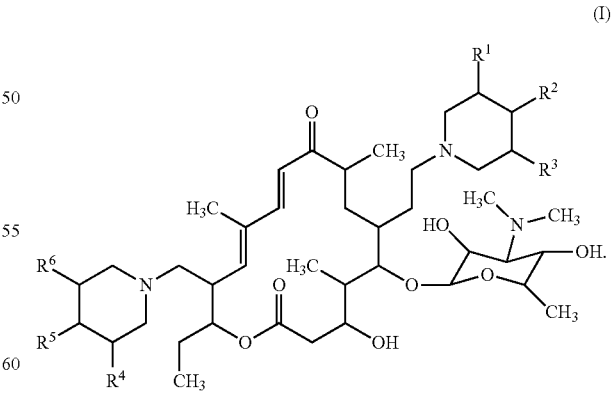

Here:

$R^1$ and $R^3$ are each methyl, and $R^2$ is hydrogen; $R^1$ and $R^3$ are each hydrogen, and $R^2$ is methyl; or $R^1$, $R^2$, and $R^3$ are each hydrogen; and $R^4$ and $R^6$ are each methyl, and $R^5$ is hydrogen; $R^4$ and $R^6$ are each hydrogen, and $R^5$ is methyl; or $R^4$, $R^5$, and $R^6$ are each hydrogen.

Such compounds include, e.g., 20,23-dipiperidinyl-5-O-mycaminosyl-tylonolide, which has the following structure:

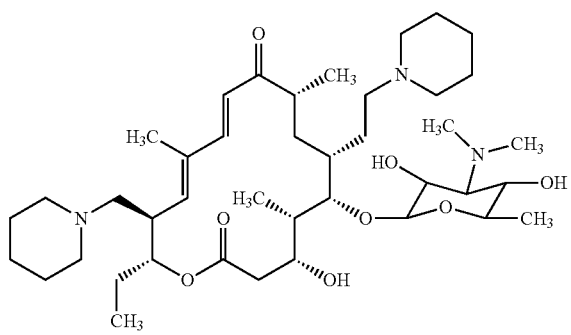 [SMILES: CC[C@H]1OC(=O)C[C@@H](O)[C@H](C)[C@@H](OC2OC(C)C(O)C(N(C)C)C2O)[C@@H](CCN2CCCCC2)C[C@@H](C)C(=O)/C=C/C(C)=C/[C@@H]1CN1CCCCC1]

These compounds, and particularly 20,23-dipiperidinyl-5-O-mycaminosyl-tylonolide, are believed to have pharmacokinetic and pharmacodynamic attributes for safe and effective treatment of, e.g., pasteurellosis, bovine respiratory disease, and swine respiratory disease. A discussion relating to the use of these compounds to treat livestock and poultry diseases is included in U.S. Pat. No. 6,514,946. That discussion is incorporated by reference herein. Applicants are not aware of any stable crystalline form of 20,23-dipiperidinyl-5-O-mycaminosyl-tylonolide being described.

Various approaches for making macrolides have been reported.

In EP 0103465B1, e.g., Debono et al. discuss various process steps for making compounds within their recited genus. These processes include, e.g., the following reduction:

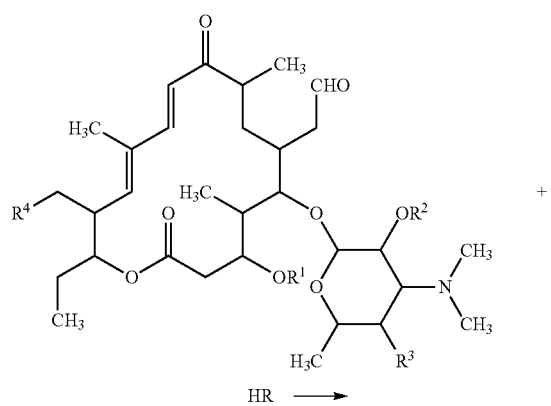

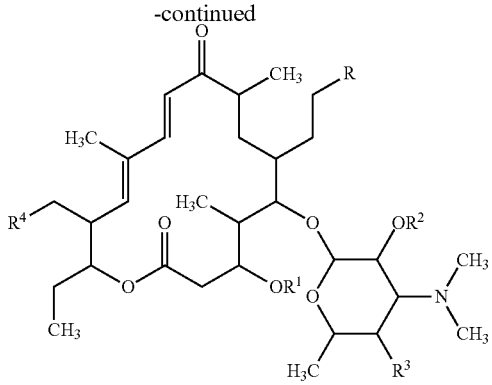

Here, R, $R^1$, $R^2$, $R^3$, and $R^4$ are defined as various substituents. R, in particular, is defined as a nitrogen-containing ring system that has up to 3 unsaturated or saturated rings that are optionally substituted. Debono et al. report that the preferred reducing agent is a cyanoborohydride, and that sodium cyanoborohydride is "the reducing agent of choice." Debono et al. also state that the solvent for this reaction will normally be an inert polar solvent, such as a $C_1$-$C_4$ alkanol. See page 6, lines 7-14. In a later-filed patent in the same patent family, Debono et al. further discuss reductive amination of various aldehyde compounds (including tylosin) with an amine. Sodium cyanoborohydride and sodium borohydride are cited as suitable reducing agents, and anhydrous methanol is cited as a suitable solvent. See U.S. Pat. No. 4,820,695, col. 7, lines 60-68.

In U.S. Pat. No. 6,664,240, Phan et al. also discuss a reductive amination:

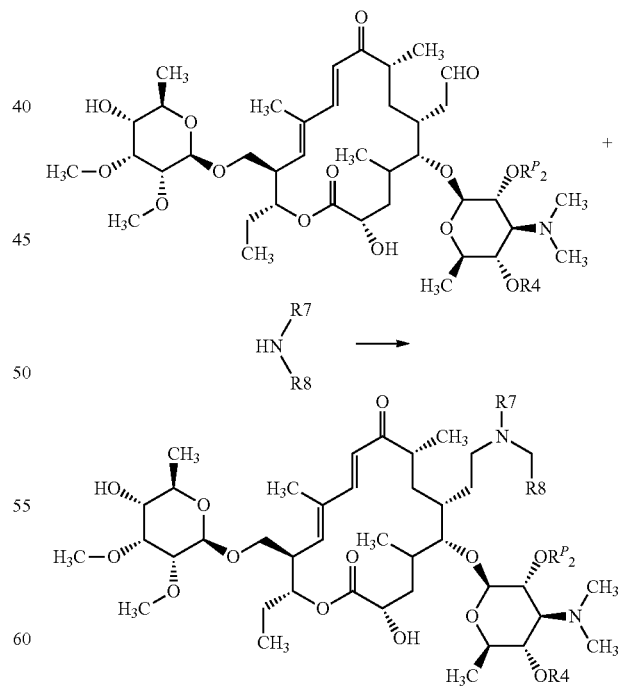

Here, $R^P{}_2$, R4, R7 and R8 are defined as various substituents. $R^7$ and $R^8$, in particular, are each defined as being independent substituents, or, alternatively, as together forming a 3- to 7-member heterocyclic ring. Phan et al. discuss conducting this reaction with a borohydride reagent in an alcohol or acetonitrile solvent. Sodium borohydride and sodium cyanoborohydride are listed as example borohydride reagents; and methanol, ethanol, and isopropanol are listed as example alcohol solvents. See, e.g., col. 15, line 64 to col. 16, line 42; and col. 22, lines 41-49.

In EP 0240264B1, Tao et al. also discuss a reductive amination:

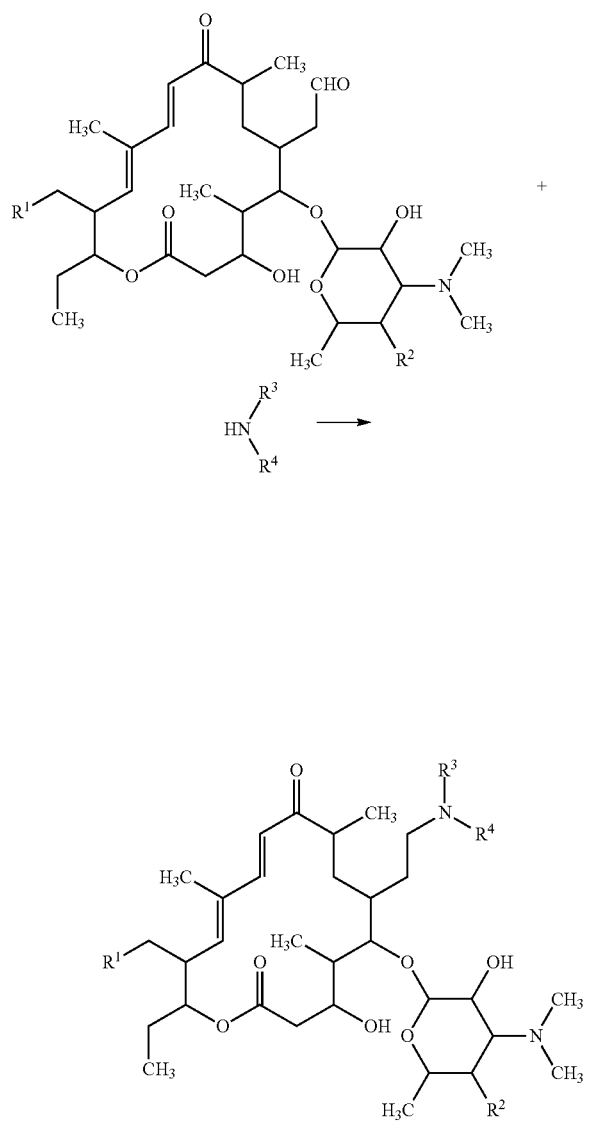

Here, $R^1$, $R^2$, $R^3$, and $R^4$ are defined as various substituents. $R^3$ and $R^4$, in particular, are defined as each being independent substituents, or, alternatively, as together forming a heterocyclic ring system having up to 3 optionally substituted rings. Tao et al. report that this reduction may be achieved using formic acid as the reducing agent. Tao et al. further report that the solvent will ordinarily be an inert polar organic solvent. Amyl acetate and acetonitrile are cited as examples of such a solvent. See page 4, line 57 to page 5, line 10. See also, U.S. Pat. No. 4,921,947, col. 3, line 62 to col. 4, line 16.

In EP 0103465B1, Debono et al. discuss the following hydrolysis reaction:

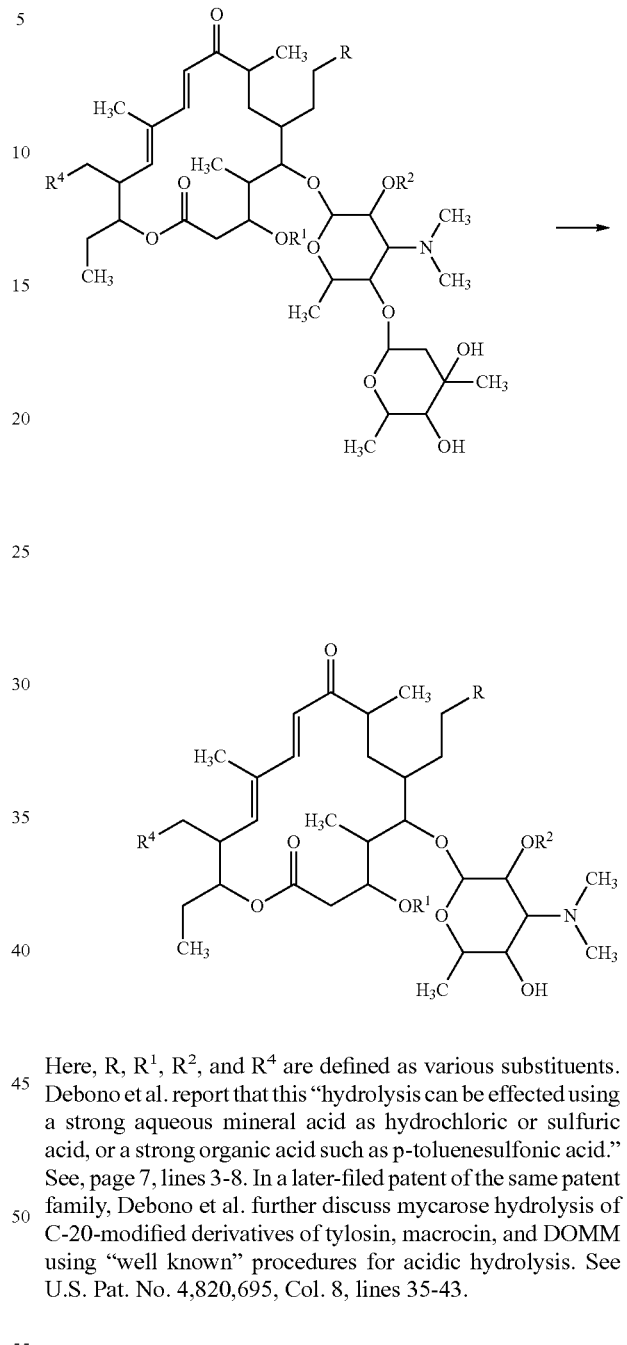

Here, R, $R^1$, $R^2$, and $R^4$ are defined as various substituents. Debono et al. report that this "hydrolysis can be effected using a strong aqueous mineral acid as hydrochloric or sulfuric acid, or a strong organic acid such as p-toluenesulfonic acid." See, page 7, lines 3-8. In a later-filed patent of the same patent family, Debono et al. further discuss mycarose hydrolysis of C-20-modified derivatives of tylosin, macrocin, and DOMM using "well known" procedures for acidic hydrolysis. See U.S. Pat. No. 4,820,695, Col. 8, lines 35-43.

SUMMARY OF THE INVENTION

Described are processes for making macrolides, and, in particular, optionally substituted 20,23-dipiperidinyl-5-O-mycaminosyl-tylonolide and derivatives thereof. Such processes include processes for making the macrolides themselves, as well as processes for making compounds that, inter alia, may be used as intermediates for making various macrolides.

Briefly, this disclosure is directed, in part, to a process for making a macrolide and salts thereof. The macrolide corresponds in structure to Formula (I):

(I)

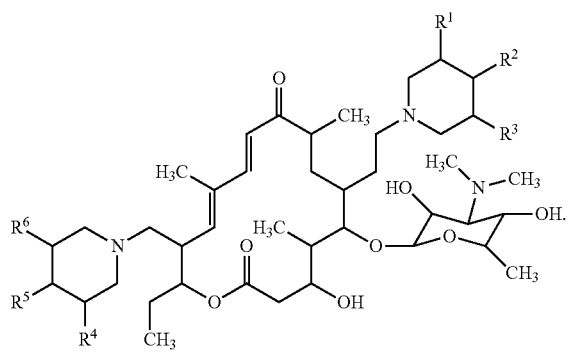

Here:
As to $R^1$, $R^2$, and $R^3$:
$R^1$ and $R^3$ are each methyl, and $R^2$ is hydrogen,
$R^1$ and $R^3$ are each hydrogen, and $R^2$ is methyl, or
$R^1$, $R^2$, and $R^3$ are each hydrogen.
As to $R^4$, $R^5$, and $R^6$:
$R^4$ and $R^6$ are each methyl, and $R^5$ is hydrogen,
$R^4$ and $R^6$ are each hydrogen, and $R^5$ is methyl, or
$R^4$, $R^5$, and $R^6$ are each hydrogen.

In some embodiments, the process comprises reacting tylosin (e.g., tylosin A or a salt thereof), a piperidinyl compound of Formula (II), and formic acid in the presence of a non-polar solvent. In these embodiments, the piperidinyl compound of Formula (II) corresponds in structure to:

(II)

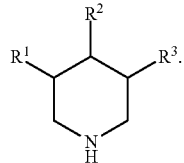

In some embodiments, the process comprises reacting a 20-piperidinyl-tylosin compound with an acid. In these embodiments, the 20-piperidinyl-tylosin compound corresponds in structure to Formula (III):

(III)

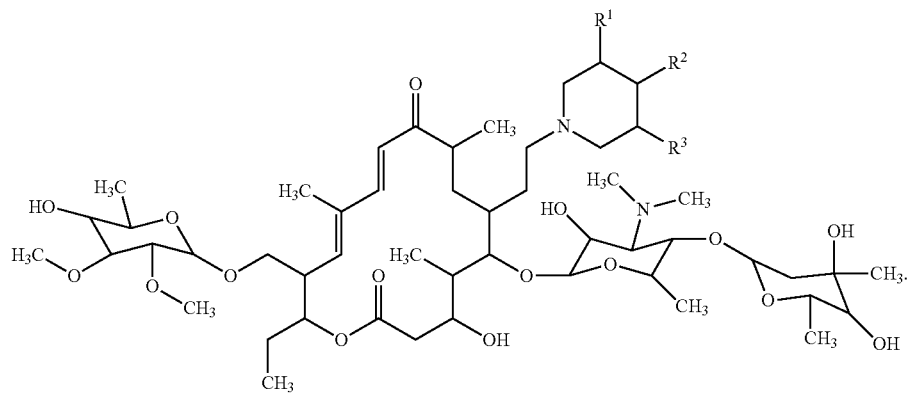

In some embodiments, the process comprises reacting a 23-O-mycinosyl-20-piperidinyl-5-O-mycaminosyl-tylonolide compound with an acid. In these embodiments, the 23-O-mycinosyl-20-piperidinyl-5-O-mycaminosyl-tylonolide compound corresponds in structure to Formula (IV):

(IV)

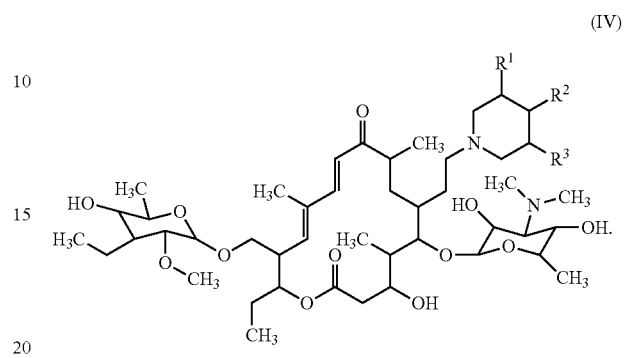

In some embodiments, the process comprises activating a 23-hydroxyl-20-piperidinyl-5-O-mycaminosyl-tylonolide compound with an activating agent to form an activated compound. In these embodiments, the 23-hydroxyl-20-piperidinyl-5-O-mycaminosyl-tylonolide compound corresponds in structure to Formula (V):

(V)

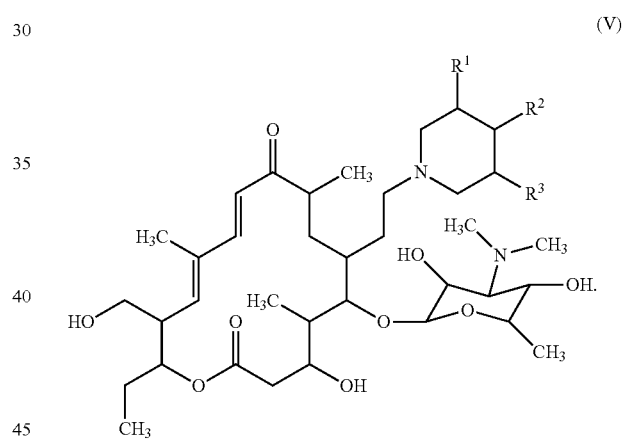

The activated compound (also referred to as a "23-L-20-piperidinyl-5-O-mycaminosyl-tylonolide compound") corresponds in structure to Formula (VI):

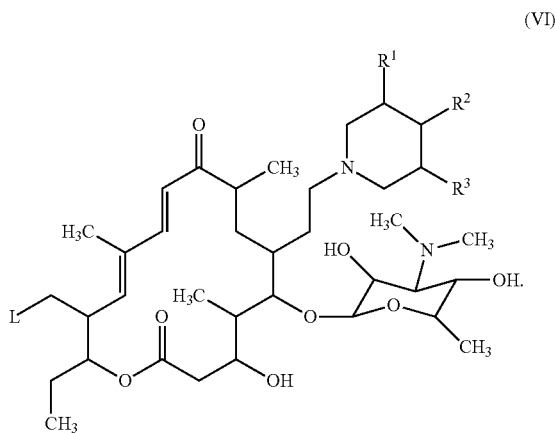

(VI)

And L is a leaving group.

In other embodiments, the process comprises reacting an activated compound of Formula (VI) with a piperidinyl compound of Formula (VII). In these embodiments, the piperidinyl compound of Formula (VII) corresponds in structure to:

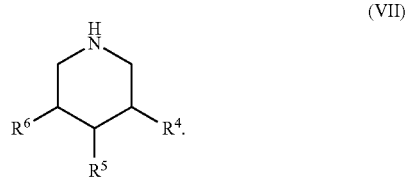

(VII)

In some embodiments, the process comprises a combination of the above embodiments to make a macrolide of Formula (I) or salt thereof.

In some embodiments, the process comprises one or more of the above embodiments to make, e.g., an amorphous, crystalline, co-crystalline, or solvate form of the macrolide of Formula (I) or a salt thereof.

This disclosure also is directed, in part, to a process for making 20-piperidinyl-tylosin compound of Formula (III) or a salt thereof. In such embodiments, the process comprises reacting tylosin (e.g., tylosin A), the piperidinyl compound of Formula (II), and formic acid in the presence of a non-polar solvent.

This disclosure is also directed, in part, to a process for making the 23-O-mycinosyl-20-piperidinyl-5-O-mycaminosyl-tylonolide compound of Formula (IV) or a salt thereof. In these embodiments, the process comprises reacting the 20-piperidinyl-tylosin compound of Formula (III) with HBr.

This disclosure is also directed, in part, to a process for making a 23-hydroxyl-20-piperidinyl-5-O-mycaminosyl-tylonolide compound of Formula (V) or a salt thereof. In these embodiments, the process comprises reacting the 23-O-mycinosyl-20-piperidinyl-5-O-mycaminosyl-tylonolide compound of Formula (IV) with an acid.

This disclosure is also directed, in part, to a process for making an activated compound of Formula (VI) or a salt thereof. In these embodiments, the process comprises activating a 23-hydroxyl-20-piperidinyl-5-O-mycaminosyl-tylonolide compound of Formula (V) with an activating agent.

Also described are methods of using compounds of Formula (I) (and pharmaceutically acceptable salts thereof) prepared in accordance with this disclosure in methods for treating a disease, such as pasteurellosis, swine respiratory disease, or bovine respiratory disease. More specifically, this disclosure includes, in part, a method that comprises preparing a compound of Formula (I) (or a pharmaceutically acceptable salt thereof) in accordance with one or more of the cited methods, and then administering a therapeutically effective amount of the compound or salt to an animal in need of the treatment. This disclosure is also directed, in part, to using a compound of Formula (I) (or a pharmaceutically acceptable salt thereof) prepared in accordance with this invention to prepare a medicament, particularly a medicament for use in the above treatments.

Also described are crystalline forms of 20,23-dipiperidinyl-5-O-mycaminosyl-tylonolide.

This disclosure is directed, in part, to a first crystalline 20,23-dipiperidinyl-5-O-mycaminosyl-tylonolide form (identified in this disclosure as the "Form I polymorph"). The Form I polymorph generally may be characterized as having, e.g., at least one (and typically more than one) of the following characteristics:
  a. an FT-Raman spectrum comprising an absorption band at one or more frequencies selected from the group consisting of about 2935, about 1633, about 1596, about 1712, about 1683, and about 781 cm$^{-1}$;
  b. a powder X-ray diffraction spectrum comprising at least one peak selected from the group consisting of 5.0 (±0.2) and 5.6 (±0.2) degrees 2Θ;
  c. an attenuated total reflection infrared spectrum comprising an absorption band at one or more frequencies selected from the group consisting of about 2932, about 1711, about 1682, about 1635, about 1599, about 1442, about 1404, about 1182, about 1079, about 1053, about 1008, about 985, about 842, and about 783 cm$^{-1}$;
  d. a melting point of from about 192 to about 195° C.; or
  e. a melting enthalpy of about 57 J/g.

This disclosure is also directed, in part, to a second crystalline 20,23-dipiperidinyl-5-O-mycaminosyl-tylonolide form (identified in this disclosure as the "Form II polymorph"). The Form II polymorph generally may be characterized as having, e.g., at least one (and typically more than one) of the following characteristics:
  a. an FT-Raman spectrum comprising an absorption band at one or more frequencies selected from the group consisting of about 2929, about 1625, about 1595, about 1685, and 783 cm$^{-1}$;
  b. a powder X-ray diffraction spectrum comprising a peak at 6.5 (±0.2) degrees 2Θ;
  c. an attenuated total reflection infrared spectrum comprising an absorption band at one or more frequencies selected from the group consisting of about 2935, about 1736, about 1668, about 1587, about 1451, about 1165, about 1080, about 1057, about 1042, about 1005, about 981, about 838, and about 755 cm$^{-1}$;
  d. a melting point of from about 113 to about 119° C.; or
  e. a melting enthalpy of about 15 J/g.

This disclosure is also directed, in part, to a third crystalline 20,23-dipiperidinyl-5-O-mycaminosyl-tylonolide form (identified in this disclosure as the "Form III polymorph"). The Form III polymorph generally may be characterized as having, e.g., at least one (and typically more than one) of the following characteristics:
  a. an FT-Raman spectrum comprising an absorption band at one or more frequencies selected from the group consisting of about 2943, about 2917, about 1627, about 1590, about 1733, about 1669, about 1193, about 1094, and about 981 cm$^{-1}$;

b. a powder X-ray diffraction spectrum comprising at least one peak selected from the group consisting of 5.6 (+0.2) and 6.1 (±0.2) degrees 2Θ;

c. an attenuated total reflection infrared spectrum comprising an absorption band at one or more frequencies selected from the group consisting of about 2931, about 1732, about 1667, about 1590, about 1453, about 1165, about 1081, about 1057, about 1046, about 1005, about 981, about 834, and about 756 cm$^{-1}$;

d. a melting point of from about 107 to about 134° C.; or e. a melting enthalpy of about 38 J/g.

This disclosure is also directed, in part, to a fourth crystalline 20,23-dipiperidinyl-5-O-mycaminosyl-tylonolide form (identified in this disclosure as the "Form IV polymorph"). The Form IV polymorph generally may be characterized as having, e.g., at least one (and typically both) of the following characteristics:

a. an attenuated total reflection infrared spectrum comprising an absorption band at one or more frequencies selected from the group consisting of about 3559, about 2933, about 1743, about 1668, about 1584, about 1448, about 1165, about 1075, about 1060, about 1045, about 1010, about 985, about 839, and about 757 cm$^{-1}$; or b. a melting point of from about 149 to about 155° C.

This disclosure is also directed, in part, to solvated crystalline forms of 20,23-dipiperidinyl-5-O-mycaminosyl-tylonolide.

In some embodiments, the solvated crystalline form comprises an ethyl acetate (or "EtOAc"), ethanol, or diethyl ketone solvated crystalline form of 20,23-dipiperidinyl-5-O-mycaminosyl-tylonolide; as well as any other crystalline solvate that is isomorphic to the ethyl acetate, ethanol, or diethyl ketone solvated crystalline form. These crystalline solvates are collectively identified in this disclosure as "S1 crystalline solvates."

In some embodiments, the solvated crystalline form comprises a tert-butyl methyl ether (or "tBME") solvated crystalline form of 20,23-dipiperidinyl-5-O-mycaminosyl-tylonolide, as well as any other crystalline solvate that is isomorphic to the tBME solvated crystalline form. These crystalline solvates are collectively identified in this disclosure as "S2 crystalline solvates."

In some embodiments, the solvated crystalline form comprises a tetrahydrofuran (or "THF") solvated crystalline form of 20,23-dipiperidinyl-5-O-mycaminosyl-tylonolide, as well as any other crystalline solvate that is isomorphic to the THF solvated crystalline form. These crystalline solvates are collectively identified in this disclosure as "S3 crystalline solvates."

In some embodiments, the solvated crystalline form comprises a methyl acetate or ethyl formate solvated crystalline form of 20,23-dipiperidinyl-5-O-mycaminosyl-tylonolide, as well as any other crystalline solvate that is isomorphic to the methyl acetate or ethyl formate solvated crystalline form. These crystalline solvates are collectively identified in this disclosure as "S4 crystalline solvates."

This disclosure is also directed, in part, to compositions comprising 20,23-dipiperidinyl-5-O-mycaminosyl-tylonolide. In these embodiments, an amount (generally at least a detectable quantity) of the 20,23-dipiperidinyl-5-O-mycaminosyl-tylonolide in the composition consists of one of the above-discussed solvated or non-solvated crystalline forms of 20,23-dipiperidinyl-5-O-mycaminosyl-tylonolide.

This disclosure is also directed, in part, to a method for treating a disease, such as pasteurellosis, swine respiratory disease, or bovine respiratory disease. The method comprises combining a therapeutically effective amount of an above-discussed crystal-containing composition with at least one excipient to form a pharmaceutical composition, and administering the pharmaceutical composition to an animal in need of such treatment. In some such embodiments, e.g., a therapeutically effective amount of the crystal-containing composition is dissolved in a liquid excipient(s) to form a solution that may, in turn, be used for parenteral or oral administration. In other such embodiments, a therapeutically effective amount of the crystal-containing composition is suspended in a liquid excipient(s) to form a suspension that may, in turn, be used for parenteral or oral administration.

This disclosure is also directed, in part, to a use of a therapeutically effective amount of an above-discussed crystal-containing composition to prepare a medicament for treating a disease (e.g., pasteurellosis, swine respiratory disease, or bovine respiratory disease) in an animal.

This disclosure is also directed, in part, to a pharmaceutical composition prepared by a process comprising combining at least one excipient with a therapeutically effective amount of an above-discussed crystal-containing composition. In some such embodiments, e.g., a therapeutically effective amount of the crystal-containing composition is dissolved in a liquid excipient(s) to form a solution that may, in turn, be used for parenteral or oral administration. In other such embodiments, e.g., a therapeutically effective amount of the crystal-containing composition is suspended in a liquid excipient(s) to form a suspension that may, in turn, be used for parenteral or oral administration.

This disclosure is also directed, in part, to a kit. The kit comprises: a therapeutically effective amount of an above-discussed crystal-containing composition, and instructions for combining the crystal-containing composition with at least one excipient. The kit may further (or alternatively) comprise additional components, such as, e.g., one or more excipients, one or more additional pharmaceutical or biological materials, and/or one or more diagnostic tools.

DETAILED DESCRIPTION OF PREFERRED EMBODIMENTS

A. Macrolides that May be Prepared

Figure 1:
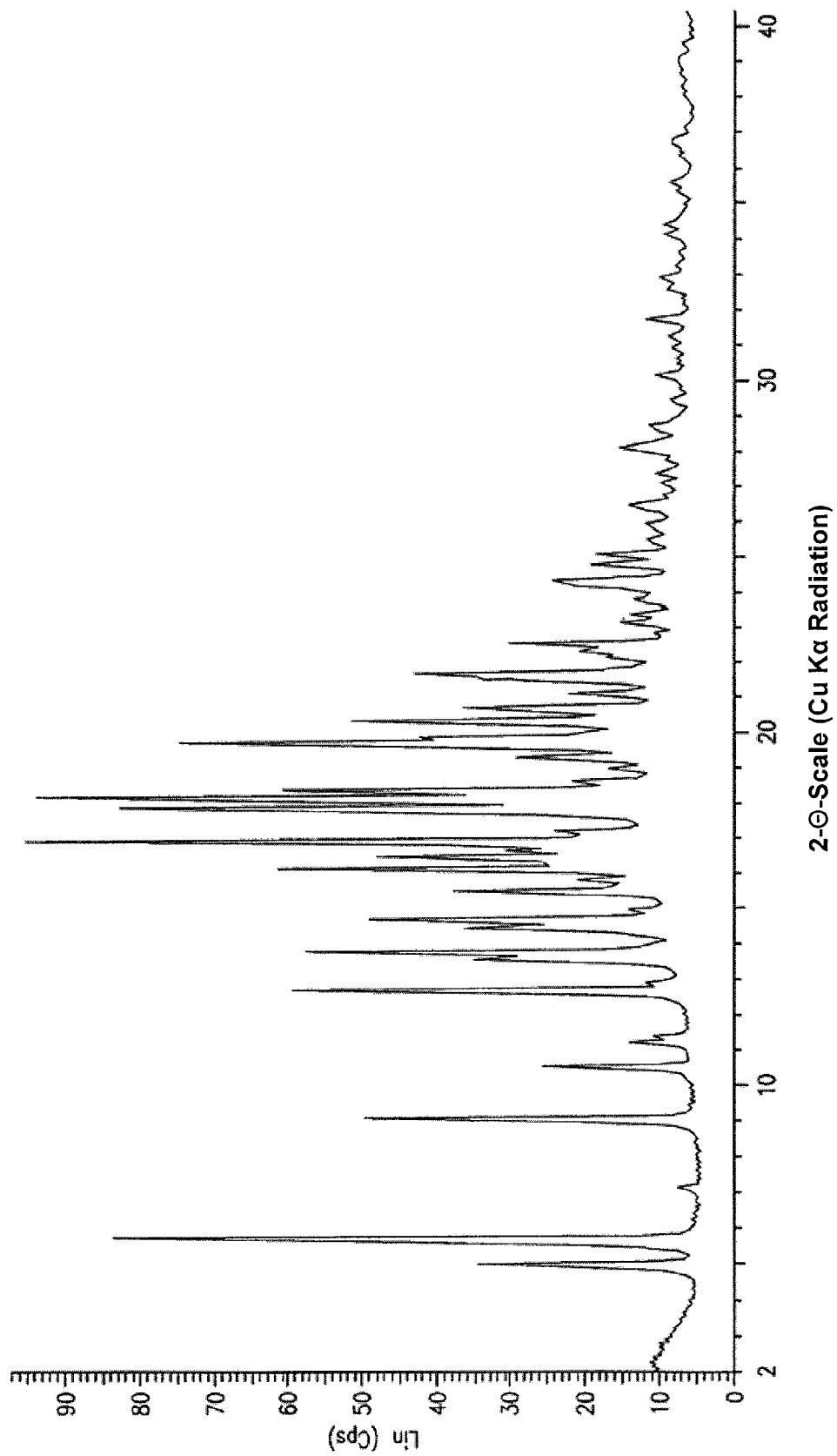
FIG. 1 shows an illustrative powder X-ray diffraction ("PXRD") spectrum for the Form I polymorph of 20,23-dipiperidinyl-5-O-mycaminosyl-tylonolide.

Compounds that may be prepared by the process of this invention include compounds corresponding in structure to Formula (I):

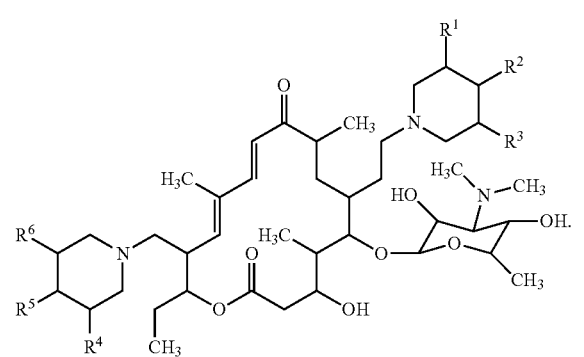

Here:
$R^1$ and $R^3$ are each methyl, and $R^2$ is hydrogen; $R^1$ and $R^3$ are each hydrogen, and $R^2$ is methyl; or $R^1$, $R^2$, and $R^3$ are each hydrogen; and $R^4$ and $R^6$ are each methyl, and $R^5$ is hydrogen; $R^4$ and $R^6$ are each hydrogen, and $R^5$ is methyl; or $R^4$, $R^5$, and $R^6$ are each hydrogen.

In some embodiments, the piperidinyl substituents of Formula (I) are identical, i.e.:

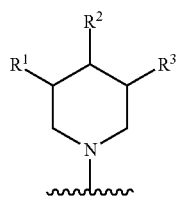

IS THE SAME AS

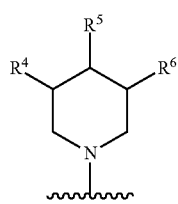

In some such embodiments, e.g., both piperidinyl substituents are piperidine (i.e., $R^1$, $R^2R^3$, $R^4$, $R^5$, and $R^6$ are each hydrogen), such that the compound is 20,23-dipiperidinyl-5-O-mycaminosyl-tylonolide:

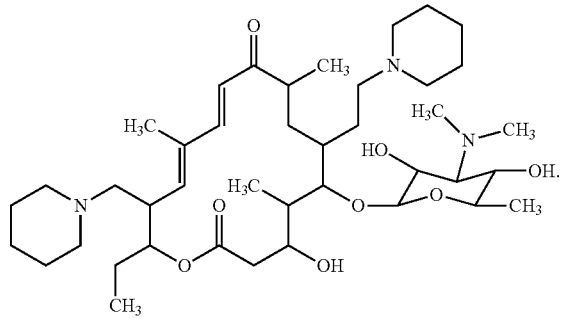 [SMILES: CCC1OC(=O)CC(O)C(C)C(OC2OC(C)C(O)C(N(C)C)C2O)C(CCN2CCCCC2)CC(C)C(=O)/C=C/C(C)=C/C1CN1CCCCC1]

Such compounds include, for example:

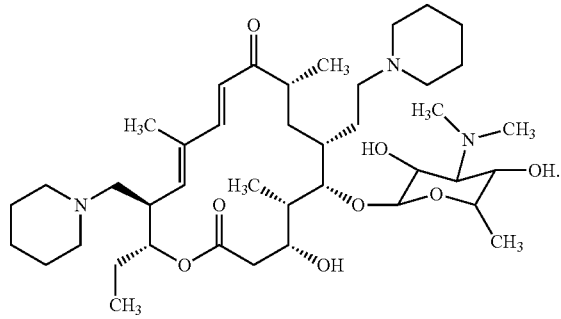 [SMILES: CC[C@H]1OC(=O)C[C@@H](O)[C@H](C)[C@@H](OC2OC(C)C(O)C(N(C)C)C2O)[C@@H](CCN2CCCCC2)C[C@@H](C)C(=O)/C=C/C(C)=C/[C@@H]1CN1CCCCC1]

Other compounds having identical piperidinyl substituents include:

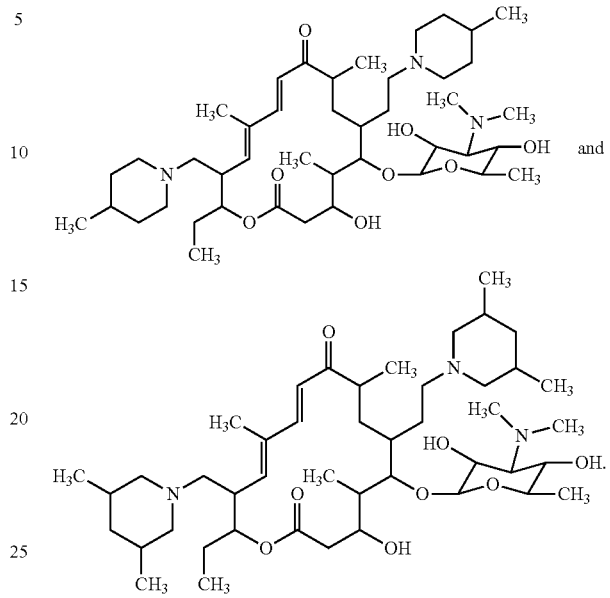

In some embodiments, the piperidinyl substituents of Formula (I) are not identical, i.e.:

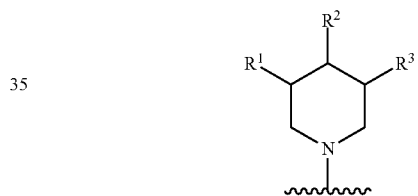

IS DIFFERENT THAN

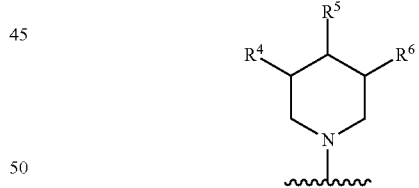

Compounds having different piperidinyl substituents include:

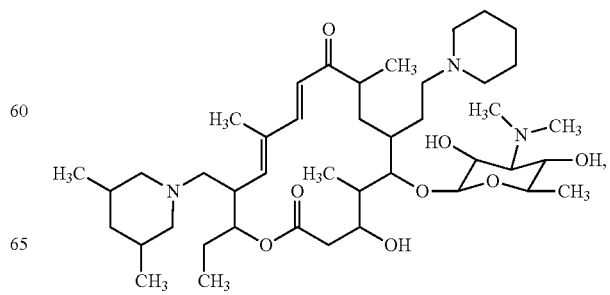

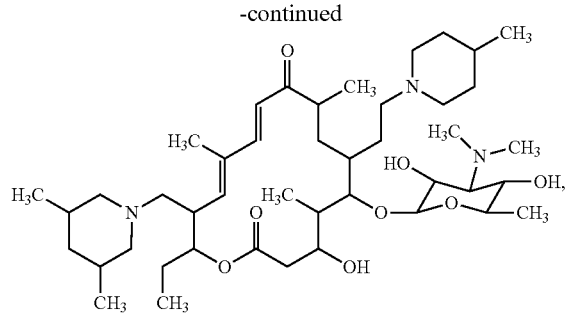
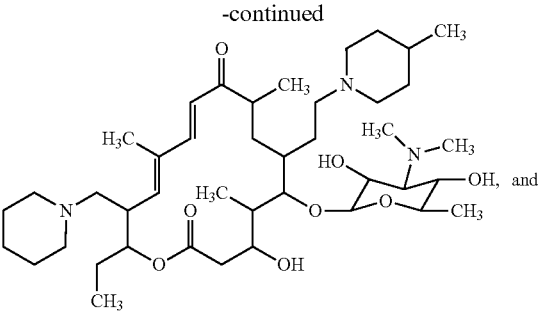
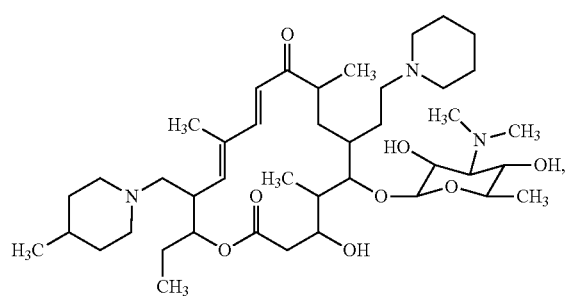
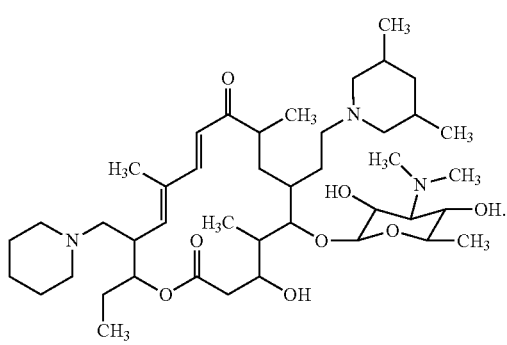
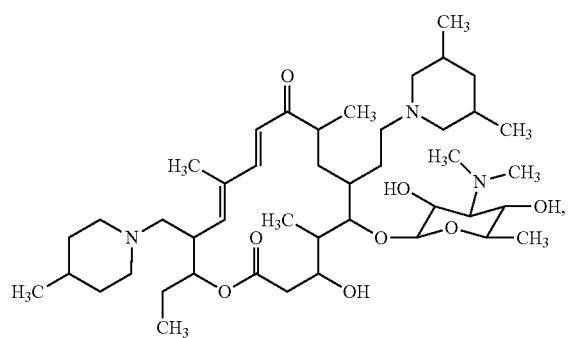
B. Macrolide Synthesis
This invention may be used to synthesize macrolides from materials generally available in the art.
B-1. Preparation of 20-Piperidinyl-Tylosin Compound
In some embodiments, the macrolide synthesis begins by or includes preparing a 20-piperidinyl-tylosin compound, and particularly a compound corresponding in structure to Formula (III):
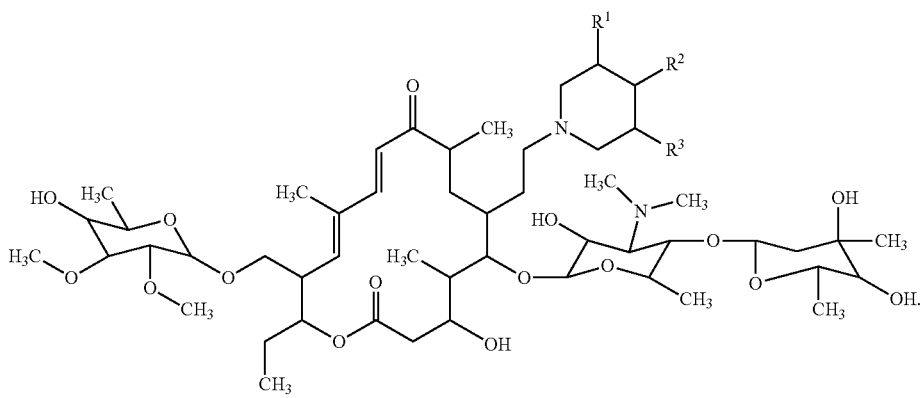

In some embodiments, $R^1$ and $R^3$ are each methyl, and $R^2$ is hydrogen; or $R^1$ and $R^3$ are each hydrogen, and $R^2$ is methyl. In other embodiments, $R^1$, $R^2$, and $R^3$ are each hydrogen, such that the compound corresponds in structure to:

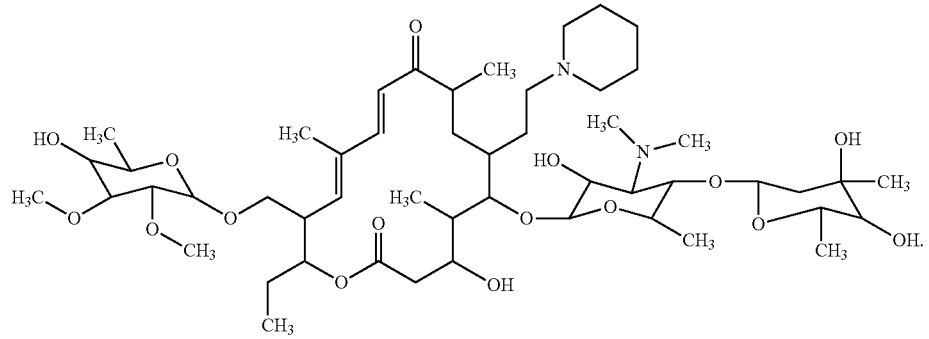 [SMILES: CCC1OC(=O)CC(O)C(C)C(OC2OC(C)C(OC3CC(C)(O)C(O)C(C)O3)C(N(C)C)C2O)C(CCN2CCCCC2)CC(C)C(=O)/C=C/C(C)=C/C1COC1OC(C)C(O)C(OC)C1OC]

20

The 20-piperidinyl-tylosin compound may be prepared from tylosin A and a piperidinyl compound via a reductive amination reaction using a reducing agent comprising formic acid (or "HCOOH"):

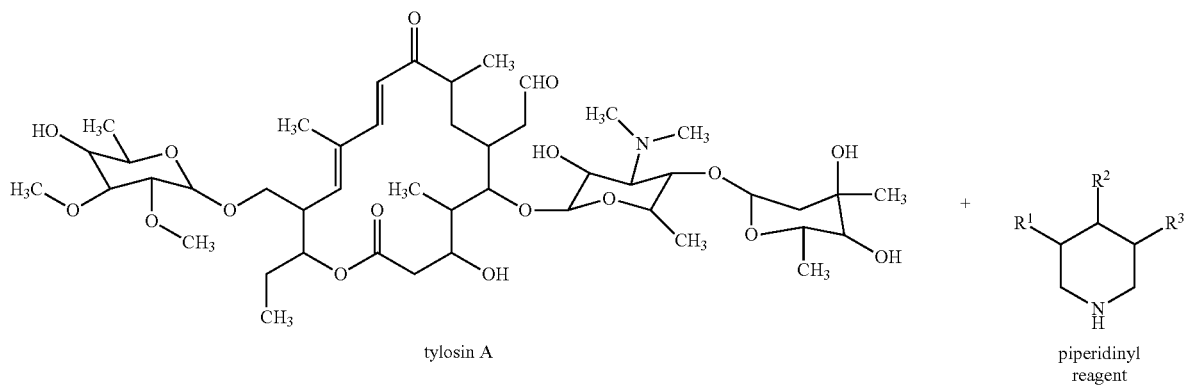

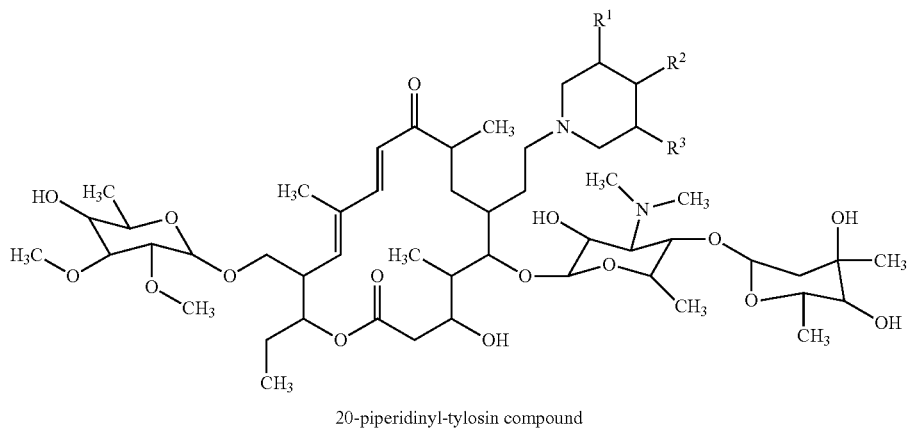

Where $R^1$, $R^2$, and $R^3$ are each hydrogen, this reaction is as follows:

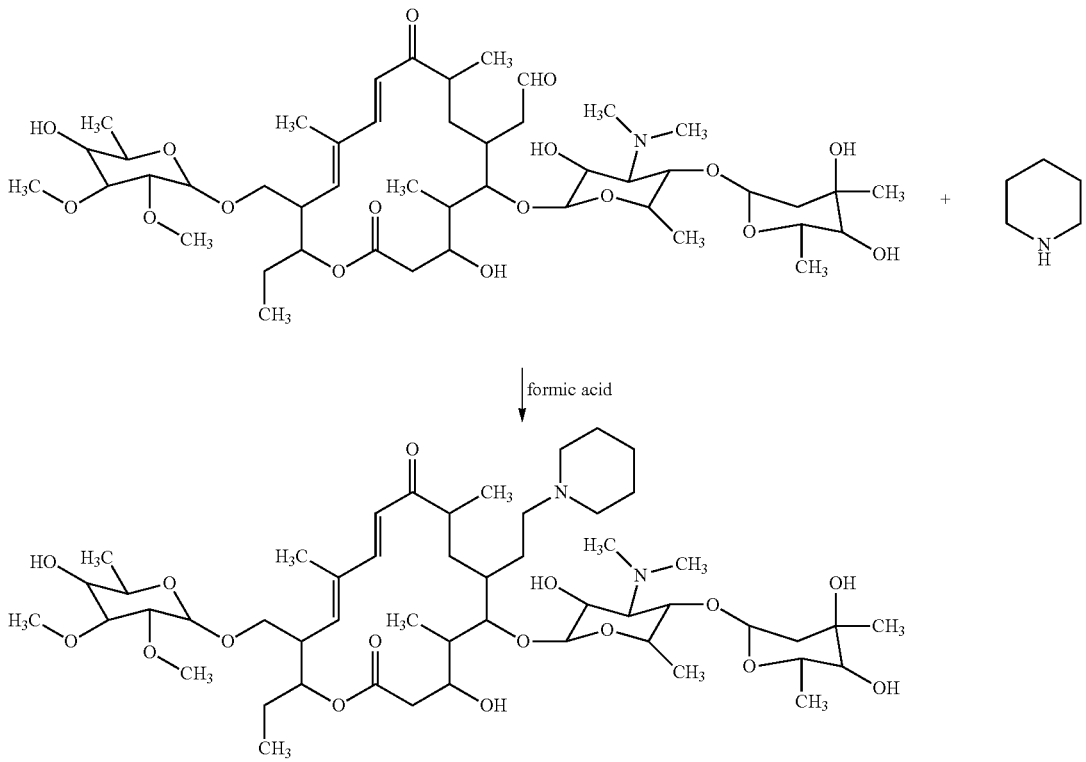

Tylosin A, piperidinyl compounds, and formic acid are commercially available.

The tylosin A reagent may, e.g., be pure (or at least essentially pure) tylosin A. Alternatively, as noted below in Section B-7, the tylosin A reagent may be part of a mixture, such as, e.g., a mixture comprising tylosin A as well as one or more tylosin A derivatives, such as tylosin B, tylosin C, and/or tylosin D.

The tylosin A may be in the form of its free base, or, alternatively, in the form of a salt. The tylosin A derivatives likewise are optionally in the form of one or more salts. It is contemplated that a variety of salts may be suitable. In some embodiments, e.g., the salt comprises a phosphate salt. In other embodiments, the salt comprises a tartrate salt. In still other embodiments, the salt comprises a citrate or sulfate salt. Further discussion relating to salts may be found below in Section C.

The solvent may comprise one or more solvents. Although the solvent may comprise one or more polar solvents in some embodiments, the solvent preferably instead comprises one or more non-polar solvents. A "non-polar solvent" is a solvent that does not ionize sufficiently to be electrically conductive, and cannot (or at least essentially cannot) dissolve polar compounds (e.g., various inorganic salts), but can dissolve non-polar compounds (e.g., hydrocarbons and resins). In general, the solvent preferably is non-reactive with the reagents, products, and any other ingredients in the reaction mixture. The solvent may comprise, e.g., chloroform (or "$CHCl_3$"); tetrahydrofuran (or "THF"); dichloromethane (or "$CH_2Cl_2$" or "DCM" or "methylene chloride"); carbon tetrachloride (or "$CCl_4$"); ethyl acetate (or "$CH_3COOC_2H_5$"); diethyl ether (or "$CH_3CH_2OCH_2CH_3$"); cyclohexane (or "$C_6H_{12}$"); or aromatic hydrocarbon solvents, such as benzene (or "$C_6H_6$"), toluene (or "$C_6H_5CH_3$"), xylene (or "$C_6H_4(CH_3)_2$" or "dimethylbenzene" (including 1,3-dimethylbenzene (or "m-xylene"), 1,2-dimethylbenzene (or "o-xylene"), or 1,4-dimethylbenzene (or "p-xylene")), ethylbenzene, or mixtures thereof (e.g., mixtures of m-xylene, o-xylene, p-xylene, and/or ethylbenzene). In some embodiments, the solvent comprises dichloromethane, chloroform, or ethyl acetate. In other embodiments, the solvent comprises xylene. In still other embodiments, the solvent comprises toluene. In some such embodiments, toluene is particularly preferred because of its ease of use at typical reaction temperatures.

In some embodiments, the solvent comprises a mixture of solvents. In some such embodiments, e.g., the solvent comprises a mixture of toluene and DCM. Here, the toluene/DCM ratio may be, e.g., from about 1:1 to about 100:1, or from about 5:1 to about 8:1 (v/v). In some of these embodiments, the ratio is, e.g., about 8:1 (v/v). In others, the ratio is, e.g., about 5.3:1 (v/v).

To perform the amination, the tylosin A reagent, piperidinyl compound, formic acid (or a source of formic acid), and solvent normally are charged to a reactor and mixed. These ingredients may generally be charged to the reactor in any sequence.

The reactor may comprise various reactor types. In some embodiments, e.g., the reactor is a stirred-tank reactor. Glass and glass-lined reactors are often preferred, although any composition stable when exposed to the reaction mixture may be used. For example, stainless steel reactors generally may be used as well.

Typically, equimolar amounts of the tylosin A reagent, piperidinyl compound, and formic acid may be used. Normally, however, excess amounts of the piperidinyl compound and formic acid are used, relative to the molar amount of tylosin A reagent.

In some embodiments, from 1 to about 3 equivalents (or from 1.05 to about 3 equivalents) of the piperidinyl compound are charged to the reactor. In some such embodiments, e.g., from 1.05 to about 1.2 equivalents of piperidinyl compound are charged to the reactor. In other such embodiments, from about 1.07 to about 1.5 equivalents of piperidinyl compound are charged to the reactor. Here, e.g., about 1.3 equivalents of the piperidinyl compound may be charged to the reactor. In some embodiments, the piperidinyl compound is charged to the reactor in two or more separate charges over time, preferably with the subsequent charge(s) being less than the first charge. In some embodiments, e.g., the piperidinyl compound is charged to the reactor in two charges, with the amount of the second charge being about 10% of the first charge. Applicants have discovered that this can be beneficial for increasing conversion.

In some embodiments, from 1 to about 10 equivalents (or from 1.05 to about 10 equivalents, from about 2 to about 5 equivalents, or from about 2.5 to about 4.5 equivalents) of formic acid are used. In some such embodiments, e.g., about 4.5 equivalents of formic acid are used. In other such embodiments, from about 2.5 to about 4 equivalents of formic acid are used. For example, in some such embodiments, about 3.0 equivalents of formic acid are used.

Typically, the amount of solvent is sufficient to, e.g., prevent (or essentially prevent) the reagents, products, and other ingredients in the reaction mixture from sticking to the reactor, and promote homogenous distribution of the reagents. In some embodiments, the amount of solvent is at least about 1 L per kg tylosin A reagent (or, where the tylosin A reagent is part of a mixture of tylosin A reagent and derivates thereof, per kg of the total tylosin mixture). The amount of solvent generally is less than about 40 L per kg tylosin A reagent (or tylosin mixture). In some embodiments, the amount of solvent is from about 2 to about 15 L (or from about 5 to about 15 L, from about 5 to about 12 L, from about 5 to about 10 L, or from about 8 to about 10 L) per kg tylosin A reagent (or tylosin mixture). To illustrate, in some such embodiments, the solvent comprises toluene or a mixture of toluene and DCM, and the amount of solvent is from about 8 to about 10 L per kg tylosin A reagent (or tylosin mixture). Here, e.g., the amount of solvent may be about 8 L per kg tylosin A reagent (or tylosin mixture).

At least a portion of the reaction (or the entire reaction) is typically conducted at greater than about 20° C., greater than about 25° C., or greater than about 60° C. In general, at least a portion of the reaction (or the entire reaction) is conducted at a temperature that is not greater than the boiling point of the solvent, and, more typically, is less than the boiling point. When, e.g., the solvent is toluene, at least a portion of the reaction (or the entire reaction) is typically conducted at less than about 110° C. Illustrating further, when the solvent is xylene, at least a portion of the reaction (or the entire reaction) is normally conducted at less than about 165° C. In general, at least a portion of the reaction (or the entire reaction) is conducted at from about 60 to about 95° C., from about 70 to about 85° C., from about 70 to about 80° C., or from about 75 to about 80° C. In some embodiments, e.g., the reaction temperature for at least a portion of the reaction (or the entire reaction) is about 80° C. In other embodiments, e.g., the reaction temperature for at least a portion of the reaction (or the entire reaction) is about 76° C. Although lesser temperatures than the above ranges may be used, such temperatures tend to coincide with slower reaction rates. And, although greater temperatures than the above ranges may be used, such temperatures tend to coincide with greater production of undesirable byproducts.

This reaction may be conducted over a wide range of pressures, including atmospheric pressure, less than atmospheric pressure, and greater than atmospheric pressure. It is typically preferred, however, to conduct the reaction at about atmospheric pressure. In preferred embodiments, this reaction is conducted under an inert atmosphere (e.g., $N_2$).

The reaction time may depend on various factors including, e.g., the reaction temperature, characteristics of the solvent, relative amounts of the ingredients, and the desired conversion. In a batch reactor, the reaction time is generally at least about 1 minute, typically at least about 5 minutes, and more typically at least about 1 hour. The reaction time is generally less than about 24 hours. In some embodiments, e.g., the reaction time is from about 0.5 to about 12 hours, or from about 1 to about 4 hours. In some such embodiments, the reaction time is about 3.5 hours. In other such embodiments, the reaction time is from about 1 to about 3 hours. In these embodiments, the reaction time may be, e.g., about 2 hours. Although lesser reaction times than these ranges may be used, such reaction times tend to coincide with lesser conversions. And, although greater reaction times may be used, such reaction times tend to coincide with greater production of impurities and inefficient use of equipment and manpower.

Purification or isolation of the product may be achieved using, e.g., various methods known in the art. Alternatively, the product may be used in the next step without further purification or isolation.

B-2. Preparation of 23-O-Mycinosyl-20-Piperidinyl-5-O-Mycaminosyl-Tylonolide Compound (Hydrolysis of Mycarosyloxy Substituent)

In some embodiments, the macrolide synthesis begins by or includes preparing a 23-O-mycinosyl-20-piperidinyl-5-O-mycaminosyl-tylonolide compound, and particularly a compound corresponding in structure to Formula (IV):

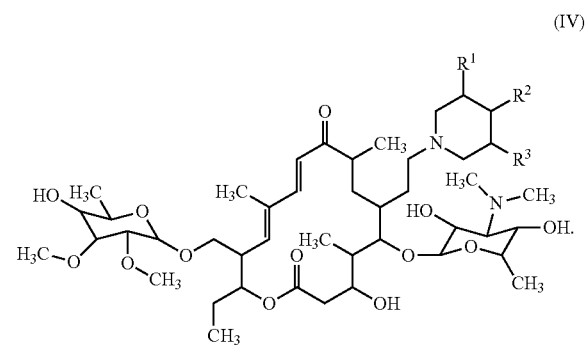

(IV)

In some embodiments, $R^1$ and $R^3$ are each methyl, and $R^2$ is hydrogen; or $R^1$ and $R^3$ are each hydrogen, and $R^2$ is methyl. In other embodiments, $R^1$, $R^2$, and $R^3$ are each hydrogen such that the compound corresponds in structure to:

The 23-O-mycinosyl-20-piperidinyl-5-O-mycaminosyl-tylonolide compound may be prepared via acid hydrolysis of a 20-piperidinyl-tylosin compound:

When $R^1$, $R^2$, and $R^3$ are each hydrogen, this reaction is as follows:

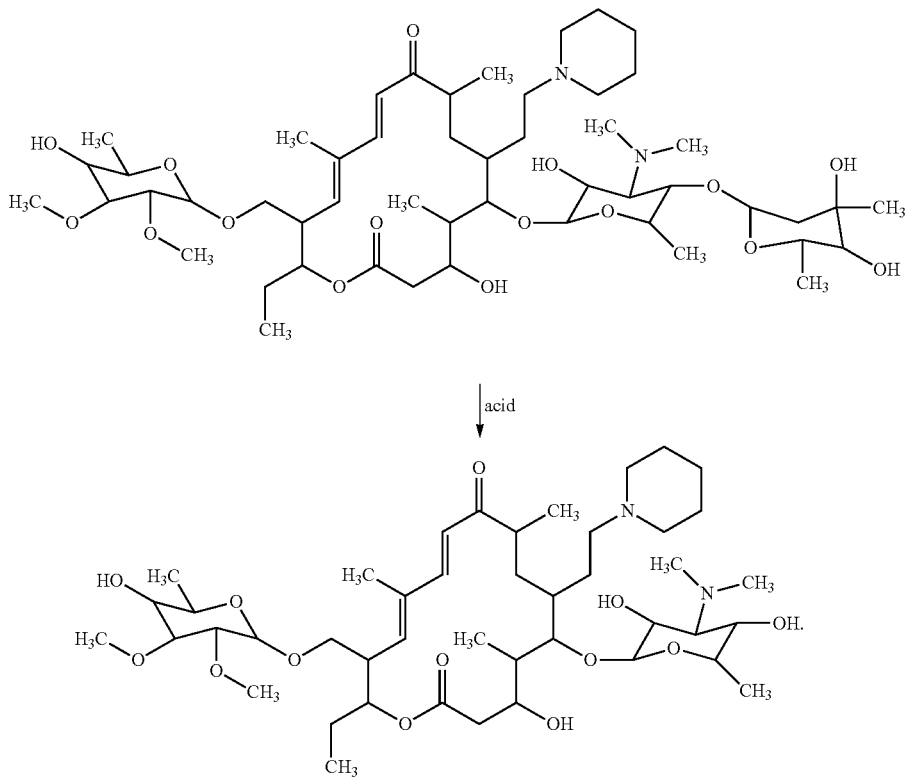

The 20-piperidinyl-tylosin compound used in the above reaction may be prepared using a process discussed above in Section B-1, prepared using a different process (e.g., a process using a borohydride as reducing agent), or obtained from a commercial vendor. In some embodiments, the 20-piperidinyl-tylosin compound is prepared using a process discussed above in Section B-1.

The acid may, e.g., be a strong mineral acid, such as hydrochloric acid (or "HCl"), nitric acid (or "HNO$_3$"), fluoroboric acid (or "HBF$_4$"), sulfuric acid (or "H$_2$SO$_4$"), phosphoric acid (or "H$_3$PO$_4$"), polyphosphonic acid (or "PPA"), or hydrobromic acid (or "HBr"); or a strong organic acid, such as p-toluenesulfonic acid or trifluoroacetic acid ("CF$_3$COOH"). In some embodiments, the acid comprises HCl. In other embodiments, the acid comprises HBr. Use of HBr tends to coincide with less impurities in the product mixture relative to the product obtained using, e.g., HCl. In some embodiments, a mixture of acids (particularly a strong acid with another acid) is used.

In general, sufficient acid is mixed with the 20-piperidinyl-tylosin compound to hydrolyze (i.e., cleave) the mycarosyloxy substituent to form a hydroxyl group. Typically, the amount of acid will be at least about one equivalent, based on the amount of 20-piperidinyl-tylosin compound. In general, the acid is added to the reaction mixture in the form of a concentrated composition. The concentration typically is not greater than about 50% (mass/vol), not greater than about 48% (mass/vol), from about 1 to about 30% (mass/vol), or from about 1 to about 24% (mass/vol). In some embodiments, e.g., the acid is HBr, and the concentration of the acid solution added to the reaction mixture is about 24% (mass/vol). In some embodiments, the concentrated acid comprises a mixture of acids, such as, e.g., HBr with another acid.

The ingredients may generally be charged to the reactor in any sequence. The reactor may comprise various reactor types. In some embodiments, e.g., the reactor is a stirred-tank reactor. Glass and glass-lined reactors are often preferred, although any composition stable when exposed to the acidic reaction mixture may be used.

At least a portion of the hydrolysis (or the entire hydrolysis) normally is conducted at a temperature that is greater than the freezing point of the mixture, allows the mixture to be stirred, and allows for the mixture to be homogenous. A temperature of at least about 10° C. (or greater than about 15° C., or greater than about 25° C.) is typically preferred. In general, the reaction temperature is not greater than the boiling point of the solvent (e.g., water), and typically is less than the boiling point. In some embodiments, at least a portion of the reaction (or the entire reaction) is conducted at a temperature that is not greater than about 100° C. (or not greater than about 65° C.). In some embodiments where the acid is HCl or HBr, the reaction temperature over at least a portion of the reaction (or the entire reaction) is from about 20 to about 60° C. In some such embodiments, the reaction temperature over at least a portion of the reaction (or the entire reaction) is not greater than about 40° C. In such instances, the reaction temperature over at least a portion of the reaction (or the entire reaction) may be, e.g., from about 20 to about 40° C., from about 25 to about 40° C., or from about 30 to about 40° C. In other embodiments where the acid is HCl or HBr, the reaction temperature over at least a portion of the reaction (or the entire reaction) is from about 45 to about 60° C., or from about 50 to about 56° C. To illustrate, in such embodiments, the reaction temperature over at least a portion of the reaction (or the entire reaction) may be, e.g., about 56° C. Although greater temperatures than these ranges may be used, such temperatures tend to coincide with greater production of undesirable byproducts. And, although lesser temperatures than these ranges may be used, such temperatures tend to coincide with slower reaction rates. Such rates, however, may still be suitable, given the ease with which this hydrolysis occurs.

The reaction mixture may be maintained at a temperature that is slightly less than the desired reaction temperature while the acid is being charged to the reactor. In such embodiments, the temperature tends to increase once the acid has been charged to the reactor.

This reaction may be conducted over a wide range of pressures, including atmospheric pressure, less than atmospheric pressure, and greater than atmospheric pressure. It is typically preferred, however, to conduct the reaction at about atmospheric pressure.

The reaction time will depend on various factors including, e.g., the reaction temperature, relative amounts of the ingredients, and the desired conversion. In a batch reactor, the reaction time may be less than a minute, essentially spontaneous, or spontaneous. Generally, however, the reaction time is at least about 1 minute, more typically at least about 5 minutes, and still more typically at least about 15 minutes. Normally, the reaction time is less than about 3 hours. In some embodiments, e.g., the reaction time is from about 0.25 to about 2 hours, from about 0.25 to about 1.5 hours, or from about 0.25 to about 1.1 hours. Although lesser reaction times may be used, such reaction times may coincide with lesser conversions. And, although greater reaction times may be used, such reaction times tend to coincide with greater production of impurities and inefficient use of equipment and manpower.

Purification or isolation of the product may be achieved using, e.g., various methods known in the art. Alternatively, the product may be used in the next step without further purification or isolation.

B-3. Preparation of 23-Hydroxyl-20-Piperidinyl-5-O-Mycaminosyl-Tylonolide Compound (Hydrolysis of Mycinosyloxy Substituent)

In some embodiments, the macrolide synthesis begins by or includes preparing a 23-hydroxyl-20-piperidinyl-5-O-mycaminosyl-tylonolide compound, and particularly a compound corresponding in structure for Formula (V):

(V)

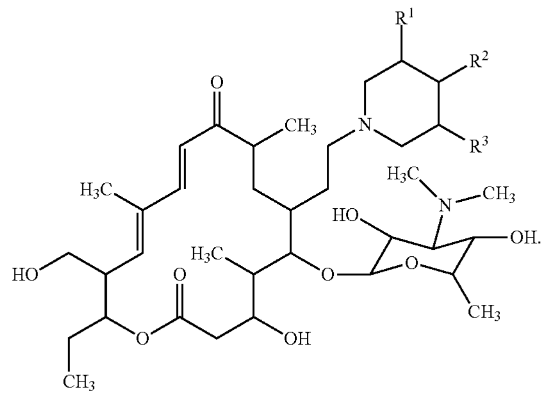

In some embodiments, $R^1$ and $R^3$ are each methyl, and $R^2$ is hydrogen; or $R^1$ and $R^3$ are each hydrogen, and $R^2$ is methyl. In other embodiments, $R^1$, $R^2$, and $R^3$ are each hydrogen:

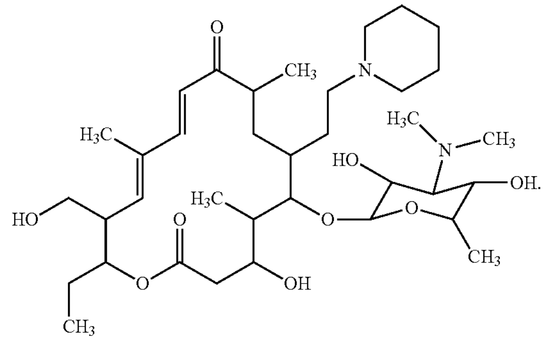 [SMILES: CCC1OC(=O)CC(O)C(C)C(OC2OC(C)C(O)C(N(C)C)C2O)C(CCN2CCCCC2)CC(C)C(=O)/C=C/C(C)=C/C1CO]

The 23-hydroxyl-20-piperidinyl-5-O-mycaminosyl-tylonolide compound may be prepared via an acid hydrolysis reaction from a 23-O-mycinosyl-20-piperidinyl-5-O-mycaminosyl-tylonolide compound:

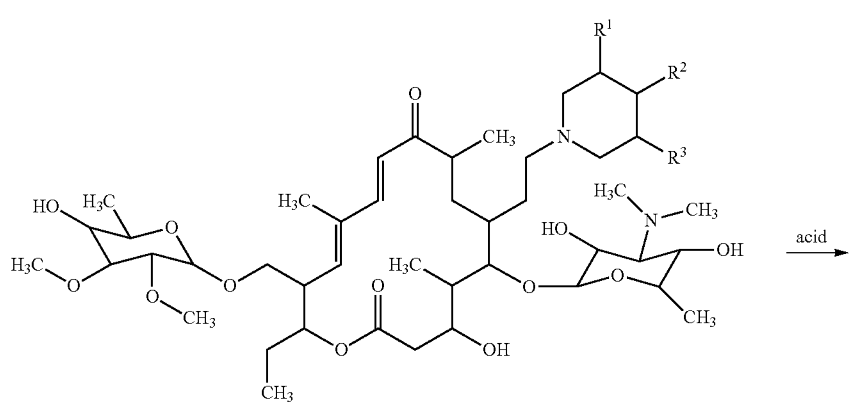

23-O-mycinosyl-20-piperidinyl-5-O-mycaminosyl-tylonodide compound

-continued

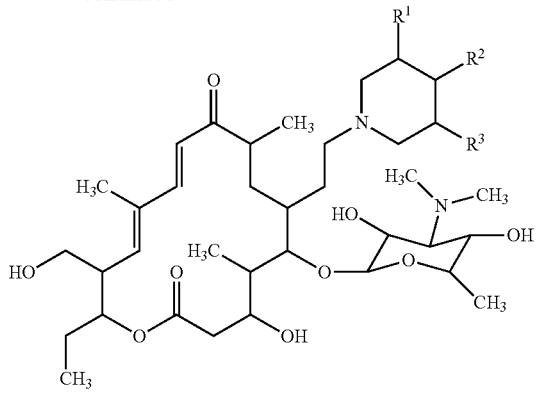

23-hydroxy-20-piperidinyl-5-O-mycaminosyl-tylonodide compound

Where $R^1$, $R^2$, and $R^3$ are each hydrogen, this reaction is as follows:

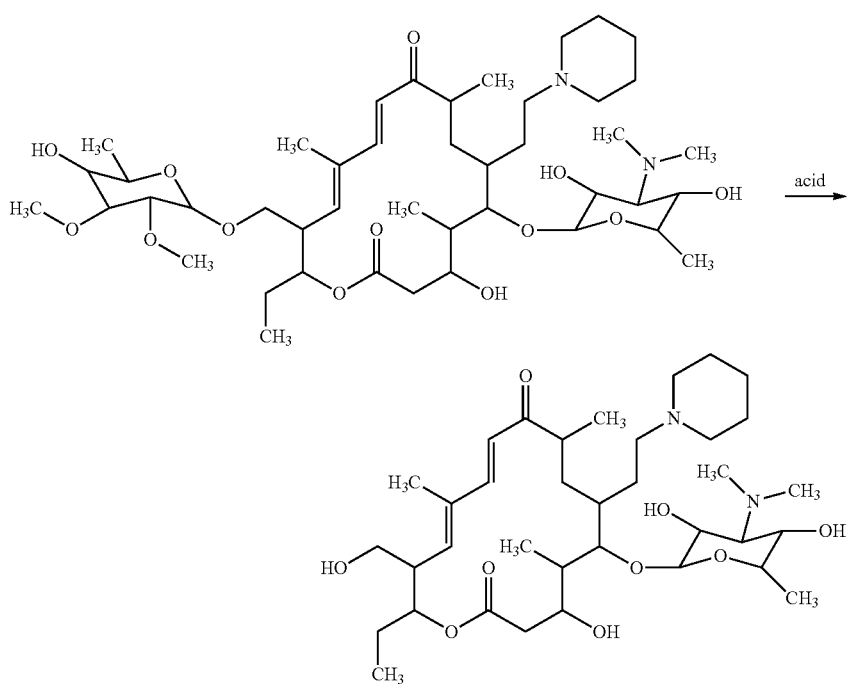

The 23-O-mycinosyl-20-piperidinyl-5-O-mycaminosyl-tylonolide compound used in the above reaction may be prepared using a process discussed above in Section B-2, prepared using a different process, or obtained from a commercial vendor. In some preferred embodiments, the 23-O-mycinosyl-20-piperidinyl-5-O-mycaminosyl-tylonolide compound is prepared using a process discussed above in Section B-2.

The acid may, e.g., be a strong mineral acid, such as hydrochloric acid, nitric acid, fluoroboric acid, sulfuric acid, phosphoric acid, polyphosphonic acid, or hydrobromic acid; or a strong organic acid, such as p-toluenesulfonic acid or trifluoroacetic acid. In some embodiments, the acid comprises HCl. In some preferred embodiments, the acid comprises HBr. As with the hydrolysis discussed above in Section B-2, this preference stems from the tendency of HBr to coincide with less impurities in the product mixture relative to, e.g., HCl. In some embodiments, a mixture of acids (particularly a mixture of a strong acid with another acid) is used.

In embodiments where the mycinosyloxy hydrolysis occurs after the acid hydrolysis of mycarosyloxy discussed above in Section B-2, the acids used in the mycinosyloxy and mycarosyloxy hydrolysis reactions may be different, although it is generally more preferred for the acids to be the same. In some embodiments, e.g., HCl is used in both reactions. In other embodiments, HBr is used in both reactions.

In general, sufficient acid is mixed with the 23-O-mycinosyl-20-piperidinyl-5-O-mycaminosyl-tylonolide compound to hydrolyze the mycinosyloxy substituent to form a hydroxyl group. Typically, the amount of acid will be greater than about one equivalent, based on the molar amount of 23-O-mycinosyl-20-piperidinyl-5-O-mycaminosyl-tylonolide compound. In general, the acid is added to the reaction mixture in the form of a concentrated composition. The concentration typically is not greater than about 50% (mass/vol), not greater than about 48% (mass/vol), from about 1 to about 30% (mass/vol), or from about 1 to about 24% (mass/vol). In some embodiments, e.g., the acid is HBr, and concentration of the acid solution added to the reaction mixture is about 24% (mass/vol). In some embodiments, the concentrated acid comprises a mixture of acids, such as, e.g., HBr with another acid.

The ingredients may generally be charged to the reactor in any sequence. The reactor may comprise various reactor types. In some embodiments, e.g., the reactor is a stirred-tank reactor. Glass and glass-lined reactors are often preferred, although any composition stable when exposed to the acidic reaction mixture may be used.

The mixture normally is maintained at a temperature that is greater than the freezing point of the mixture, allows the mixture to be stirred, and allows for the mixture to be homogenous. The reaction temperature over at least a portion of the reaction (or the entire reaction) preferably is not greater than the boiling point of the solvent (e.g., water), and typically is less than the boiling point. In general, at least a portion of the reaction (or the entire reaction) is conducted at a temperature of at least about 10° C., greater than about 25° C., or at least about 48° C. The reaction temperature over at least a portion of the reaction (or the entire reaction) typically is not greater than about 100° C., or not greater than about 65° C. In some embodiments, e.g., the reaction temperature over at least a portion of the reaction (or the entire reaction) is from about 10 to about 100° C. In some embodiments when the acid is HCl or HBr, the reaction temperature over at least a portion of the reaction (or the entire reaction) preferably is from about 48 to about 60° C. In some such embodiments, e.g., the temperature over at least a portion of the reaction (or the entire reaction) is from about 55 to about 60° C. In other such embodiments, the temperature over at least a portion of the reaction (or the entire reaction) is from about 51 to about 57° C. (e.g., about 54° C.). In still other such embodiments, the temperature over at least a portion of the reaction (or the entire reaction) is from about 50 to about 56° C. Although lesser temperatures than these ranges may be used, such temperatures tend to coincide with slower reaction rates. And, although greater temperatures than these ranges may be used, such temperatures tend to coincide with greater production of undesirable byproducts.

As with the mycarosyloxy hydrolysis discussed above in Section B-2, the mycinosyloxy hydrolysis reaction mixture may be maintained at a temperature that is slightly less than the desired reaction temperature while at least a portion of the acid (or all the acid) is being charged to the reactor.

This reaction may be conducted over a wide range of pressures, including atmospheric pressure, less than atmospheric pressure, and greater than atmospheric pressure. It is typically preferred, however, to conduct the reaction at about atmospheric pressure.

The reaction time depends on various factors including, e.g., the reaction temperature, relative amounts of the ingredients, and the desired conversion. In a batch reactor, the reaction time is generally at least about 1 minute, and more typically at least about 15 minutes. Typically, the reaction time is less than about 7 hours. In some embodiments, e.g., the reaction time is from about 0.5 to about 7 hours. In some such embodiments, e.g., the reaction time is from about 1 to about 5 hours, or from about 3 to about 5 hours. Although lesser reaction times than these ranges may be used, such reaction times tend to coincide with lesser conversions. And, although greater reaction times may be used, such reaction times tend to coincide with greater production of impurities and inefficient use of equipment and manpower.

When the mycinosyloxy hydrolysis occurs after the mycarosyloxy hydrolysis discussed above in Section B-2, the two reactions (i.e., those described above in Section B-2 and this Section B-3) may be carried out as two discrete steps or as a single reaction. When the reactions are carried out as a single reaction, the reaction mixture may be maintained at the same temperature or changed (typically increased) over time. If the reaction mixture is maintained at the same temperature, the mixture normally is maintained at a temperature of at least about 10° C., typically greater than about 25° C., more typically at least about 30° C., and still more typically at least about 45° C. In some embodiments, the temperature is maintained at from about 10 to about 100° C. In some such embodiments, e.g., the temperature is from about 48 to about 70° C. In other such embodiments, e.g., the temperature is from about 50 to about 56° C. In other such embodiments, e.g., the temperature is from about 55 to about 60° C. In still other such embodiments, the temperature is from about 65 to about 70° C. If the temperature of the mixture is increased over time, the temperature of the mixture at the beginning of the hydrolysis normally is at least about 15° C., or at least about 25° C. As the reaction progresses from the mycarosyloxy hydrolysis to the mycinosyloxy hydrolysis, the temperature preferably is increased to at least about 30° C., at least about 45° C., or from about 48 to about 70° C. In some such embodiments, the increased temperature is from about 50 to about 56° C. In other such embodiments, the increased temperature is from about 55 to about 60° C. In still other such embodiments, the increased temperature is from about 65 to about 70° C. In some embodiments, the reaction mixture is maintained at a temperature that is slightly less than the desired reaction temperature while the acid is being charged to the reactor. In those embodiments, the temperature tends to increase once the acid has been charged to the reactor.

The total reaction time when the two hydrolysis reactions are combined depends on various factors including, e.g., reaction temperature, relative amounts of the ingredients, and the desired conversion. Generally, however, the reaction time for the combined hydrolysis reactions in a batch reactor is at least about 4 hours. In some embodiments, the combined reaction time is from about 4 to about 6 hours. In some such embodiments, e.g., the combined reaction time is about 4 hours. Such a reaction time may be particularly suitable where, e.g., the reaction temperature is from about 65 to about 70° C. In other embodiments, the reaction time is about 5 hours. Such a reaction time may be particularly suitable where, e.g., the reaction temperature is from about 55 to about 60° C.

Purification or isolation of the product may be achieved using, e.g., various methods known in the art. Alternatively, the product may be used in the next step without further purification or isolation.

B-4. Preparing the Activated Compound

In some embodiments, the macrolide synthesis begins by or includes preparing an activated compound, and particularly a compound that corresponds in structure to Formula (VI):

(VI)

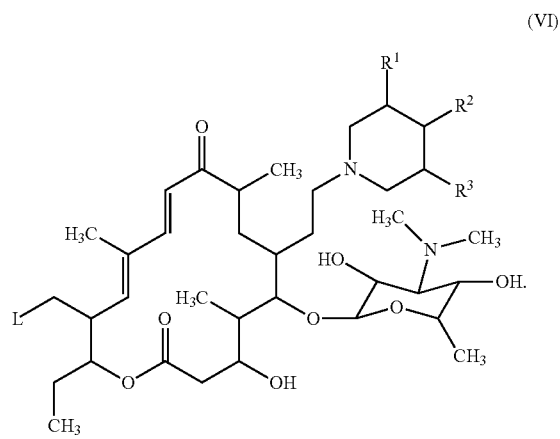

In some embodiments, $R^1$ and $R^3$ are each methyl, and $R^2$ is hydrogen; or $R^1$ and $R^3$ are each hydrogen, and $R^2$ is methyl. In other embodiments, $R^1$, $R^2$, and $R^3$ are each hydrogen, such that the compound corresponds in structure to:

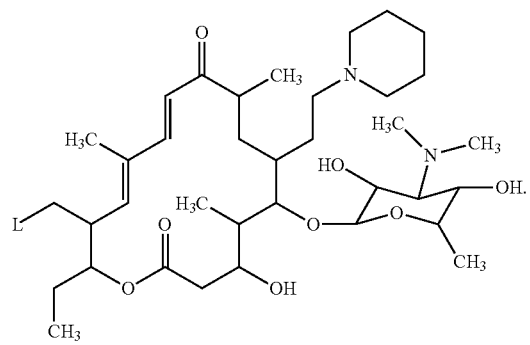

L is a leaving group. In general, the leaving group is a group that may be replaced with a piperidinyl group (normally via nucleophilic displacement) using piperidine in an amination reaction, such as the amination reaction discussed below in Section B-5. In some embodiments, e.g., L is iodo (—I), bromo (—Br), alkylsulfonate, and arylsulfonate. The alkylsulfonate and arylsulfonate are optionally substituted with one or more substituents independently selected from the group consisting of halo, alkyl, and haloalkyl. In some such embodiments, e.g., L is iodo, bromo, methylsulfonate (or "—OS(O)$_2$CH$_3$" or "mesylate"), trifluoromethylsulfonate (or "—OS(O)$_2$CF$_3$" or "triflate"), or 4-methylphenylsulfonate (or "p-toluenesulfonate" or "tosylate"). In some embodiments, L is iodo, and the activated compound corresponds in structure to:

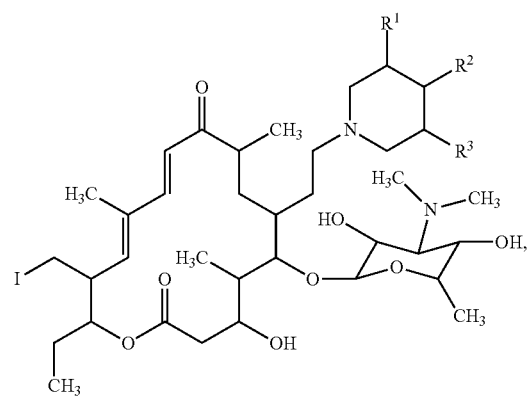

or, when $R^1$, $R^2$, and $R^3$ are each hydrogen, corresponds in structure to:

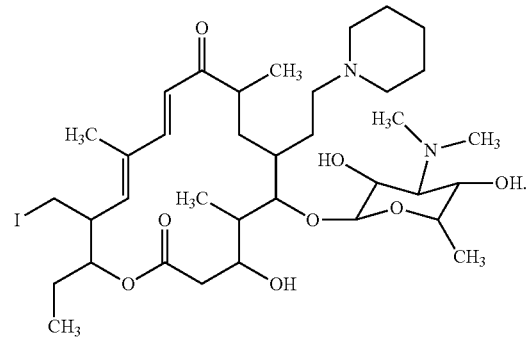 [SMILES: CCC1OC(=O)CC(O)C(C)C(OC2OC(C)C(O)C(N(C)C)C2O)C(CCN2CCCCC2)CC(C)C(=O)/C=C/C(C)=C/C1CI]

In some embodiments, L is mesylate, and the activated compound corresponds in structure to:

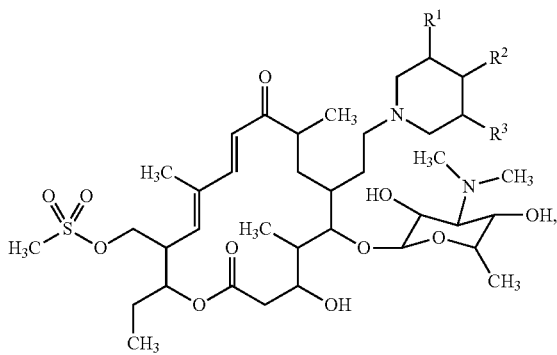

or, when $R^1$, $R^2$, and $R^3$ each are hydrogen, corresponds in structure to:

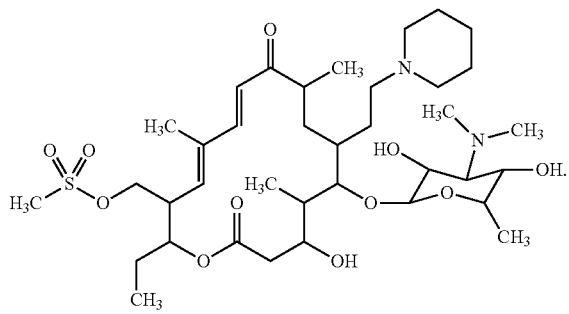 [SMILES: CCC1OC(=O)CC(O)C(C)C(OC2OC(C)C(O)C(N(C)C)C2O)C(CCN2CCCCC2)CC(C)C(=O)/C=C/C(C)=C/C1COS(C)(=O)=O]

In some embodiments, L is tosylate, and the activated compound corresponds in structure to:

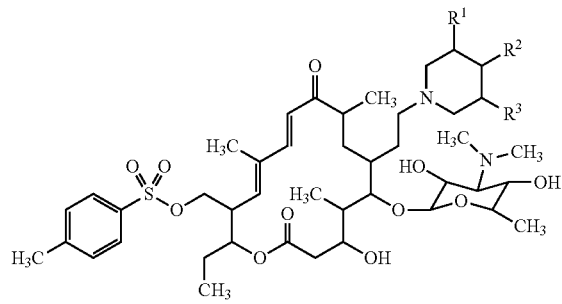

or, when $R^1$, $R^2$, and $R^3$ each are hydrogen, corresponds in structure to:

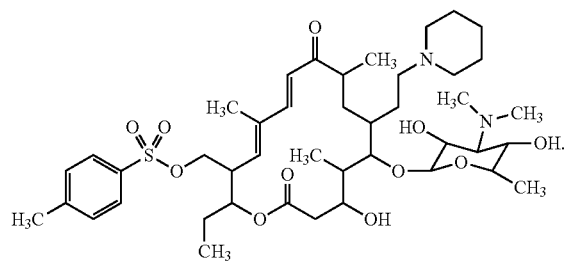

In some embodiments, L is triflate, and the activated compound corresponds in structure to:

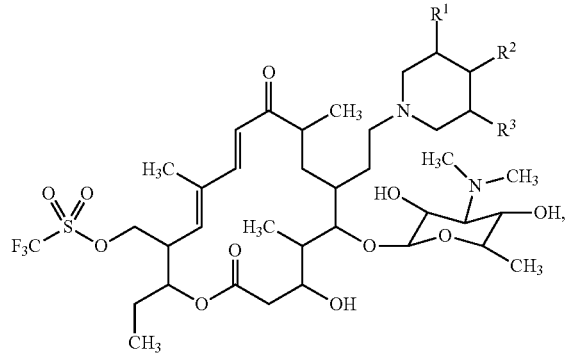

or, when $R^1$, $R^2$, and $R^3$ each are hydrogen, corresponds in structure to:

The activated compound may be prepared via an activation reaction from a 23-hydroxyl-20-piperidinyl-5-O-mycaminosyl-tylonolide compound and an activating agent (i.e., a compound comprising an electron withdrawing group):

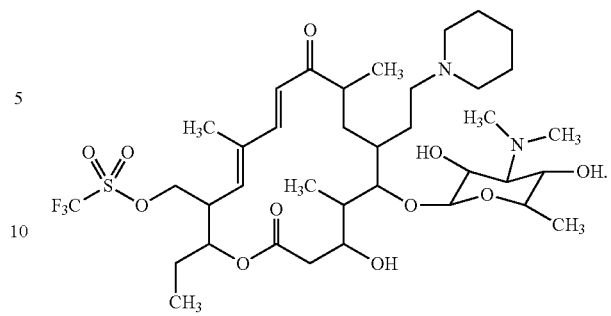

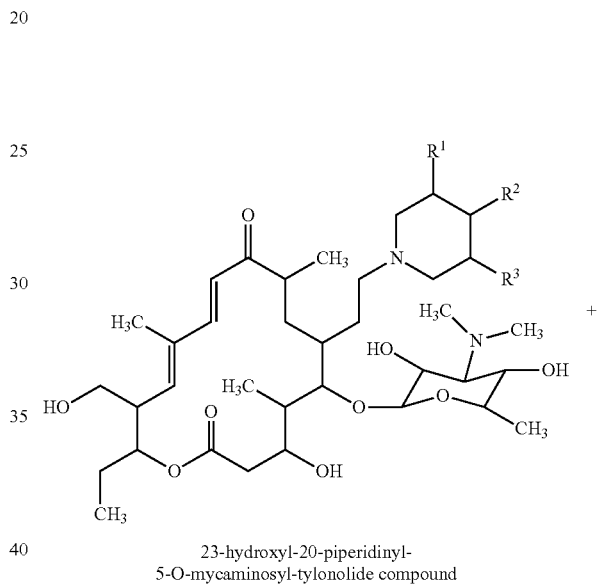

23-hydroxyl-20-piperidinyl-
5-O-mycaminosyl-tylonolide compound

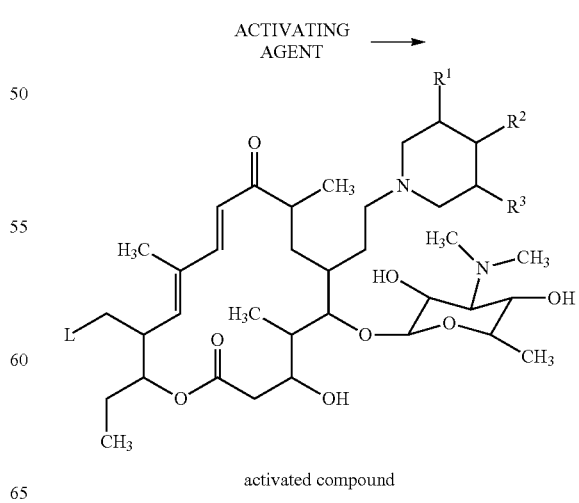

activated compound

Where R¹, R², and R³ are each hydrogen, this reaction is as follows:

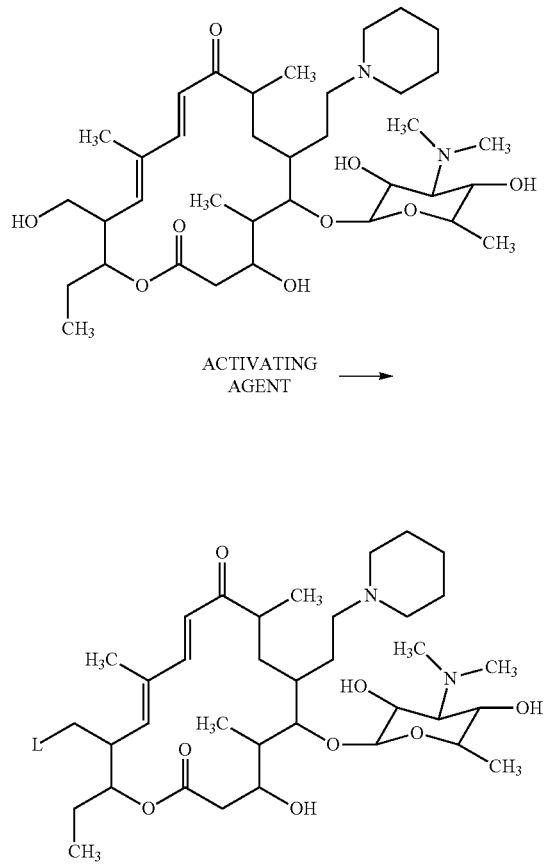

The 23-hydroxyl-20-piperidinyl-5-O-mycaminosyl-tylonolide compound used in the above reaction may be prepared using a process discussed above in Section B-3, prepared using a different process, or obtained from a commercial vendor. In some preferred embodiments, the 23-hydroxyl-20-piperidinyl-5-O-mycaminosyl-tylonolide compound is prepared using a process discussed above in Section B-3.

In some embodiments, L is iodo, and the activating agent is formed by mixing I₂ and triphenylphosphine:

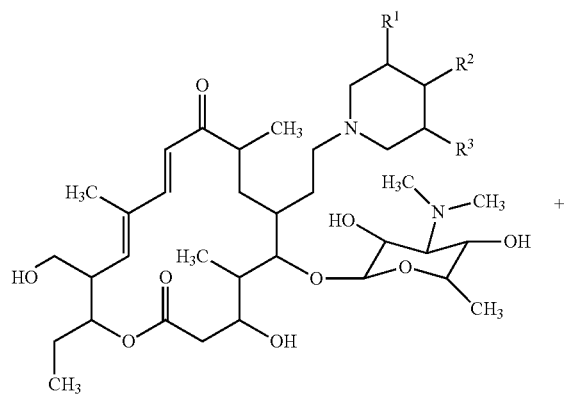

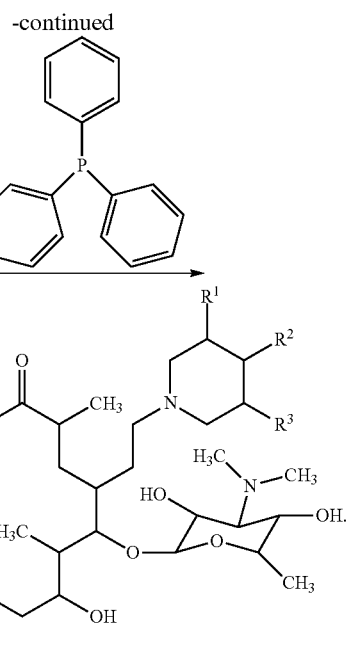

Typically, this reaction is conducted in the presence of one or more solvents. In general, the solvent is non-reactive with the reagents, products, and any other ingredients in the reaction mixture (although, as noted below, the solvent may, e.g., act as a helping base). The solvent may be, e.g., one or more of dichloromethane ("DCM"), acetone, acetonitrile ("ACN"), tert-butyl methyl ether (or "tBME"), toluene, and pyridine. In some embodiments, e.g., the solvent comprises tetrahydrofuran ("THF"). In other embodiments, the solvent comprises pyridine, which also may act as a helping base. In still other embodiments, the solvent comprises dichloromethane. In some such embodiments, e.g., the solvent comprises both dichloromethane and toluene. In some embodiments, the ratio of dichloromethane to toluene is, e.g., be at least about 1:1, from about 3:1 to about 10:1, or from about 3:1 to about 5:1. In some embodiments, at least a portion of the solvent comprises solvent from a process step used during the preparation and/or purification of the 23-hydroxyl-20-piperidinyl-5-O-mycaminosyl-tylonolide compound.

In general, the amount of solvent is sufficient to, e.g., prevent (or essentially prevent) the reagents, products, and other ingredients in the reaction mixture from sticking to the reactor, dissolve the reagents (particularly the 23-hydroxyl-20-piperidinyl-5-O-mycaminosyl-tylonolide compound), and promote homogenous distribution of the reagents. The amount of solvent typically is at least about 1 L per kilogram of the 23-hydroxyl-20-piperidinyl-5-O-mycaminosyl-tylonolide compound. The amount of solvent typically is not greater than about 100 L per kilogram of the 23-hydroxyl-20-piperidinyl-5-O-mycaminosyl-tylonolide compound. In some embodiments, the amount of solvent is from about 5 to about 20 L (or from about 5 to about 15 L, or from about 10 to about 12 L) per kilogram of 23-hydroxyl-20-piperidinyl-5-O-mycaminosyl-tylonolide compound. To illustrate, in some embodiments, the amount of solvent is about 10 L DCM per kilogram. In other embodiments, the amount of solvent is about 12 L DCM per kilogram. In still other embodiments, the solvent is a mixture of DCM and toluene (about 4:1 vol/vol), and the amount of solvent is about 10 L per kilogram.

As indicated above, this reaction may be conducted in the presence of a base (or "helping base"). The base may be a single base, or a combination of bases. This base may comprise, e.g., triethylamine, pyridine, imidazole, potassium carbonate, and/or 4-dimethylaminopyridine (or "DMAP"). The presence of the base may increase the reaction rate. In some embodiments, the base comprises pyridine. In some such embodiments, e.g., the activating agent comprises $I_2$ and triphenylphosphine. In other embodiments, the base comprises imidazole. In other embodiments, the base comprises a combination of potassium carbonate and 4-dimethylaminopyridine. In some such embodiments, e.g., the activating agent comprises p-toluenesulfonyl chloride. In some embodiments, the helping base is attached to a solid support (e.g., a resin).

When a base is used, the molar amount of the base is typically at least equivalent to the molar amount of 23-hydroxyl-20-piperidinyl-5-O-mycaminosyl-tylonolide compound. In some embodiments, the amount of the base is at least 1.05 equivalents. For example, in some embodiments, the molar amount of the base is from about 1.1 to about 10 equivalents, from about 1.1 to about 5 equivalents, or from about 1.1 to about 3 equivalents. In some such embodiments, the molar amount of base is from about 1.1 to about 1.4 equivalents (e.g., about 1.15 or about 1.3 equivalents). In other such embodiments, the molar amount of the base is about 2.8 equivalents. When a combination of bases is used, the total molar amount of base preferably falls within the ranges described above. For example, when the source of the activating agent comprises p-toluenesulfonyl chloride, an example of a contemplated amount of base is about 1.5 equivalents of potassium carbonate and about 1.0 equivalents of 4-dimethylaminopyridine, based on the amount of the 23-hydroxyl-20-piperidinyl-5-O-mycaminosyl-tylonolide compound.

When the source of the activating agent is $I_2$ and triphenylphosphine, the $I_2$, triphenylphosphine, and base (if present) are typically first combined in the presence of solvent to form the activating agent before they are combined with the 23-hydroxyl-20-piperidinyl-5-O-mycaminosyl-tylonolide compound. The reactor in which the activating agent is formed may be the same reactor in which the activating agent is combined with the 23-hydroxyl-20-piperidinyl-5-O-mycaminosyl-tylonolide compound. Alternatively, the activating agent may be formed in a different reactor, and then charged to the reactor to which the 23-hydroxyl-20-piperidinyl-5-O-mycaminosyl-tylonolide compound is charged. The $I_2$ may be added in one or more doses to the triphenylphosphine or vice versa. In some embodiments, the $I_2$ is added to the triphenylphosphine in two or more portions (e.g., 5 portions) or vice versa. The portions may be equal or different amounts. Generally, the combination of the $I_2$ and triphenylphosphine takes place in the presence of a solvent, which may, e.g., comprise the solvent(s) that is used in the substitution reaction. If a base (e.g., pyridine) is present, it is typically combined with the triphenylphosphine before the $I_2$ is added. The mixture preferably is maintained at from about 15 to about 35° C. (or from about 20 to about 30° C., e.g., about 25° C.) during the addition of $I_2$ to the triphenylphosphine, and then maintained at a temperature of from about 15 to about 35° C. (or from about 20 to about 30° C., e.g., about 25° C.) after the addition for at least about one minute (e.g., about 2 minutes), or for at least about 5 minutes, from about 5 to about 60 minutes, or from about 30 to about 60 minutes (e.g., about 40 minutes). Afterward, the temperature preferably is adjusted to a temperature that is approximately equal to the temperature at which the substitution reaction is to be initiated.

To perform the substitution reaction, equimolar amounts of the 23-hydroxyl-20-piperidinyl-5-O-mycaminosyl-tylonolide compound and activating agent generally may be used. Normally, however, an excess of the activating agent is used, and typically at least 1.05 equivalents are used, based on the molar amount of 23-hydroxyl-20-piperidinyl-5-O-mycaminosyl-tylonolide compound.

In some embodiments when the activating agent is formed from $I_2$ and triphenylphosphine, the molar amounts of $I_2$ and triphenylphosphine are each at least 1.05 equivalents, based on the molar amount of 23-hydroxyl-20-piperidinyl-5-O-mycaminosyl-tylonolide compound. For example, in some such embodiments, the molar amounts of $I_2$ and triphenylphosphine are each from 1.05 to about 10 equivalents, from 1.05 to about 5 equivalents, or from 1.05 to about 3 equivalents. Although the equivalents of each of $I_2$ and triphenylphosphine may be the same, the equivalents of triphenylphosphine typically exceeds the equivalents of $I_2$. To illustrate, suitable molar amounts of $I_2$ and triphenylphosphine may be about 2.5 and 2.6 equivalents, respectively, based on the molar amount of 23-hydroxyl-20-piperidinyl-5-O-mycaminosyl-tylonolide compound. In other embodiments, suitable molar amounts of $I_2$ and triphenylphosphine are about 1.9 and 2.0 equivalents, respectively, based on the molar amount of 23-hydroxyl-20-piperidinyl-5-O-mycaminosyl-tylonolide compound. In still other embodiments, a suitable molar amount of $I_2$ is from 1.05 to about 1.2 equivalents, based on the molar amount of 23-hydroxyl-20-piperidinyl-5-O-mycaminosyl-tylonolide compound; and a suitable amount of triphenylphosphine is from about 1.09 to about 1.25 equivalents, based on the molar amount of 23-hydroxyl-20-piperidinyl-5-O-mycaminosyl-tylonolide compound. For example, suitable molar amounts of $I_2$ and triphenylphosphine may be about 1.06 and about 1.13 equivalents, respectively, based on the molar amount of 23-hydroxyl-20-piperidinyl-5-O-mycaminosyl-tylonolide compound. Exemplifying further, suitable molar amounts of $I_2$ and triphenylphosphine may alternatively be about 1.2 and about 1.25 equivalents, respectively, based on the molar amount of 23-hydroxyl-20-piperidinyl-5-O-mycaminosyl-tylonolide compound.

In some embodiments when the activating agent is p-toluenesulfonyl chloride, the molar amount of p-toluenesulfonyl chloride is from about 1.1 to about 10 equivalents, from about 1.2 to about 5 equivalents, or from about 1.2 to about 3 equivalents, based on the molar amount of 23-hydroxyl-20-piperidinyl-5-O-mycaminosyl-tylonolide compound. A suitable molar amount of p-toluenesulfonyl chloride may be, e.g., 1.2 equivalents.

The substitution reaction may be conducted over a wide range of pressures, including atmospheric pressure, less than atmospheric pressure, and greater than atmospheric pressure. It is typically preferred, however, to conduct the reaction at about atmospheric pressure.

The reaction temperature for at least a portion of the substitution reaction (or the entire substitution reaction) typically is greater than the freezing point of the solvent. In general, the reaction temperature over at least a portion of the substitution (or the entire substitution) is not greater than the boiling point of the solvent, and typically is less than the boiling point. In some embodiments, e.g., the solvent is dichloromethane, and at least a portion of the reaction (or the entire reaction) is conducted at a temperature that is not greater than about 45° C. In some embodiments, at least a portion of the reaction (or the entire reaction) is conducted at a temperature that is not greater than about 32° C., or not greater than about 25° C. In some such embodiments, e.g., at least a portion of the reaction (or the entire reaction) is conducted at from about −10° C. to about 25° C. For example, in some embodiments, at least a portion of the reaction (or the entire reaction) is conducted at from about zero to about 20° C., or from about 12 to about 18° C. (e.g., about 13° C.). In other embodiments, at least a portion of the reaction (or the entire reaction) is conducted at from about −10° C. to about 45° C., or from about 25 to about 45° C. In still other embodiments, at least a portion of the reaction (or the entire reaction) is conducted at from about −10 to about 0° C., or from about −6 to about −5° C. Although lesser temperatures than these ranges may be used, such temperatures tend to coincide with slower reaction rates. And, although greater temperatures than these ranges may be used, such temperatures tend to coincide with greater production of undesirable byproducts. Use of some sources of the activating agent (e.g., toluenesulfonyl chloride), however, may allow for greater temperatures to be used (e.g., from about 25 to about 45° C.). When the activating agent is iodine, it is typically preferred to conduct the substitution reaction within a temperature range that does not produce an unacceptable level of impurities resulting from di-iodination of the 23-hydroxyl-20-piperidinyl-5-O-mycaminosyl-tylonolide compound.

The reaction time depends on various factors including, e.g., the reaction temperature, characteristics of the solvent, relative amounts of the ingredients, and the desired conversion. In a batch reactor, the total reaction time is typically at least about 1 minute, and more typically at least about 45 minutes. In general, the total reaction time is less than about 24 hours. In some embodiments, e.g., the total reaction time is less than about 5 hours. To illustrate, in some embodiments, the reaction time is from about 45 minutes to about 5 hours, or from about 1 to about 3 hours. In some such embodiments, e.g., the reaction time is from about 2 to about 3 hours, or from about 2 to about 2.5 hours (e.g., about 2 or about 2.2 hours). In other embodiments, the reaction time is from about 5 to about 10 hours, from about 6 to about 10 hours, from about 7 to about 10 hours, or from about 7 to about 8 hours. Although lesser reaction times than these ranges may be used, such reaction times tend to coincide with lesser conversions. And, although greater reaction times may be used, such reaction times tend to coincide with greater production of impurities and inefficient use of equipment and manpower.

Due to the exothermic nature of the substitution reaction, in some embodiments (particularly those using a batch reactor), the 23-hydroxyl-20-piperidinyl-5-O-mycaminosyl-tylonolide compound is combined with the activating agent over time (or in multiple separate doses) rather than all at once. In some embodiments, this occurs over a period of at least one minute, at least 5 minutes, from about 5 to about 60 minutes, or from about 30 to about 60 minutes (e.g., about 50 minutes). To illustrate, in some embodiments, the substitution reaction is conducted at a maximum temperature of about 25° C., and the dosing of the activating agent occurs over from about 0.5 to about 1 hour, followed by an additional reaction time of about 1 hour. In other embodiments, the substitution reaction is conducted at a maximum temperature of about −5° C., and the dosing of the activating agent occurs over from about 0.7 to about 1 hour, followed by an additional reaction time of about 7 hours.

In some embodiments, the substitution reaction is quenched to inactivate any residual iodine, and, therefore, reduce (and preferably prevent) by-product formation due to such residual iodine. For example, in some such embodiments, the reaction is quenched with aqueous sodium sulfite (i.e., $Na_2SO_3$). Purification or isolation of the product may be achieved using, e.g., various methods known in the art. Alternatively, the product may be used in the next step without further purification or isolation.

Both the activating agent formation reaction and the substitution reaction may be conducted in various reactor types. In some embodiments, e.g., the reactor is a stirred-tank reactor. The reactor may be made of any composition that remains stable when exposed to the reaction mixture. Such materials include, e.g., various materials, such as glass (including glass-lining) or stainless steel.

B-5. Preparing the Macrolide

As noted above, the macrolides prepared in accordance with this invention correspond in structure to Formula (I):

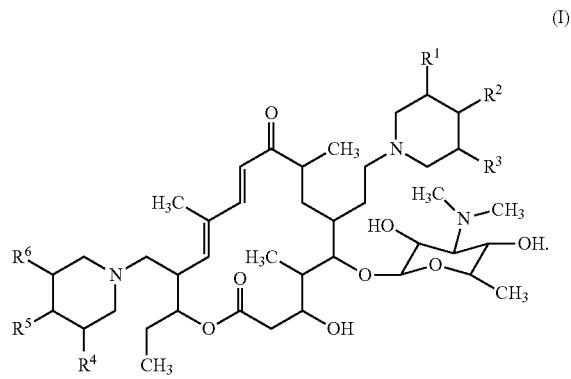

(I)

Here:

As to $R^1$, $R^2$, and $R^3$:

$R^1$ and $R^3$ are each methyl, and $R^2$ is hydrogen;

$R^1$ and $R^3$ are each hydrogen, and $R^2$ is methyl; or $R^1$, $R^2$, and $R^3$ are each hydrogen.

As to $R^4$, $R^5$, and $R^6$:

$R^4$ and $R^6$ are each methyl, and $R^5$ is hydrogen;

$R^4$ and $R^6$ are each hydrogen, and $R^5$ is methyl; or $R^4$, $R^5$, and $R^6$ are each hydrogen.

In some embodiments, $R^1$, $R^2$, $R^3$, $R^4$, $R^5$, and $R^6$ are each hydrogen:

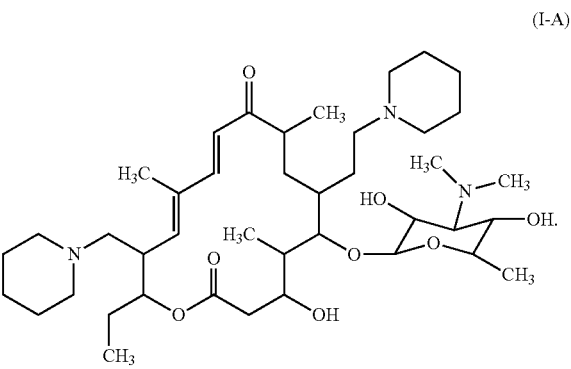 [SMILES: CCC1OC(=O)CC(O)C(C)C(OC2OC(C)C(O)C(N(C)C)C2O)C(CCN2CCCCC2)CC(C)C(=O)/C=C/C(C)=C/C1CN1CCCCC1]

(I-A)

In some such embodiments, e.g., the compound corresponds in structure to the following formula:

In some embodiments, the preparation of the macrolide begins by or includes an amination reaction of an activated compound with a piperidinyl compound:

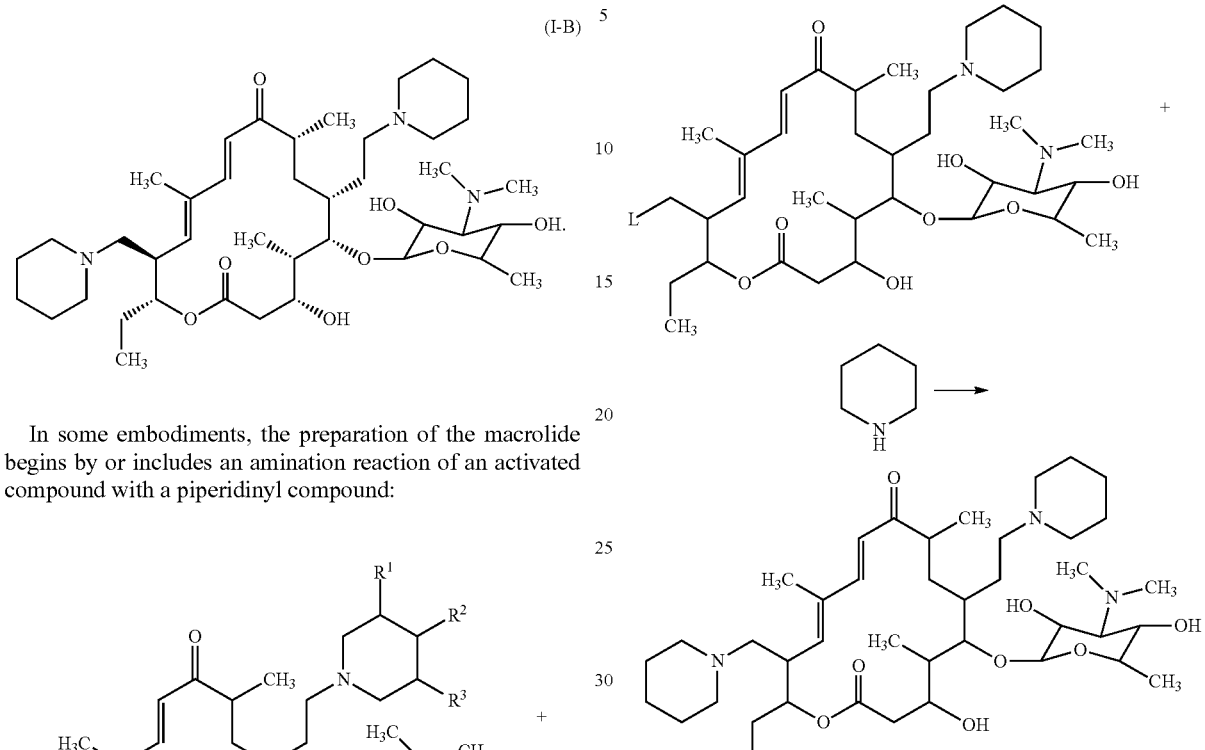

Where $R^1$, $R^2$, $R^3$, $R^4$, $R^5$, and $R^6$ are each hydrogen, this reaction is as follows:

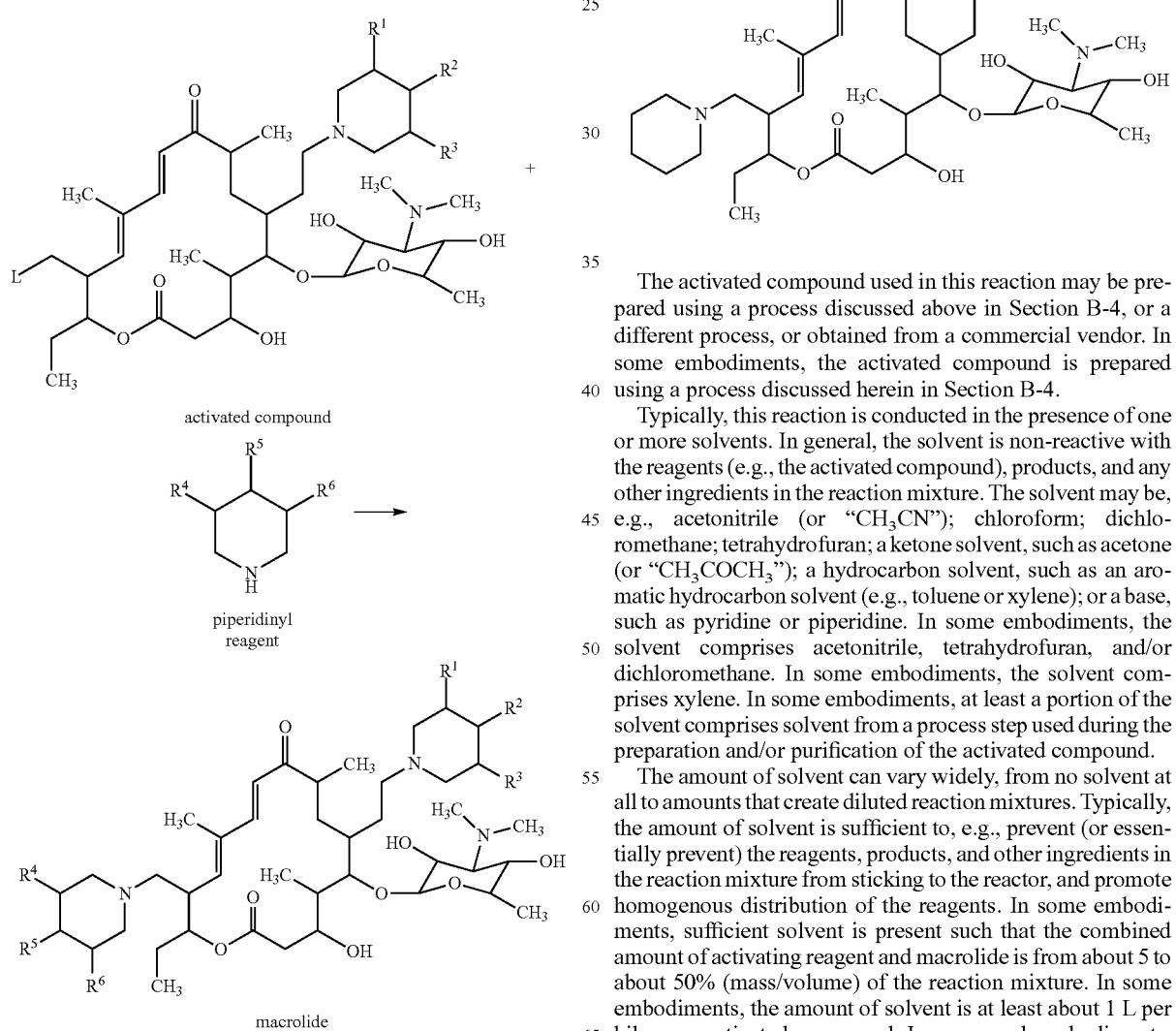

The activated compound used in this reaction may be prepared using a process discussed above in Section B-4, or a different process, or obtained from a commercial vendor. In some embodiments, the activated compound is prepared using a process discussed herein in Section B-4.

Typically, this reaction is conducted in the presence of one or more solvents. In general, the solvent is non-reactive with the reagents (e.g., the activated compound), products, and any other ingredients in the reaction mixture. The solvent may be, e.g., acetonitrile (or "$CH_3CN$"); chloroform; dichloromethane; tetrahydrofuran; a ketone solvent, such as acetone (or "$CH_3COCH_3$"); a hydrocarbon solvent, such as an aromatic hydrocarbon solvent (e.g., toluene or xylene); or a base, such as pyridine or piperidine. In some embodiments, the solvent comprises acetonitrile, tetrahydrofuran, and/or dichloromethane. In some embodiments, the solvent comprises xylene. In some embodiments, at least a portion of the solvent comprises solvent from a process step used during the preparation and/or purification of the activated compound.

The amount of solvent can vary widely, from no solvent at all to amounts that create diluted reaction mixtures. Typically, the amount of solvent is sufficient to, e.g., prevent (or essentially prevent) the reagents, products, and other ingredients in the reaction mixture from sticking to the reactor, and promote homogenous distribution of the reagents. In some embodiments, sufficient solvent is present such that the combined amount of activating reagent and macrolide is from about 5 to about 50% (mass/volume) of the reaction mixture. In some embodiments, the amount of solvent is at least about 1 L per kilogram activated compound. In some such embodiments, e.g., the amount of solvent is from about 1 to about 100 L (or from about 1 to about 20 L) per kilogram of activated compound. To illustrate, in some embodiments, about 5 L of solvent (e.g., xylene or tetrahydrofuran) are used per kilogram of activated compound. Illustrating further, in other embodiments, about 10 L of solvent (e.g., acetonitrile) are used per kilogram of activated compound.

In some embodiments, the amination is conducted in the presence of a base. In some embodiments, the base comprises an un-hydrated base. The base may be, e.g., potassium carbonate (or "$K_2CO_3$"), sodium carbonate (or "$Na_2CO_3$"), or a tertiary amine. The presence of such a base tends to coincide with a greater reaction rate and less impurities. It is believed that such advantages may stem from the base deprotonating protonated piperidinyl compound. The base preferably is not so strong as to cause hydrolysis of the lactone in the macrolide core. Generally, equimolar amounts of the activated compound and base may be used. Normally, however, an excess of base is used. In some embodiments, at least 1.05 (or from about 1.1 to about 50, from about 2 to about 30, from about 2 to about 20, or from about 2 to about 10) equivalents of base are used, based on the molar amount of activated compound charged to the reactor. In some such embodiments, about 6.2 equivalents of base are used. In other some such embodiments, about 10 equivalents of base are used. In still other such embodiments, from about 1.1 to about 10 (or from about 2 to about 8, or from about 4 to about 6) equivalents of base are used, based on the molar amount of activated compound charged to the reactor. To illustrate, a suitable amount of base may be, e.g., about 5 equivalents.

To perform the amination, the activated compound, piperidinyl compound, and solvent, as well as any base (to the extent present), are normally charged to a reactor and mixed. These ingredients generally may be charged to the reactor in any sequence. The reactor may comprise various reactor types. In some embodiments, e.g., the reactor is a stirred-tank reactor. Glass, glass-lined, and stainless steel reactors are often preferred, although any composition stable when exposed to the reaction mixture may be used.

Generally, equimolar amounts of the activated compound and piperidinyl compound may be used. Normally, however, an excess of the piperidinyl compound is used. In some embodiments, at least 1.05 (or from about 1.1 to about 50, from about 2 to about 30, from about 2 to about 20, or from about 2 to about 10) equivalents of the piperidinyl compound are used, based upon the molar amount of activated compound charged to the reactor. In some such embodiments, about 10 equivalents of the piperidinyl compound are used. In other such embodiments, from about 2 to about 8 (or from about 4 to about 6) equivalents are used, based upon the molar amount of activated compound charged to the reactor. To illustrate, a suitable amount of piperidinyl compound may be, e.g., about 4.7 equivalents. A contemplated suitable amount of piperidinyl compound also may be, e.g., about 5.7-5.8 equivalents.

At least a portion of the reaction (or the entire reaction) normally is conducted at greater than about 20° C., or greater than about 25° C. The optimal reaction temperature depends on, e.g., the solvent. Typically, at least a portion of the reaction (or the entire reaction) is conducted at a temperature that is not greater than the boiling point of the solvent, and typically is less than the boiling point. In general, at least a portion of the reaction (or the entire reaction) is conducted at from about 50 to about 110° C. In some embodiments, e.g., at least a portion of the reaction (or the entire reaction) is conducted at from about 60 to about 110° C., or from about 75 to about 110° C. To illustrate, when the solvent comprises acetonitrile or toluene, a suitable contemplated reaction temperature for at least a portion of the reaction (or the entire reaction) is from about 78° C. to about 110° C. (e.g., about 78° C.). To illustrate further, when the solvent comprises xylene, a suitable contemplated reaction temperature for at least a portion of the reaction (or the entire reaction) is from about 95 to about 105° C., and a suitable reaction time for the reaction is about 15 hours. In other embodiments, the solvent comprises tetrahydrofuran, and at least a portion of the reaction (or the entire reaction) is conducted at from about 55 to about 75° C. Although lesser temperatures than these ranges may be used, such temperatures tend to coincide with slower reaction rates. And, although greater temperatures than these ranges may be used, such temperatures tend to coincide with greater production of undesirable byproducts. Typically, lesser temperatures may be used with solvents having greater polarities. The temperature can be adapted accordingly by one skilled in the art.

In some embodiments, the amination reaction is conducted at more than one temperature. For example, the reaction may be conducted at one temperature initially, and then slowly increased to another temperature as the reaction progresses.

The amination may be conducted over a wide range of pressures, including atmospheric pressure, less than atmospheric pressure, and greater than atmospheric pressure. It is typically preferred, however, to conduct the reaction at about atmospheric pressure.

The reaction time depends on various factors including, e.g., the reaction temperature, characteristics of the solvent, relative amounts of the ingredients, and the desired conversion. In a batch reactor, the reaction time is generally at least about 1 minute, at least about 5 minutes, or at least about 45 minutes. The reaction time is generally no greater than about 24 hours. In some embodiments, the reaction time is from about 2 to about 15 hours. In other embodiments, the reaction time is from about 1 to about 5 hours, from about 2 to about 4 hours, or from about 2 to about 3 hours (e.g., about 2.5 hours). In other such embodiments, the reaction time is from about 6 to about 15 hours. Although lesser reaction times than these ranges may be used, such reaction times tend to coincide with lesser conversions.

Further purification or isolation of the product may be achieved using, e.g., various methods known in the art.

B-6. Examples of Contemplated Reaction Schemes

This invention contemplates any processes that use any of the above reactions. In some embodiments, the process will comprise one of the above reactions. In other embodiments, the process will comprise two, three, four, or all the above reactions. The following Scheme I generically illustrates a scenario where all the above reactions are used:

Scheme I
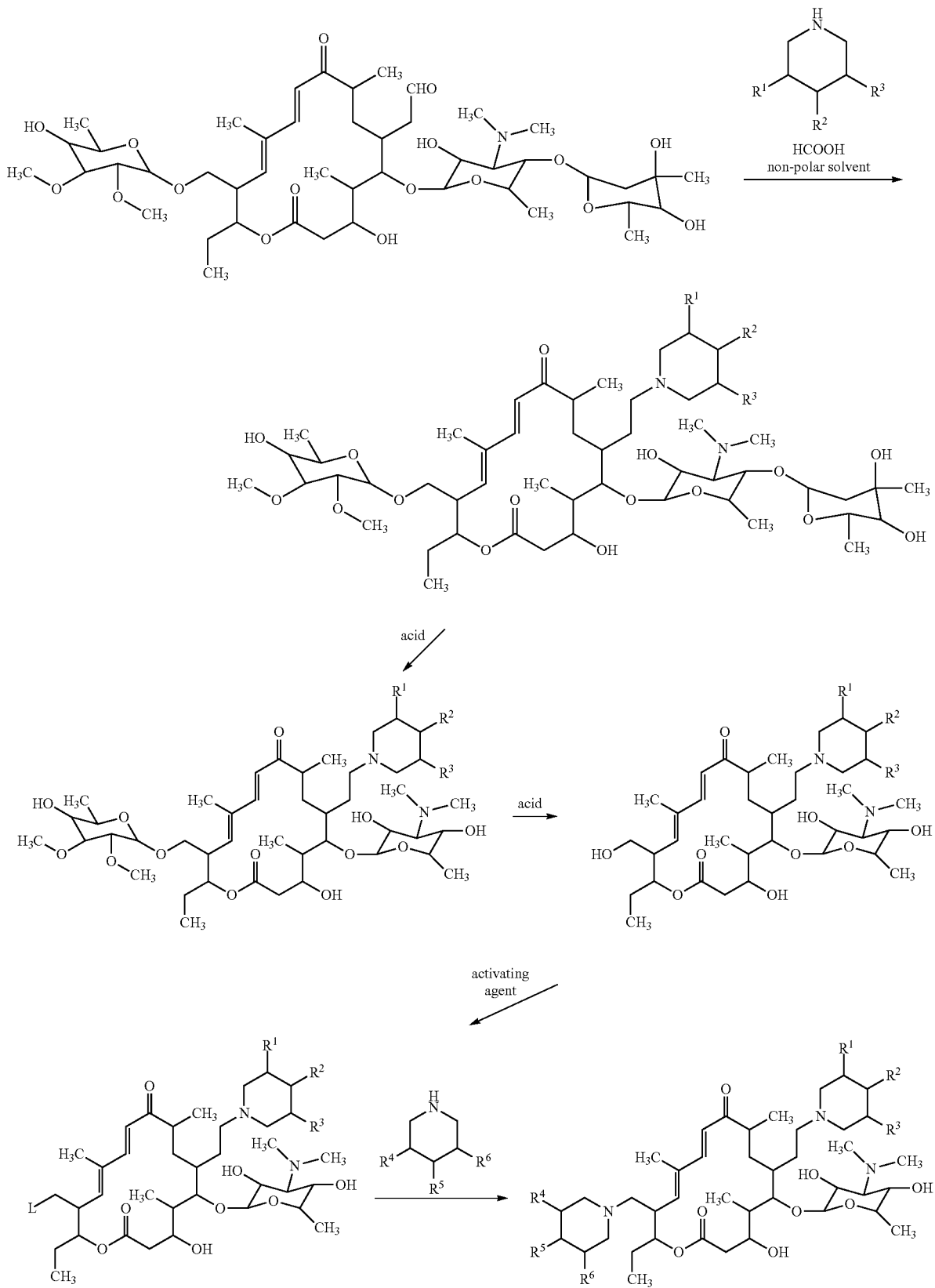

Here:
As to $R^1$, $R^2$, and $R^3$:
$R^1$ and $R^3$ are each methyl, and $R^2$ is hydrogen;
$R^1$ and $R^3$ are each hydrogen, and $R^2$ is methyl; or
$R^1$, $R^2$, and $R^3$ are each hydrogen.
As to $R^4$, $R^5$, and $R^6$:
$R^4$ and $R^6$ are each methyl, and $R^5$ is hydrogen;
$R^4$ and $R^6$ are each hydrogen, and $R^5$ is methyl; or
$R^4$, $R^5$, and $R^6$ are each hydrogen.
L is a leaving group.

The following Scheme II generically illustrates the above scenario where the non-polar solvent in the reductive amination comprises toluene; the acids in the hydrolysis reactions comprise HBr; the source of the activating agent comprises $I_2$, triphenylphosphine, and pyridine; and the final amination reaction mixture comprises potassium carbonate:

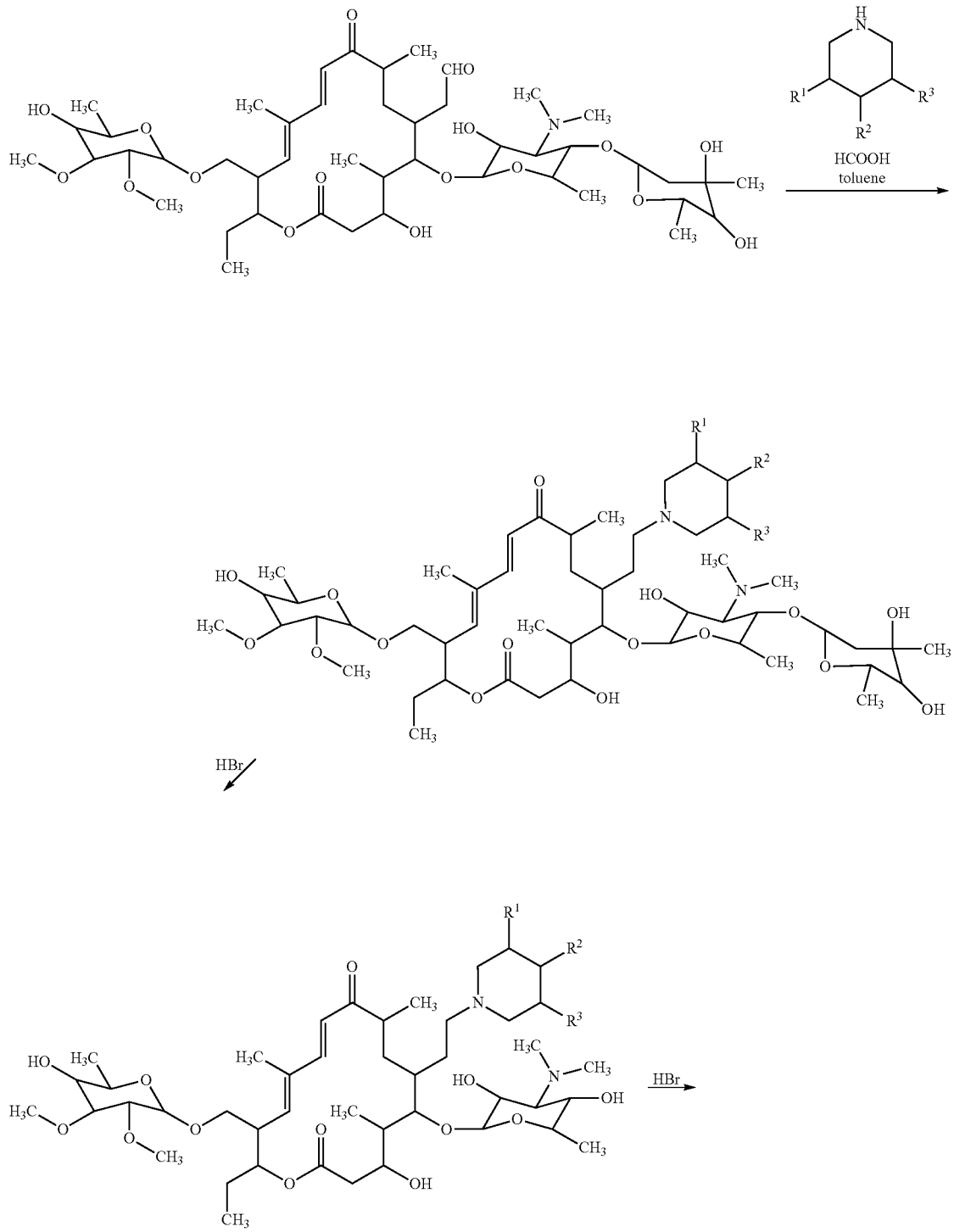

-continued
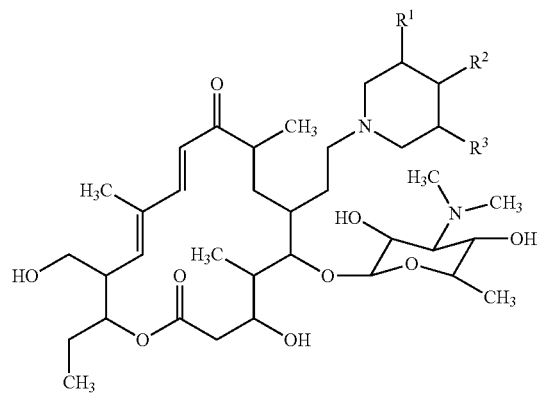
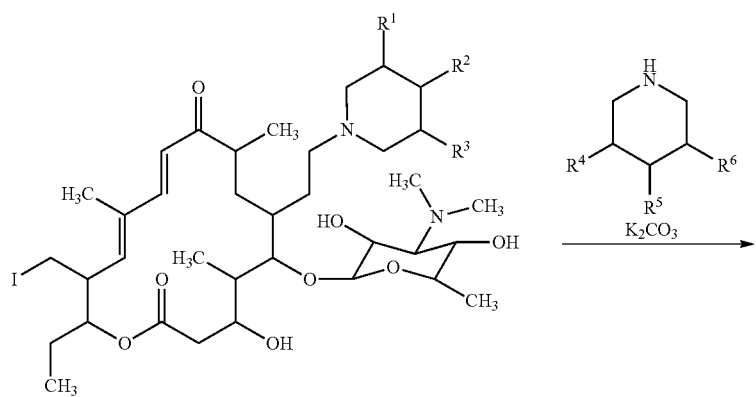
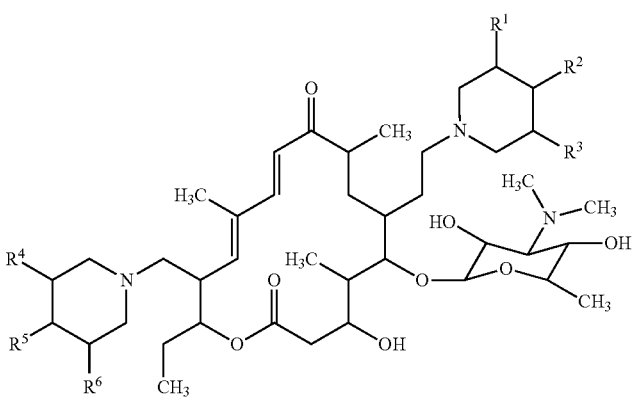

The following Scheme III generically illustrates the scenario of Scheme I where the two hydrolysis reactions are conducted without stopping the first hydrolysis or isolating product from the first hydrolysis before conducting the second hydrolysis:
Scheme III
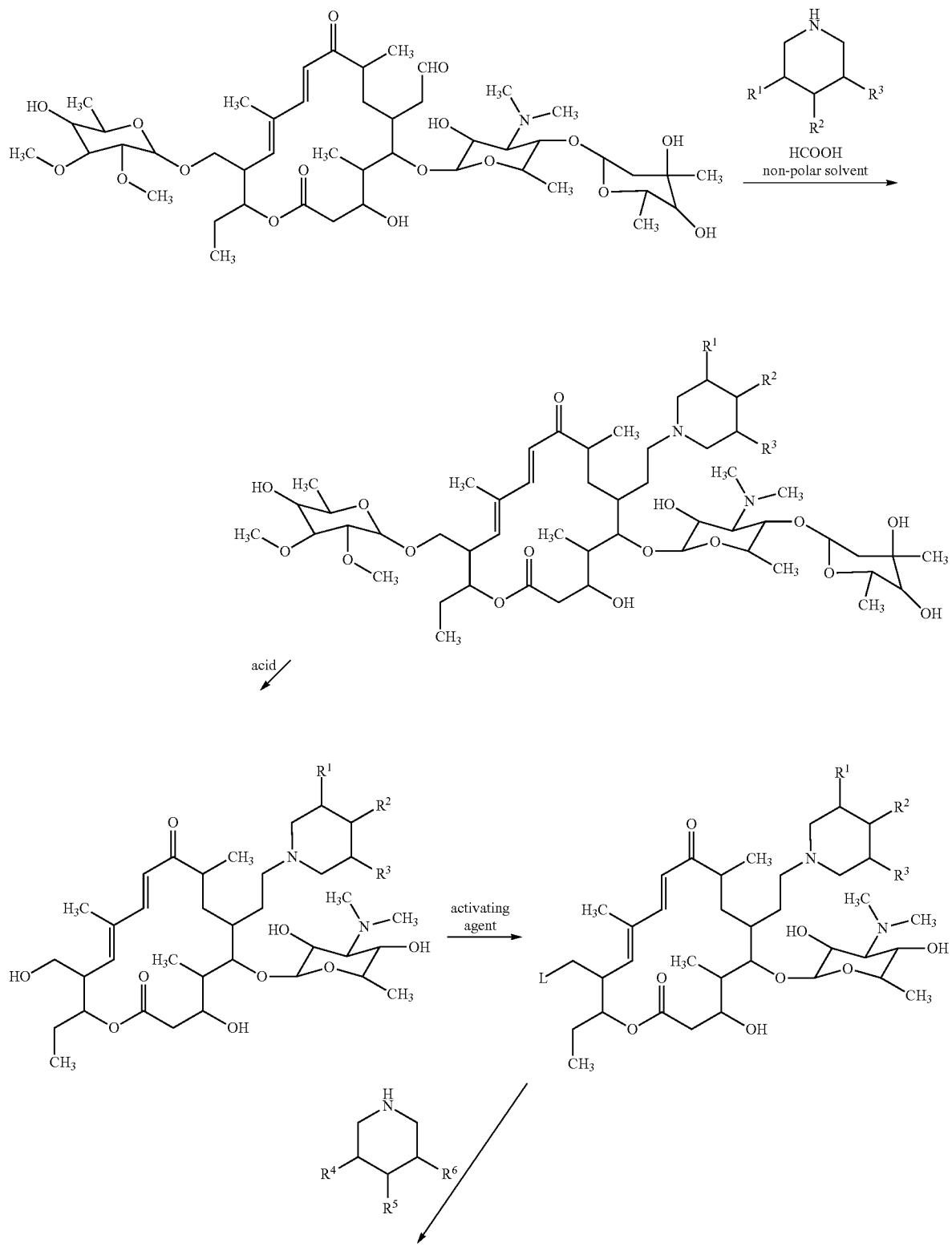

-continued

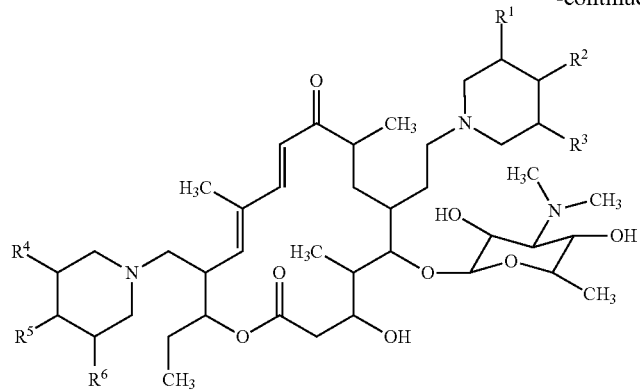

The following Scheme IV generically illustrates the scenario of Scheme I where the non-polar solvent in the reductive amination comprises toluene; the acids in the hydrolysis reactions comprise HBr; the first hydrolysis is not stopped and the product of the first hydrolysis is not isolated before conducting the second hydrolysis; the source of the activating agent comprises $I_2$, triphenylphosphine, and pyridine; and the final amination reaction mixture comprises potassium carbonate:

Scheme IV

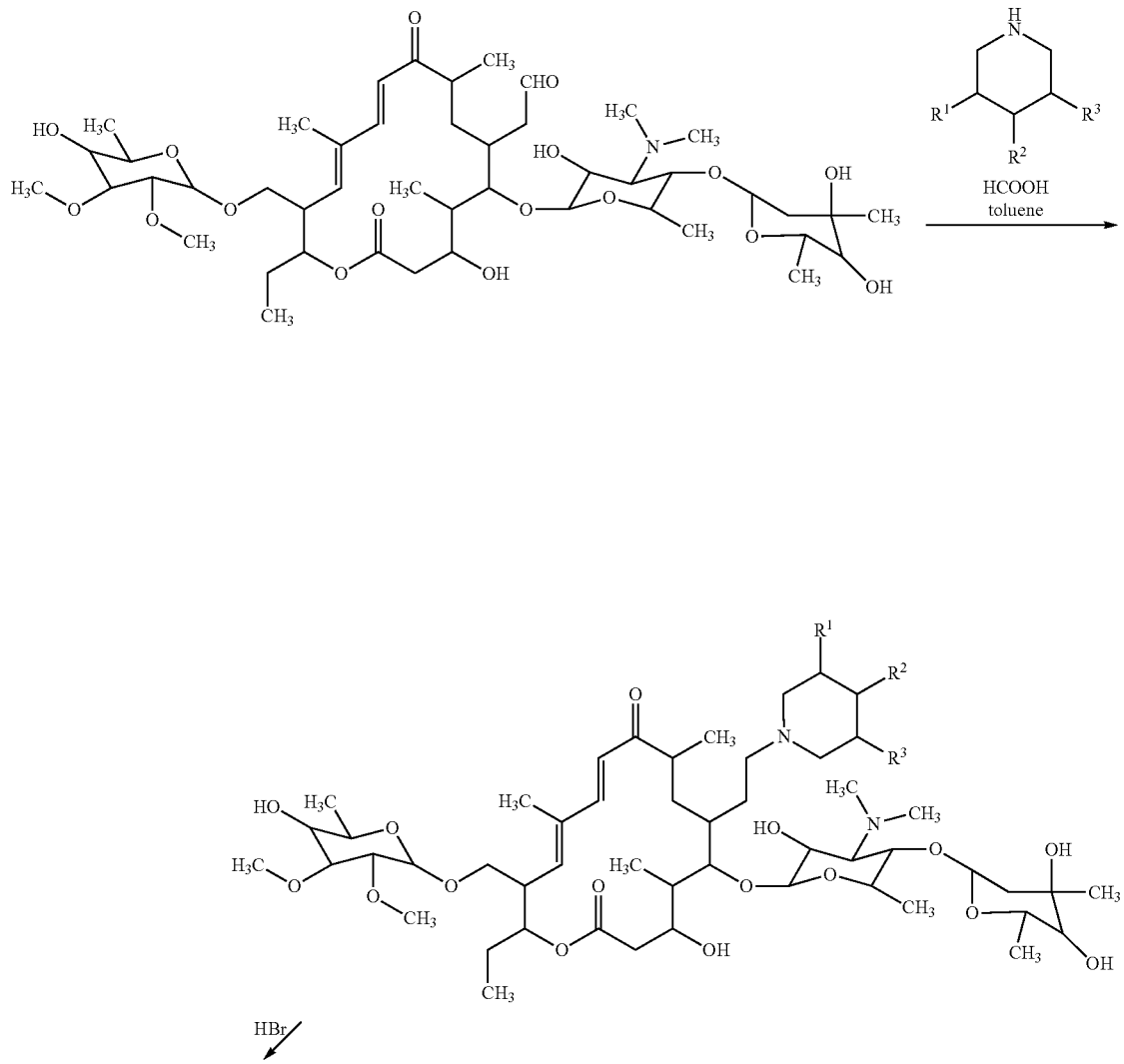

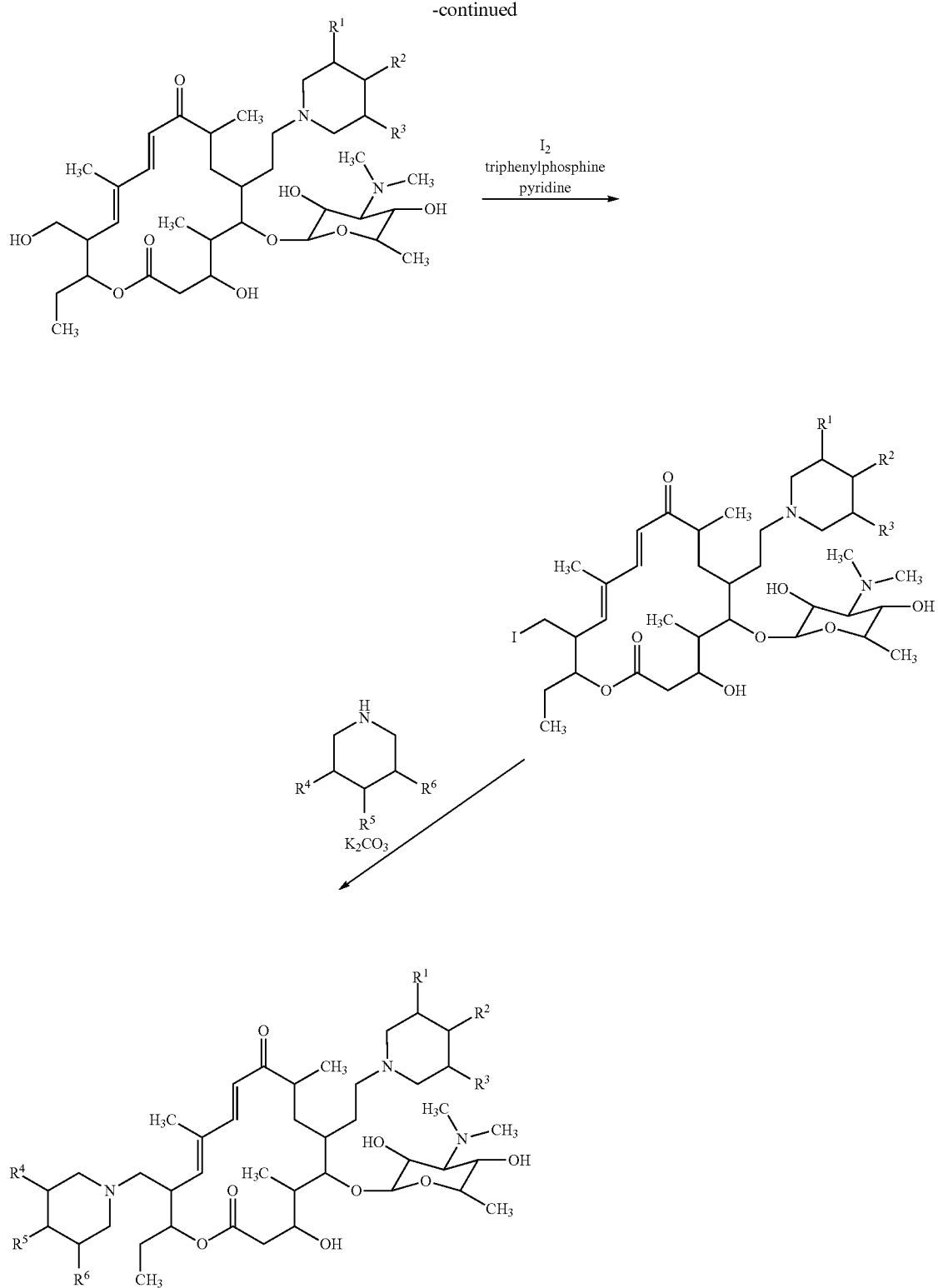

The following Scheme V generically illustrates a 2-stage scenario of Scheme I where the non-polar solvent in the reductive amination comprises toluene; the acids in the hydrolysis reactions comprise HBr; the reductive amination and first hydrolysis are not stopped and the products of the reductive amination and first hydrolysis are not isolated before conducting the second hydrolysis; the source of the activating agent comprises $I_2$, triphenylphosphine, and pyridine; the final amination reaction mixture comprises potassium carbonate; and the activation reaction is not stopped and the product of the activation reaction is not isolated before conducting the final amination reaction:

61  62
Scheme V
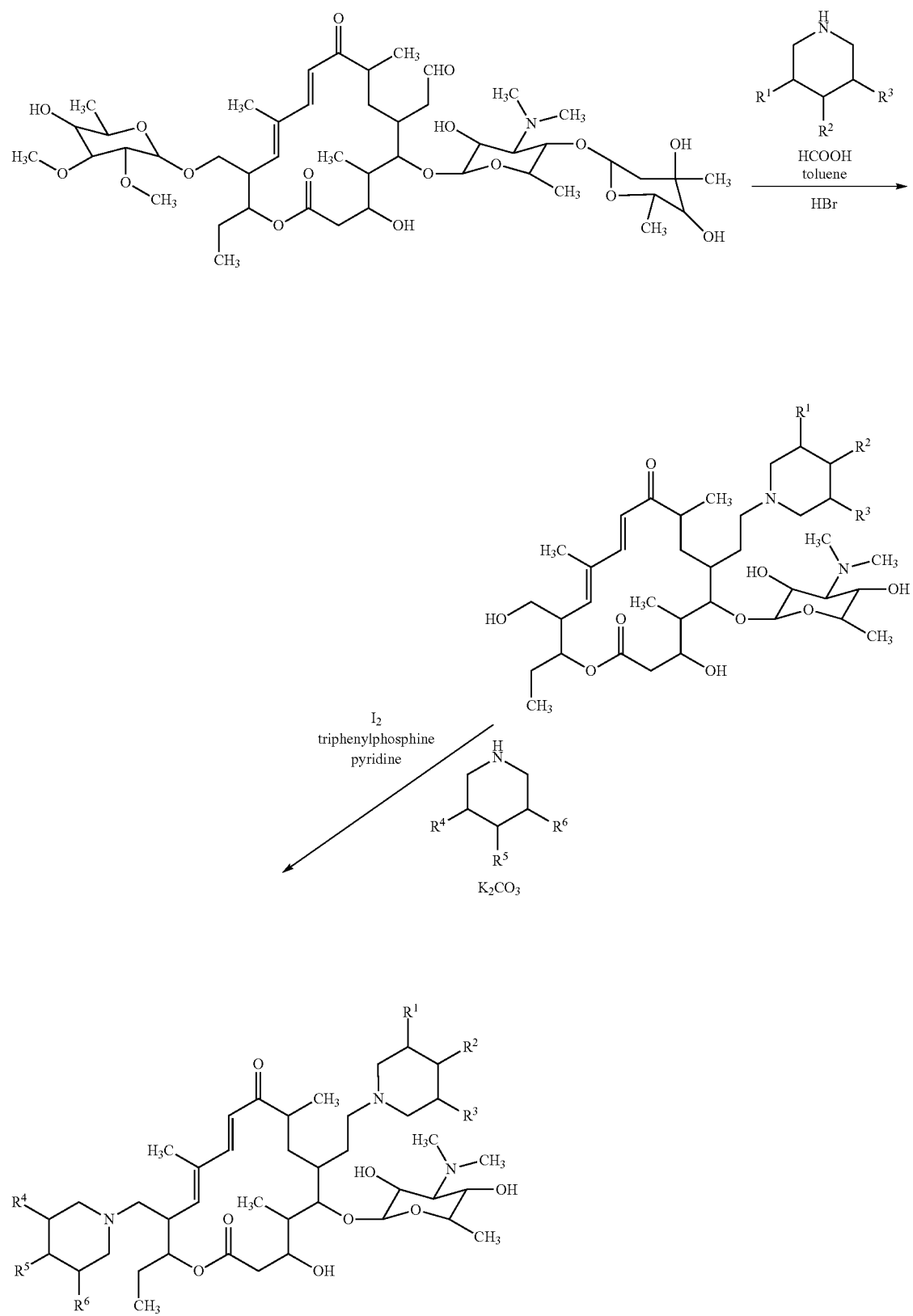

B-7. Tylosin Reagent

In general, the tylosin reagent used in the processes of this invention comprises tylosin A (or a salt thereof):

Tylosin A

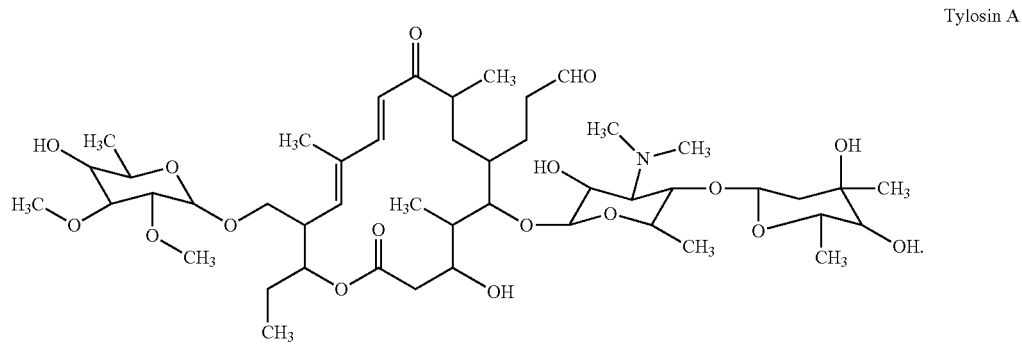 [SMILES: CCC1OC(=O)CC(O)C(C)C(OC2OC(C)C(OC3CC(C)(O)C(O)C(C)O3)C(N(C)C)C2O)C(CCC=O)CC(C)C(=O)/C=C/C(C)=C/C1COC1OC(C)C(O)C(OC)C1OC]

Although this invention contemplates the use of pure (or at least essentially pure) tylosin A (or a salt thereof), various commercially available tylosin compositions additionally or alternatively may comprise one or more derivatives of tylosin A, including:

tylosin B

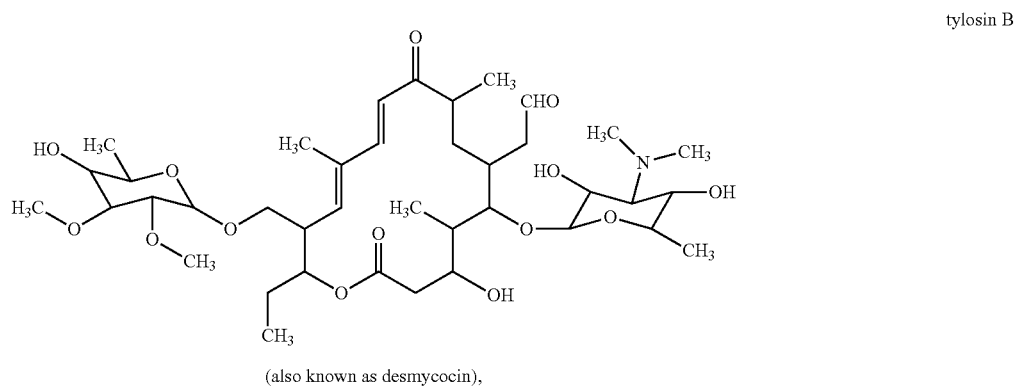

(also known as desmycocin), tylosin C

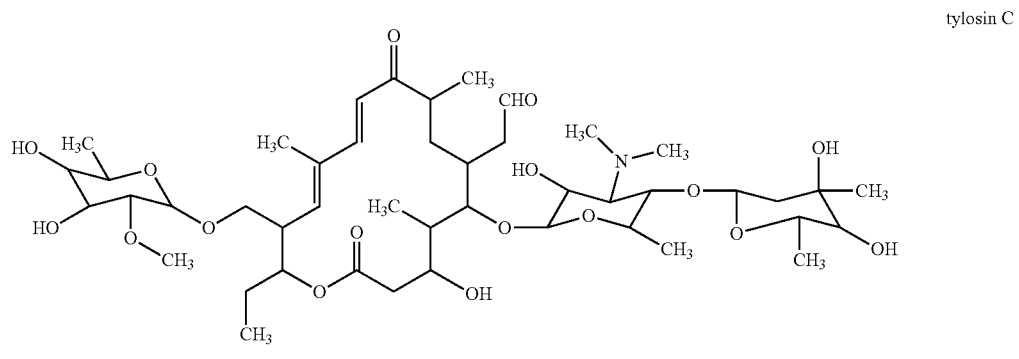

(also known as macrocin), and

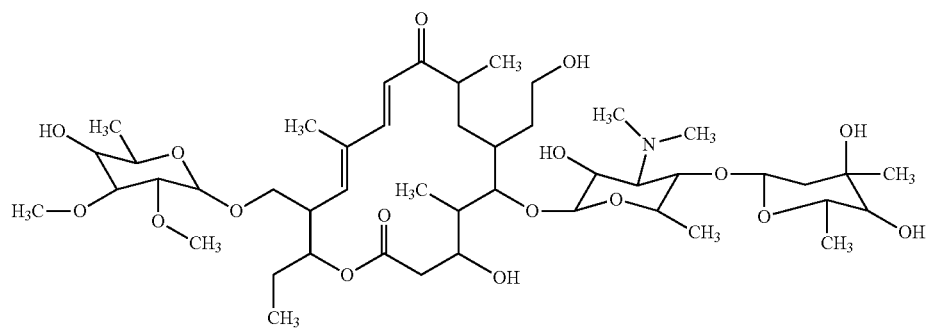

tylosin D (also known as relomycin).

In general, these derivatives, if present, are present in only small amounts. In some embodiments, the weight ratio of tylosin A to the total combined amount of tylosin A derivatives in the composition is at least about 1:1. In some such embodiments, e.g., the ratio is at least about 4:1, at least about 10:1, at least about 95:5, at least about 98:2, or at least about 99:1. In other such embodiments, about 100% (by weight) of the tylosin compounds (i.e., tylosin A and tylosin A derivatives) in the composition consists of tylosin A. Other embodiments are contemplated wherein the tylosin A makes up less than 50% (by weight) of the tylosin compounds in the composition. To illustrate, in some such embodiments, the weight ratio of tylosin D to the total combined amounts of tylosin A and other tylosin A derivatives is at least about 1:1, at least about 4:1, at least about 9:1, at least about 95:5, at least about 98:2, or at least about 99:1. In other such embodiments, about 100% (by weight) of the tylosin compounds in the composition consists of tylosin D.

The methods discussed above for making 20,23-dipiperidinyl-5-O-mycaminosyl-tylonolide from tylosin A generally can be used (and, to the extent desirable, modified) for making 20,23-dipiperidinyl-5-O-mycaminosyl-tylonolide from tylosin B, C, and/or D in addition to (or instead of) tylosin A.

Tylosin B, e.g., has a hydroxyl instead of a mycarosyl substituent on the 5-mycanimosyl. Thus, a 20-piperidinyl intermediate derived from tylosin B does not require the first hydrolysis reaction discussed above in Section B-2. To the extent such an intermediate is exposed to the hydrolysis method discussed in Section B-2, the intermediate will generally remain non-reactive or begin hydrolyzing at the 23-mycinosyloxy substituent.

Tylosin C has a hydroxyl rather than a methoxy at the 3-position of the 23-mycinosyloxy substituent. This difference generally has no effect with respect to the above-described methods. The sugar normally will cleave (i.e., hydrolyze) in the same manner and under the same conditions as the 23-mycinosyloxy of tylosin A during the hydrolysis described above in Section B-3.

Tylosin D has a hydroxyl rather than a carbonyl at the 20-position. This hydroxyl is generally not transformed into a piperidinyl using the reductive amination method described above in Section B-1. Depending on the reaction conditions, however, it may become activated during the activation reaction described above in Section B-4, and then aminated with piperidine along with the 23-position during the amination method described above in Section B-5.

C. Salts of Intermediates and Macrolides

This invention may be used to prepare macrolide compounds or intermediates both in the form of free compounds and in the form of salts. In addition, the reagents used in this invention may be in the form of salts. Salts may be, e.g., acid addition salts. In general, an acid addition salt can be prepared using any inorganic or organic acid. Depending on the particular compound (and/or its crystalline structure), a salt of a compound may be advantageous due to one or more of the salt's chemical or physical properties, such as stability in differing temperatures and humidities, or a desirable solubility in water, oil, or other solvent. In some instances, a salt of a compound also may be used as an aid in the isolation or purification of a compound. In some embodiments (particularly where the salt is intended to be administered to an animal, as opposed to, e.g., being used in an in vitro context), the salt is pharmaceutically acceptable.

Salts can typically be formed by, e.g., mixing the free macrolide or intermediate compound with an acid using various known methods in the art. Examples of often suitable inorganic acids include hydrochloric, hydrobromic, hydroiodic, nitric, carbonic, sulfuric, and phosphoric acid. Examples of often suitable organic acids include, e.g., aliphatic, cycloaliphatic, aromatic, araliphatic, heterocyclic, carboxylic, and sulfonic classes of organic acids. Specific examples of often suitable organic salts include cholate, sorbate, laurate, acetate, trifluoroacetate (or "$CF_3COOH$" or "TFA"), formate, propionate, succinate, glycolate, gluconate, digluconate, lactate, malate, tartrate (and derivatives thereof, such as dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some embodiments, the salt comprises a hydrochlorate, trifluoroacetate, mesylate, tosylate, tartrate, or citrate salt.

D. Crystalline Forms of
20,23-Dipiperidinyl-5-O-Mycaminosyl-Tylonolide

The chemical and physical properties of macrolides, and particularly 20,23-dipiperidinyl-5-O-mycaminosyl-tylonolide, are often important in their commercial development. These properties include, for example: (1) physical stability; (2) chemical stability; (3) packing properties, such as molar volume, density, and hygroscopicity; (4) thermodynamic properties, such as melting temperature, vapor pressure, and solubility; (5) kinetic properties, such as dissolution rate and stability (including stability at ambient conditions, especially to moisture and under storage conditions); (6) surface properties, such as surface area, wettability, interfacial tension, and shape; (7) mechanical properties, such as hardness, tensile strength, compactability, handling, flow, and blend; (8) filtration properties; and (9) chemical purity. These properties can affect, e.g., processing and storage of pharmaceutical compositions comprising 20,23-dipiperidinyl-5-O-mycaminosyl-tylonolide. While Applicants believe that all the solid-state forms of 20,23-dipiperidinyl-5-O-mycaminosyl-tylonolide described in this disclosure are therapeutically effective, solid-state forms that provide an improvement in one or more of the above-listed properties relative to other solid-state forms of 20,23-dipiperidinyl-5-O-mycaminosyl-tylonolide are generally desirable, as are solid-state forms that may be used as intermediates in processes for making the desired solid-state forms.

In accordance with the invention, several crystalline forms of 20,23-dipiperidinyl-5-O-mycaminosyl-tylonolide have been prepared. These crystalline forms generally possess one or more of the above-described advantageous chemical and/or physical properties relative to other solid-state forms of 20,23-dipiperidinyl-5-O-mycaminosyl-tylonolide and/or are useful as intermediates in the preparation of one or more other solid-state forms of 20,23-dipiperidinyl-5-O-mycaminosyl-tylonolide. Specific crystalline forms of 20,23-dipiperidinyl-5-O-mycaminosyl-tylonolide that have been discovered include the following:

(1) A first anhydrous and non-solvated crystalline form of 20,23-dipiperidinyl-5-O-mycaminosyl-tylonolide possessing unique properties relative to other solid-state forms of 20,23-dipiperidinyl-5-O-mycaminosyl-tylonolide (identified in this disclosure as the "Form I polymorph");

(2) a second anhydrous and non-solvated crystalline form of 20,23-dipiperidinyl-5-O-mycaminosyl-tylonolide possessing unique properties relative to other solid-state forms of 20,23-dipiperidinyl-5-O-mycaminosyl-tylonolide (identified in this disclosure as the "Form II polymorph");

(3) a third anhydrous and non-solvated crystalline form of 20,23-dipiperidinyl-5-O-mycaminosyl-tylonolide possessing unique properties relative to other solid-state forms of 20,23-dipiperidinyl-5-O-mycaminosyl-tylonolide (identified in this disclosure as the "Form III polymorph");

(4) a fourth anhydrous and non-solvated crystalline form of 20,23-dipiperidinyl-5-O-mycaminosyl-tylonolide possessing unique properties relative to other solid-state forms of 20,23-dipiperidinyl-5-O-mycaminosyl-tylonolide (identified in this disclosure as the "Form IV polymorph");

(5) isomorphic ethyl acetate, ethanol, and diethyl ketone solvated crystalline forms of 20,23-dipiperidinyl-5-O-mycaminosyl-tylonolide (collectively identified in this disclosure as "S1 crystalline solvates");

(6) a tert-butyl methyl ether solvated crystalline form of 20,23-dipiperidinyl-5-O-mycaminosyl-tylonolide (identified in this disclosure as an "S2 crystalline solvate");

(7) a tetrahydrofuran solvated crystalline form of 20,23-dipiperidinyl-5-O-mycaminosyl-tylonolide (identified in this disclosure as an "S3 crystalline solvate"); and (8) isomorphic methyl acetate and ethyl formate solvated crystalline forms of 20,23-dipiperidinyl-5-O-mycaminosyl-tylonolide (collectively identified in this disclosure as "S4 crystalline solvates").

In some embodiments, the invention is directed to the Form I polymorph of 20,23-dipiperidinyl-5-O-mycaminosyl-tylonolide. Illustrative methods for making the Form I polymorph include, e.g., those shown in Examples 3 (Part F) and 12-16. Based on Applicants' observations, it is believed that the Form I polymorph generally possesses greater stability at ambient temperature than the other above-listed solid-state forms of 20,23-dipiperidinyl-5-O-mycaminosyl-tylonolide, particularly in the absence of solvent. In many embodiments, it is desirable to use a solid-state form, such as the Form I polymorph, that typically does not require special processing or storage conditions, and avoids the need for frequent inventory replacement. For example, selecting a solid-state form that is physically stable during a manufacturing process (such as during milling to obtain a material with reduced particle size and increased surface area) can avoid the need for special processing conditions and the increased costs generally associated with such special processing conditions. Similarly, selection of a solid-state form that is physically stable over a wide range of storage conditions (especially considering the different possible storage conditions that can occur during the lifetime of a 20,23-dipiperidinyl-5-O-mycaminosyl-tylonolide product) can help avoid polymorphic or other degradative changes in the 20,23-dipiperidinyl-5-O-mycaminosyl-tylonolide that can lead to product loss or deterioration of product efficacy. Thus, the selection of a solid-state form having greater physical stability provides a meaningful benefit over less-stable solid-state forms of 20,23-dipiperidinyl-5-O-mycaminosyl-tylonolide. The Form I polymorph also tends to exhibit less water uptake than other solid-state forms of 20,23-dipiperidinyl-5-O-mycaminosyl-tylonolide under, e.g., ambient conditions (e.g., 25° C.). It is further hypothesized that the Form I polymorph exhibits advantageous packing properties, thermodynamic properties, kinetic properties, surface properties, mechanical properties, filtration properties, or chemical purity relative to other solid-state forms of 20,23-dipiperidinyl-5-O-mycaminosyl-tylonolide.

The Form I polymorph may be identified using various analytical techniques. In some embodiments, the Form I polymorph is defined as having one (and typically two, three, four, or all five) of the following characteristics:

a. an FT-Raman spectrum comprising an absorption band at one or more frequencies selected from the group consisting of about 2935, about 1633, about 1596, about 1712, about 1683, and about 781 $cm^{-1}$;

b. a powder X-ray diffraction spectrum comprising at least one peak selected from the group consisting of 5.0 (±0.2) and 5.6 (+0.2) degrees 2Θ;

c. an attenuated total reflection infrared spectrum comprising an absorption band at one or more frequencies selected from the group consisting of about 2932, about 1711, about 1682, about 1635, about 1599, about 1442, about 1404, about 1182, about 1079, about 1053, about 1008, about 985, about 842, and about 783 $cm^{-1}$.

d. a melting point of from about 192 to about 195° C.; or e. a melting enthalpy of about 57 J/g.

In some embodiments, the Form I polymorph is defined as having an FT-Raman spectrum comprising an absorption band at about 2935 $cm^{-1}$. In other embodiments, the Form I polymorph is defined as having an FT-Raman spectrum comprising an absorption band at about 1633 cm$^{-1}$.

In some embodiments, the Form I polymorph is defined as having a powder X-ray diffraction spectrum comprising a peak at 5.0 (±0.2) degrees 2Θ.

In some embodiments, the Form I polymorph is defined as having an attenuated total reflection infrared spectrum comprising an absorption band at one or more frequencies selected from the group consisting of about 1711, about 1682, about 1635, about 1599, about 1404, about 1182, and about 783 cm$^{-1}$. In some such embodiments, e.g., the Form I polymorph is defined as having an attenuated total reflection infrared spectrum comprising an absorption band at one or more frequencies selected from the group consisting of about 1711 and about 1682 cm$^{-1}$. In other such embodiments, the Form I polymorph is defined as having an attenuated total reflection infrared spectrum comprising an absorption band at one or more frequencies selected from the group consisting of about 1635, about 1404, and about 1182 cm$^{-1}$.

Figure 2:
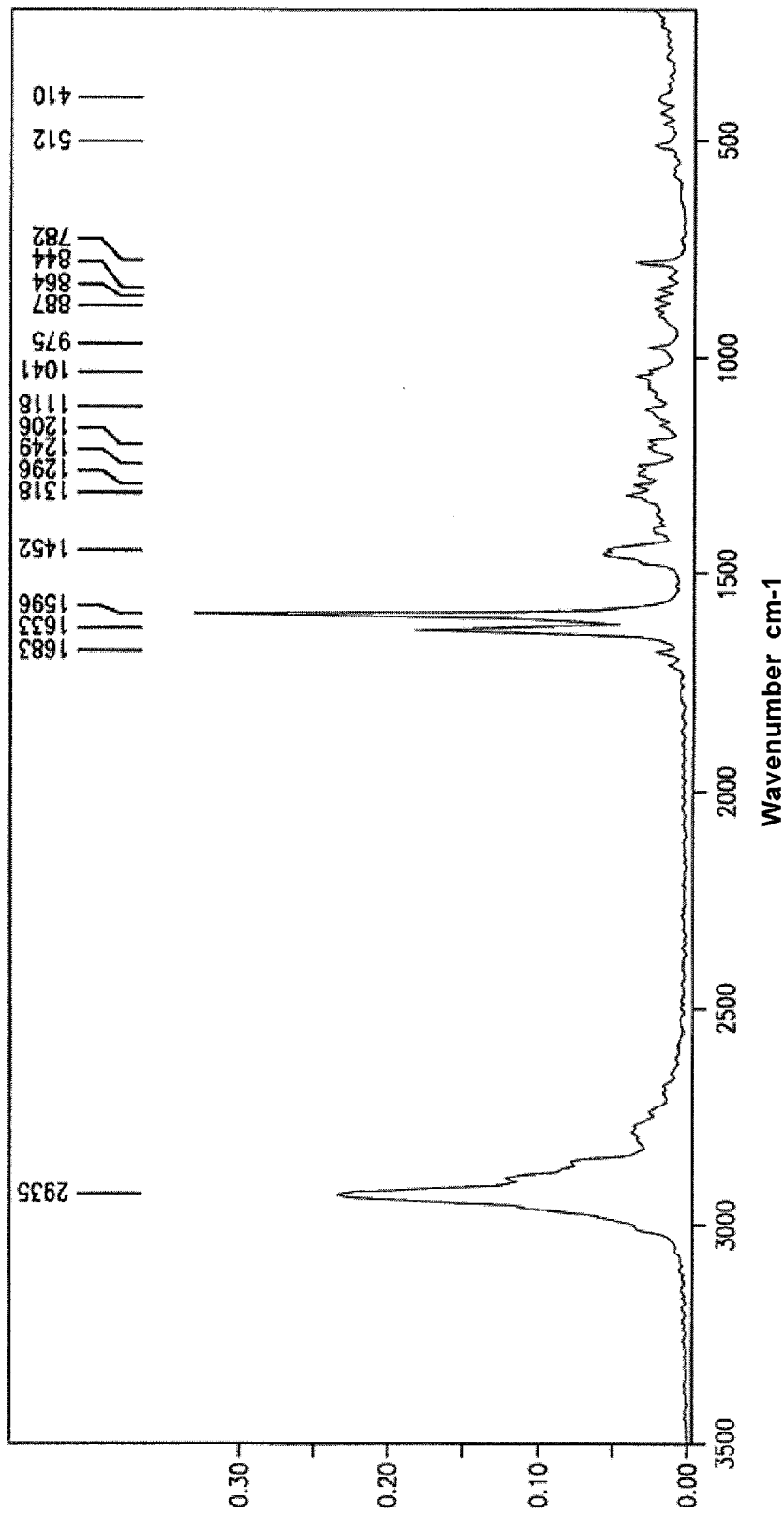
FIG. 2 shows an illustrative Fourier-transform Raman ("FT-Raman") spectrum for the Form I polymorph of 20,23-dipiperidinyl-5-O-mycaminosyl-tylonolide.
Figure 6:
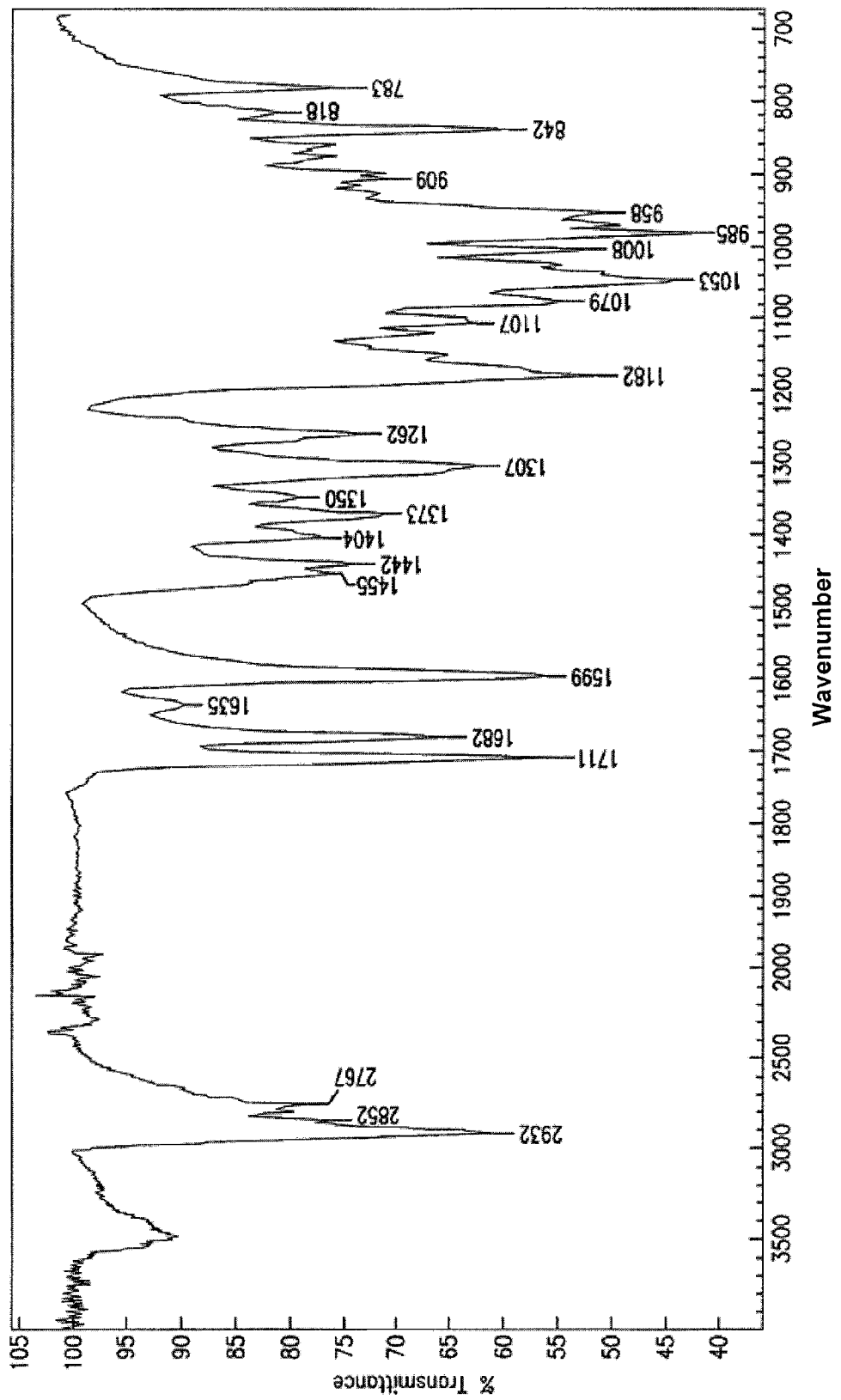
FIG. 6 shows an illustrative attenuated total reflection infrared ("ATR-IR") spectrum (or "absorption band profile") for the Form I polymorph of 20,23-dipiperidinyl-5-O-mycaminosyl-tylonolide.

In some embodiments, the Form I polymorph is defined as having one (and typically two or all three) of the following characteristics:
a. a powder X-ray diffraction spectrum substantially as shown in FIG. 1,
b. an attenuated FT-Raman spectrum substantially as shown in FIG. 2, or
c. an attenuated total reflection infrared spectrum substantially as shown in FIG. 6.

Some embodiments are directed to compositions comprising 20,23-dipiperidinyl-5-O-mycaminosyl-tylonolide, wherein at least a detectable amount of the 20,23-dipiperidinyl-5-O-mycaminosyl-tylonolide in the composition is the Form I polymorph. In some such embodiments, e.g., at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the Form I polymorph. In other such embodiments, a therapeutically effective amount of the 20,23-dipiperidinyl-5-O-mycaminosyl-tylonolide in the composition is the Form I polymorph. In still other such embodiments, the 20,23-dipiperidinyl-5-O-mycaminosyl-tylonolide in the composition is substantially phase-pure Form I crystalline 20,23-dipiperidinyl-5-O-mycaminosyl-tylonolide.

In other embodiments, the invention is directed to the Form II polymorph of 20,23-dipiperidinyl-5-O-mycaminosyl-tylonolide. Methods for making the Form II polymorph include, e.g., the method shown in Example 4. As with the Form I polymorph, the Form II polymorph tends to exhibit less water uptake than other solid-state forms of 20,23-dipiperidinyl-5-O-mycaminosyl-tylonolide under, e.g., ambient conditions. It is hypothesized that the Form II polymorph exhibits advantageous physical stability, chemical stability, packing properties, thermodynamic properties, kinetic properties, surface properties, mechanical properties, filtration properties, or chemical purity relative to other solid-state forms of 20,23-dipiperidinyl-5-O-mycaminosyl-tylonolide. The Form II polymorph also is useful as an intermediate for preparing various other solid-state forms. Table 1 summarizes examples of such methods.

TABLE 1

Use of the Form II Polymorph to Make Other Crystalline Forms of 20,23-Dipiperidinyl-5-O-Mycaminosyl-Tylonolide

| Crystalline form made from Form II polymorph | Example of method that may be used | Illustrations of example method |
|---|---|---|
| Form I polymorph | Dissolve the Form II polymorph in a tBME/heptane solvent, and remove the solvent | Examples 12, 13, and 16 |
| Form III polymorph | Dissolve the Form II polymorph in acetonitrile solvent, subject the resulting mixture to repeated heating and cooling cycles, and remove the solvent | Example 11 |
| Ethyl acetate S1 crystalline solvate | Dissolve the Form II polymorph in ethyl acetate solvent, and remove the solvent | Examples 6, 8, and 9 |
| Ethanol S1 crystalline solvate | Dissolve the Form II polymorph in ethanol solvent, and remove the solvent | Example 17 |
| Diethyl ketone S1 crystalline solvate | Dissolve the Form II polymorph in diethyl ketone solvent, and remove the solvent | Example 18 |
| tBME S2 crystalline solvate | Dissolve the Form II polymorph in tBME solvent, and remove the solvent | Example 19 |
| THF S3 crystalline solvate | Dissolve the Form II polymorph in THF solvent, and remove the solvent | Example 20 |
| Methyl acetate S4 crystalline solvate | Dissolve the Form II polymorph in methyl acetate solvent, and remove the solvent | Example 21 |
| Ethyl formate S4 crystalline solvate | Dissolve the Form II polymorph in ethyl formate solvent, and remove the solvent | Example 22 |

The Form II polymorph may be identified using various analytical techniques. In some embodiments, the Form II polymorph is defined as having one (and typically two, three, four, or all five) of the following characteristics:

a. an FT-Raman spectrum comprising an absorption band at one or more frequencies selected from the group consisting of about 2929, about 1625, about 1595, about 1685, and 783 cm$^{-1}$;

b. a powder X-ray diffraction spectrum comprising a peak at 6.5 (±0.2) degrees 2Θ;

c. an attenuated total reflection infrared spectrum comprising an absorption band at one or more frequencies selected from the group consisting of about 2935, about 1736, about 1668, about 1587, about 1451, about 1165, about 1080, about 1057, about 1042, about 1005, about 981, about 838, and about 755 cm$^{-1}$;

d. a melting point of from about 113 to about 119° C.; or e. a melting enthalpy of about 15 J/g.

In some embodiments, the Form II polymorph is defined as having an FT-Raman spectrum comprising an absorption band at about 2929 cm$^{-1}$. In other embodiments, the Form II polymorph is defined as having an FT-Raman spectrum comprising an absorption band at about 1685 cm$^{-1}$.

In some embodiments, the Form II polymorph is defined as having a powder X-ray diffraction spectrum comprising a peak at 6.5 (±0.2) degrees 2Θ.

Figure 8:
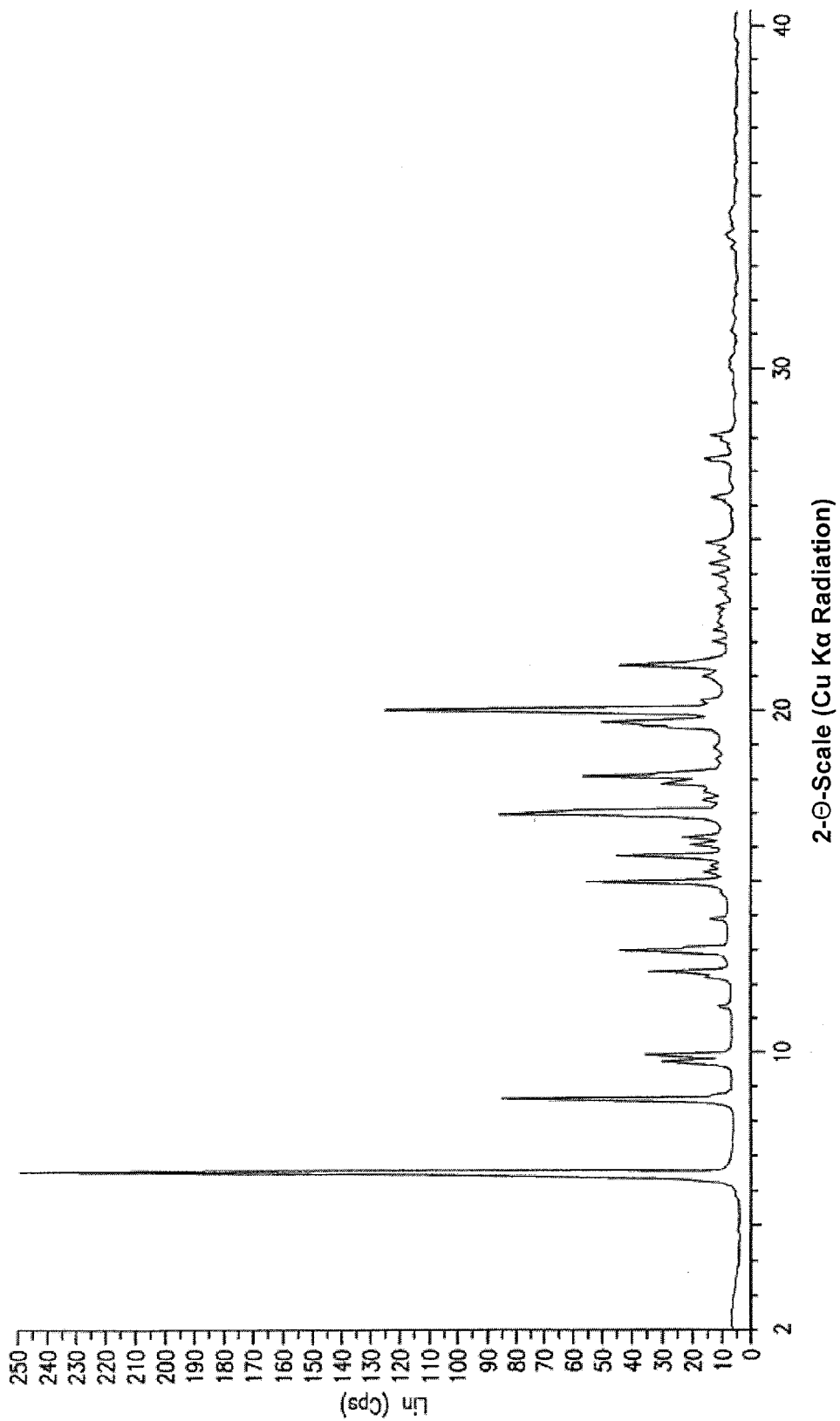
FIG. 8 shows an illustrative PXRD spectrum for the Form II polymorph of 20,23-dipiperidinyl-5-O-mycaminosyl-tylonolide.
Figure 9:
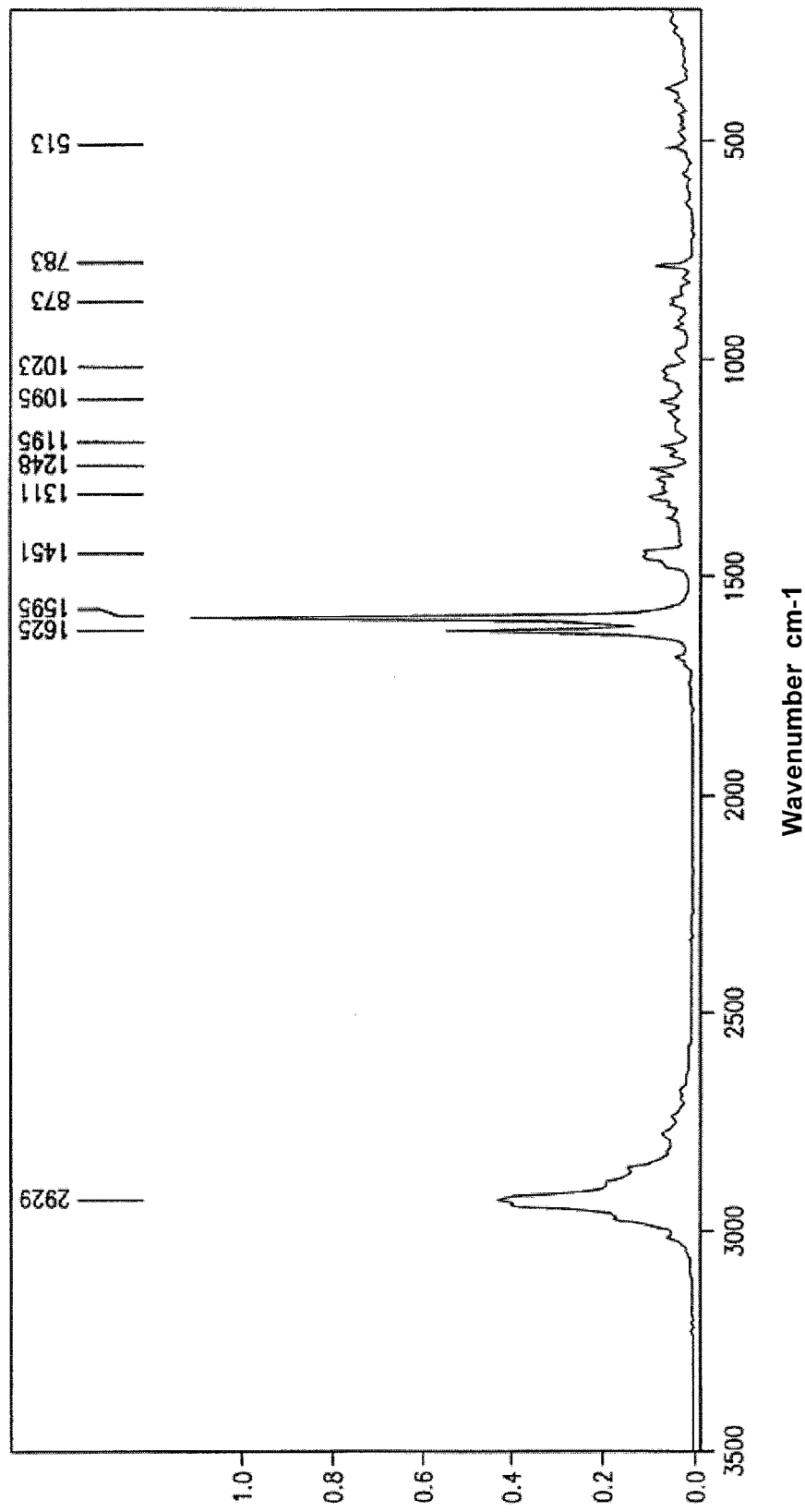
FIG. 9 shows an illustrative FT-Raman spectrum for the Form II polymorph of 20,23-dipiperidinyl-5-O-mycaminosyl-tylonolide.
Figure 13:
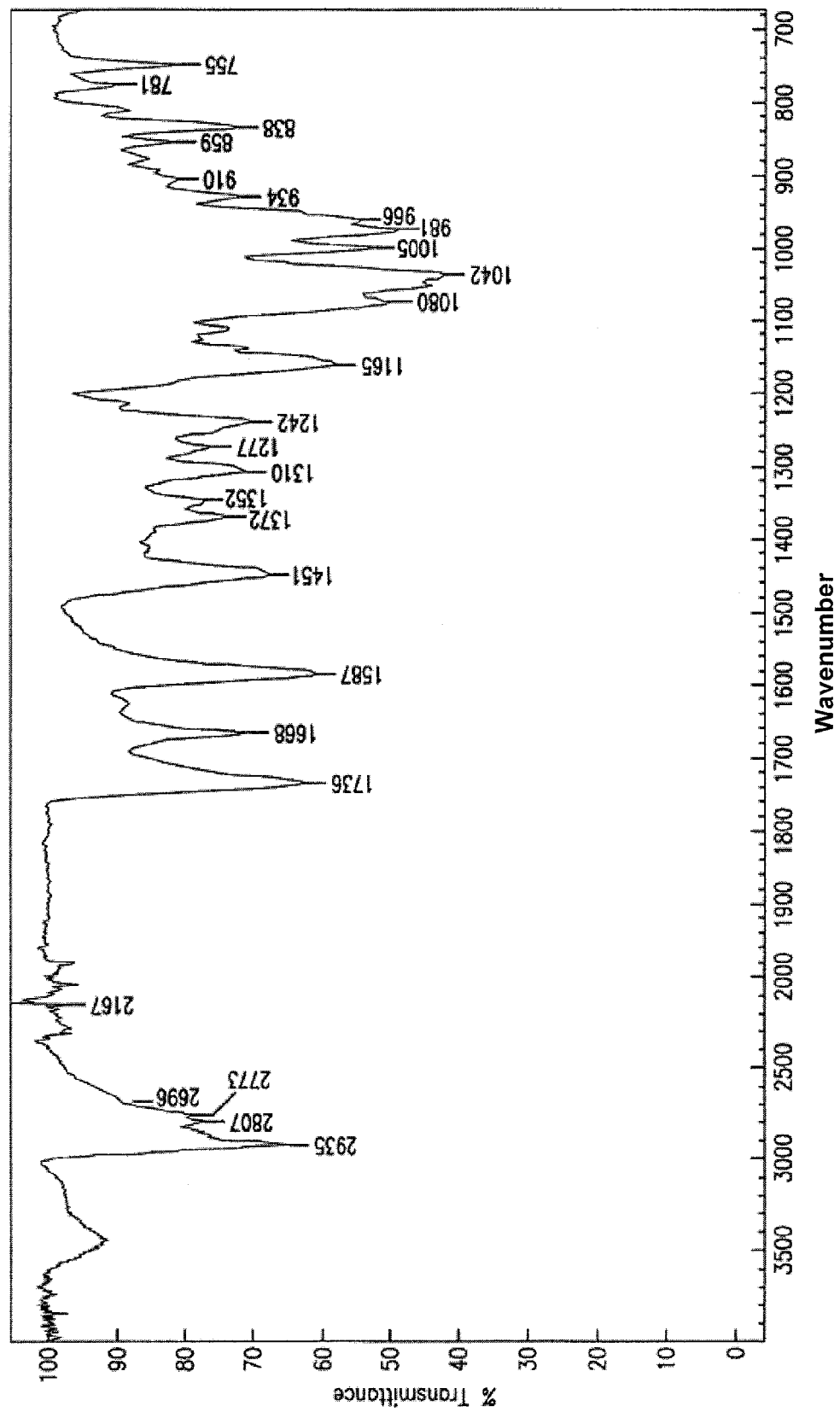
FIG. 13 shows an illustrative ATR-IR spectrum for the Form II polymorph of 20,23-dipiperidinyl-5-O-mycaminosyl-tylonolide.

In some embodiments, the Form II polymorph is defined as having one (and typically two or all three) of the following characteristics:

a. a powder X-ray diffraction spectrum substantially as shown in FIG. 8, b. an FT-Raman spectrum substantially as shown in FIG. 9, or c. an attenuated total reflection infrared spectrum substantially as shown in FIG. 13.

Some embodiments hereof are directed to compositions comprising 20,23-dipiperidinyl-5-O-mycaminosyl-tylonolide wherein at least a detectable amount of the 20,23-dipiperidinyl-5-O-mycaminosyl-tylonolide in the composition is the Form II polymorph. In some such embodiments, e.g., at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the Form II polymorph. In other such embodiments, a therapeutically effective amount of the 20,23-dipiperidinyl-5-O-mycaminosyl-tylonolide in the composition is the Form II polymorph. In still other such embodiments, the 20,23-dipiperidinyl-5-O-mycaminosyl-tylonolide in the composition is substantially phase-pure Form II crystalline 20,23-dipiperidinyl-5-O-mycaminosyl-tylonolide.

In other embodiments, the disclosure is directed to the Form III polymorph of 20,23-dipiperidinyl-5-O-mycaminosyl-tylonolide. Illustrative methods for making the Form III polymorph include, e.g., those shown in Examples 7, 10, and 11. It is believed that the Form III polymorph exhibits greater stability relative to other solid-state forms of 20,23-dipiperidinyl-5-O-mycaminosyl-tylonolide. It also is hypothesized that the Form III polymorph exhibits advantageous packing properties, thermodynamic properties, kinetic properties, surface properties, mechanical properties, filtration properties, or chemical purity relative to other solid-state forms of 20,23-dipiperidinyl-5-O-mycaminosyl-tylonolide. The Form III polymorph also is, e.g., useful for making the Form I polymorph of 20,23-dipiperidinyl-5-O-mycaminosyl-tylonolide. This may be achieved by, e.g., dissolving Form III polymorph crystals in a tBME/heptane solvent, and removing the solvent. See, e.g., Example 15.

The Form III polymorph may be identified using various analytical techniques. In some embodiments, the Form III polymorph is defined as having one (and typically two, three, four, or all five) of the following characteristics:

a. an FT-Raman spectrum comprising an absorption band at one or more frequencies selected from the group consisting of about 2943, about 2917, about 1627, about 1590, about 1733, about 1669, about 1193, about 1094, and about 981 cm$^{-1}$;

b. a powder X-ray diffraction spectrum comprising at least one peak selected from the group consisting of 5.6 (+0.2) and 6.1 (±0.2) degrees 2Θ;

c. an attenuated total reflection infrared spectrum comprising an absorption band at one or more frequencies selected from the group consisting of about 2931, about 1732, about 1667, about 1590, about 1453, about 1165, about 1081, about 1057, about 1046, about 1005, about 981, about 834, and about 756 cm$^{-1}$;

d. a melting point of from about 107 to about 134° C.; or e. a melting enthalpy of about 38 J/g.

In some embodiments, the Form III polymorph is defined as having an FT-Raman spectrum comprising an absorption band at one or more frequencies selected from the group consisting of about 2943, about 2917, about 1590, about 1733, about 1669, about 1193, about 1094, and about 981 cm$^{-1}$. In some such embodiments, e.g., the Form III polymorph is defined as having an FT-Raman spectrum comprising an absorption band at one or more frequencies selected from the group consisting of about 2943, about 2917, about 1590, about 1733, about 1094, and about 981 cm'.

In some embodiments, the Form III polymorph is defined as having a powder X-ray diffraction spectrum comprising a peak at 6.1 (±0.2) degrees 2Θ.

Figure 15:
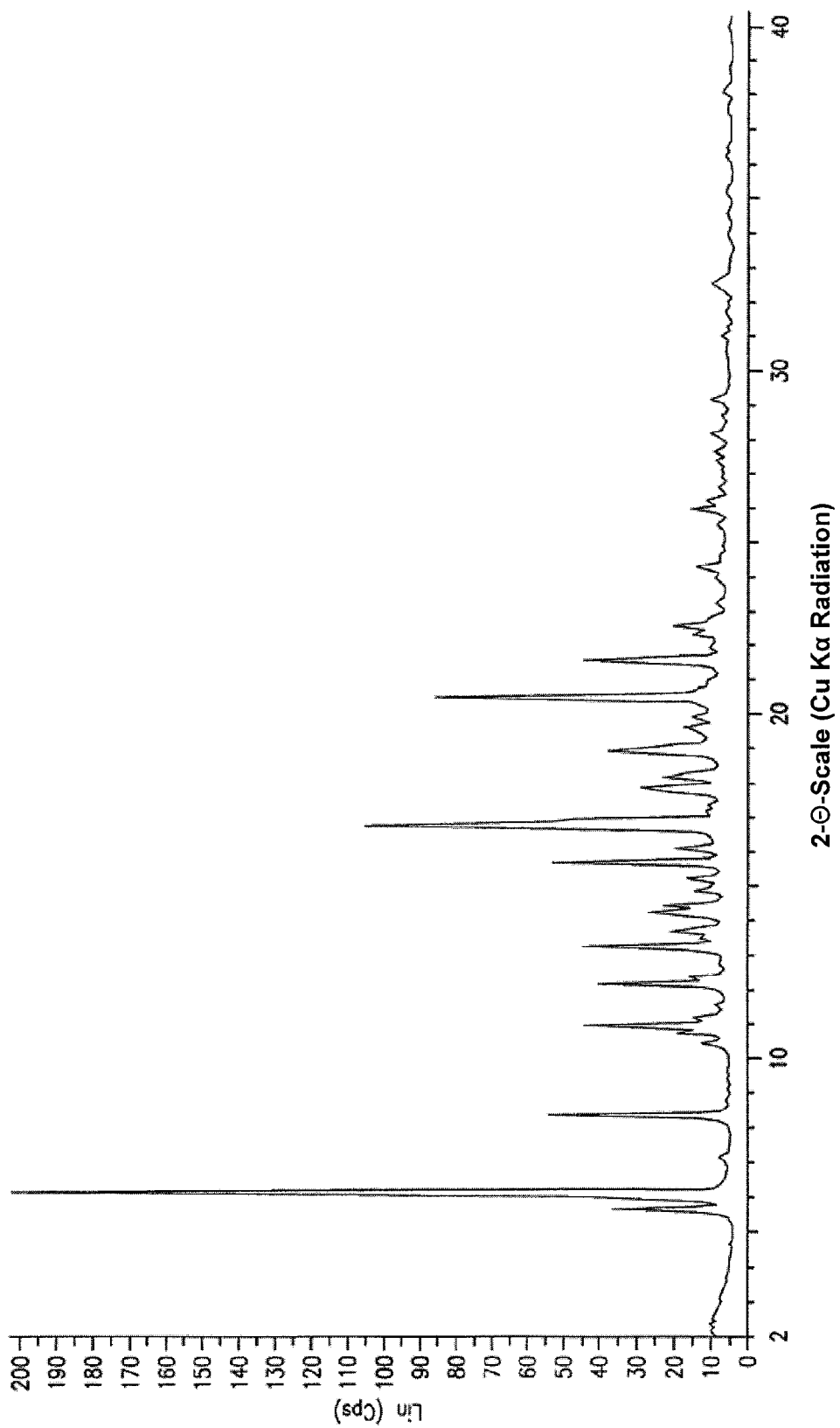
FIG. 15 shows an illustrative PXRD spectrum for the Form III polymorph of 20,23-dipiperidinyl-5-O-mycaminosyl-tylonolide.
Figure 16:
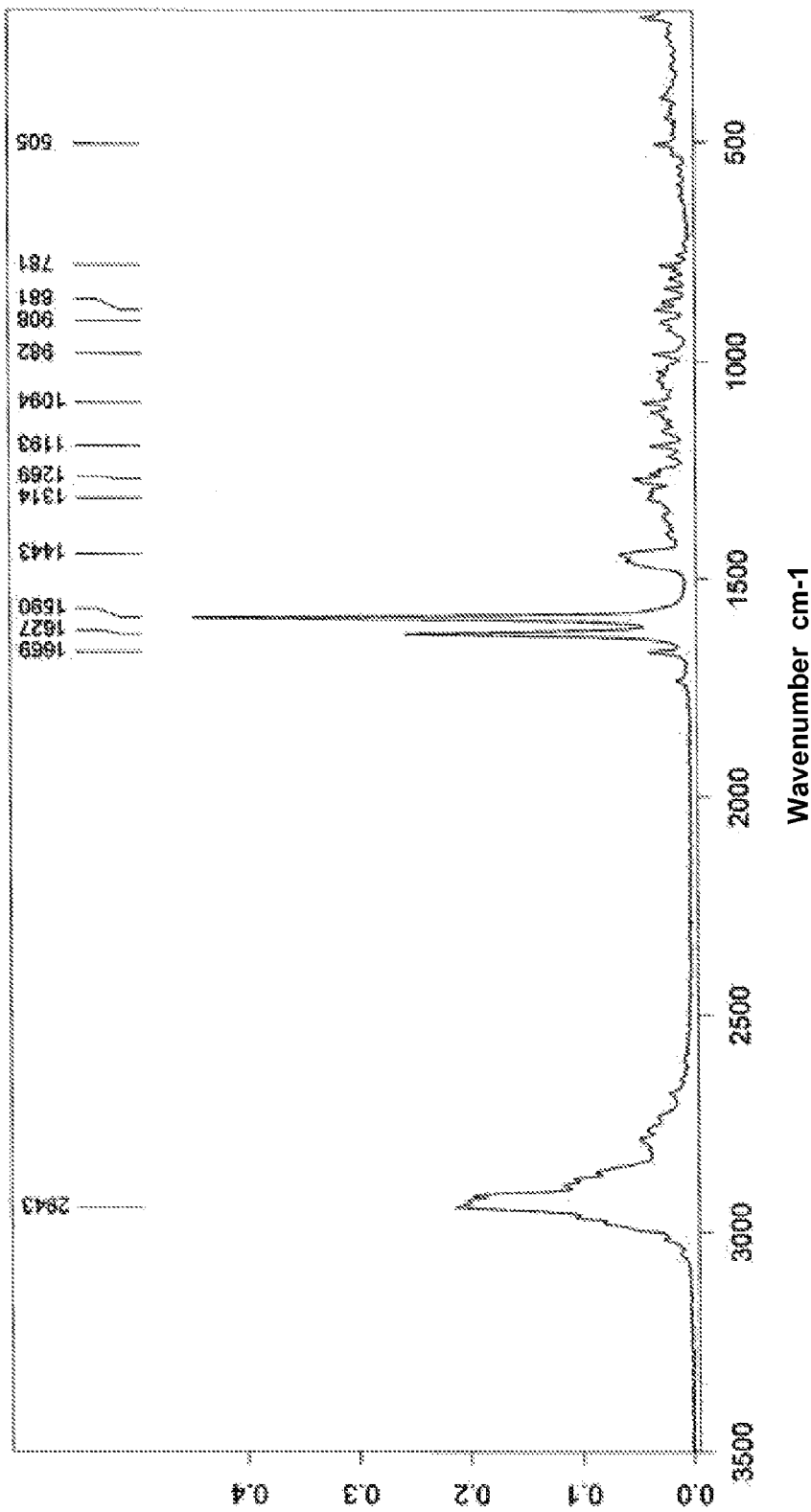
FIG. 16 shows an illustrative FT-Raman spectrum for the Form III polymorph of 20,23-dipiperidinyl-5-O-mycaminosyl-tylonolide.
Figure 20:
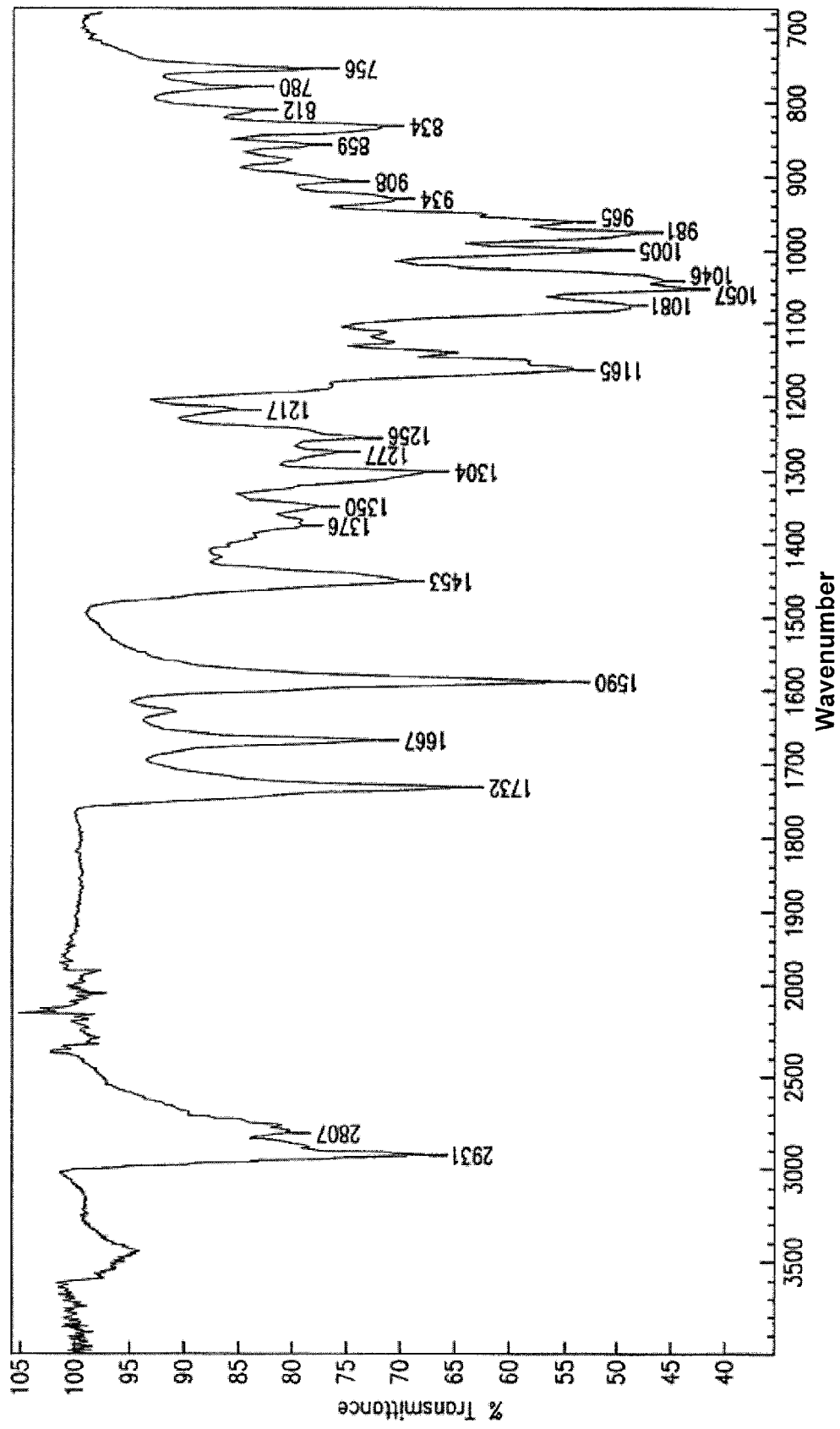
FIG. 20 shows an illustrative ATR-IR spectrum for the Form III polymorph of 20,23-dipiperidinyl-5-O-mycaminosyl-tylonolide.

In some embodiments, the Form III polymorph is defined as having one (and typically two or all three) of the following characteristics:

a. a powder X-ray diffraction spectrum substantially as shown in FIG. 15, b. an FT-Raman spectrum substantially as shown in FIG. 16, or c. an attenuated total reflection infrared spectrum substantially as shown in FIG. 20.

Some embodiments are directed to compositions comprising 20,23-dipiperidinyl-5-O-mycaminosyl-tylonolide wherein at least a detectable amount of the 20,23-dipiperidinyl-5-O-mycaminosyl-tylonolide in the composition is the Form III polymorph. In some such embodiments, e.g., at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the Form III polymorph. In other such embodiments, a therapeutically effective amount of the 20,23-dipiperidinyl-5-O-mycaminosyl-tylonolide in the composition is the Form III polymorph. In still other such embodiments, the 20,23-dipiperidinyl-5-O-mycaminosyl-tylonolide in the composition is substantially phase-pure Form III crystalline 20,23-dipiperidinyl-5-O-mycaminosyl-tylonolide.

In other embodiments, the invention is directed to the Form IV polymorph of 20,23-dipiperidinyl-5-O-mycaminosyl-tylonolide. Methods for making the Form IV polymorph include, e.g., the method shown in Example 23. It is hypothesized that the Form IV polymorph exhibits advantageous physical stability, chemical stability, packing properties, thermodynamic properties, kinetic properties, surface properties, mechanical properties, filtration properties, or chemical purity relative to other solid-state forms of 20,23-dipiperidinyl-5-O-mycaminosyl-tylonolide.

The Form IV polymorph may be identified using various analytical techniques. In some embodiments, the Form IV polymorph is defined as having one (and typically both) of the following characteristics:
  a. an attenuated total reflection infrared spectrum comprising an absorption band at one or more frequencies selected from the group consisting of about 3559, about 2933, about 1743, about 1668, about 1584, about 1448, about 1165, about 1075, about 1060, about 1045, about 1010, about 985, about 839, and about 757 cm$^{-1}$; or
  b. a melting point of from about 149 to about 155° C.

In some embodiments, the Form IV polymorph is defined as having an attenuated total reflection infrared spectrum having an absorption band at 1743 cm$^{-1}$. In other embodiments, the Form IV polymorph is defined as having an attenuated total reflection infrared spectrum comprising an absorption band at 3559 cm$^{-1}$.

Figure 22:
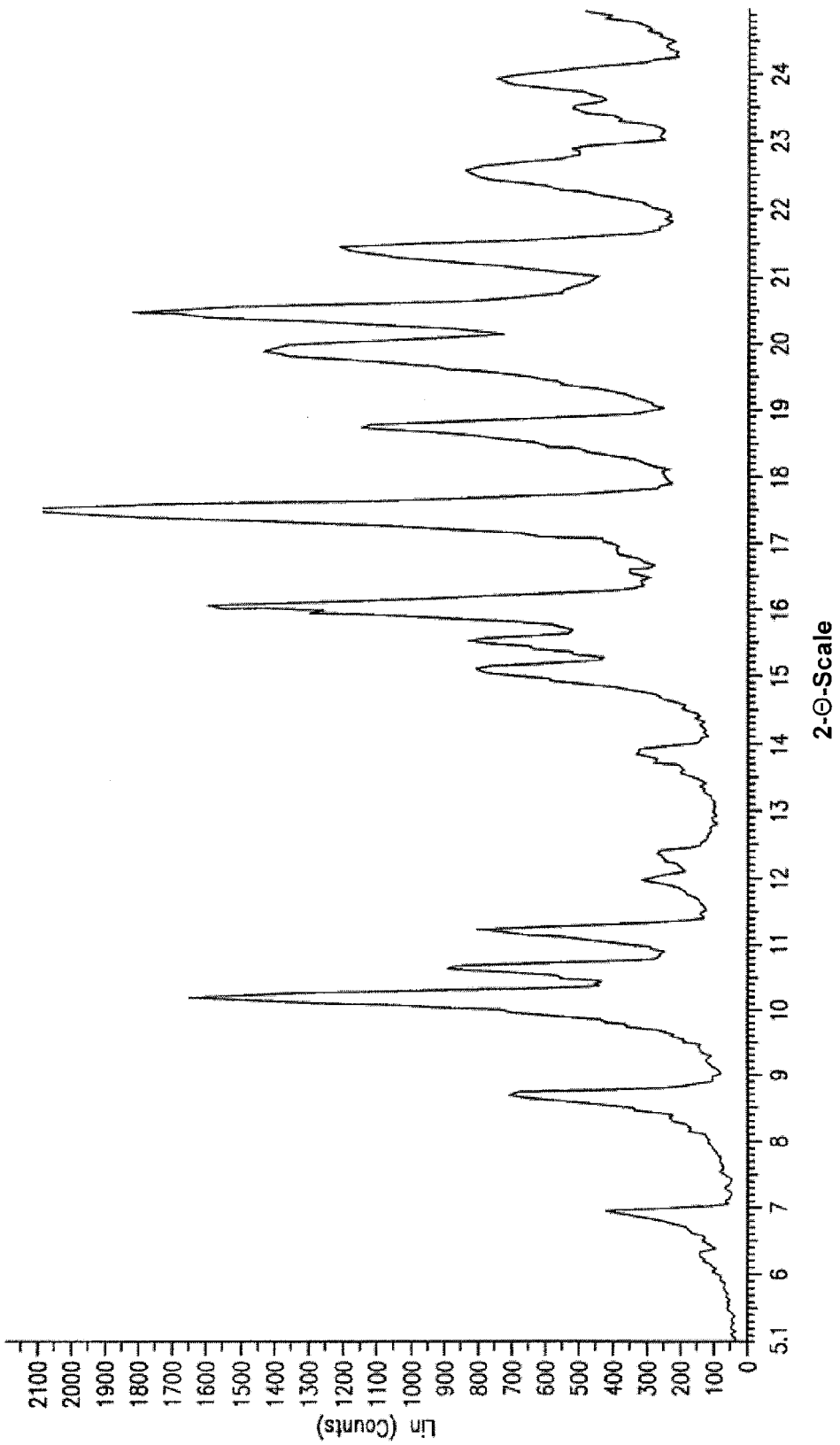
FIG. 22 shows an illustrative PXRD spectrum for the Form IV polymorph of 20,23-dipiperidinyl-5-O-mycaminosyl-tylonolide.
Figure 24:
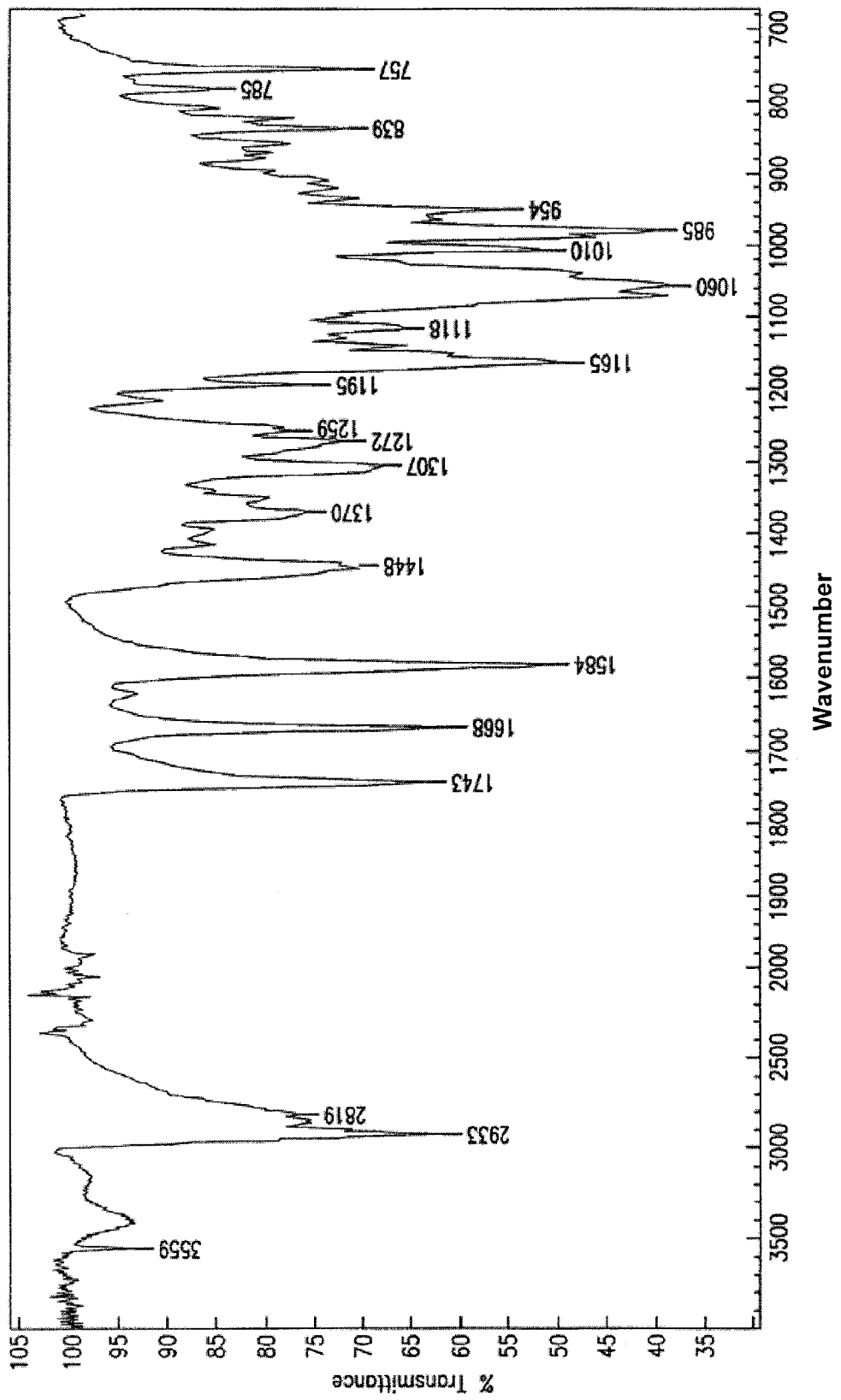
FIG. 24 shows an illustrative ATR-IR spectrum for the Form IV polymorph of 20,23-dipiperidinyl-5-O-mycaminosyl-tylonolide.

In other embodiments, the Form IV polymorph is defined as having one (and typically both) of the following characteristics:
  a. a powder X-ray diffraction spectrum substantially as shown in FIG. 22, or
  b. an attenuated total reflection infrared spectrum substantially as shown in FIG. 24.

Some embodiments are directed to compositions comprising 20,23-dipiperidinyl-5-O-mycaminosyl-tylonolide wherein at least a detectable amount of the 20,23-dipiperidinyl-5-O-mycaminosyl-tylonolide in the composition is the Form IV polymorph. In some such embodiments, e.g., at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the Form IV polymorph. In other such embodiments, a therapeutically effective amount of the 20,23-dipiperidinyl-5-O-mycaminosyl-tylonolide in the composition is the Form IV polymorph. In still other such embodiments, the 20,23-dipiperidinyl-5-O-mycaminosyl-tylonolide in the composition is substantially phase-pure Form IV crystalline 20,23-dipiperidinyl-5-O-mycaminosyl-tylonolide.

In other embodiments, the crystalline form of 20,23-dipiperidinyl-5-O-mycaminosyl-tylonolide comprises a solvated crystalline form. In some embodiments, the solvated crystalline forms of particular interest are those that can be converted into a more desirable solid-state form. In other embodiments, pharmaceutically acceptable solvated crystalline forms of 20,23-dipiperidinyl-5-O-mycaminosyl-tylonolide are used directly in pharmaceutical compositions. It is hypothesized, e.g., that some crystalline solvates tend to exhibit advantageous physical stability, chemical stability, packing properties, thermodynamic properties, kinetic properties, surface properties, mechanical properties, filtration properties, or chemical purity relative to other solid-state forms of 20,23-piperidinyl-5-O-mycaminosyl-tylonolide. It also is believed that the solvated crystalline forms collectively can offer a range of different dissolution rates in, e.g., solid dosage forms. When used directly in pharmaceutical compositions, the solvated crystalline forms preferably are substantially exclusive of solvents that are not pharmaceutically acceptable.

In some embodiments, the crystalline form of 20,23-dipiperidinyl-5-O-mycaminosyl-tylonolide comprises the S1 crystalline solvate of 20,23-dipiperidinyl-5-O-mycaminosyl-tylonolide. Illustrative methods for making the ethyl acetate S1 crystalline solvate include, e.g., those shown in Examples 3 (Part E), 6, 8, and 9. Methods for making the ethanol S1 crystalline solvate include, e.g., the method shown in Example 17. And methods for making the diethyl ketone S1 crystalline solvate include, e.g., the method shown in Example 18. The ethyl acetate S1 crystalline solvate, e.g., is useful as an intermediate for preparing other solid-state forms. Table 2 summarizes examples of such methods.

TABLE 2

Use of Ethyl Acetate Crystalline Solvate to Make Other Crystalline Forms of 20,23-Dipiperidinyl-5-O-Mycaminosyl-Tylonolide

| Crystalline form made from S1 solvate | Example of method that may be used | Illustrations of example method |
| --- | --- | --- |
| Form I polymorph | Combine ethyl acetate S1 solvate crystals with heptane, heat the resulting mixture, and remove the heptane | Example 3, Part F |
| Form III polymorph | Dry ethyl acetate S1 solvate crystals under vacuum | Examples 7 and 10 |
| Form IV polymorph | Combine ethyl acetate S1 crystals with heptane; heat the resulting mixture to at least, e.g., about 80° C. for an extended period while stirring; and remove the heptane | Example 23 |

In some embodiments, the crystalline form of 20,23-dipiperidinyl-5-O-mycaminosyl-tylonolide comprises the S2 crystalline solvate of 20,23-dipiperidinyl-5-O-mycaminosyl-tylonolide. Methods for making the S2 crystalline solvate include, e.g., the method shown in Example 19. It is contemplated that the S2 crystalline solvate (i.e., the tBME solvated crystalline form) may be particularly suitable for use directly in pharmaceutical compositions. This crystalline solvate exhibits stability at, e.g., 60° C. at 1 mbar (absolute) for 1 day.

In some embodiments, the crystalline form of 20,23-dipiperidinyl-5-O-mycaminosyl-tylonolide comprises the S3 crystalline solvate of 20,23-dipiperidinyl-5-O-mycaminosyl-tylonolide. Methods for making the S3 crystalline solvate include, e.g., the method shown in Example 20.

In some embodiments, the crystalline form of 20,23-dipiperidinyl-5-O-mycaminosyl-tylonolide comprises the S4 crystalline solvate of 20,23-dipiperidinyl-5-O-mycaminosyl-tylonolide. Methods for making the methyl acetate S4 crystalline solvate include, e.g., the method shown in Example 21. And methods for making the ethyl formate S4 crystalline solvate include, e.g., the method shown in Example 22.

Some embodiments are directed to compositions comprising 20,23-dipiperidinyl-5-O-mycaminosyl-tylonolide wherein at least a detectable amount of the 20,23-dipiperidinyl-5-O-mycaminosyl-tylonolide in the composition is one of the above-referenced crystalline solvate forms. In some embodiments, e.g., at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the crystalline solvate form. In some such embodiments, at least about 50% (or at least about 75%, at least about 85%, at least about 90%, at least about 95%, at least about 99%, or at least about 99.9%) of the 20,23-dipiperidinyl-5-O-mycaminosyl-tylonolide in the composition is the ethyl acetate S1 crystalline solvate. In other embodiments, a therapeutically effective amount of the 20,23-dipiperidinyl-5-O-mycaminosyl-tylonolide in the composition is in one of the above-listed crystalline solvate forms. In still other embodiments, the 20,23-dipiperidinyl-5-O-mycaminosyl-tylonolide in the composition is substantially phase-pure as to one of the above-discussed crystalline solvate forms. In some such embodiments, e.g., the 20,23-dipiperidinyl-5-O-mycaminosyl-tylonolide in the composition is substantially phase-pure ethyl acetate S1 crystalline solvate.

Some embodiments are directed to a combination of two or more solid-state forms selected from the group consisting of the Form I polymorph, Form II polymorph, Form III polymorph, Form IV polymorph, and solvated crystalline forms of 20,23-dipiperidinyl-5-O-mycaminosyl-tylonolide. Such combinations may be useful in, e.g., the preparation of solid pharmaceutical compositions having a variety of dissolution profiles, including controlled-release compositions. In one embodiment, a combination comprises the Form I polymorph in at least a detectable amount, with the remaining 20,23-dipiperidinyl-5-O-mycaminosyl-tylonolide being one or more solid-state forms selected from the group consisting of the Form II polymorph, Form III polymorph, Form IV polymorph, and solvated crystalline forms. In another embodiment, the combination comprises the Form II polymorph in at least a detectable amount, with the remaining 20,23-dipiperidinyl-5-O-mycaminosyl-tylonolide being one or more solid-state forms selected from the group consisting of the Form I polymorph, Form III polymorph, Form IV polymorph, and solvated crystalline forms. In another embodiment, the combination comprises the Form III polymorph in at least a detectable amount, with the remaining 20,23-dipiperidinyl-5-O-mycaminosyl-tylonolide being one or more solid-state forms selected from the group consisting of the Form I polymorph, Form II polymorph, Form IV polymorph, and solvated crystalline forms. In still another embodiment, the combination comprises the Form IV polymorph in at least a detectable amount, with the remaining 20,23-dipiperidinyl-5-O-mycaminosyl-tylonolide being one or more solid-state forms selected from the group consisting of the Form I polymorph, Form II polymorph, Form III polymorph, and solvated crystalline forms.

Depending on the intended use of the solid-state form of 20,23-dipiperidinyl-5-O-mycaminosyl-tylonolide, processing considerations may favor selection of a specific solid-state form or a specific combination of such solid-state forms. The ease of preparing solid-state forms of 20,23-dipiperidinyl-5-O-mycaminosyl-tylonolide (or solid-state forms of 20,23-dipiperidinyl-5-O-mycaminosyl-tylonolide having a minimum phase purity) generally differs from one solid-state form to another.

Characterization of Solid-State Forms

Techniques

Samples of the solid-state forms of 20,23-dipiperidinyl-5-O-mycaminosyl-tylonolide prepared in accordance with this invention have been characterized using several different techniques. These techniques include the following.

Powder X-Ray diffraction ("PXRD") spectra for all samples but the Form IV polymorph were obtained with a Bruker D8 Advance X-ray diffractometer using Cu Kα radiation (wavelength for calculating d values: $\lambda$=1.5418 Å); 35 kV/45 mA tube power; a VANTEC1 detector; and a 0.017° 2Θ step size, 105±5 sec per step, and 2°-50° 2Θ scanning range. Silicon single-crystal sample holders having a 12 mm diameter and a 0.1 mm depth were used. The PXRD spectrum for the Form IV polymorph was obtained with a Siemens D5000 x-ray diffractometer using Diffract Plus software, a 0.04° 2Θ step size, a 2 sec step time, a 5.0°-80.0 2Θ scanning range, the divergence slit set at V20, the anti-scatter slit set at V20, the detector slit out, rotation, 40 kV generator tension, 30 mA generator current, a high sensitivity scintillation counter, and a Cu x-ray tube.

Fourier-transform Raman ("FT-Raman") spectra were obtained with a Bruker RFS100 FT-Raman spectrometer with an Nd:YAG laser using 1064 nm excitation wavelength, 100 mW laser power, a Ge-detector, 64 scans, a range of 50-3500 $cm^{-1}$, a 2 $cm^{-1}$ resolution, and an aluminum sample holder.

Measurements of thermogravimetry coupled to Fourier transform infrared spectroscopy ("TG-FTIR") were obtained using a Netzsch Thermo-Microbalance TG 209 with a Bruker Vector 22 FT-IR Spectrometer using an aluminum crucible (with micro-hole or open), $N_2$ atmosphere, heating rate of 10° C./min, and temperature range of 25-250° C.

Thermogravimetry ("TG") measurements were obtained with a Perkin Elmer TGS 2 thermogravimetric analyzer using an aluminum crucible (open), $N_2$ atmosphere, heating rate of 10° C./min, and temperature range of 25-500° C.

Differential scanning calorimetry ("DSC") measurements were obtained for the Form I, II, and III polymorphs with a Perkin Elmer DSC 7 differential scanning calorimeter using gold crucibles; a heating rate of 10° C./min. These measurements were performed in hermetically sealed sample pans closed under inert gas (i.e., in the absence of oxygen) after removal of any residual solvent and moisture. One scan was performed with the Form I polymorph. That scan was performed from −50° C. to about 210° C. Two scans were performed for the Form II and III polymorphs, with the first scan being performed from −50° C. to 150° C., and the second scan being performed from −50° C. to 200° C. DSC measurements were obtained for the Form IV polymorph with a Mettler DSC-822e using an aluminum crucible, air as the cover gas, a 10K/min heating rate, a heating range of 30 to 200° C., and a 5 mg sample size. Applicants believe DSC is particularly prone to variations, and should, therefore, be used cautiously.

Dynamic vapor sorption ("DVS") measurements were obtained with a Projekt Messtechnik SPS11-100n water vapor sorption analyzer. The samples were placed into aluminum crucibles on a microbalance, and allowed to equilibrate at 25° C. and 50% relative humidity before initiating the following pre-defined humidity program at 25° C.: 50-95-0-50% relative humidity, and scanning with a 5% change in relative humidity per hour and with iso-humid equilibration periods at extreme values.

Infrared ("IR") spectra were obtained using an Excalibur FT-IR spectrometer from Portmann Instruments AG (now Varian). Two techniques were used. The first technique was attenuated total reflection ("ATR") infrared spectroscopy. To obtain a spectrum using ATR, a spatula tip of sample was placed onto the sample area of the ATR cell (torque 120 n*cm), and the infrared spectra were recorded from 3600 to 700 $cm^{-1}$. The second technique used a sample mulled in nujol (i.e., a nujol suspension). To obtain a spectrum using such a sample, a spatula tip of sample was ground thoroughly in a motar with two or three drops of nujol until a homogenous paste was obtained. The paste, in turn, was spread on a NaCl plate, and pressed with a second NaCl plate to form a thin homogenous film. For these samples, the infrared spectra were recorded from 3600 to 600 $cm^{-1}$.

Finally, Applicants made various observations regarding the shapes and sizes of the 20,23-dipiperidinyl-5-O-mycaminosyl-tylonolide solid-state forms, and have summarized those observations below. Applicants note, however, that this information should be used with caution because other shapes and/or sizes of the crystalline forms might exist, depending on the procedure used to make the solid-state forms.

Form I Polymorph

The following discussion provides various observed characteristics of the Form I polymorph.

i. Appearance of the Form I Polymorph

The Form I polymorph was generally in the form of small particles.

ii. Powder X-Ray Diffraction Spectrum for the Form I Polymorph

The observed PXRD spectrum for the Form I polymorph is shown in FIG. 1, and the corresponding data is shown in the following Table 3:

TABLE 3

X-Ray Diffraction Data for the Form I Polymorph

| Angle (2-Θ degrees) | d Value (Å) | Intensity (cps) | Rel. Intensity (%) |
|---|---|---|---|
| 5.0 | 17.673 | 34 | 36.0 |
| 5.6 | 15.781 | 84 | 87.8 |
| 9.0 | 9.826 | 50 | 52.2 |
| 10.5 | 8.425 | 26 | 26.7 |
| 11.2 | 7.900 | 14 | 14.3 |
| 12.6 | 7.025 | 59 | 62.3 |
| 13.5 | 6.559 | 35 | 37.0 |
| 13.7 | 6.463 | 58 | 60.7 |
| 14.4 | 6.151 | 36 | 37.7 |
| 14.6 | 6.067 | 49 | 51.3 |
| 15.5 | 5.717 | 38 | 39.3 |
| 15.8 | 5.609 | 21 | 21.7 |
| 16.1 | 5.505 | 62 | 65.0 |
| 16.4 | 5.405 | 48 | 50.6 |
| 16.6 | 5.340 | 31 | 32.0 |
| 16.8 | 5.277 | 95 | 100.0 |
| 17.8 | 4.983 | 83 | 86.9 |
| 18.1 | 4.901 | 94 | 98.3 |
| 18.3 | 4.848 | 61 | 63.6 |
| 19.3 | 4.599 | 29 | 30.6 |
| 19.6 | 4.529 | 75 | 78.3 |
| 20.3 | 4.375 | 51 | 53.8 |
| 20.6 | 4.311 | 36 | 38.2 |
| 21.1 | 4.210 | 22 | 23.1 |
| 21.6 | 4.114 | 43 | 45.1 |
| 22.5 | 3.952 | 30 | 31.5 |
| 23.1 | 3.850 | 15 | 15.9 |
| 24.3 | 3.663 | 24 | 25.2 |
| 24.8 | 3.590 | 19 | 19.8 |
| 25.1 | 3.548 | 18 | 19.2 |
| 26.5 | 3.363 | 14 | 14.5 |
| 28.1 | 3.175 | 15 | 16.2 |
| 31.7 | 2.823 | 12 | 12.3 |

Characteristic features of the spectrum include the initial peaks at 2Θ=5.0° and 5.6°.

With some samples, the PXRD spectrum showed contamination to some extent with amorphous 20,23-dipiperidinyl-5-O-mycaminosyl-tylonolide. It is believed, however, that there was essentially no such amorphous material in the sample corresponding to the above-discussed PXRD spectrum.

iii. FT-Raman Spectrum for the Form I Polymorph

The observed FT-Raman spectrum for the Form I polymorph is shown in FIG. 2, and the corresponding data is shown in the following Table 4:

TABLE 4

FT-Raman Data for the Form I Polymorph

| Position (cm$^{-1}$) | Intensity |
|---|---|
| 2935 | 0.234 |
| 2894 | 0.122 |
| 2788 | 0.038 |
| 1712 | 0.013 |
| 1683 | 0.022 |
| 1633 | 0.182 |
| 1596 | 0.330 |
| 1452 | 0.058 |
| 1394 | 0.023 |
| 1318 | 0.042 |
| 1295 | 0.036 |
| 1249 | 0.034 |
| 1206 | 0.027 |
| 1156 | 0.020 |
| 1118 | 0.029 |
| 1041 | 0.035 |
| 975 | 0.026 |
| 887 | 0.023 |
| 864 | 0.023 |
| 844 | 0.022 |
| 781 | 0.036 |
| 512 | 0.023 |
| 464 | 0.018 |
| 440 | 0.020 |
| 410 | 0.022 |
| 86 | 0.080 |

Characteristic features of the spectrum include intense peaks at 2935 cm$^{-1}$, 1633 cm$^{-1}$, and 1596 cm$^{-1}$; and smaller peaks at 1712 cm$^{-1}$, 1683 cm$^{-1}$, and 781 cm$^{-1}$.

iv. Thermogravimetry for the Form I Polymorph

Figure 3:
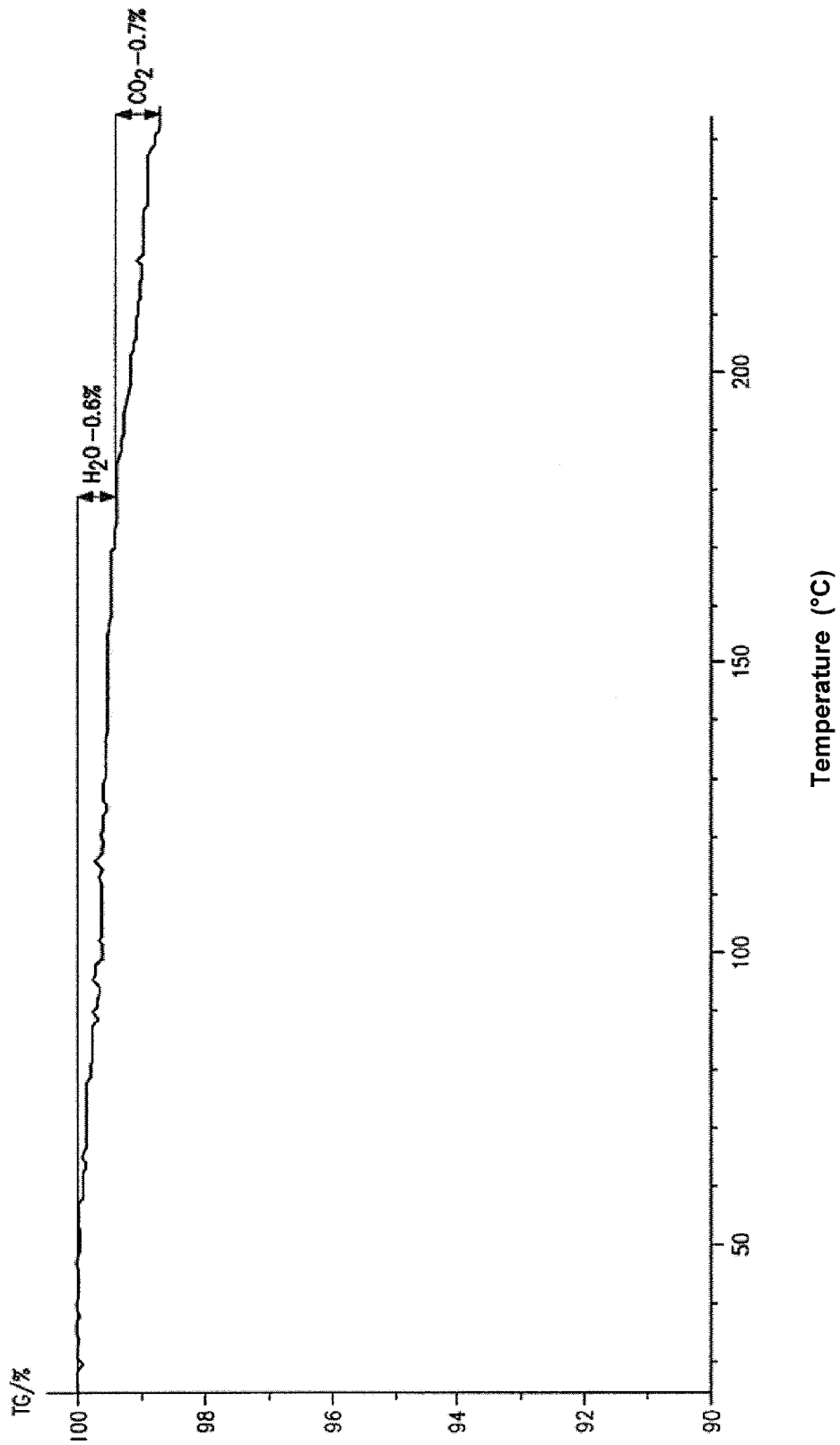
FIG. 3 shows illustrative thermogravimetry coupled to Fourier transform infrared spectroscopy ("TG-FTIR") results for the Form I polymorph of 20,23-dipiperidinyl-5-O-mycaminosyl-tylonolide.

FIG. 3 shows the results from a TG-FTIR analysis of the Form I polymorph. A weight loss of 0.6% was observed in the temperature range of from 60 to 180° C. Applicants believe this is attributable to water loss. Due to the small amount, Applicants further believe that this water loss resulted from surface-absorbed water rather than being attributable to a hydrate.

v. Differential Scanning Calorimetry for the Form I Polymorph

Figure 4:
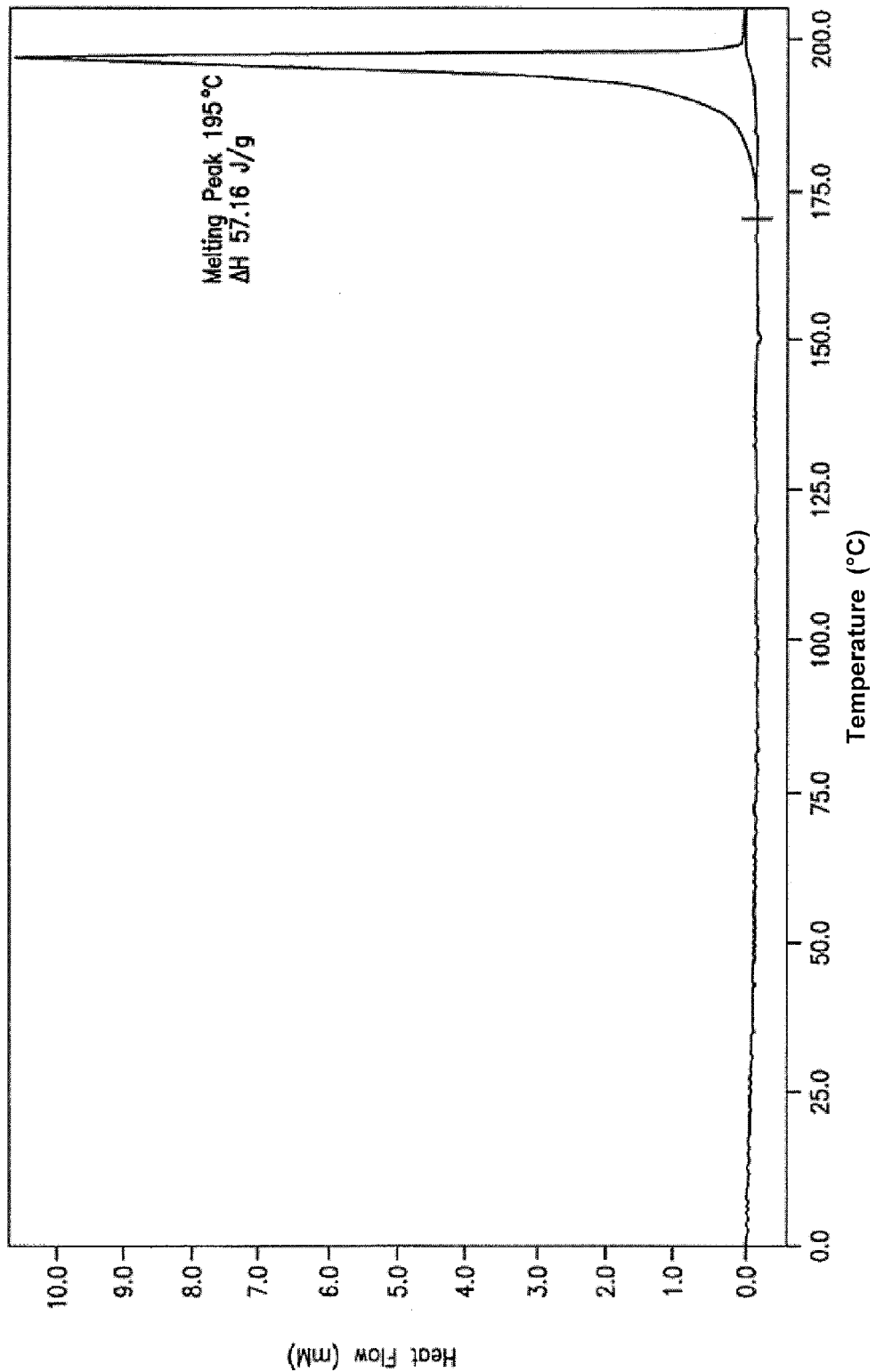
FIG. 4 shows illustrative differential scanning calorimetry ("DSC") results for the Form I polymorph of 20,23-dipiperidinyl-5-O-mycaminosyl-tylonolide.

FIG. 4 shows the results from a DSC analysis for the Form I polymorph. There is a sharp melting peak at 195° C. with a melting enthalpy of $\Delta H_{fus}$ of 57 J/g. These are both greater than the melting points and melting enthalpies for the Form II and Form III polymorphs. In FIG. 4, the $T_g$ step is barely discernable. It is believed that this confirms that the sample was greater than 90% crystalline.

Samples of the Form I polymorph were independently analyzed to determine the melting point. Samples having a purity of about 98% (w/w) exhibited a melting point of 192 to 195° C.

vi. Dynamic Vapor Sorption for the Form I Polymorph

Figure 5:
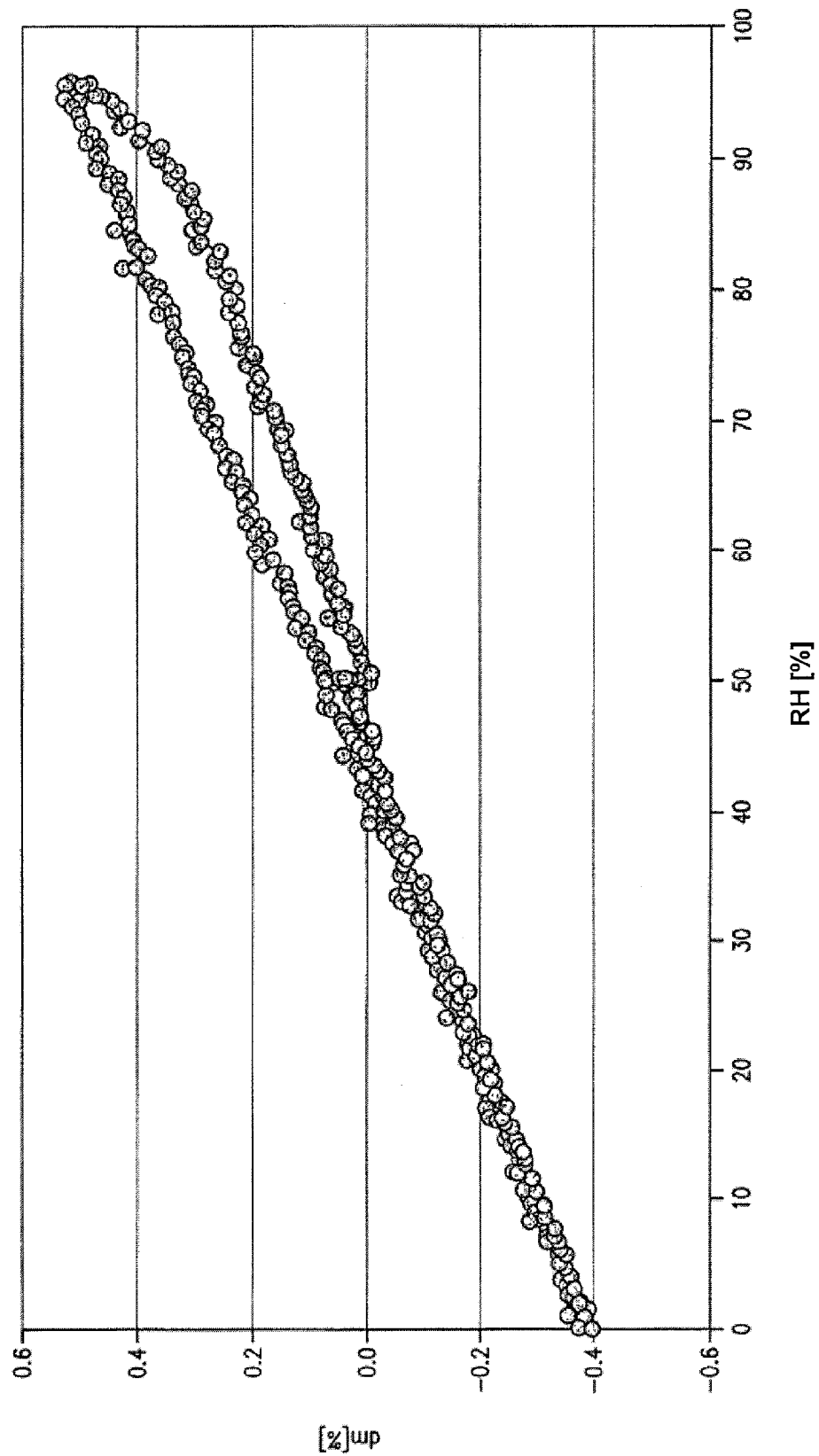
FIG. 5 shows illustrative dynamic vapor sorption ("DVS") results for the Form I polymorph of 20,23-dipiperidinyl-5-O-mycaminosyl-tylonolide.

FIG. 5 shows the results for a DVS analysis of the Form I polymorph, which was conducted at 25° C. A maximum water uptake less than 1% (w/w) at 95% relative humidity was observed.

vii. IR Spectrum for the Form I Polymorph

Figure 7:
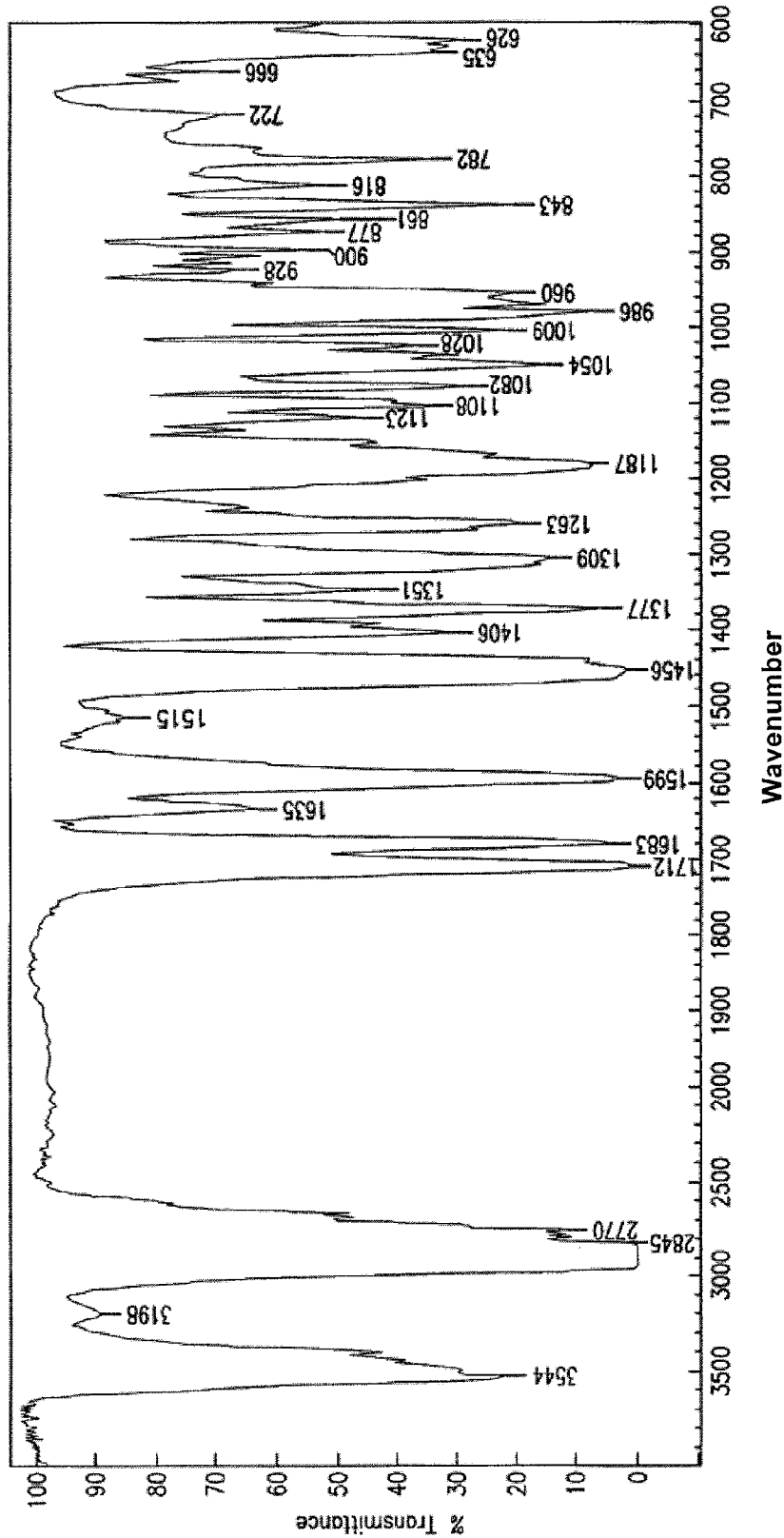
FIG. 7 shows an illustrative IR spectrum for a nujol suspension containing the Form I polymorph of 20,23-dipiperidinyl-5-O-mycaminosyl-tylonolide.

FIG. 6 shows ATR-IR spectrum for the Form I polymorph, and FIG. 7 provides the IR spectrum for the Form I polymorph in a nujol suspension. The corresponding data are shown in the following Table 5:

TABLE 5

IR Data for the Form I Polymorph

| Frequencies of intense IR absorption bands observed with ATR technique (cm$^{-1}$) | Frequencies of intense IR absorption bands observed with Nujol technique (cm$^{-1}$) |
|---|---|
|  | 3544 |
| 2932 | overlaps with nujol vibration band |
| 1711 | 1712 |
| 1682 | 1683 |
| 1635 | 1635 |
| 1599 | 1599 |
| 1442 | overlaps with nujol vibration band |
| 1404 | 1406 |
| 1373 | overlaps with nujol vibration band |
| 1350 | 1351 |
| 1307 | 1309 |
| 1262 | 1263 |
| 1182 | 1187 |
|  | 1123 |
| 1107 | 1108 |
| 1079 | 1082 |
| 1053 | 1054 |
| 1008 | 1009 |
| 985 | 986 |
| 958 | 960 |
|  | 928 |
| 909 | 900 |
|  | 877 |
|  | 861 |
| 842 | 843 |
| 818 | 816 |
| 783 | 782 |
|  | 722 |

Characteristic features of the spectra, particularly the ATR spectrum, include intense absorption bands at 2932 cm$^{-1}$, 1711 cm$^{-1}$, 1682 cm$^{-1}$, 1599 cm$^{-1}$, 1442 cm$^{-1}$, 1182 cm$^{-1}$, 1079 cm$^{-1}$, 1053 cm$^{-1}$, 1008 cm$^{-1}$, 985 cm$^{-1}$, 842 cm$^{-1}$, and 783 cm$^{-1}$. Absorption bands at 1711 cm$^{-1}$ and 1682 cm$^{-1}$ appear to be particularly unique to this polymorph. Absorption bands at 1635 cm$^{-1}$, 1404 cm$^{-1}$, and 1182 cm$^{-1}$ also appear to be particularly unique to this polymorph.

Form II Polymorph

The following discussion provides various observed characteristics of the Form II polymorph.

i. Appearance of the Form II Polymorph

The Form II polymorph was generally in the form of prismatic crystals with a size of up to several hundred microns.

ii. Powder X-Ray Diffraction Spectrum for the Form II Polymorph

The observed PXRD spectrum for the Form II polymorph is shown in FIG. 8, and the corresponding data is shown in the following Table 6:

TABLE 6

X-Ray Diffraction Data for the Form II Polymorph

| Angle (2-Θ degrees) | d Value (Å) | Intensity (cps) | Rel. Intensity (%) |
|---|---|---|---|
| 6.5 | 13.598 | 250.71 | 100.0 |
| 8.7 | 10.164 | 86.09 | 34.3 |

TABLE 6-continued

X-Ray Diffraction Data for the Form II Polymorph

| Angle (2-Θ degrees) | d Value (Å) | Intensity (cps) | Rel. Intensity (%) |
|---|---|---|---|
| 9.7 | 9.118 | 29.90 | 11.9 |
| 9.9 | 8.934 | 35.38 | 14.1 |
| 12.4 | 7.138 | 34.12 | 13.6 |
| 13.0 | 6.810 | 43.56 | 17.4 |
| 15.0 | 5.906 | 55.07 | 22.0 |
| 15.8 | 5.609 | 44.94 | 17.9 |
| 16.1 | 5.505 | 19.86 | 7.9 |
| 16.3 | 5.438 | 22.40 | 8.9 |
| 17.0 | 5.216 | 85.44 | 34.1 |
| 17.9 | 4.955 | 30.02 | 12.0 |
| 18.1 | 4.901 | 56.47 | 22.5 |
| 19.7 | 4.506 | 50.08 | 20.0 |
| 20.0 | 4.439 | 125.24 | 50.0 |
| 21.3 | 4.171 | 43.10 | 17.2 |
| 24.9 | 3.576 | 14.93 | 6.0 |
| 26.3 | 3.389 | 12.77 | 5.1 |
| 27.4 | 3.255 | 15.40 | 6.1 |

Characteristic features of the spectrum include the initial and most intense peak being at 2Θ=6.5°.

iii. FT-Raman Spectrum for the Form II Polymorph

The observed FT-Raman spectrum for the Form II polymorph is shown in FIG. 9, and the corresponding data is shown in the following Table 7:

TABLE 7

FT-Raman Data for the Form II Polymorph

| Position (cm$^{-1}$) | Intensity |
|---|---|
| 2929 | 0.435 |
| 1685 | 0.044 |
| 1625 | 0.550 |
| 1595 | 1.118 |
| 1451 | 0.114 |
| 1361 | 0.062 |
| 1311 | 0.100 |
| 1270 | 0.085 |
| 1248 | 0.100 |
| 1195 | 0.074 |
| 1117 | 0.060 |
| 1095 | 0.075 |
| 1023 | 0.073 |
| 984 | 0.047 |
| 925 | 0.051 |
| 873 | 0.058 |
| 783 | 0.084 |
| 513 | 0.063 |
| 379 | 0.066 |
| 87 | 0.198 |

Characteristic features of the spectrum include intense peaks at 2929 cm$^{-1}$, 1625 cm$^{-1}$, and 1595 cm$^{-1}$; and smaller, but sharp, peaks at 1685 cm$^{-1}$ and 783 cm$^{-1}$.

iv. Thermogravimetry for the Form II Polymorph

Figure 10:
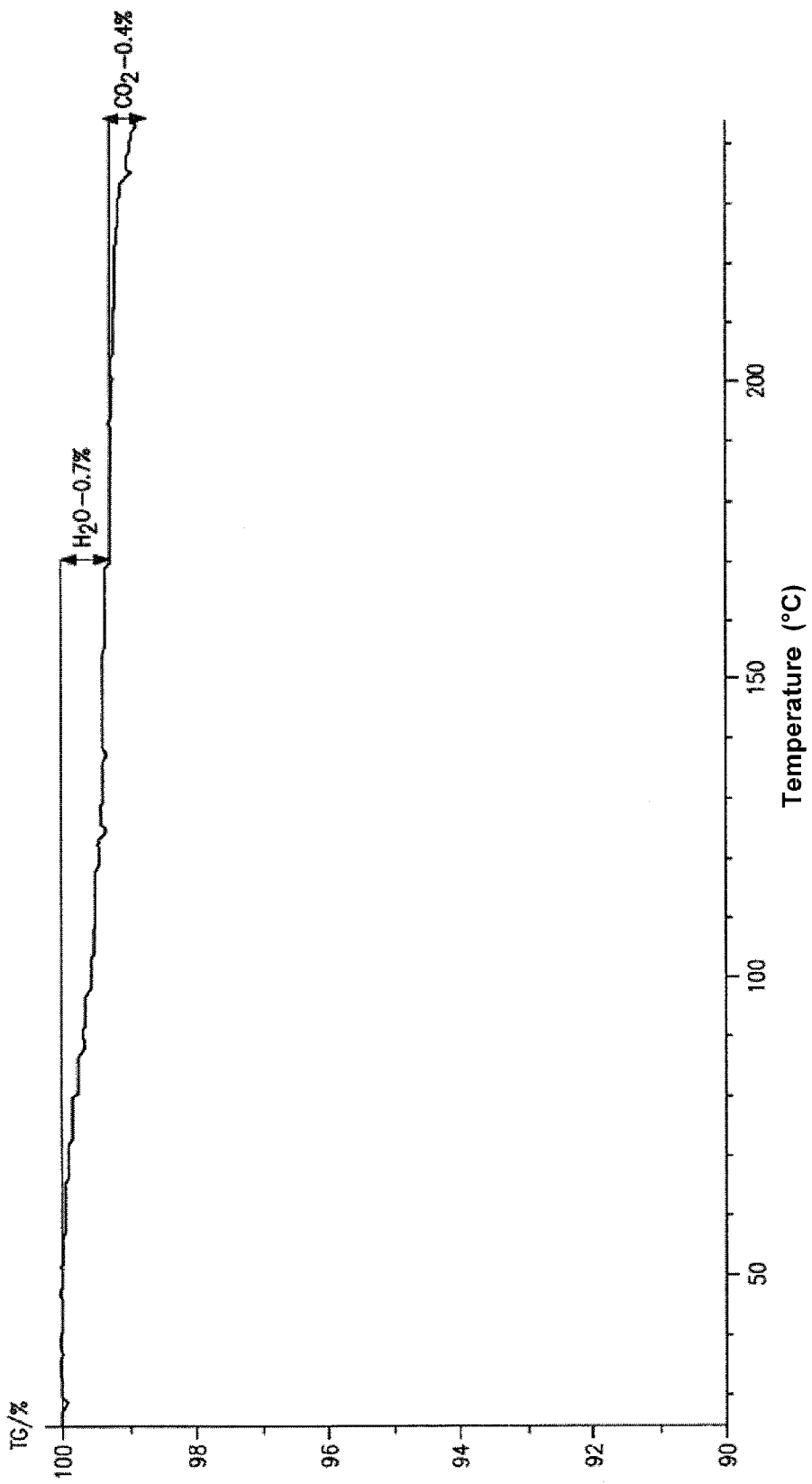
FIG. 10 shows illustrative TG-FTIR results for the Form II polymorph of 20,23-dipiperidinyl-5-O-mycaminosyl-tylonolide.

FIG. 10 shows the results from a TG-FTIR analysis of the Form II polymorph. A weight loss of 0.7% was observed, mainly in the temperature range of from 50 to 100° C. Applicants believe this is attributable to water loss. Decomposition began at a temperature of greater than 220° C.

v. Differential Scanning Calorimetry for the Form II Polymorph

Figure 11:
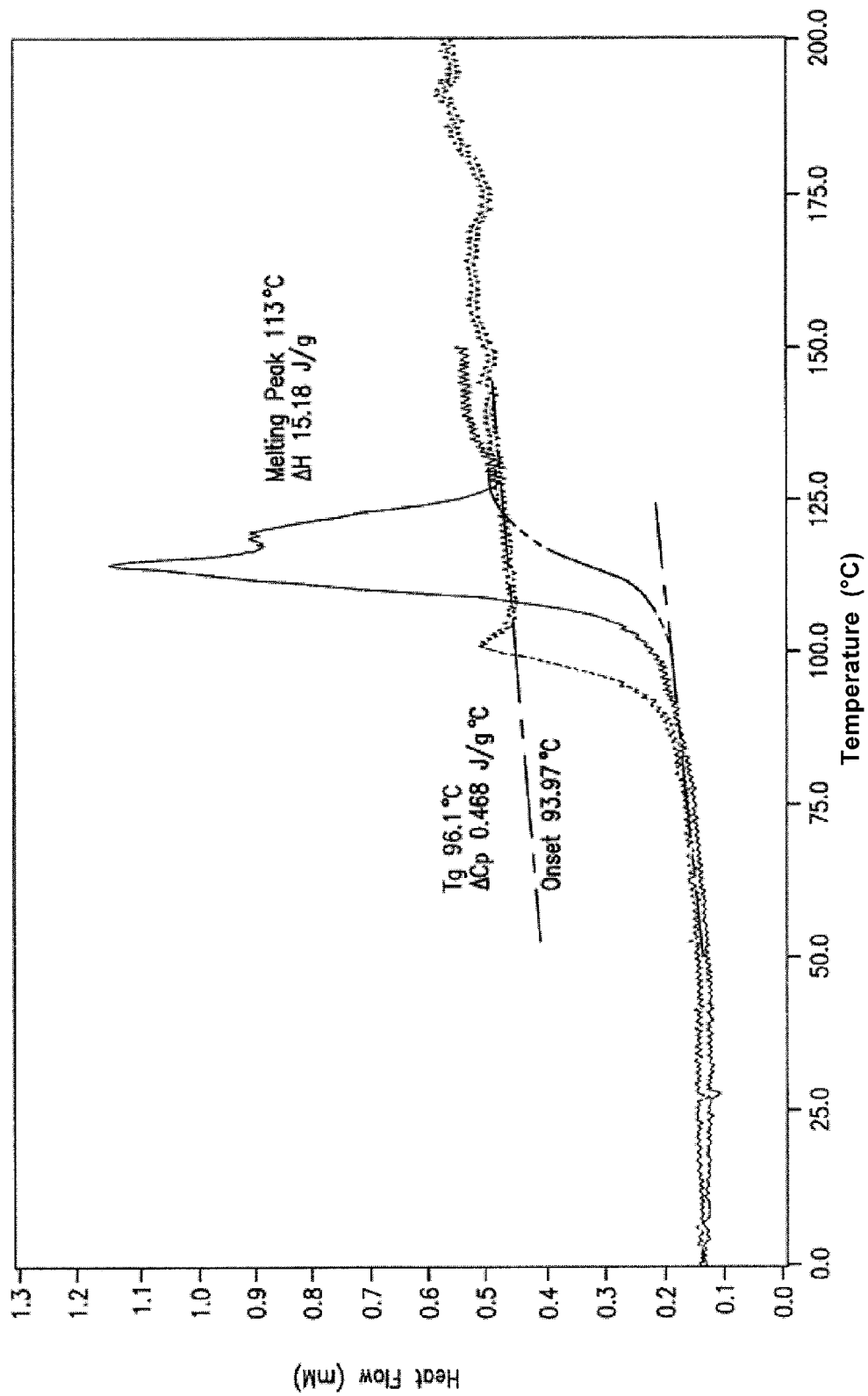
FIG. 11 shows illustrative DSC results for the Form II polymorph of 20,23-dipiperidinyl-5-O-mycaminosyl-tylonolide. The continuous line corresponds to the first scan, and the dashed line corresponds to the second scan.

FIG. 11 shows the results from a DSC analysis of the Form II polymorph. The first scan (the continuous line) shows a melting peak at 113° C. with a melting enthalpy of $\Delta H_{fus}$=15 J/g. The second scan (the dotted line) shows a glass transition temperature ("$T_g$") of 96.1° C. Re-crystallization was not observed.

Samples of the Form II polymorph were independently analyzed to determine the melting point. Samples having a purity of about 96% (w/w) exhibited a melting point of from 113 to 119° C.

vi. Dynamic Vapor Sorption for the Form II Polymorph

Figure 12:
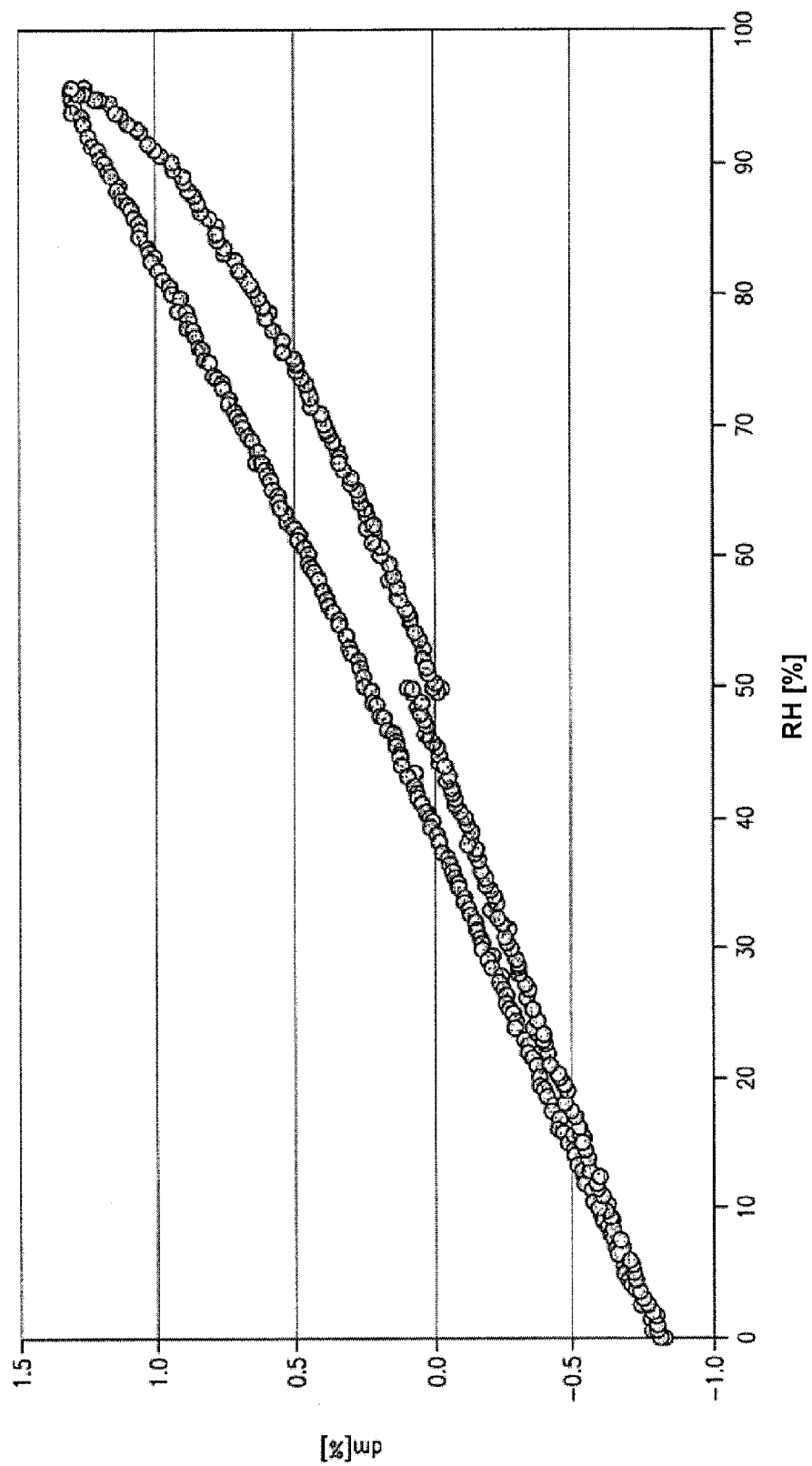
FIG. 12 shows illustrative DVS results for the Form II polymorph of 20,23-dipiperidinyl-5-O-mycaminosyl-tylonolide.

FIG. 12 shows the results from a DVS analysis of the Form II polymorph. This analysis was conducted at 25° C. A maximum water uptake of about 2% (by weight) at 95% relative humidity was observed.

vii. IR Spectrum for the Form II Polymorph

Figure 14:
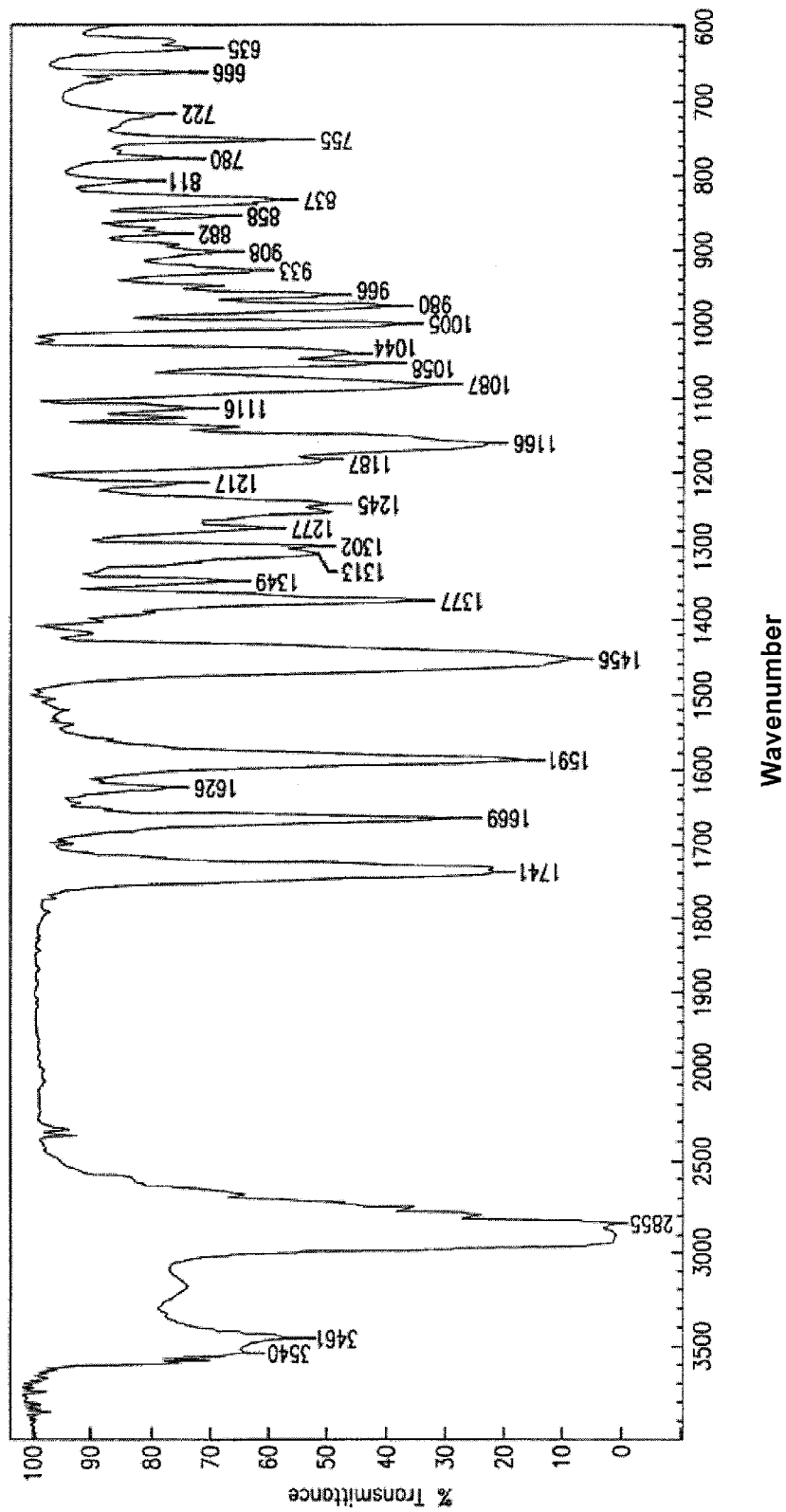
FIG. 14 shows an illustrative IR spectrum for a nujol suspension containing the Form II polymorph of 20,23-dipiperidinyl-5-O-mycaminosyl-tylonolide.

FIG. 13 shows ATR-IR spectrum for the Form II polymorph, and FIG. 14 provides the IR spectrum for the Form II polymorph in a nujol suspension. The corresponding data are shown in the following Table 8:

TABLE 8

IR Data for the Form II Polymorph

| Frequencies of intense IR absorption bands observed with ATR technique (cm$^{-1}$) | Frequencies of intense IR absorption bands observed with Nujol technique (cm$^{-1}$) |
|---|---|
|  | 3540 |
| 2935 | overlaps with nujol vibration band |
| 1736 | 1741 |
| 1668 | 1669 |
|  | 1626 |
| 1587 | 1591 |
| 1451 | overlaps with nujol vibration band |
| 1372 | overlaps with nujol vibration band |
| 1352 | 1349 |
| 1310 | 1313 |
|  | 1302 |
| 1277 | 1277 |
| 1242 | 1245 |
|  | 1217 |
|  | 1187 |
| 1165 | 1166 |
|  | 1116 |
| 1080 | 1087 |
| 1057 | 1058 |
| 1042 | 1044 |
| 1005 | 1005 |
| 981 | 980 |
| 966 | 966 |
| 934 | 933 |
| 910 | 908 |
|  | 882 |
| 859 | 858 |
| 838 | 837 |
|  | 811 |
| 781 | 780 |
| 755 | 755 |
|  | 722 |

Characteristic features of the spectra, particularly the ATR spectrum, include intense absorption bands at 2935 cm$^{-1}$, 1736 cm$^{-1}$, 1668 cm$^{-1}$, 1587 cm$^{-1}$, 1451 cm$^{-1}$, 1165 cm$^{-1}$, 1080 cm$^{-1}$, 1057 cm$^{-1}$, 1042 cm$^{-1}$, 1005 cm$^{-1}$, 981 cm$^{-1}$, 838 cm$^{-1}$, and 755 cm$^{-1}$.

Form III Polymorph

The following discussion provides various observed characteristics of the Form III polymorph.

i. Appearance of the Form III Polymorph

The Form III polymorph was generally in the form of fine needles.

ii. Powder X-Ray Diffraction Spectrum for the Form III Polymorph

The observed PXRD spectrum for the Form III polymorph is shown in FIG. 15, and the corresponding data is shown in the following Table 9:

TABLE 9

X-Ray Diffraction Data for the Form III Polymorph

| Angle (2-Θ degrees) | d Value (Å) | Intensity (cps) | Rel. Intensity (%) |
|---|---|---|---|
| 5.6 | 15.781 | 36 | 17.3 |
| 6.1 | 14.489 | 209 | 100.0 |
| 8.3 | 10.653 | 54 | 25.8 |
| 11.0 | 8.043 | 44 | 21.2 |
| 12.2 | 7.255 | 40 | 19.2 |
| 13.2 | 6.707 | 45 | 21.4 |
| 13.7 | 6.463 | 21 | 9.8 |
| 14.2 | 6.237 | 26 | 12.4 |
| 15.2 | 5.829 | 16 | 7.9 |
| 15.7 | 5.644 | 53 | 25.2 |
| 16.1 | 5.505 | 19 | 9.2 |
| 16.8 | 5.277 | 105 | 50.1 |
| 17.9 | 4.955 | 28 | 13.3 |
| 18.2 | 4.874 | 22 | 10.6 |
| 18.9 | 4.695 | 37 | 17.8 |
| 19.6 | 4.529 | 17 | 8.1 |
| 20.5 | 4.332 | 86 | 41.1 |
| 21.6 | 4.114 | 44 | 21.2 |
| 22.5 | 3.952 | 20 | 9.4 |
| 24.3 | 3.663 | 14 | 6.6 |
| 26.0 | 3.427 | 15 | 7.1 |

Characteristic features of the spectrum include the most intense peak being at 2Θ=6.1°, which is accompanied by a smaller peak at 2Θ=5.6°. It has been observed that the relative intensity of these two peaks varies from batch to batch, as do the relative intensities of other peaks in the spectrum. Such variations are not uncommon to PXRD. Often, they originate from orientation effects, particularly in the context of anisotropic (i.e., needle- and plate-like) crystals. These variations, however, generally do not influence the identification of the polymorphic form because this normally depends on peak positions rather than intensities.

iii. FT-Raman Spectrum for the Form III Polymorph

The observed FT-Raman spectrum for the Form III polymorph is shown in FIG. 16, and the corresponding data is shown in the following Table 10:

TABLE 10

FT-Raman Data for the Form III Polymorph

| Position (cm$^{-1}$) | Intensity |
|---|---|
| 2943 | 0.214 |
| 2917 | 0.199 |
| 2785 | 0.049 |
| 1733 | 0.014 |
| 1669 | 0.038 |
| 1627 | 0.256 |
| 1590 | 0.447 |
| 1443 | 0.064 |
| 1314 | 0.040 |
| 1269 | 0.051 |

TABLE 10-continued

FT-Raman Data for the Form III Polymorph

| Position (cm$^{-1}$) | Intensity |
|---|---|
| 1257 | 0.037 |
| 1217 | 0.021 |
| 1193 | 0.037 |
| 1116 | 0.035 |
| 1094 | 0.043 |
| 1041 | 0.029 |
| 981 | 0.034 |
| 908 | 0.026 |
| 881 | 0.031 |
| 863 | 0.025 |
| 833 | 0.022 |
| 810 | 0.018 |
| 781 | 0.027 |
| 505 | 0.030 |
| 444 | 0.021 |
| 399 | 0.025 |
| 216 | 0.042 |
| 173 | 0.033 |
| 108 | 0.070 |
| 84 | 0.068 |

Characteristic features of the spectrum include intense peaks at 2943 cm$^{-1}$, 2917 cm$^{-1}$, 1627 cm$^{-1}$, and 1590 cm$^{-1}$; and smaller peaks at 1733 cm$^{-1}$, 1669 cm$^{-1}$, 1193 cm$^{-1}$, 1094 cm$^{-1}$, and 981 cm$^{-1}$.

iv. Thermogravimetry for the Form III Polymorph

TG-FTIR analysis of one sample showed a weight loss of 1.7% up to 220° C., with most of the loss occurring between 50 and 120° C. It is hypothesized that this weight loss was due to water or acetonitrile in the sample (the sensitivity of the IR-detector to acetonitrile is low).

Figure 17:
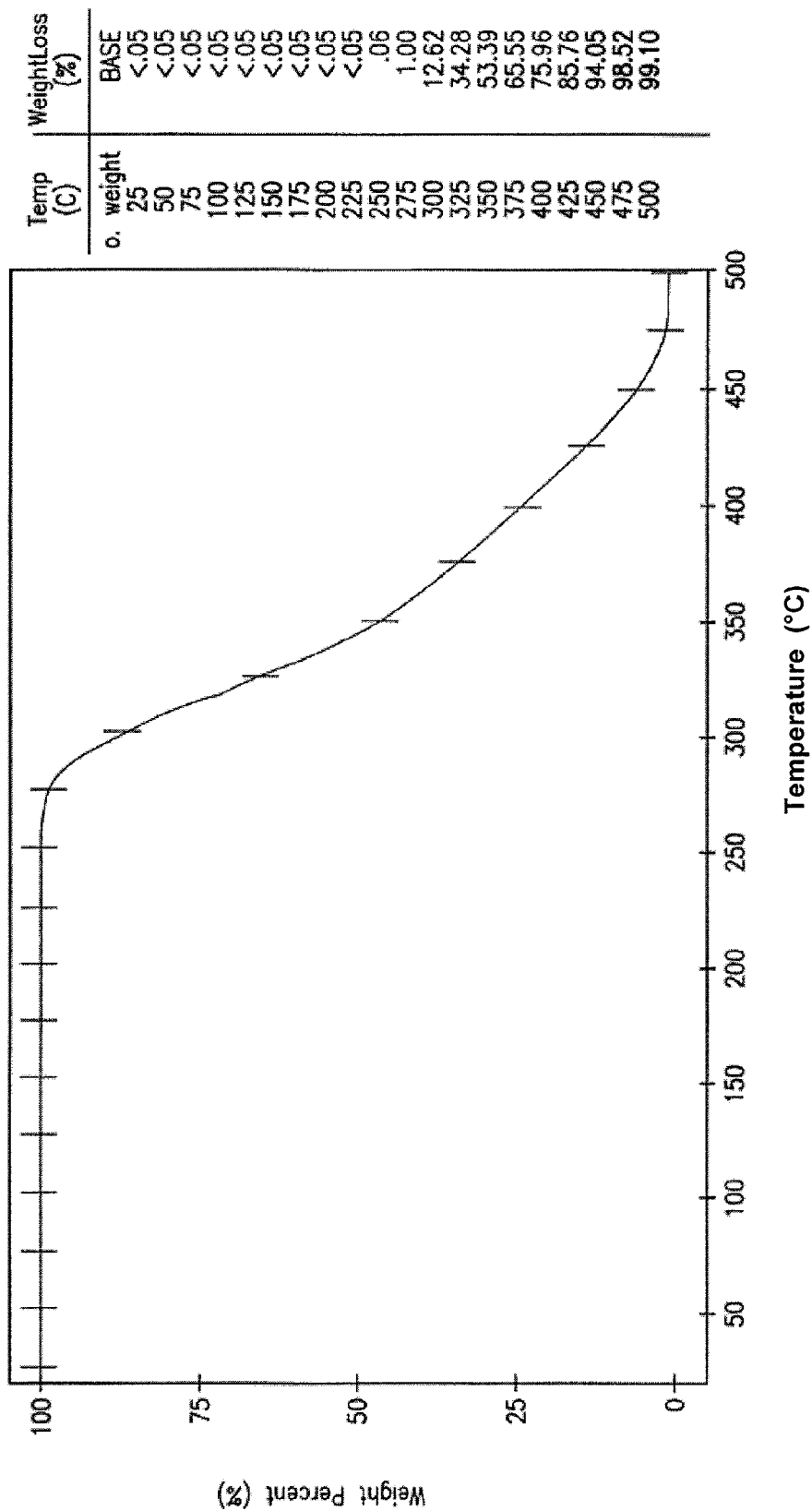
FIG. 17 shows illustrative TG results for the Form III polymorph of 20,23-dipiperidinyl-5-O-mycaminosyl-tylonolide.

FIG. 17 shows the results from a TG analysis of the Form III polymorph. A weight loss of less than 0.05% was observed up to 200° C. Decomposition began at a temperature of greater than 270° C.

v. Differential Scanning Calorimetry for the Form III Polymorph

Figure 18:
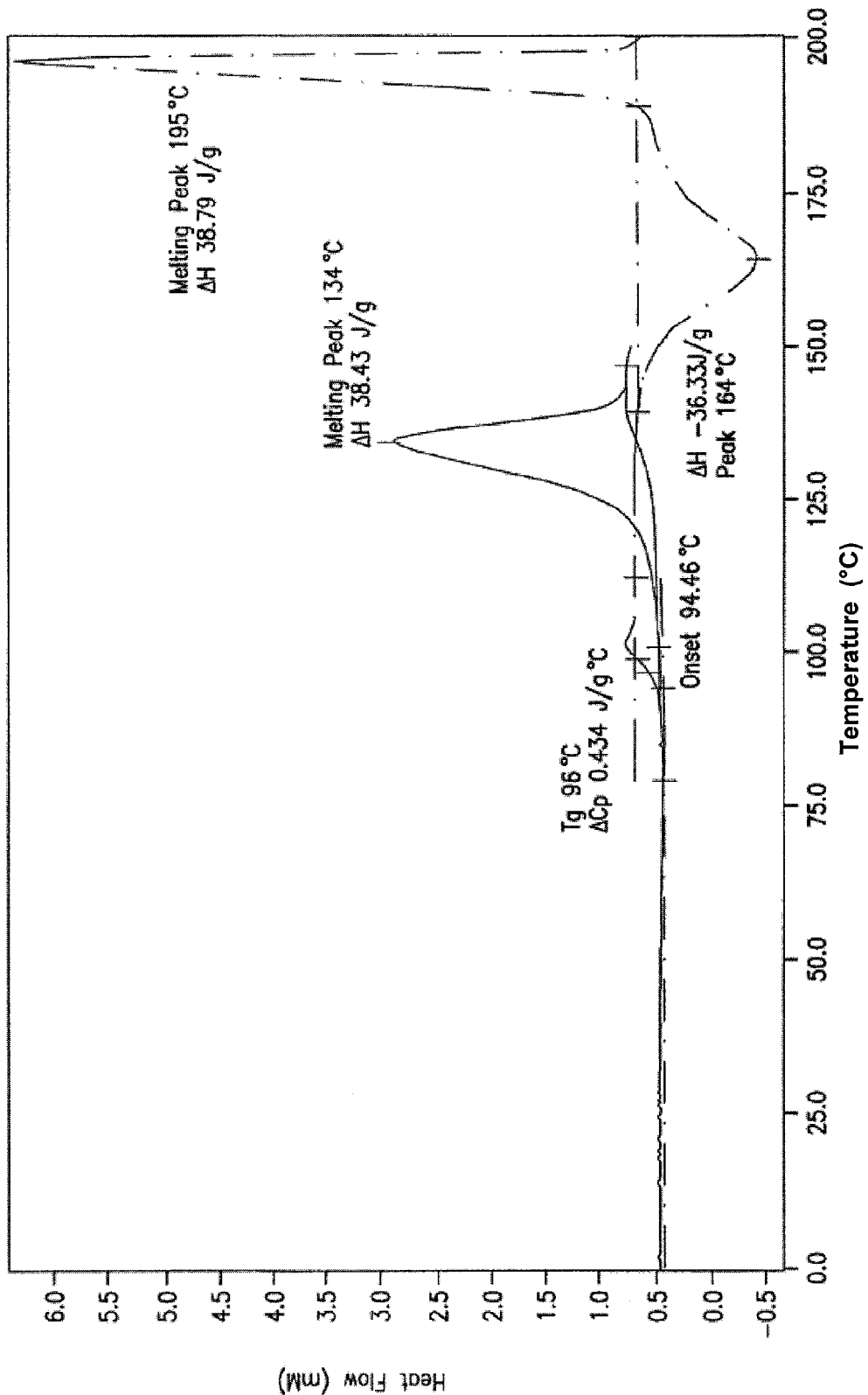
FIG. 18 shows illustrative DSC results for the Form III polymorph of 20,23-dipiperidinyl-5-O-mycaminosyl-tylonolide. The continuous line corresponds to the first scan, and the dashed line corresponds to the second scan.

FIG. 18 shows the results from a DSC analysis of the Form III polymorph. The first scan (the continuous line) shows a melting peak at 134° C. with a melting enthalpy of $\Delta H_{fus}$=38 J/g. Upon cooling, the material solidified into the amorphous state. The second scan (the dotted line) shows a $T_g$ of 96° C., re-crystallization, and melting again at 195° C.

Samples of the Form III polymorph were independently analyzed to determine the melting point. Samples having a purity of about 99% exhibited a melting point of from 122 to 126° C.

vi. Dynamic Vapor Sorption for the Form III Polymorph

Figure 19:
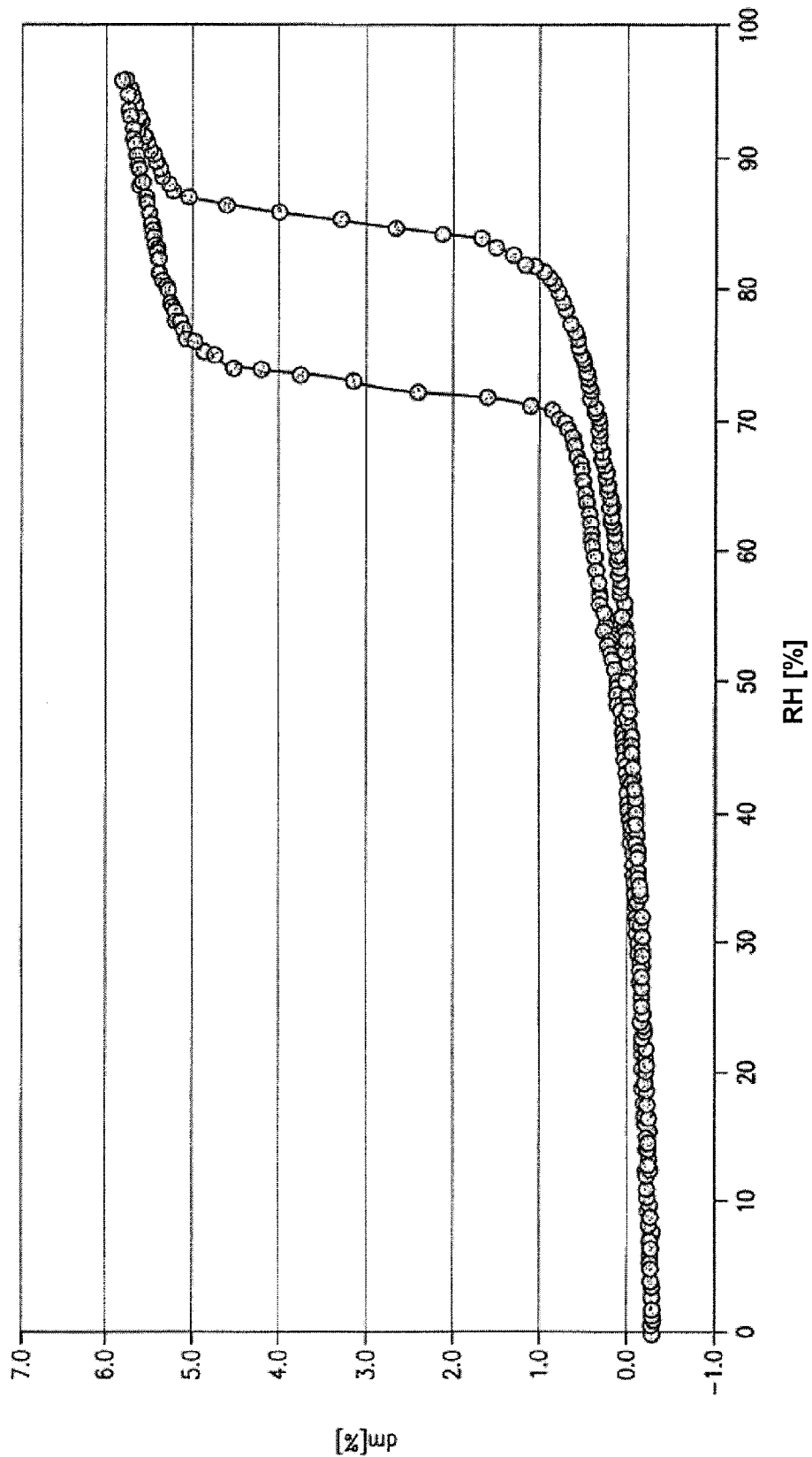
FIG. 19 shows illustrative DVS results for the Form III polymorph of 20,23-dipiperidinyl-5-O-mycaminosyl-tylonolide.

FIG. 19 shows the results from a DVS analysis of the Form III polymorph. This analysis was conducted at 25° C. A water uptake of about 6% was observed between 70 and 85% relative humidity.

vii. IR Spectrum for the Form III Polymorph

Figure 21:
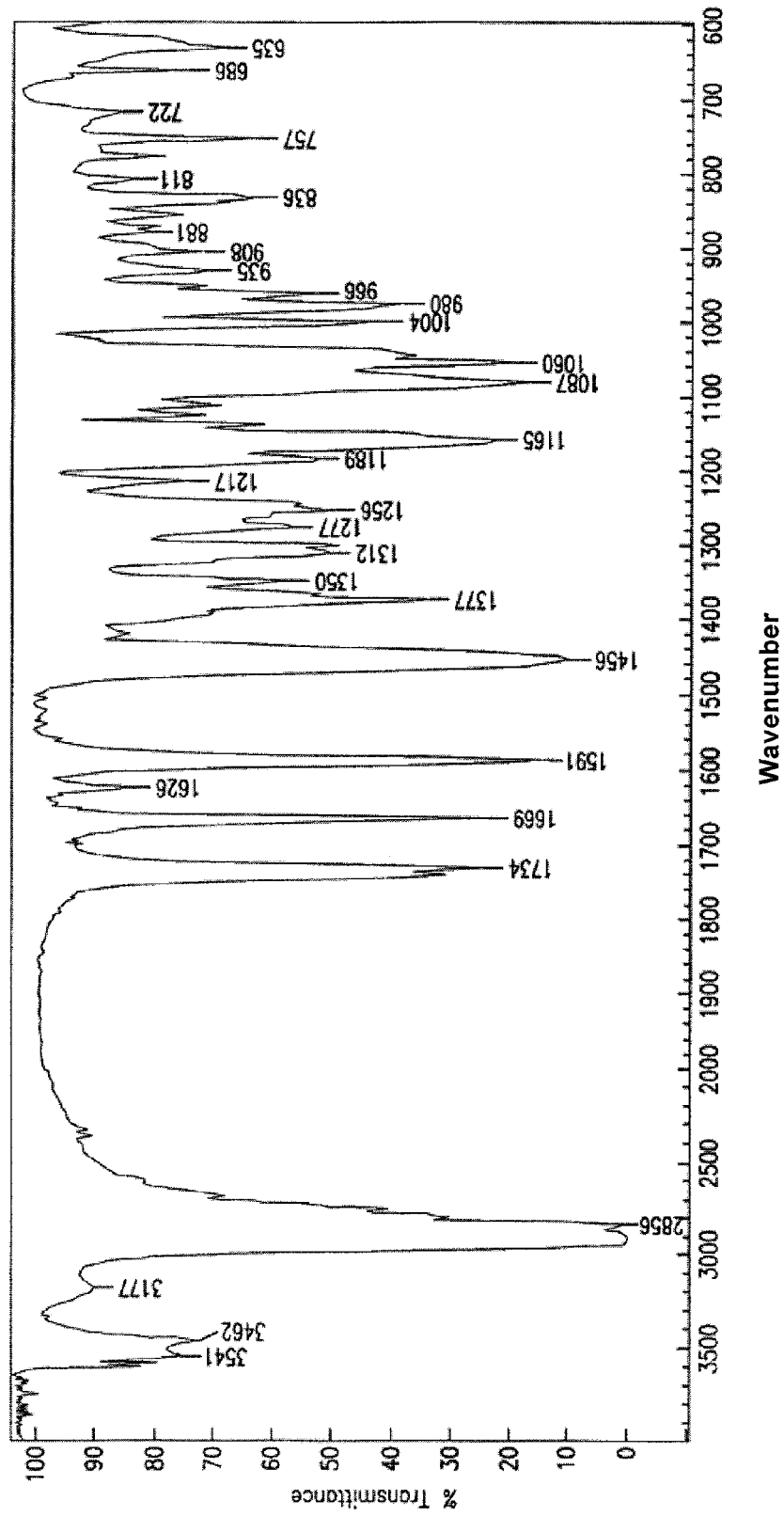
FIG. 21 shows an illustrative IR spectrum for a nujol suspension containing the Form III polymorph of 20,23-dipiperidinyl-5-O-mycaminosyl-tylonolide.

FIG. 20 shows ATR-IR spectrum for the Form III polymorph, and FIG. 21 provides the IR spectrum for the Form III polymorph in a nujol suspension. The corresponding data are shown in the following Table 11:

TABLE 11

| IR Data for the Form III Polymorph | |
|---|---|
| Frequencies of intense IR absorption bands observed with ATR technique (cm$^{-1}$) | Frequencies of intense IR absorption bands observed with Nujol technique (cm$^{-1}$) |
|---|---|
|  | 3541 |
| 2931 | overlaps with nujol vibration band |
| 1732 | 1734 |
| 1667 | 1669 |
|  | 1626 |
| 1590 | 1591 |
| 1453 | overlaps with nujol vibration band |
| 1376 | overlaps with nujol vibration band |
| 1350 | 1350 |
| 1304 | 1312 |
| 1277 | 1277 |
| 1256 | 1256 |
| 1217 | 1217 |
|  | 1189 |
| 1165 | 1165 |
| 1081 | 1087 |
| 1057 | 1060 |
| 1046 |  |
| 1005 | 1004 |
| 981 | 980 |
| 965 | 966 |
| 934 | 935 |
| 908 | 908 |
|  | 881 |
| 859 |  |
| 834 | 836 |
| 812 | 811 |
| 780 |  |
| 756 | 757 |
| 722 |  |

Characteristic features of the spectra, particularly the ATR spectrum, include intense absorption bands at 2931 cm$^{-1}$, 1732 cm$^{-1}$, 1667 cm$^{-1}$, 1590 cm$^{-1}$, 1453 cm$^{-1}$, 1165 cm$^{-1}$, 1081 cm$^{-1}$, 1057 cm$^{-1}$, 1046 cm$^{-1}$, 1005 cm$^{-1}$, 981 cm$^{-1}$, 834 cm$^{-1}$, and 756 cm$^{-1}$.

Form IV Polymorph

The following discussion provides various observed characteristics of the Form IV polymorph.

i. Powder X-Ray Diffraction Spectrum for the Form IV Polymorph

The observed PXRD spectrum for the Form IV polymorph is shown in FIG. 22, and the corresponding data is shown in the following Table 12:

TABLE 12

X-Ray Diffraction Data for the Form IV Polymorph

| Angle (2-Θ degrees) | d Value (Å) | Intensity (cps) | Rel. Intensity (%) |
|---|---|---|---|
| 6.232 | 14.171 | 135 | 6.4 |
| 6.848 | 12.898 | 367 | 17.5 |
| 8.653 | 10.211 | 709 | 33.8 |
| 10.16 | 8.7007 | 1650 | 78.7 |
| 10.64 | 8.3119 | 887 | 42.3 |
| 11.18 | 7.9106 | 706 | 33.7 |
| 11.95 | 7.4034 | 314 | 15.0 |
| 12.29 | 7.1957 | 253 | 12.1 |
| 13.84 | 6.3955 | 328 | 15.6 |
| 15.06 | 5.8779 | 804 | 38.3 |

TABLE 12-continued

X-Ray Diffraction Data for the Form IV Polymorph

| Angle (2-Θ degrees) | d Value (Å) | Intensity (cps) | Rel. Intensity (%) |
|---|---|---|---|
| 15.49 | 5.7158 | 831 | 39.6 |
| 16.06 | 5.5147 | 1600 | 76.3 |
| 17.50 | 5.0638 | 2097 | 100 |
| 18.75 | 4.7291 | 1144 | 54.6 |
| 19.93 | 4.4510 | 1435 | 68.4 |
| 20.49 | 4.3321 | 1815 | 86.6 |
| 21.40 | 4.1473 | 1189 | 56.7 |
| 22.59 | 3.9328 | 838 | 40.0 |
| 23.50 | 3.7830 | 517 | 24.7 |
| 23.96 | 3.7118 | 745 | 35.5 |
| 25.06 | 3.5507 | 493 | 23.5 |
| 25.32 | 3.5147 | 522 | 24.9 |
| 25.74 | 3.4588 | 574 | 27.4 |
| 26.92 | 3.3091 | 464 | 22.1 |
| 27.83 | 3.2036 | 691 | 33.0 |
| 28.24 | 3.1576 | 470 | 22.4 |
| 29.02 | 3.0748 | 389 | 18.6 |
| 29.36 | 3.0396 | 335 | 16.0 |
| 30.92 | 2.8902 | 454 | 21.6 |
| 31.30 | 2.8554 | 506 | 24.1 |
| 32.42 | 2.7594 | 650 | 31.0 |
| 33.60 | 2.6649 | 361 | 17.2 |
| 35.38 | 2.5347 | 436 | 20.8 |
| 35.85 | 2.5027 | 390 | 18.6 |
| 36.66 | 2.4492 | 345 | 16.5 |
| 37.66 | 2.3869 | 426 | 20.3 |
| 38.63 | 2.3287 | 426 | 20.3 | ii. Differential Scanning Calorimetry for the Form IV Polymorph

Figure 23:
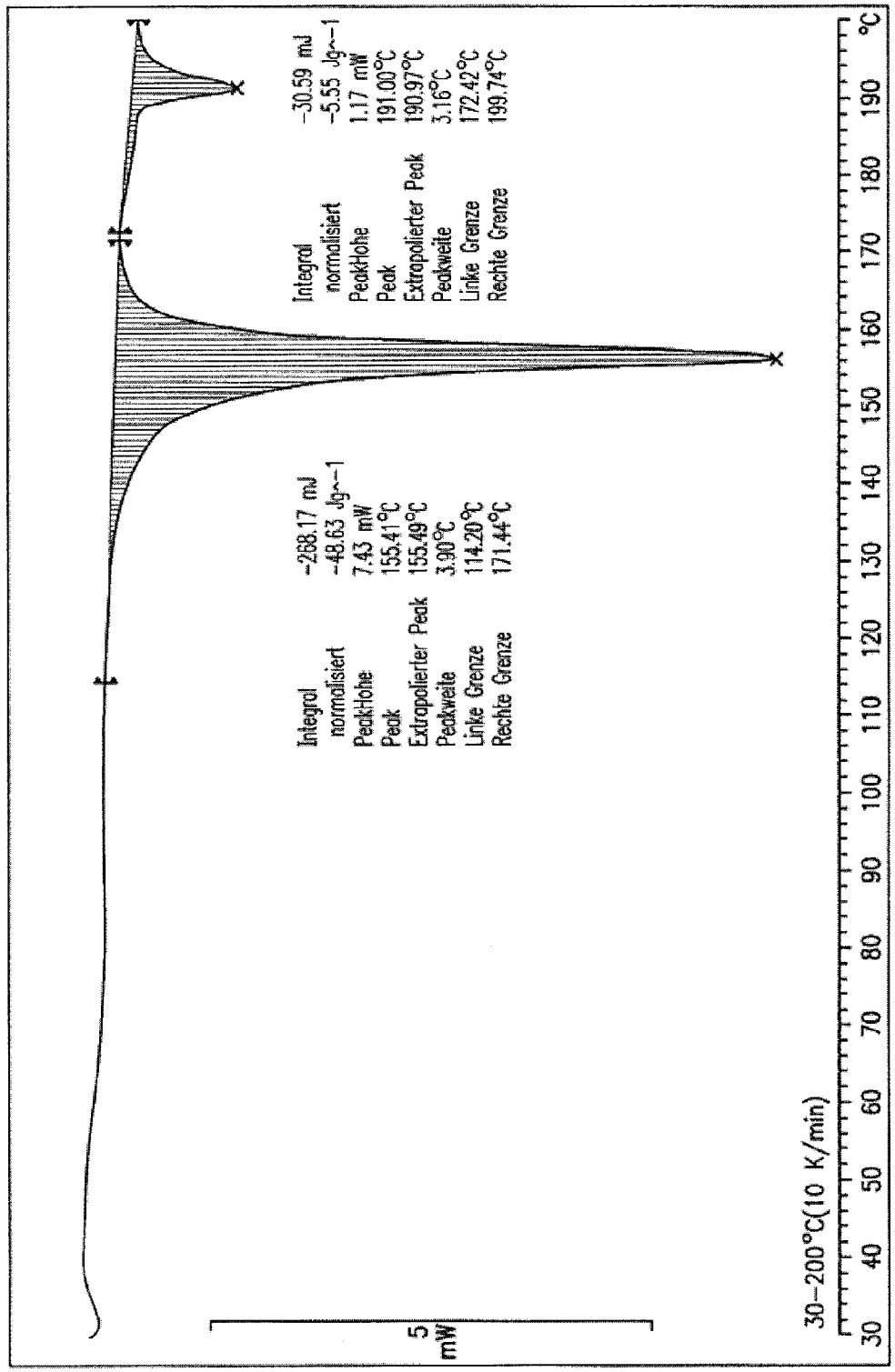
FIG. 23 shows illustrative DSC results for the Form IV polymorph of 20,23-dipiperidinyl-5-O-mycaminosyl-tylonolide.

FIG. 23 shows the results from a DSC analysis of the Form IV polymorph. The curve shows a peak at 155° C., believed to correspond to the Form IV polymorph. The curve also shows a peak at 191° C., believed to correspond to the Form I polymorph. It is believed that the sample contained both of the Form I and Form IV polymorphs, or that the Form IV polymorph converts to the Form I polymorph during heating. Samples of the Form IV polymorph were independently analyzed to determine the melting point. Samples being about 90.0% (w/w) pure exhibited melting points of from 149-152° C.

iv. IR Spectrum for the Form IV Polymorph

Figure 25:
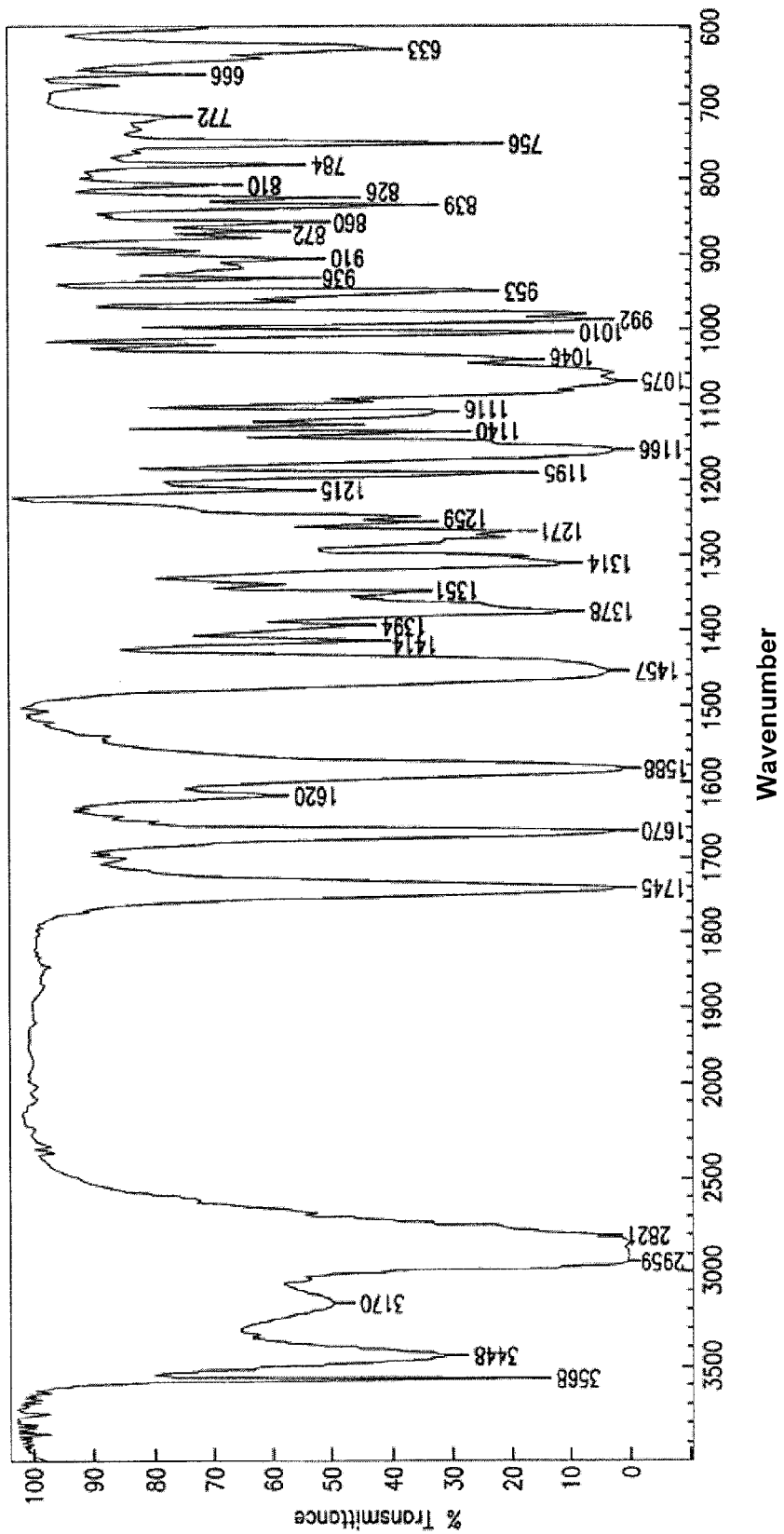
FIG. 25 shows an illustrative IR spectrum for a nujol suspension containing the Form IV polymorph of 20,23-dipiperidinyl-5-O-mycaminosyl-tylonolide.

FIG. 24 shows ATR-IR spectrum for the Form IV polymorph, and FIG. 25 provides the IR spectrum for the Form IV polymorph in a nujol suspension. The corresponding data are shown here:

TABLE 13

IR Data for the Form IV Polymorph

| Frequencies of intense IR absorption bands observed with ATR technique (cm$^{-1}$) | Frequencies of intense IR absorption bands observed with Nujol technique (cm$^{-1}$) |
|---|---|
| 3559 | 3568 |
| 2933 | overlaps with nujol vibration band |
| 1743 | 1745 |
| 1668 | 1670 |
|  | 1620 |
| 1584 | 1588 |
| 1448 | overlaps with nujol vibration band |
|  | 1441 |
|  | 1394 |
| 1370 | overlaps with nujol vibration band |
|  | 1351 |
|  | 1314 |
| 1307 |  |
| 1272 | 1271 |
| 1259 | 1259 |
|  | 1215 |
| 1195 | 1195 |
| 1165 | 1166 |
|  | 1140 |
| 1118 | 1116 |
| 1075 | 1075 |
| 1060 |  |
| 1045 | 1046 |
| 1010 | 1010 |
| 985 | 992 |
| 954 | 953 |
|  | 936 |
|  | 910 |
|  | 872 |
|  | 860 |
| 839 | 839 |
|  | 810 |
| 785 | 784 |
| 757 | 756 |
|  | 722 |

Characteristic features of the spectra, particularly the ATR spectrum, include intense absorption bands at 2933 cm$^{-1}$, 1743 cm$^{-1}$, 1668 cm$^{-1}$, 1584 cm$^{-1}$, 1448 cm$^{-1}$, 1165 cm$^{-1}$, 1075 cm$^{-1}$, 1060 cm$^{-1}$, 1045 cm$^{-1}$, 1010 cm$^{-1}$, 985 cm$^{-1}$, 839 cm$^{-1}$, and 757 cm$^{-1}$. The absorption band at 3559 cm$^{-1}$ appears to be particularly unique to this polymorph.

S1 Crystalline Solvate

The following discussion provides various observed characteristics of the S1 crystalline solvate. Although the PXRD and FT-Raman data below correspond to the ethyl acetate S1 crystalline solvate, this data is generally applicable to characterizing the diethyl ketone and ethanol crystalline solvates as well because they are isomorphic with the ethyl acetate crystalline solvate.

i. Appearance of the Ethyl Acetate S1 Crystalline Solvate

Figure 26:
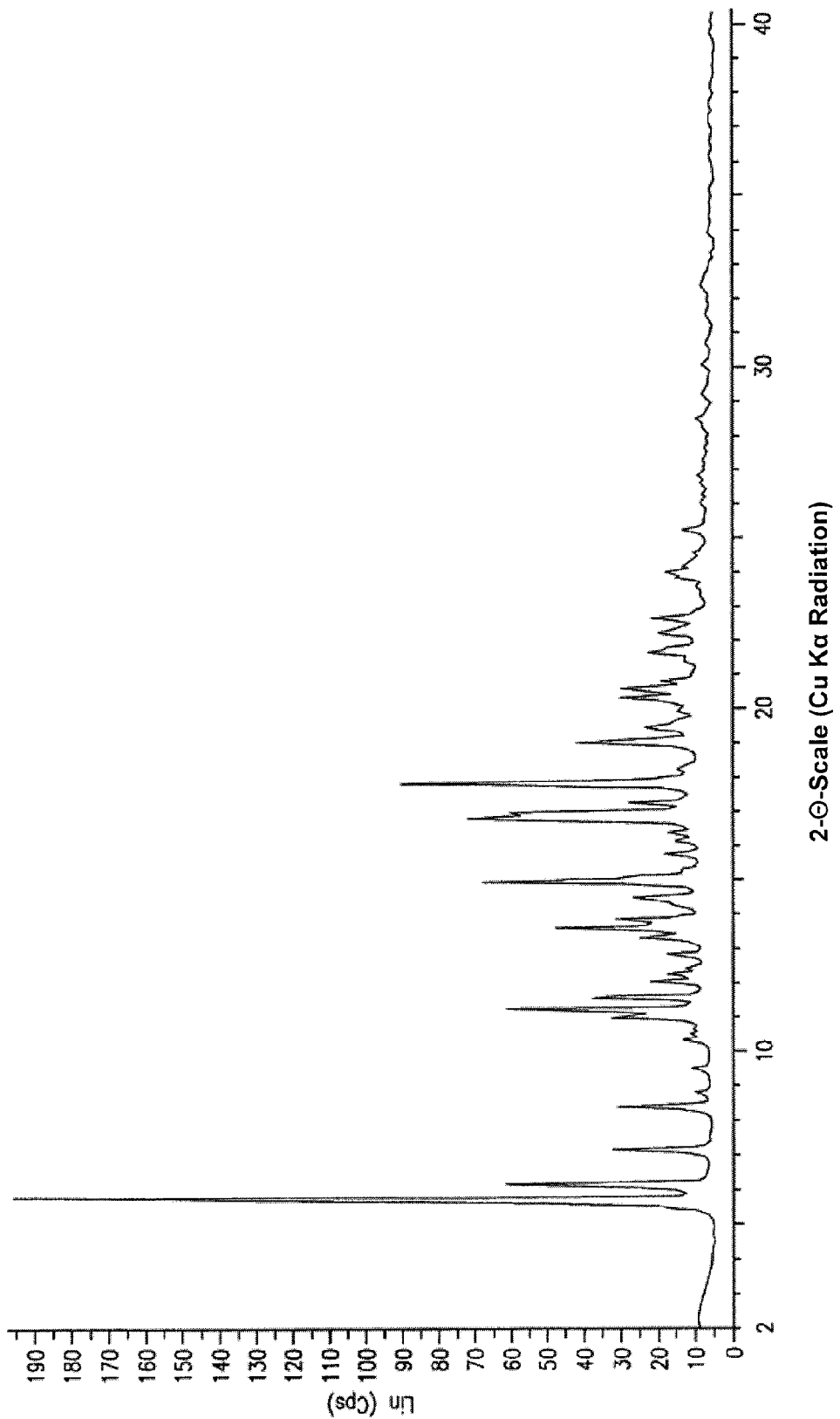
FIG. 26 shows an illustrative PXRD spectrum for an ethyl acetate S1 solvate sample of 20,23-dipiperidinyl-5-O-mycaminosyl-tylonolide.

The ethyl acetate S1 crystalline solvate was generally in the form of fine needles, or larger crystals with a tendency to break down into fibers.

ii. Powder X-Ray Diffraction Spectrum for the Ethyl Acetate S1 Crystalline Solvate The observed PXRD spectrum for the ethyl acetate S1 crystalline solvate is shown in FIG. 26, and the corresponding data is shown in the following Table 14:

TABLE 14

X-Ray Diffraction Data for the Ethyl Acetate S1 Crystalline Solvate

| Angle (2-Θ degrees) | d Value (Å) | Intensity (cps) | Rel. Intensity (%) |
|---|---|---|---|
| 5.6 | 15.781 | 199 | 100.0 |
| 6.1 | 14.489 | 62 | 31.3 |
| 7.1 | 12.450 | 32 | 15.9 |
| 8.3 | 10.653 | 30 | 15.2 |
| 11.0 | 8.043 | 32 | 15.9 |
| 11.2 | 7.900 | 62 | 31.3 |
| 11.5 | 7.695 | 37 | 18.7 |
| 12.0 | 7.375 | 22 | 10.9 |
| 12.2 | 7.255 | 17 | 8.5 |
| 12.8 | 6.916 | 17 | 8.5 |
| 13.3 | 6.657 | 24 | 12.2 |
| 13.5 | 6.559 | 47 | 23.6 |
| 13.8 | 6.417 | 31 | 15.6 |
| 14.4 | 6.151 | 26 | 13.3 |
| 14.9 | 5.946 | 68 | 34.3 |
| 15.7 | 5.644 | 18 | 8.9 |
| 16.8 | 5.277 | 71 | 36.0 |
| 17.2 | 5.155 | 27 | 13.6 |
| 17.8 | 4.983 | 89 | 44.8 |
| 19.0 | 4.671 | 41 | 20.8 |
| 19.4 | 4.575 | 23 | 11.5 |
| 20.3 | 4.375 | 29 | 14.8 |
| 20.5 | 4.332 | 29 | 14.7 |
| 21.6 | 4.114 | 22 | 11.0 |
| 22.1 | 4.022 | 19 | 9.7 |
| 22.6 | 3.934 | 21 | 10.7 |
| 23.9 | 3.723 | 17 | 8.6 |
| 25.2 | 3.534 | 13 | 6.5 |

Characteristic features of the spectrum include initial peaks at 2Θ=5.6° and 6.1°.

iii. FT-Raman Spectrum for the Ethyl Acetate S1 Crystalline Solvate

Figure 27:
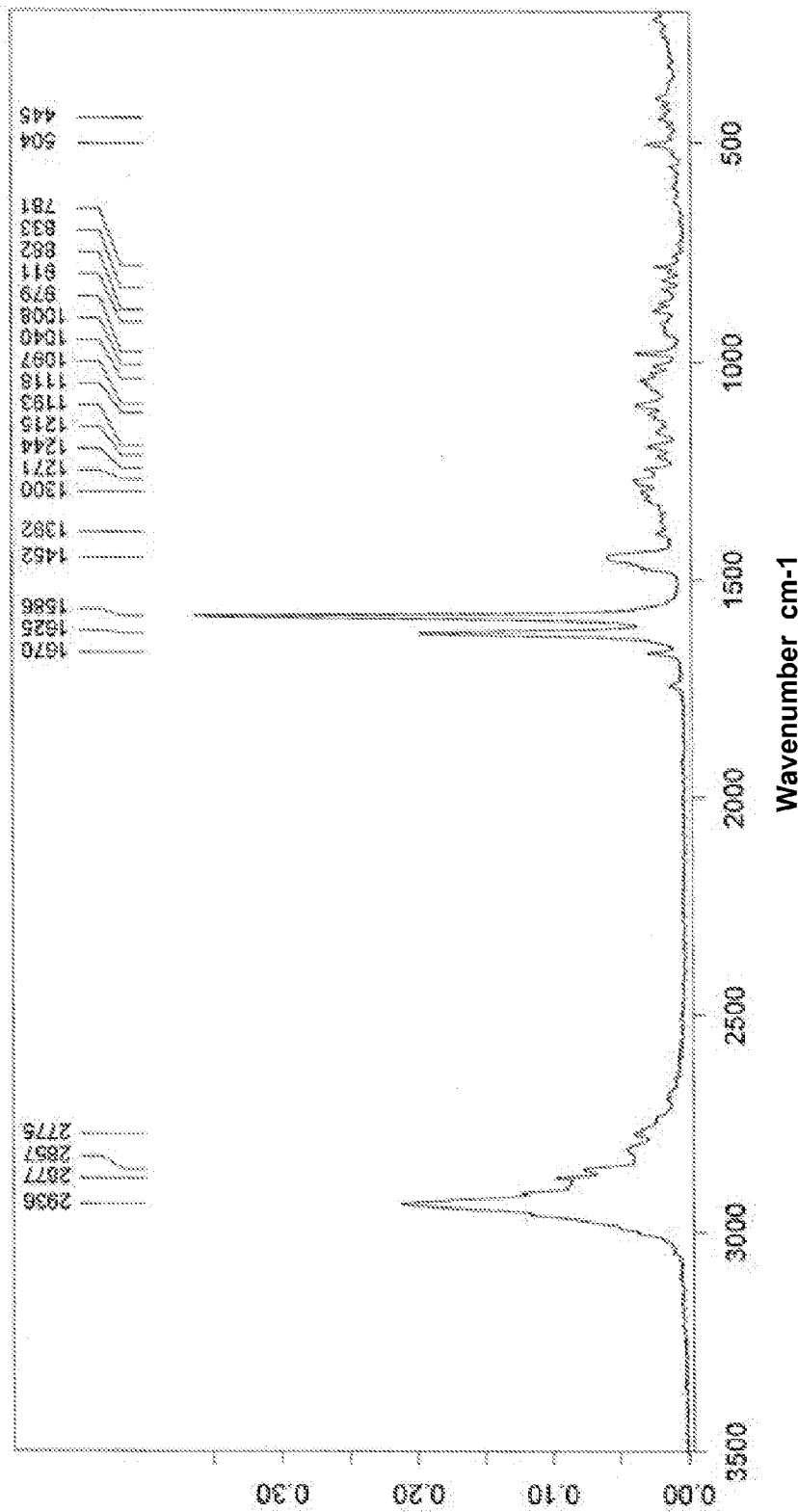
FIG. 27 shows an illustrative FT-Raman spectrum for an ethyl acetate S1 crystalline solvate sample of 20,23-dipiperidinyl-5-O-mycaminosyl-tylonolide.

The observed FT-Raman spectrum for the ethyl acetate S1 crystalline solvate is shown in FIG. 27, and the corresponding data is shown in the following Table 15:

TABLE 15

FT-Raman Data for the Ethyl Acetate S1 Crystalline Solvate

| Position (cm$^{-1}$) | Intensity |
|---|---|
| 2936 | 0.212 |
| 2877 | 0.098 |
| 2857 | 0.078 |
| 2775 | 0.040 |
| 1745 | 0.012 |
| 1669 | 0.029 |
| 1625 | 0.198 |
| 1586 | 0.363 |
| 1451 | 0.058 |
| 1392 | 0.022 |
| 1300 | 0.033 |
| 1271 | 0.039 |
| 1244 | 0.030 |
| 1215 | 0.021 |
| 1193 | 0.029 |
| 1118 | 0.028 |
| 1097 | 0.037 |
| 1040 | 0.034 |
| 1008 | 0.024 |
| 978 | 0.038 |
| 911 | 0.018 |
| 882 | 0.024 |
| 833 | 0.018 |
| 812 | 0.017 |
| 781 | 0.023 |
| 554 | 0.012 |
| 504 | 0.029 |

TABLE 15-continued

FT-Raman Data for the Ethyl Acetate S1 Crystalline Solvate

| Position (cm$^{-1}$) | Intensity |
|---|---|
| 445 | 0.019 |
| 398 | 0.021 |
| 84 | 0.076 |

Characteristic features of the spectrum include intense peaks at 2936 cm$^{-1}$, 1625-1627 cm$^{-1}$, and 1586 cm$^{-1}$; and smaller, but sharp, peaks at 1745 cm$^{-1}$, 1669 cm$^{-1}$, and 978 cm$^{-1}$.

iv. Thermogravimetry for S1 Crystalline Solvates

Figure 28:
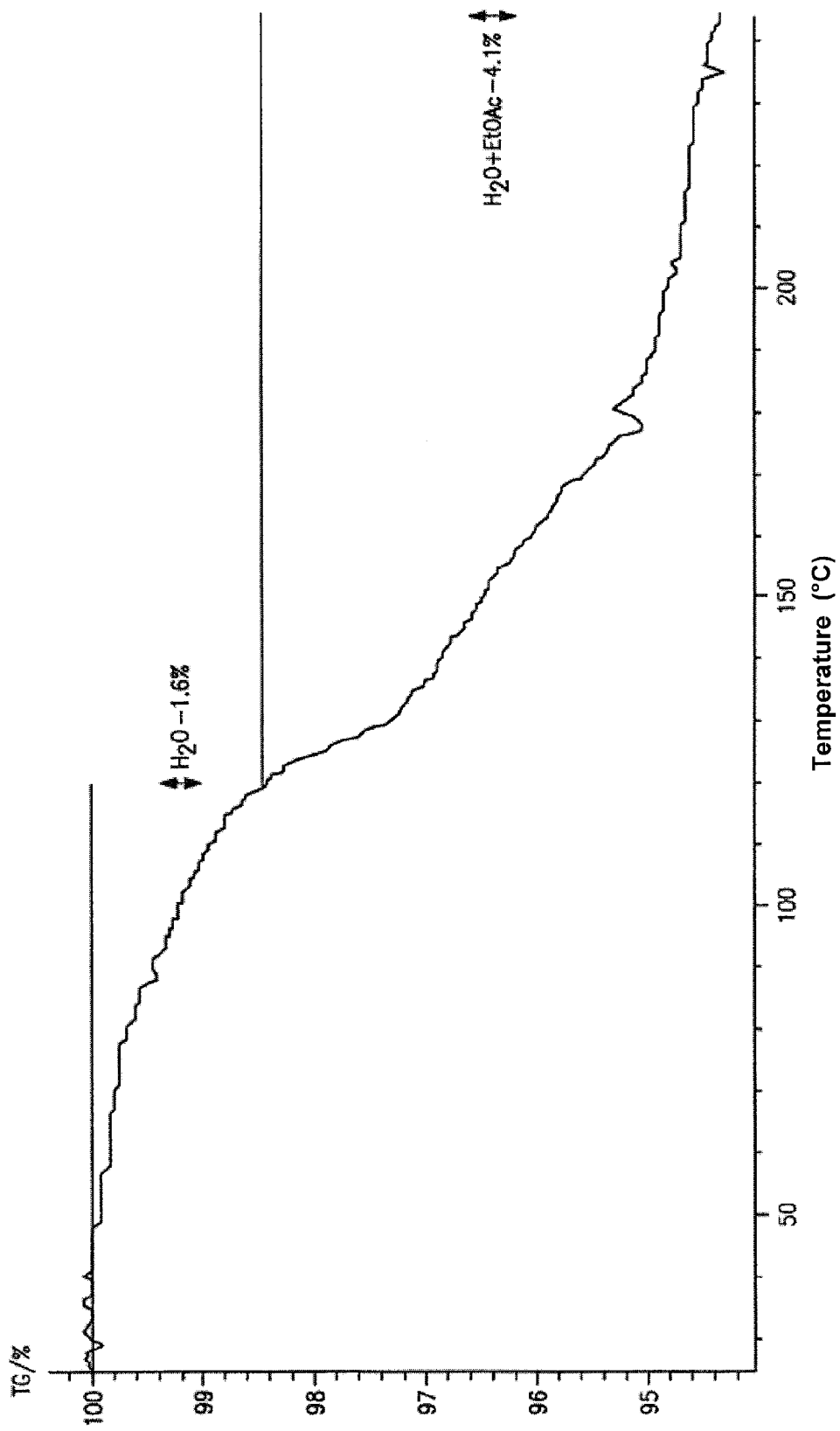
FIG. 28 shows illustrative TG-FTIR results for an ethyl acetate S1 crystalline solvate sample of 20,23-dipiperidinyl-5-O-mycaminosyl-tylonolide.
Figure 29:
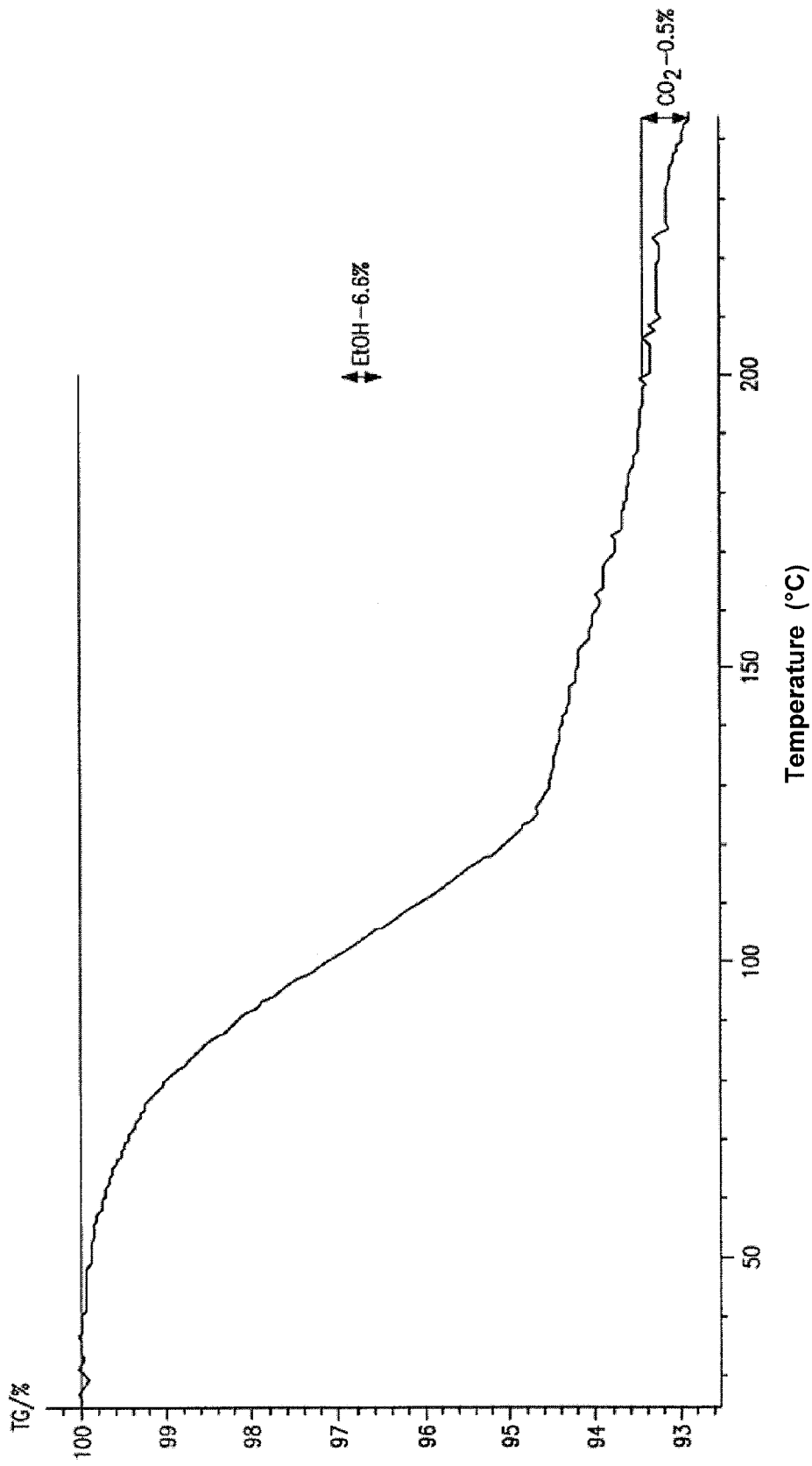
FIG. 29 shows illustrative TG-FTIR results for an ethanol S1 crystalline solvate sample of 20,23-dipiperidinyl-5-O-mycaminosyl-tylonolide.
Figure 30:
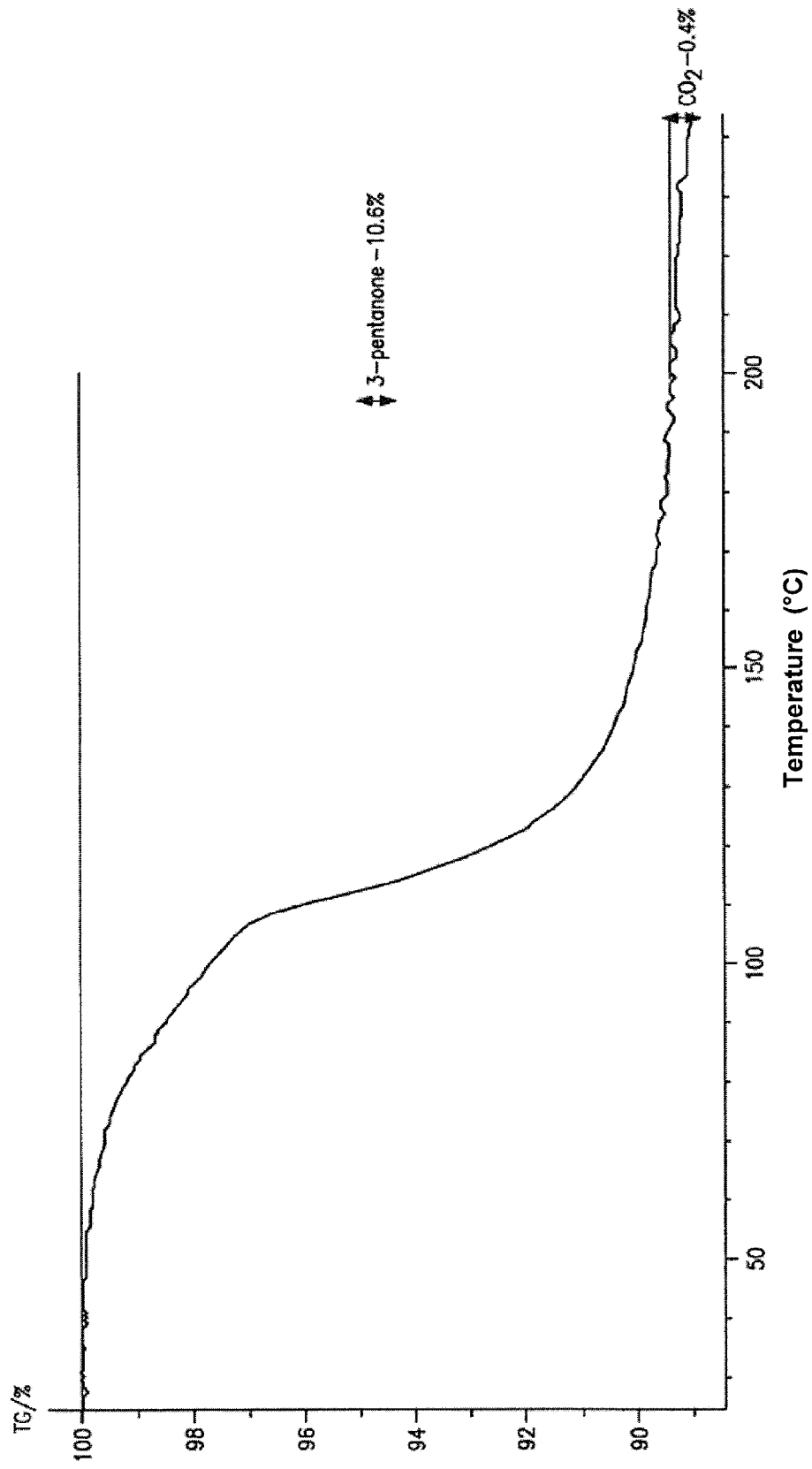
FIG. 30 shows illustrative TG-FTIR results for a diethyl ketone S1 crystalline solvate sample of 20,23-dipiperidinyl-5-O-mycaminosyl-tylonolide.

FIGS. 28, 29, and 30 show the TG-FTIR results for the ethyl acetate, ethanol, and diethyl ketone S1 crystalline solvates, respectively. These results confirm the existence of crystalline solvates with approximately one solvent molecule per 20,23-dipiperidinyl-5-O-mycaminosyl-tylonolide molecule, assuming essentially pure 20,23-dipiperidinyl-5-O-mycaminosyl-tylonolide. The ethyl acetate S1 crystalline solvate exhibited a weight loss of approximately 4.1% resulting from the liberation of ethyl acetate. This corresponds to a mole ratio of ethyl acetate to 20,23-dipiperidinyl-5-O-mycaminosyl-tylonolide of 0.36. The ethanol S1 crystalline solvate exhibited a weight loss of approximately 6.6% up to 200° C. resulting from the liberation of ethanol (the S1 crystalline solvate also may contain a small amount of water, which may have been liberated as well). This corresponds to a mole ratio of ethanol to 20,23-dipiperidinyl-5-O-mycaminosyl-tylonolide of 1.1. And the diethyl ketone S1 crystalline solvate exhibited a weight loss 10% resulting from the liberation of diethyl ketone. This corresponds to a mole ratio of diethyl ketone to 20,23-dipiperidinyl-5-O-mycaminosyl-tylonolide of 1.0. These results are summarized in Table 16:

TABLE 16

TG-FTIR Results for S1 Crystalline Solvates

| Crystalline Solvate | Detected Solvents | Solvent molecules per 20,23-dipiperidinyl-5-O-mycaminosyl-tylonolide molecule |
|---|---|---|
| ethyl acetate | ethyl acetate water | ~0.4 ethyl acetate + 0.6 water |
| ethanol | Ethanol | 1.1 ethanol |
| diethyl ketone | diethyl ketone | 1.0 diethyl ketone |

For each of the crystalline solvates, the weight loss begins at from 40 to 50° C. This indicates relatively low stability, and is consistent with the observation that the ethyl acetate crystalline solvate can, e.g., be readily converted into the Form III polymorph by vacuum drying at ambient temperature. See, e.g., Example 7. The results for the ethyl acetate crystalline solvate indicate that the solvent molecule can be substituted by water, and is consistent with the DVS results for the Form III polymorph.

S2 Crystalline Solvate

The following discussion provides various observed characteristics of the S2 crystalline solvate.

i. Appearance of the tBME S2 Crystalline Solvate

The tBME S2 crystalline solvate was generally in the form of poorly defined crystals, and did not exhibit a tendency to break down into fibers, as compared to the S1 solvate crystals.

ii. Solubility of the tBME S2 Crystalline Solvate in tBME

The solubility of the tBME S2 crystalline solvate in tBME is between 40 and 50 mg/ml. Accordingly, the solubility is at least one order of magnitude less than the solubility of the Form II polymorph in tBME.

iii. Powder X-Ray Diffraction Spectrum for the tBME S2 Crystalline Solvate

Figure 31:
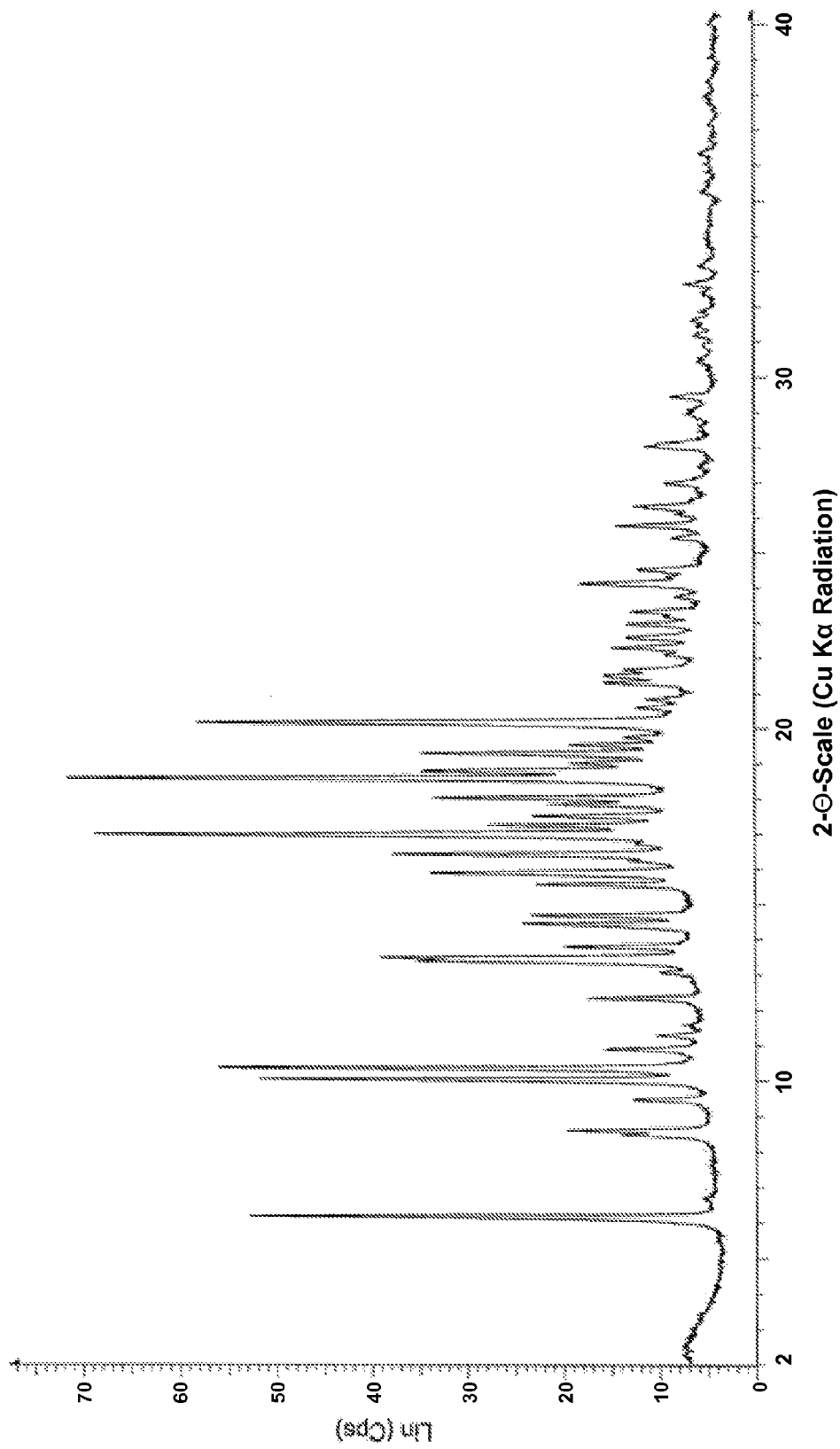
FIG. 31 shows an illustrative PXRD spectrum for a tBME S2 crystalline solvate sample of 20,23-dipiperidinyl-5-O-mycaminosyl-tylonolide.

The observed PXRD spectrum for the tBME S2 crystalline solvate is shown in FIG. 31, and the corresponding data is shown in the following Table 17:

TABLE 17

X-Ray Diffraction Data for the tBME S2 Crystalline Solvate

| Angle (2-Θ degrees) | d Value (Å) | Intensity (cps) | Rel. Intensity (%) |
|---|---|---|---|
| 6.1 | 14.489 | 54 | 73.5 |
| 8.6 | 10.282 | 20 | 26.8 |
| 9.5 | 9.309 | 13 | 17.3 |
| 10.0 | 8.845 | 52 | 71.7 |
| 10.3 | 8.588 | 56 | 77.4 |
| 10.9 | 8.117 | 16 | 21.5 |
| 12.3 | 7.196 | 18 | 24.0 |
| 13.5 | 6.559 | 39 | 53.7 |
| 13.8 | 6.417 | 20 | 27.1 |
| 14.4 | 6.151 | 24 | 33.4 |
| 14.7 | 6.026 | 23 | 32.0 |
| 15.6 | 5.680 | 23 | 31.4 |
| 15.9 | 5.574 | 34 | 46.5 |
| 16.4 | 5.405 | 38 | 52.1 |
| 17.0 | 5.216 | 70 | 95.4 |
| 17.2 | 5.155 | 28 | 38.1 |
| 18.0 | 4.928 | 33 | 45.9 |
| 18.6 | 4.770 | 73 | 100.0 |
| 18.8 | 4.720 | 35 | 48.3 |
| 19.3 | 4.599 | 35 | 48.0 |
| 20.1 | 4.418 | 58 | 79.9 |
| 21.3 | 4.171 | 16 | 21.3 |
| 21.5 | 4.133 | 16 | 21.4 |
| 22.3 | 3.986 | 15 | 20.3 |
| 22.6 | 3.934 | 13 | 18.1 |
| 23.0 | 3.867 | 13 | 18.1 |
| 23.3 | 3.818 | 13 | 17.4 |
| 24.1 | 3.693 | 18 | 24.8 |
| 25.8 | 3.453 | 14 | 19.7 |
| 26.4 | 3.376 | 12 | 17.0 |
| 28.1 | 3.175 | 11 | 15.7 |

Characteristic features of the spectrum include several peaks with similar intensity at 2Θ=6.1°, 10.0°, 10.3°, 17.0°, 18.6°, and 20.1°.

iv. FT-Raman Spectrum for the tBME S2 Crystalline Solvate

Figure 32:
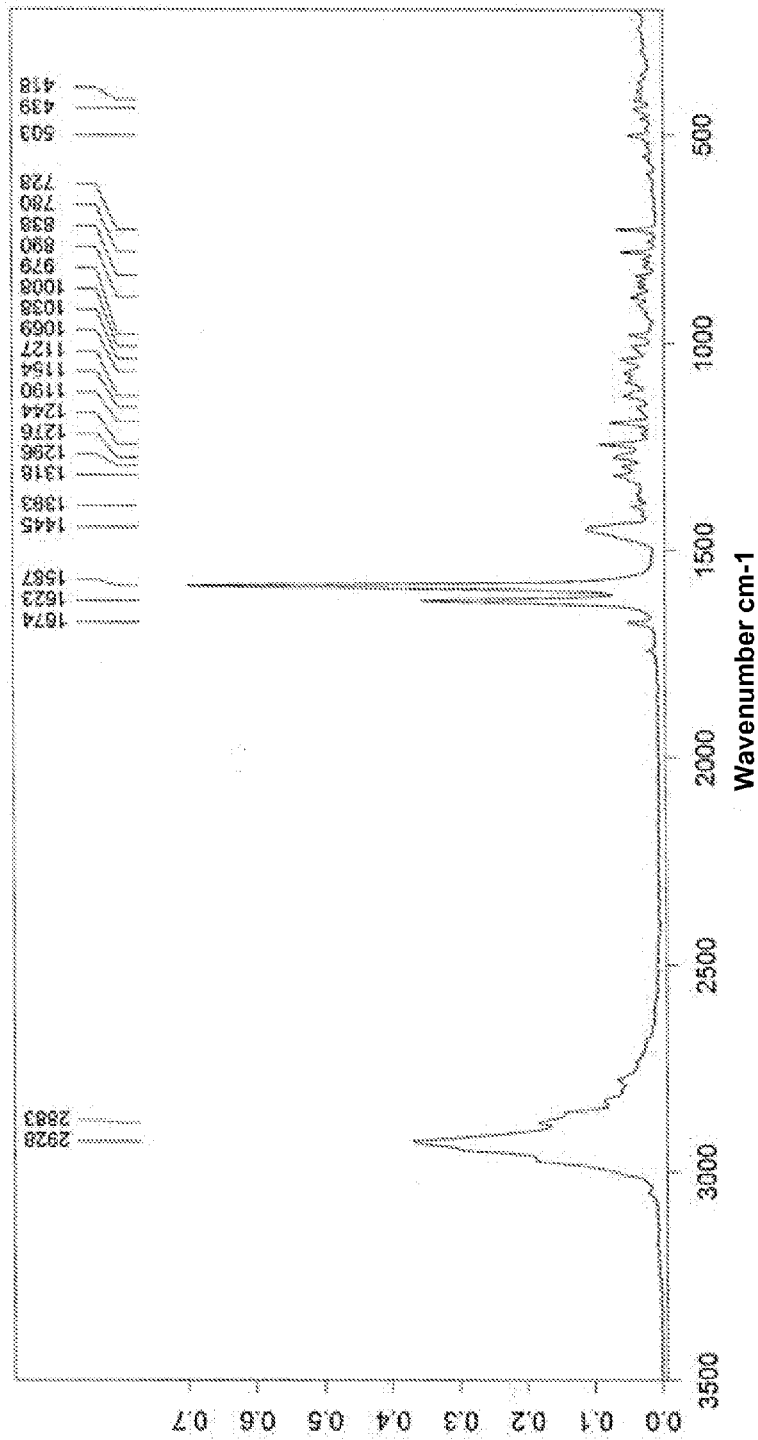
FIG. 32 shows an illustrative FT-Raman spectrum for a tBME S2 crystalline solvate sample of 20,23-dipiperidinyl-5-O-mycaminosyl-tylonolide.

The observed FT-Raman spectrum for the tBME S2 crystalline solvate is shown in FIG. 32, and the corresponding data is shown in the following Table 18:

TABLE 18

FT-Raman Data for the tBME S2 Crystalline Solvate

| Position ($cm^{-1}$) | Intensity |
|---|---|
| 2928 | 0.369 |
| 2883 | 0.184 |
| 1674 | 0.049 |
| 1623 | 0.353 |
| 1587 | 0.701 |
| 1445 | 0.108 |
| 1393 | 0.039 |
| 1318 | 0.067 |
| 1296 | 0.056 |
| 1276 | 0.066 |
| 1244 | 0.089 |
| 1190 | 0.073 |
| 1154 | 0.034 |
| 1126 | 0.053 |
| 1069 | 0.051 |
| 1038 | 0.058 |
| 1007 | 0.040 |
| 979 | 0.044 |
| 890 | 0.040 |
| 838 | 0.033 |
| 780 | 0.056 |
| 728 | 0.063 |
| 503 | 0.045 |
| 439 | 0.035 |
| 418 | 0.035 |
| 85 | 0.128 |

Characteristic features of the spectrum include intense peaks at 2928 $cm^{-1}$, 1623 $cm^{-1}$, and 1587 $cm^{-1}$; and smaller, but sharp, peaks at 1674 $cm^{-1}$, 1244 $cm^{-1}$, 1190 $cm^{-1}$, 780 $cm^{-1}$, and 728 $cm^{-1}$.

v. Thermogravimetry for the tBME S2 Crystalline Solvate

Figure 33:
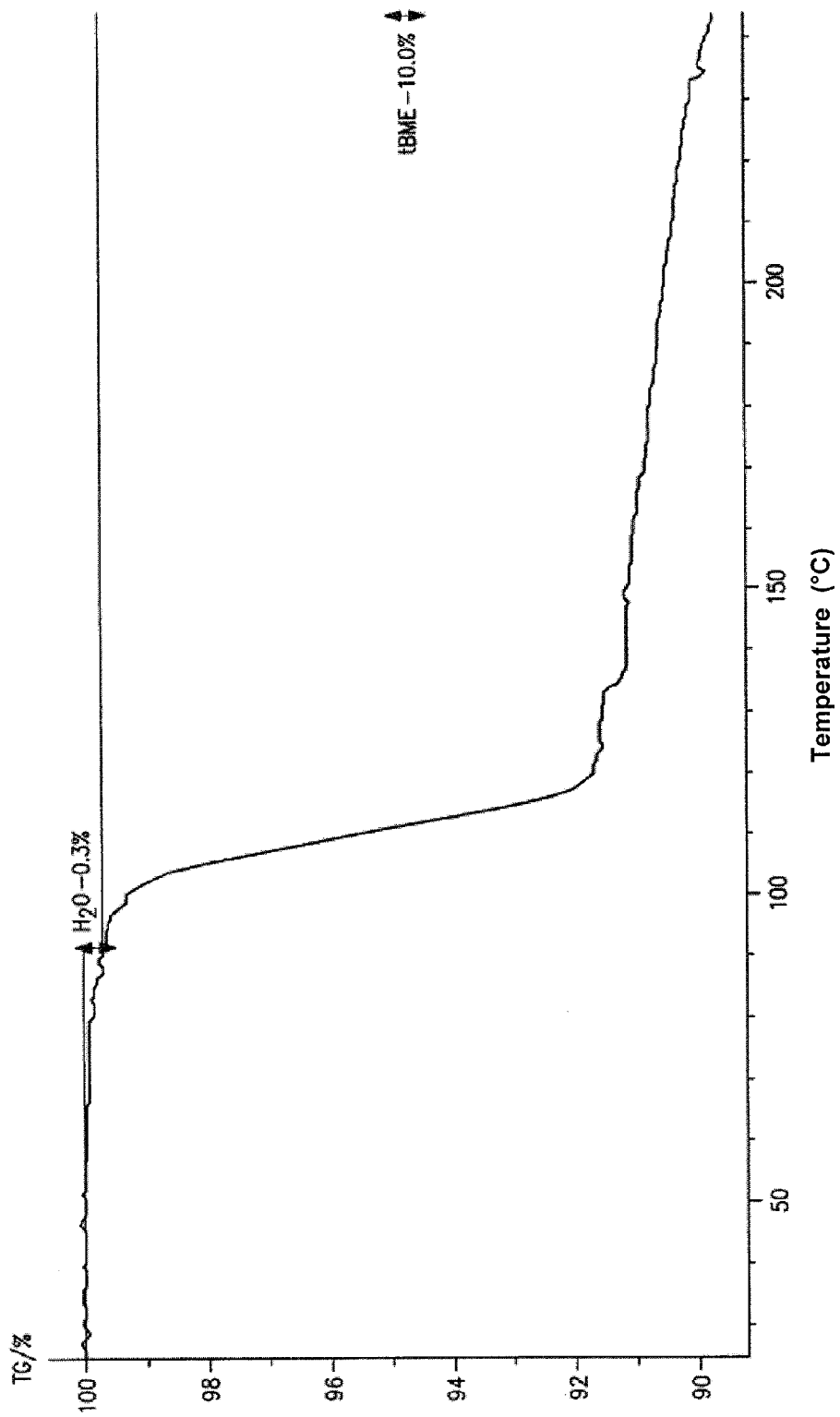
FIG. 33 shows illustrative TG-FTIR results for a tBME S2 crystalline solvate sample of 20,23-dipiperidinyl-5-O-mycaminosyl-tylonolide.

FIG. 33 shows the TG-FTIR results for a sample of the tBME S2 crystalline solvate. A weight loss of from about 8.7-10% occurred due to tBME liberation. This weight loss corresponds to about 0.8-0.9 tBME molecule per molecule of 20,23-dipiperidinyl-5-O-mycaminosyl-tylonolide, assuming essentially pure 20,23-dipiperidinyl-5-O-mycaminosyl-tylonolide. Almost all the weight loss occurs above 90° C., with a sharp step when the temperature increases to greater than 100° C. Thus, the majority of the weight loss occurs at temperatures greater than the boiling point of tBME. The tBME crystalline solvate appears to be more stable than the ethyl acetate S1 crystalline solvate. The stability was confirmed by a desolvation experiment wherein no loss of solvent was observed upon drying under vacuum at both ambient temperature and 70° C.

S3 Crystalline Solvate

The following discussion provides various observed characteristics of the S3 crystalline solvate.

i. Appearance of the THF S3 Crystalline Solvate

The THF S3 crystalline solvate was generally in the form of irregular chunks, and did not exhibit a tendency to break down into fibers, as compared to the S1 crystalline solvate crystals.

ii. Powder X-Ray Diffraction Spectrum for the THF S3 Crystalline Solvate

Figure 34:
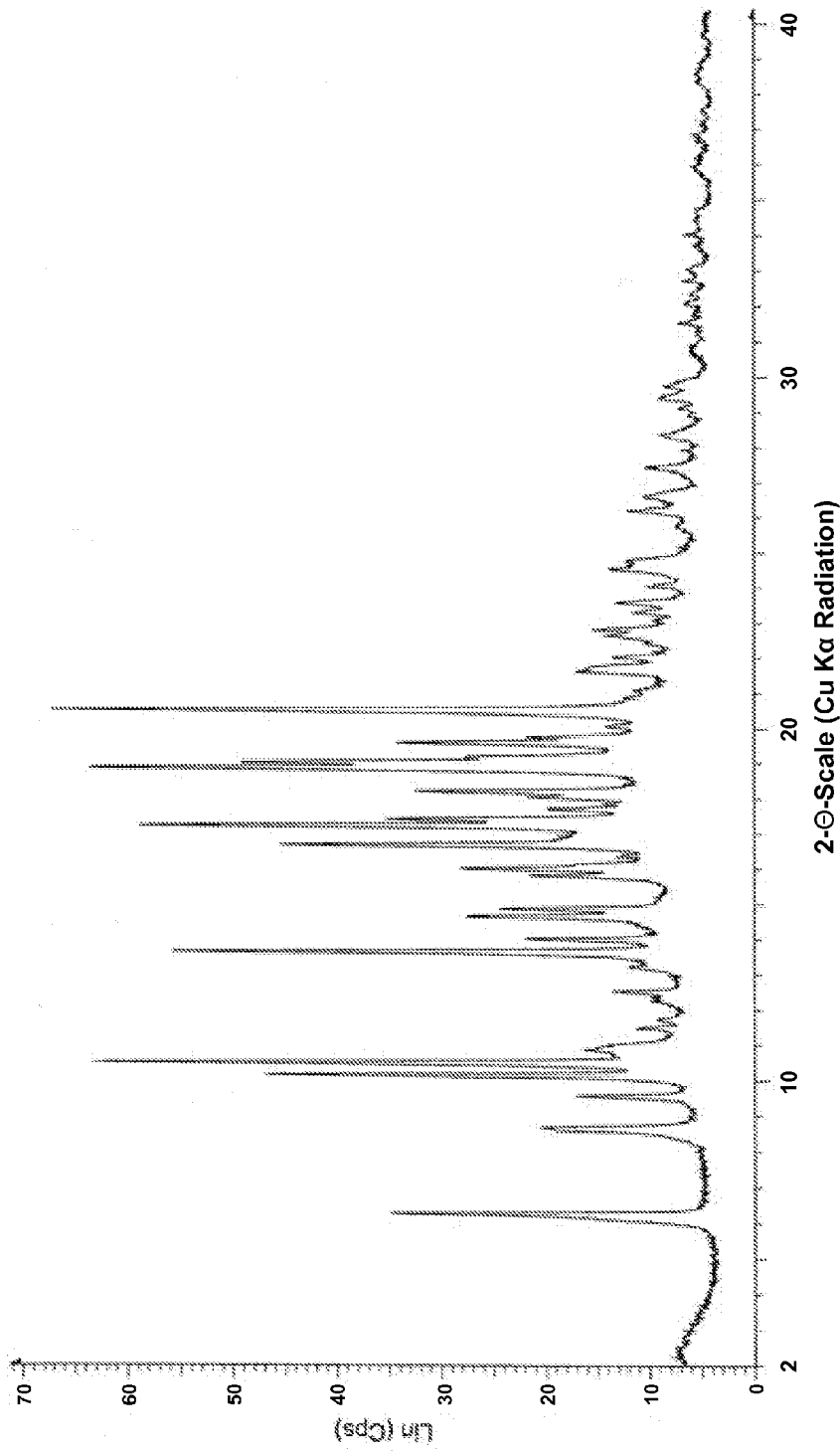
FIG. 34 shows an illustrative PXRD spectrum for a THF S3 crystalline solvate sample of 20,23-dipiperidinyl-5-O-mycaminosyl-tylonolide.

The observed PXRD spectrum for the THF S3 crystalline solvate is shown in FIG. 34, and the corresponding data is shown in the following Table 19:

TABLE 19

X-Ray Diffraction Data for the THF S3 Crystalline Solvate

| Angle (2-Θ degrees) | d Value (Å) | Intensity (cps) | Rel. Intensity (%) |
|---|---|---|---|
| 6.2 | 14.255 | 35 | 52.4 |
| 8.6 | 10.282 | 21 | 30.6 |
| 9.5 | 9.309 | 17 | 25.3 |
| 10.1 | 8.758 | 47 | 69.7 |
| 10.5 | 8.425 | 64 | 94.7 |
| 12.5 | 7.081 | 13 | 20.0 |
| 13.6 | 6.511 | 56 | 82.8 |
| 14.0 | 6.326 | 22 | 32.5 |
| 14.6 | 6.067 | 28 | 41.3 |
| 14.8 | 5.985 | 25 | 36.5 |
| 15.8 | 5.609 | 22 | 32.1 |
| 16.0 | 5.539 | 28 | 41.7 |
| 16.7 | 5.309 | 46 | 67.7 |
| 17.2 | 5.155 | 59 | 88.1 |
| 17.4 | 5.096 | 35 | 52.6 |
| 17.7 | 5.011 | 20 | 29.6 |
| 18.2 | 4.874 | 33 | 48.3 |
| 18.8 | 4.720 | 64 | 94.7 |
| 19.0 | 4.671 | 49 | 73.4 |
| 19.6 | 4.529 | 35 | 51.3 |
| 20.5 | 4.332 | 67 | 100.0 |
| 21.6 | 4.114 | 17 | 25.4 |
| 22.8 | 3.900 | 16 | 23.1 |
| 23.6 | 3.770 | 13 | 19.6 |
| 24.5 | 3.633 | 14 | 20.6 |
| 26.2 | 3.401 | 12 | 17.8 |
| 27.4 | 3.255 | 10 | 15.4 |

Characteristic features of the spectrum include several peaks with similar intensity at 2Θ=6.2°, 10.1°, 10.5°, 13.6°, 16.7°, 17.2°, 18.8°, and 20.5°.

iii. FT-Raman Spectrum for the THF S3 Crystalline Solvate

Figure 35:
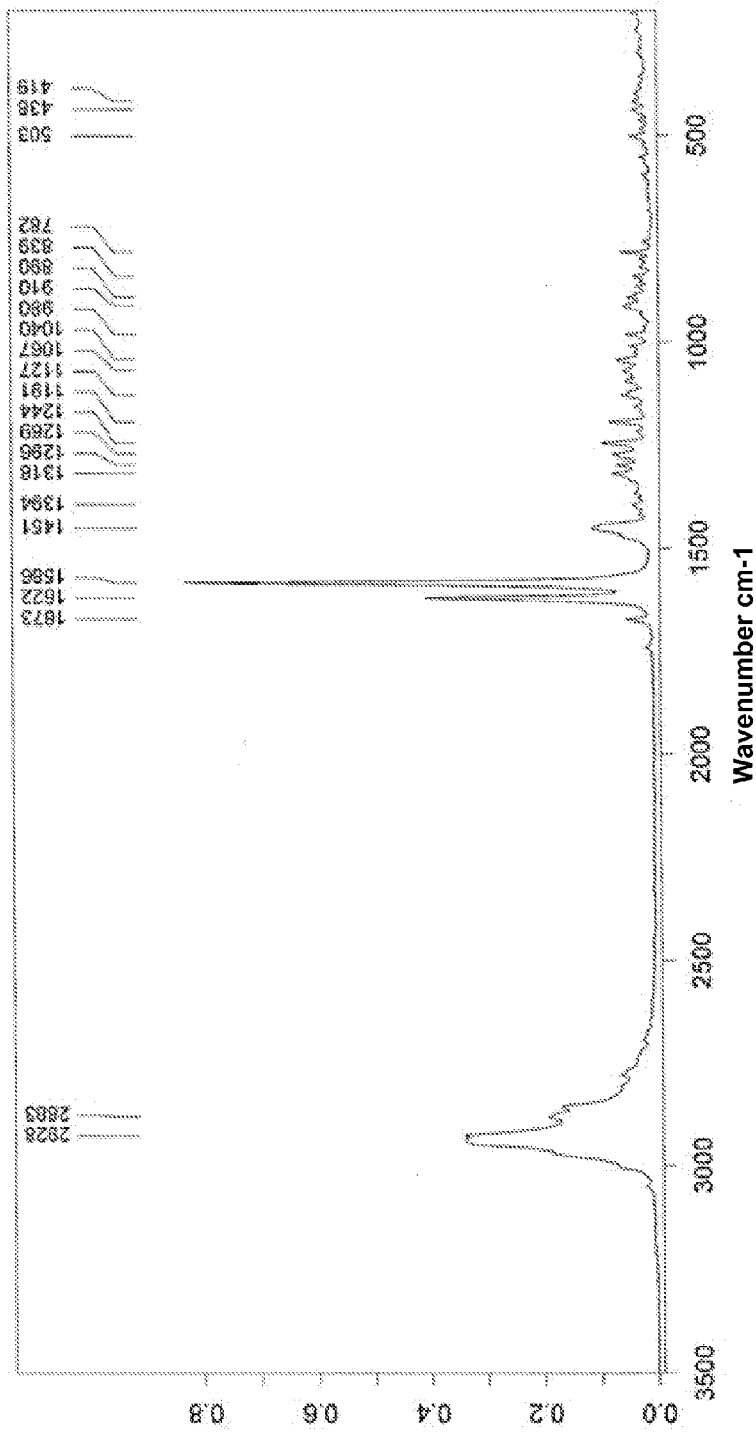
FIG. 35 shows an illustrative FT-Raman spectrum for a THF S3 crystalline solvate sample of 20,23-dipiperidinyl-5-O-mycaminosyl-tylonolide.

The observed FT-Raman spectrum for the THF S3 crystalline solvate is shown in FIG. 35, and the corresponding data is shown in the following Table 20

TABLE 20

FT-Raman Data for the THF S3 Crystalline Solvate

| Position (cm$^{-1}$) | Intensity |
|---|---|
| 2928 | 0.340 |
| 2883 | 0.192 |
| 1673 | 0.051 |
| 1622 | 0.405 |
| 1586 | 0.828 |
| 1451 | 0.111 |
| 1394 | 0.039 |
| 1318 | 0.074 |
| 1296 | 0.066 |
| 1269 | 0.073 |
| 1244 | 0.092 |
| 1191 | 0.080 |
| 1127 | 0.057 |
| 1067 | 0.052 |
| 1040 | 0.066 |
| 980 | 0.051 |
| 910 | 0.052 |
| 890 | 0.045 |
| 839 | 0.036 |
| 782 | 0.057 |
| 503 | 0.041 |
| 438 | 0.037 |
| 419 | 0.036 |
| 100 | 0.138 |

Characteristic features of the spectrum include intense peaks at 2928 cm$^{-1}$, 1622 cm$^{-1}$, and 1586 cm$^{-1}$; and smaller, but sharp, peaks at 1673 cm$^{-1}$, 1244 cm$^{-1}$, 1191 cm$^{-1}$, and 782 cm$^{-1}$.

iv. Thermogravimetry for the THF S3 Crystalline Solvate

Figure 36:
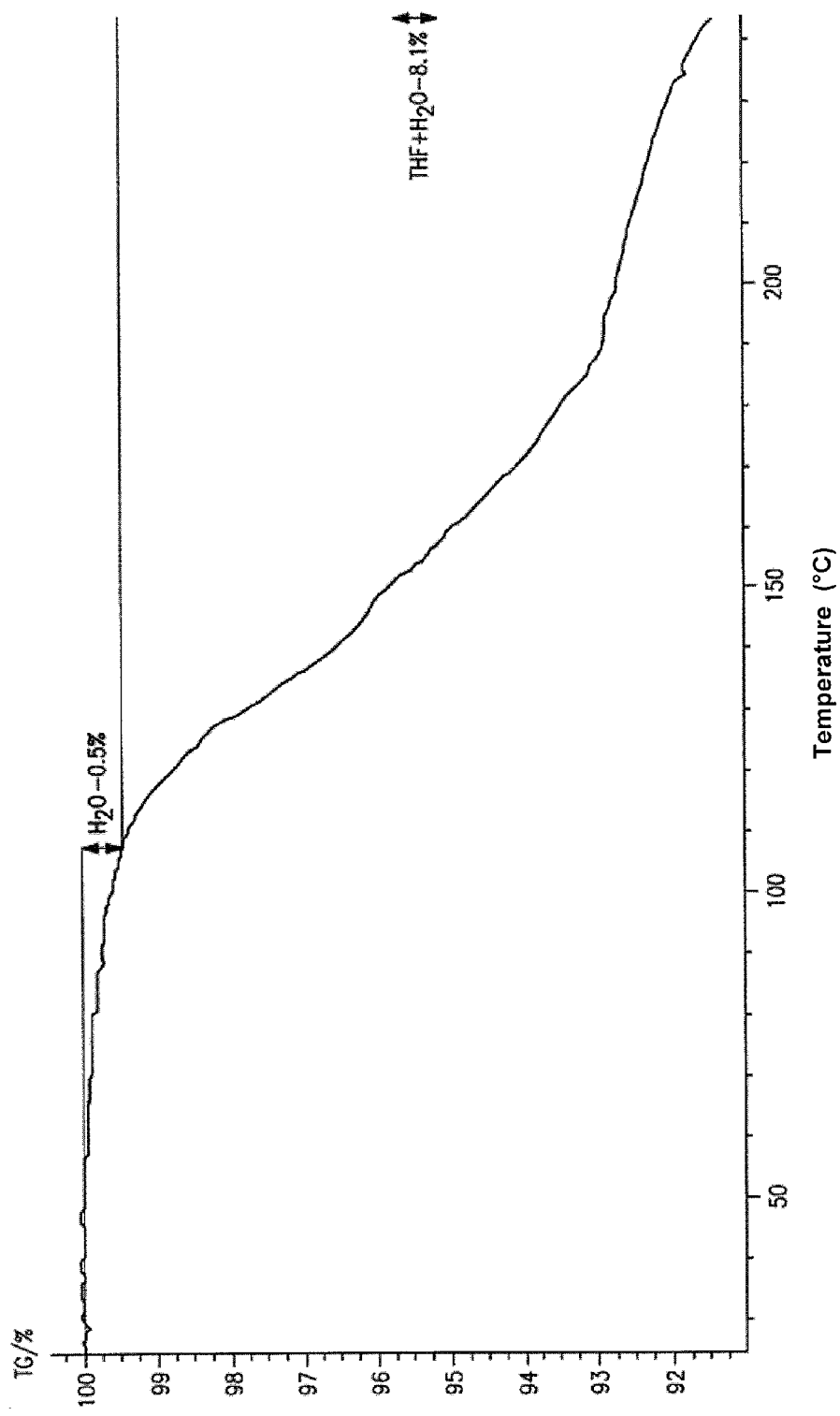
FIG. 36 shows illustrative TG-FTIR results for a THF S3 crystalline solvate sample of 20,23-dipiperidinyl-5-O-mycaminosyl-tylonolide.

FIG. 36 shows the TG-FTIR results for the THF S3 crystalline solvate. The majority of the weight loss occurred at temperatures that are greater than the boiling point of THF. Specifically, less than 10% of the weight loss occurred at from 60 to 100° C., whereas approximately 80% of the loss occurred at from 110 to 180° C. The results show a weight loss of about 8.1% occurring at temperatures greater than 100° C. due to liberation of THF. This corresponds to about 0.8 THF molecules per molecule of 20,23-dipiperidinyl-5-O-mycaminosyl-tylonolide, assuming essentially pure 20,23-dipiperidinyl-5-O-mycaminosyl-tylonolide.

S4 Crystalline Solvate

The following discussion provides various observed characteristics of the S4 crystalline solvate. Although the PXRD and FT-Raman data below correspond to the methyl acetate S4 crystalline solvate, this data is generally applicable to characterizing the ethyl formate crystalline solvate as well because it is isomorphic with the methyl acetate crystalline solvate.

i. Appearance of the Methyl Acetate S4 Crystalline Solvate

Figure 37:
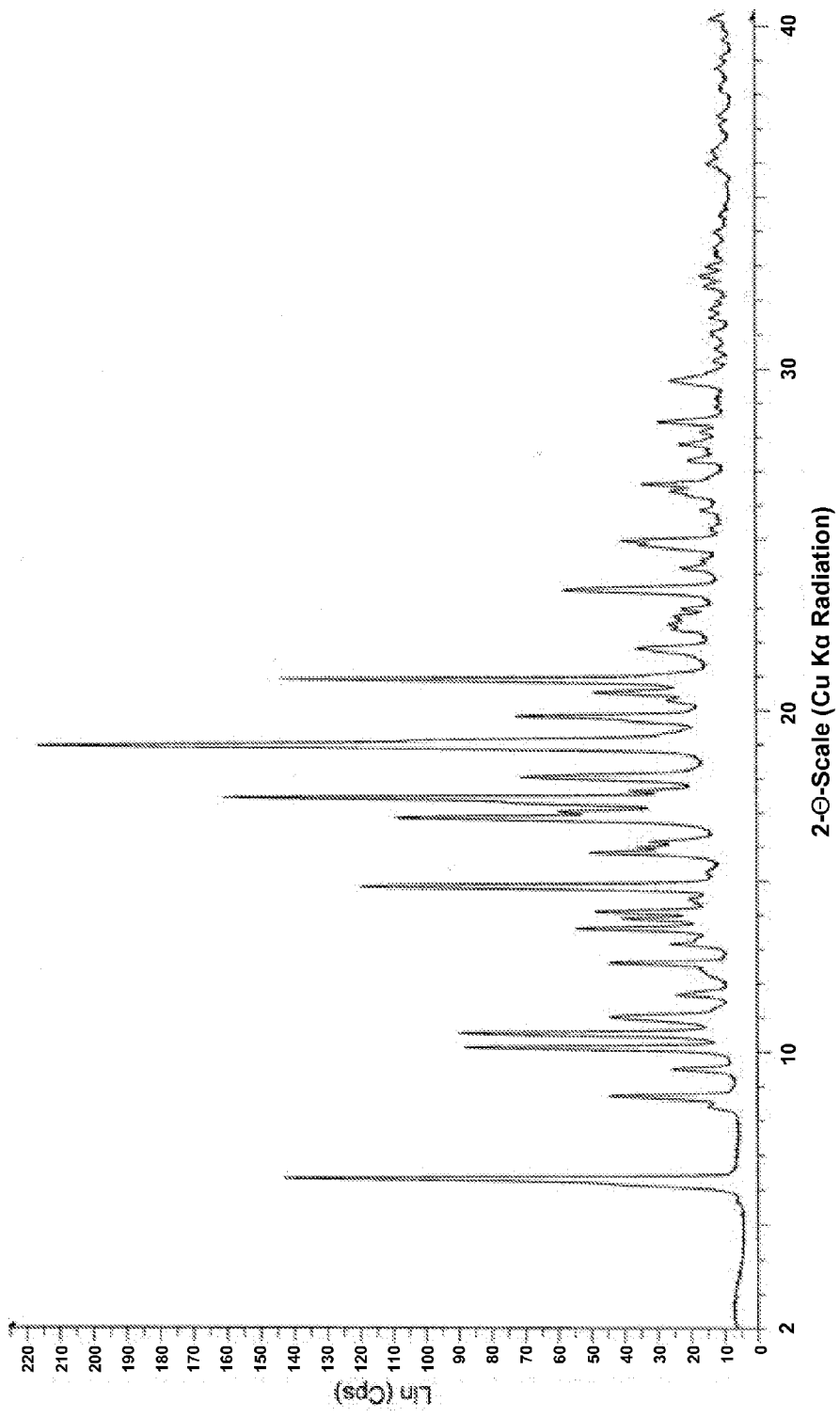
FIG. 37 shows an illustrative PXRD spectrum for a methyl acetate S4 crystalline solvate sample of 20,23-dipiperidinyl-5-O-mycaminosyl-tylonolide.

The methyl acetate S4 crystalline solvate contained some well-developed prismatic crystals. The crystals did not exhibit a tendency to break down into fibers, as compared to the S1 solvate crystals.

ii. Powder X-Ray Diffraction Spectrum for the Methyl Acetate S4 Crystalline Solvate The observed PXRD spectrum for the methyl acetate S4 crystalline solvate is shown in FIG. 37, and the corresponding data is shown in the following Table 21:

TABLE 21

X-Ray Diffraction Data for the Methyl Acetate S4 Crystalline Solvate

| Angle (2-Θ degrees) | d Value (Å) | Intensity (cps) | Rel. Intensity (%) |
|---|---|---|---|
| 6.3 | 14.029 | 144 | 66.5 |
| 8.7 | 10.164 | 44 | 20.3 |
| 9.5 | 9.309 | 25 | 11.7 |
| 10.1 | 8.758 | 88 | 40.6 |
| 10.5 | 8.425 | 90 | 41.3 |
| 11.0 | 8.043 | 44 | 20.2 |
| 11.7 | 7.563 | 24 | 11.2 |
| 12.6 | 7.025 | 44 | 20.3 |
| 13.1 | 6.758 | 26 | 11.9 |
| 13.6 | 6.511 | 54 | 25.1 |
| 13.9 | 6.371 | 40 | 18.5 |
| 14.1 | 6.281 | 49 | 22.4 |
| 14.8 | 5.985 | 120 | 55.3 |
| 15.8 | 5.609 | 50 | 23.2 |
| 16.8 | 5.277 | 109 | 50.1 |
| 17.4 | 5.096 | 161 | 74.0 |
| 18.0 | 4.928 | 71 | 32.7 |
| 18.9 | 4.695 | 217 | 100.0 |
| 19.8 | 4.484 | 73 | 33.4 |
| 20.5 | 4.332 | 49 | 22.6 |

TABLE 21-continued

X-Ray Diffraction Data for the Methyl Acetate S4 Crystalline Solvate

| Angle (2-Θ degrees) | d Value (Å) | Intensity (cps) | Rel. Intensity (%) |
|---|---|---|---|
| 20.9 | 4.250 | 145 | 66.6 |
| 21.8 | 4.077 | 36 | 16.6 |
| 22.5 | 3.952 | 26 | 12.0 |
| 23.5 | 3.786 | 58 | 26.8 |
| 24.2 | 3.678 | 23 | 10.4 |
| 25.0 | 3.562 | 41 | 18.8 |
| 26.6 | 3.351 | 34 | 15.7 |
| 27.8 | 3.209 | 23 | 10.4 |
| 28.5 | 3.132 | 29 | 13.4 |
| 29.7 | 3.008 | 25 | 11.7 |
| 32.7 | 2.739 | 17 | 7.7 |

Characteristic features of the spectrum include several peaks with similar intensity at 2Θ=6.3°, 10.1°, 10.5°, 14.8°, 16.8°, 17.4°, 18.9°, and 20.9°.

iii. FT-Raman Spectrum for the Methyl Acetate S4 Crystalline Solvate

Figure 38:
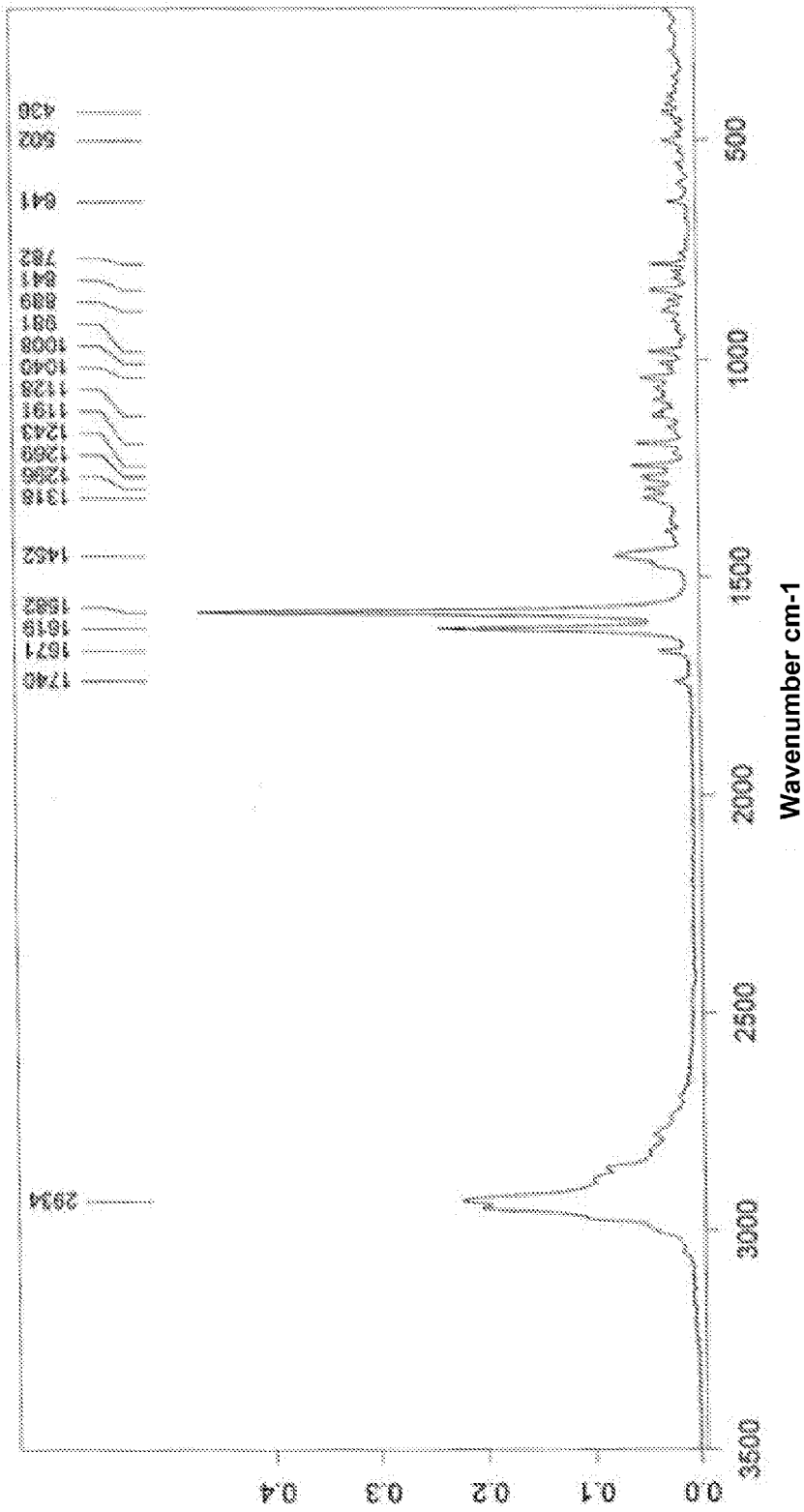
FIG. 38 shows an illustrative FT-Raman spectrum for a methyl acetate S4 crystalline solvate sample of 20,23-dipiperidinyl-5-O-mycaminosyl-tylonolide.

The observed FT-Raman spectrum for the methyl acetate S4 crystalline solvate is shown in FIG. 38, and the corresponding data is shown in the following Table 22:

TABLE 22

FT-Raman Data for the Methyl Acetate S4 Crystalline Solvate

| Position (cm$^{-1}$) | Intensity |
|---|---|
| 2949 | 0.205 |
| 2934 | 0.223 |
| 1740 | 0.019 |
| 1671 | 0.034 |
| 1619 | 0.242 |
| 1581 | 0.468 |
| 1452 | 0.075 |
| 1394 | 0.027 |
| 1318 | 0.047 |
| 1296 | 0.045 |
| 1269 | 0.048 |
| 1243 | 0.058 |
| 1191 | 0.054 |
| 1155 | 0.024 |
| 1128 | 0.038 |
| 1091 | 0.037 |
| 1040 | 0.048 |
| 1008 | 0.031 |
| 981 | 0.041 |
| 889 | 0.028 |
| 864 | 0.023 |
| 841 | 0.039 |
| 815 | 0.017 |
| 782 | 0.039 |
| 641 | 0.021 |
| 502 | 0.026 |
| 436 | 0.027 |
| 419 | 0.024 |
| 92 | 0.100 |

Characteristic features of the spectrum include intense peaks at 2949 cm$^{-1}$, 2934 cm$^{-1}$, 1619-1621 cm$^{-1}$, and 1581-1584 cm$^{-1}$; and smaller, but sharp, peaks at 1671 cm$^{-1}$, 1243 cm$^{-1}$, 1191 cm$^{-1}$, 981 cm$^{-1}$, and 782 cm$^-$.

iv. Thermogravimetry for S4 Crystalline Solvates

Figure 39:
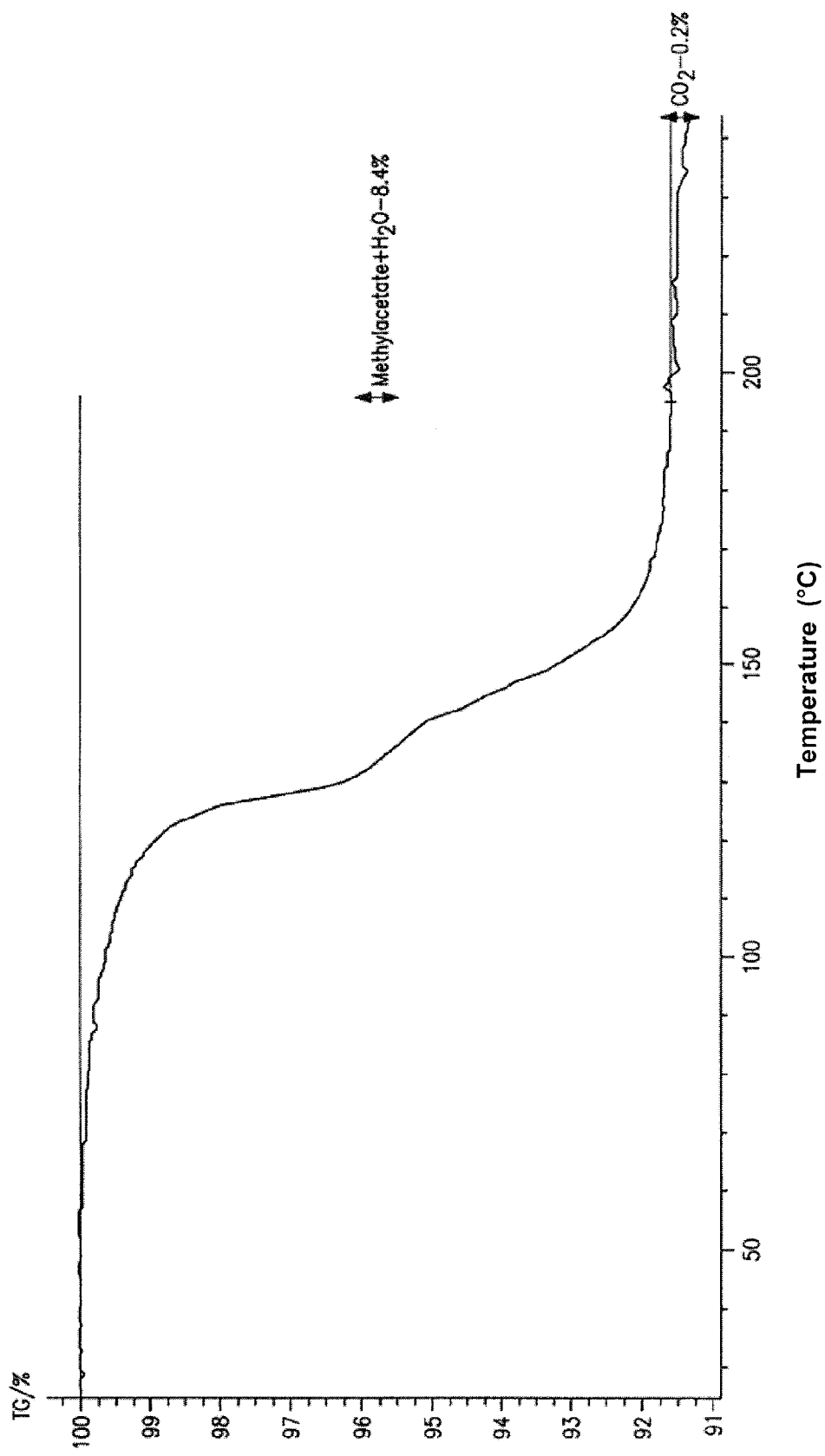
FIG. 39 shows illustrative TG-FTIR results for an methyl acetate S4 crystalline solvate sample of 20,23-dipiperidinyl-5-O-mycaminosyl-tylonolide.
Figure 40:
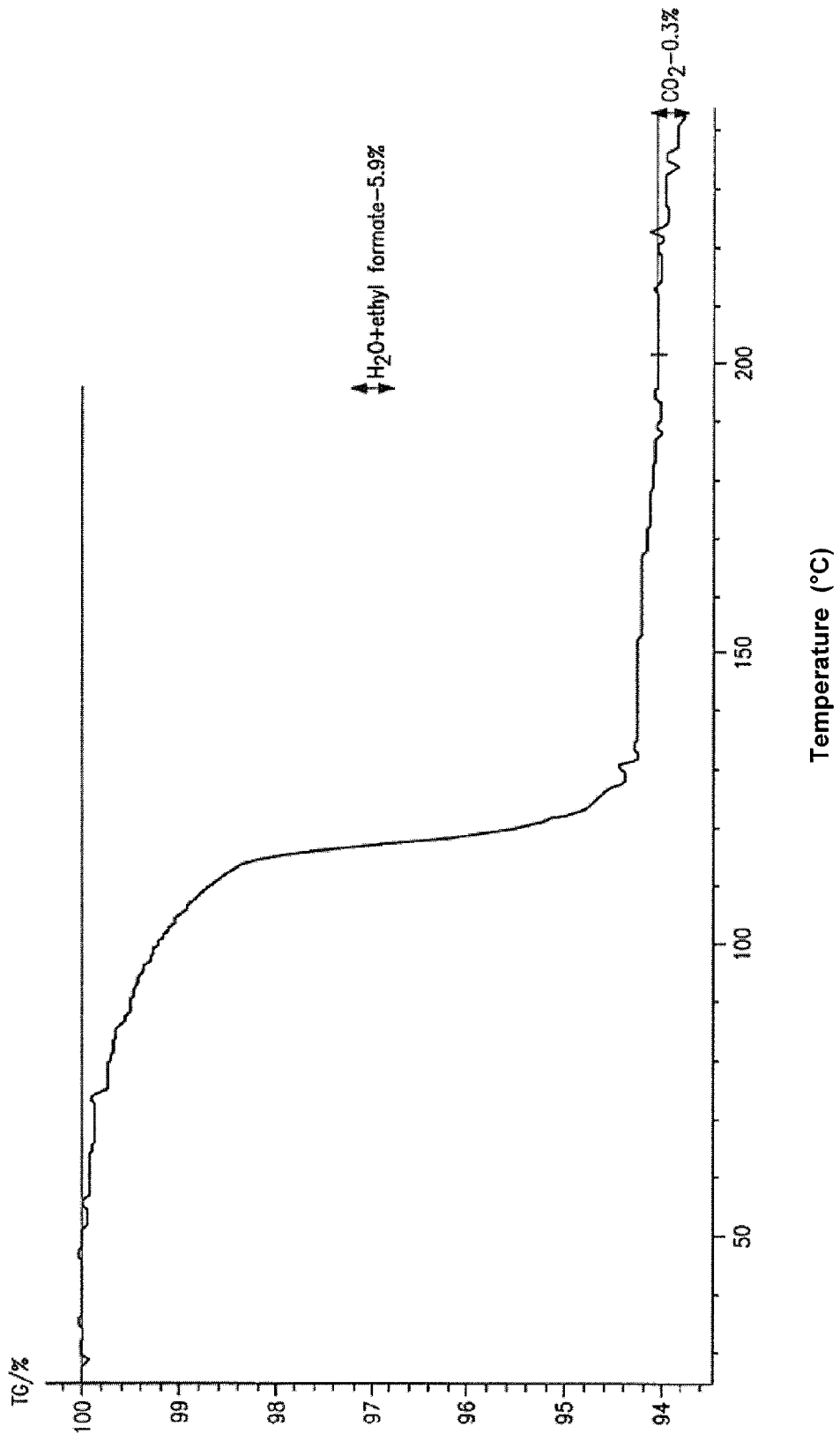
FIG. 40 shows illustrative TG-FTIR results for an ethyl formate S4 crystalline solvate sample of 20,23-dipiperidinyl-5-O-mycaminosyl-tylonolide.

FIGS. 39 and 40 show the TG-FTIR results for the methyl acetate and ethyl formate S4 crystalline solvates, respectively. These results confirm the existence of the crystalline solvates. For the methyl acetate crystalline solvate, there was a weight loss of about 8.4% due to liberation of methyl acetate. And for the ethyl formate crystalline solvate, there was a weight loss of about 7.7%. Based on the observed results, it is estimated that the methyl acetate crystalline solvate has a about 0.9 methyl acetate molecules per 20,23-dipiperidinyl-5-O-mycaminosyl-tylonolide molecule, and the ethyl formate crystalline solvate has from about 0.6 to about 0.8 ethyl formate molecules per 20,23-dipiperidinyl-5-O-mycaminosyl-tylonolide molecule. Both these estimates assume essentially pure 20,23-dipiperidinyl-5-O-mycaminosyl-tylonolide. Less than 10% of the weight loss occurred at from 70 to 110° C. for the methyl acetate crystalline solvate, and from 60 to 90° C. for the ethyl formate crystalline solvate. For both crystalline solvates, the desolvation proceeded quickly. The desolvation was nearly completed at 160° C. for the methyl acetate crystalline solvate, and 130° C. for the ethyl formate crystalline solvate.

E. Preparation of Medicaments and Methods of Treatment Using Macrolides

The macrolides described above (including macrolides prepared by the process described above, as well as the various crystalline forms of 20,23-dipiperidinyl-5-O-mycaminosyl-tylonolide described above) may be used, e.g., to treat pasteurellosis in animals, particularly livestock and poultry. In some embodiments, such a macrolide(s) is used to treat bovine animals having bovine respiratory disease (BRD) associated with *Mannheimia haemolytica*, *Pasteurella multocida* and *Histophilus somni*. In other embodiments, such a macrolide(s) is used to treat swine animals having swine respiratory disease associated with *Actinobacillus pleuropneumoniae*, *Pasteurella multocida*, and *Bordetella bronchiseptica*.

In general, a therapeutically-effective amount of one or more of such macrolides is administered to the recipient animal. As used in this disclosure, the term "therapeutically effective amount" constitutes an amount that is sufficient to prevent, reduce the risk of, delay the onset of, ameliorate, suppress, or eradicate a target pathogen(s) infection. Generally, the therapeutically effective amount is defined as the amount necessary to achieve a concentration efficacious to control the target pathogen(s) at the site of infection (or, when used to prevent, reduce the risk of, or delay the onset of infection, at a site susceptible to infection). The concentration at the site of infection (or at a site susceptible to infection) is preferably at least equal to the MIC$_{90}$ level (minimum inhibitory concentration, i.e., the concentration that inhibits the growth of 90% of the target pathogen) of the macrolide for the target pathogen. Such an amount may be administered to the animal recipient in two or more separate doses, although preferably is administered in a single dose. To the extent the macrolide(s) is administered with another active ingredient(s), the term "therapeutically effective amount" refers to the total amounts of macrolide and other active ingredient(s) that are together sufficient to prevent, reduce the risk of, delay the onset of, ameliorate, suppress, or eradicate a target pathogen(s) infection.

Factors affecting the preferred dosage regimen include the type (e.g., species and breed), age, weight, sex, diet, activity, and condition of the animal recipient; the severity of the pathological condition; the apparatus used to administer the composition, as well as the type of administration used; pharmacological considerations, such as the activity, efficacy, pharmacokinetic, and toxicology profiles of the particular composition administered; the existence of an additional active ingredient(s) in the composition; and whether the composition is being administered as part of a drug and/or vaccine combination. Thus, the dosage actually employed can vary for specific animal patients, and, therefore, can deviate from the typical dosages set forth above. Determining such dosage adjustments is generally within the skill of those in the art using conventional means.

In general, the macrolide(s) may be administered once to an animal, although it is contemplated that it may instead be administered multiple times.

For cattle, the total amount of administered macrolide(s) is typically from about 0.1 to about 40 mg per kg body weight, and more typically from about 1 to about 10 mg per kg body weight. For example, in some embodiments, the amount administered to cattle is about 4 mg per kg body weight. Although the macrolide(s) may be given to cattle at any age, in some embodiments, the macrolide(s) is administered to cattle that are from about 1 months to about 1.5 years old, or from about 6 months to about 1 year old. In some embodiments, the macrolide(s) is administered to weaned calves entering the feedlots (often at about 6 months old). In still other embodiments, the cattle are calves at from about 2 to about 12 weeks old, and the macrolide(s) is administered for prophylaxis at a dosage of from about 1 to about 10 mg per kg of the body weight; or for treating an existing infection at a dosage of from about 2 to about 20 mg per kg of the body weight.

For swine, the total amount of administered macrolide(s) is typically from about 0.1 to about 50 mg per kg body weight, and more typically from about 1 to about 10 mg per kg body weight. For example, in some embodiments, the amount administered to swine is about 4 mg per kg body weight. In other embodiments, the amount administered to swine is about 5 mg per kg body weight. Although the macrolide(s) may be given to swine at any age, in some embodiments, the macrolide(s) is administered to grower-finisher pigs.

The method of administration can be varied depending on animals, but in the case of large mammals such as cattle, swine, and horses, it is preferably administered orally or parenterally. "Parenteral administration" includes, e.g., subcutaneous injections, intravenous injections, intramuscular injections, intrasternal injections, submucosal injections, and infusion. In some embodiments, e.g., the animal recipient is a bovine animal, and the macrolide composition is administered subcutaneously, such as in the neck. In other embodiments, e.g., the animal recipient is a swine animal, and the macrolide composition is administered intramuscularly.

The macrolide(s) may be used to form a pharmaceutical composition (or "medicament"). It is contemplated that such a composition may entirely comprise one or more macrolides. Normally, however, the composition comprises other ingredients as well.

Other ingredients in the composition may comprise, e.g., other active ingredients. Alternatively (or in addition), such other ingredients may comprise one or more pharmaceutically acceptable carriers, vehicles, and/or adjuvants (collectively referred to as "excipients"). The selection of such excipients will depend on various factors, such as the mode of administration; the apparatus used to administer the composition; pharmacological considerations, such as the activity, efficacy, pharmacokinetic, and toxicology profiles of the particular composition; the existence of an additional active ingredient(s) in the composition; and whether the composition is being administered as part of a drug and/or vaccine combination.

Solid macrolide compositions may comprise, e.g., saccharides such as lactose, glucose, and sucrose; starches, such as corn starch and potato starch; cellulose derivatives, such as carboxymethylcellulose sodium, ethylcellulose, and cellulose acetate; etc.

Liquid macrolide compositions may comprise for example, water, isotonic physiological saline, Ringer's solution, ethyl alcohol, and/or phosphate buffer solution may be present. Such compositions also may comprise oils, such as peanut oil, cotton seed oil, safflower oil, sesame oil, olive oil, corn oil and soybean oil and/or polyhydric alcohols such as glycerol, propylene glycol, sorbitol, mannitol, polyethylene glycol, and poly(ethylene glycol-2-propylene glycol-2-polyethylene glycol). It also, e.g., may be desirable in some instances for the composition to comprise one or more preservatives. The presence of a preservative may, e.g., provide a benefit for compositions or solvents that may be stored over lengthy periods of time, e.g., days, weeks, months, or years. When selecting a suitable preservative, factors to consider include, e.g., its antimicrobial activity; the pH range at which it has the desired antimicrobial activity; the minimum concentration at which it has the desired antimicrobial activity; its aqueous solubility and other physical characteristics (e.g., potential to cause foaming); its suitability for parenteral use; its possible interactions with the active ingredient(s) (e.g., its effect on the solubility of an active ingredient); its possible interactions with the non-active ingredients (e.g., its effect on the stability of the solvent); and any government regulations that may be applicable where the composition or solvent is being manufactured, sold, or used. Contemplated preservatives include, e.g., parabens, propylene glycol, benzalkonium chloride, phenylethanol, chlorocresol, metacresol, ethanol, phenoxyethanol, and benzyl alcohol.

Further discussion regarding pharmaceutically acceptable excipients that may be suitable for the macrolide composition may be found in, e.g., "Gennaro, Remington: The Science and Practice of Pharmacy" (20th Edition, 2000) (incorporated by reference herein). To illustrate, other suitable excipients may include, e.g., coloring agents; flavoring agents; and thickening agents, such as povidone carboxymethylcellulose, and/or hydroxypropyl methylcellulose.

Normally, the macrolide(s) occupies at least about 0.5% by weight of the pharmaceutical composition. For example, in some embodiments for swine use, suitable macrolide concentrations for parenteral administration may be, e.g., from about 5 to about 500 mg/ml, from about 10 to about 100 mg/ml, or from about 20 to about 60 mg/ml (e.g., about 40 mg/ml). Exemplifying further, in some embodiments for bovine use, suitable macrolide concentrations for parenteral administration may be, e.g., from about 5 mg/ml to about 2.0 g/ml, from about 10 mg/ml to about 1.0 g/ml, 50 to about 500 mg/ml, or from about 100 to about 300 mg/ml (e.g., 180 mg/ml).

It should be recognized that the macrolide concentration can be varied depending on the dosage form. Where, e.g., the macrolide(s) is administered parenterally, the macrolide concentration preferably is sufficient to provide the desired therapeutically effective amount of the macrolide(s) in a volume that is acceptable for parenteral administration. The maximum acceptable volume may vary, depending on, e.g., the apparatus being used for the administration, type of parenteral administration, size of the recipient animal, and subjective desires of the user.

In some embodiments, the pharmaceutical composition comprises a liquid composition formed by a process comprising dissolving the macrolide(s) in the excipient(s). In other embodiments, the composition comprises a suspension formed by a process comprising suspending the macrolide(s) in the excipient(s).

Further discussion relating to the use of 20,23-dipiperidinyl-5-O-mycaminosyl-tylonolide and derivatives thereof to treat livestock and poultry disease may be found in, e.g., U.S. Pat. No. 6,514,946.

This disclosure is also directed to kits that are, e.g., suitable for use in performing the methods of treatment described above. In some embodiments, the kit comprises a therapeutically effective amount of at least one of the above-described crystalline forms of 20,23-dipiperidinyl-5-O-mycaminosyl-tylonolide (e.g., a therapeutically effective amount of the Form I polymorph), and instructions for combining the crystalline form with at least one excipient, such as, e.g., instructions for dissolving or suspending the crystalline form in a liquid excipient. The kit may further (or alternatively) comprise additional components, such as, e.g., one or more apparatuses (e.g., a syringe) for administering a composition comprising (or derived from) the crystalline form(s) of 20,23-dipiperidinyl-5-O-mycaminosyl-tylonolide, one or more additional pharmaceutical or biological materials, one or more excipients, and/or one or more diagnostic tools.

EXAMPLES

The following examples are merely illustrative of embodiments of the invention, and not limiting to the remainder of this disclosure in any way.

Example 1

Preparation of 20,23-dipiperidinyl-5-O-mycaminosyl-tylonolide from tylosin A

-continued
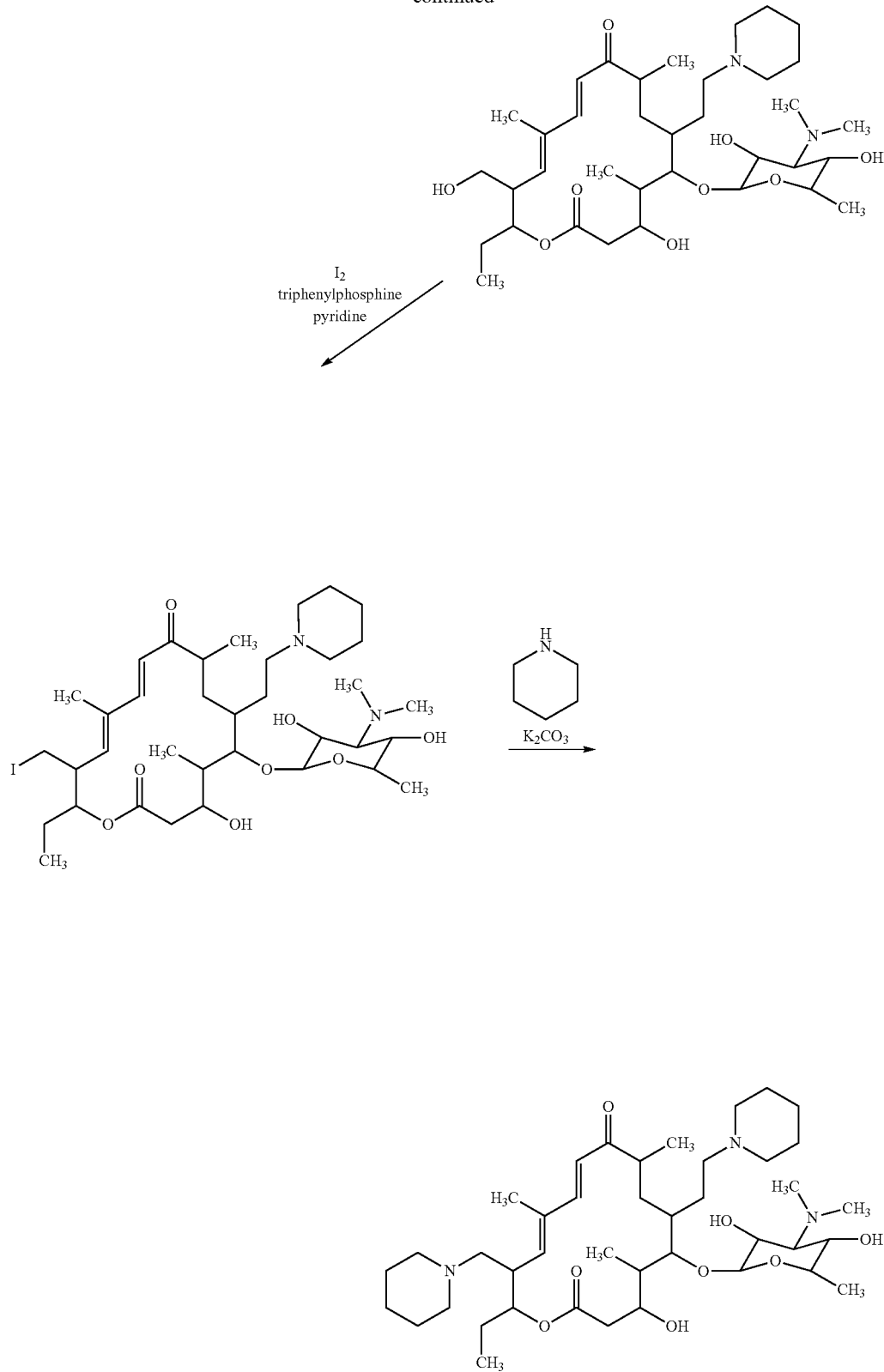
Part A. Reductive amination. Preparation of 23-O-Mycinosyl-20-Piperidinyl-5-O-Mycaminosyl-Tylonolide Compound (2).

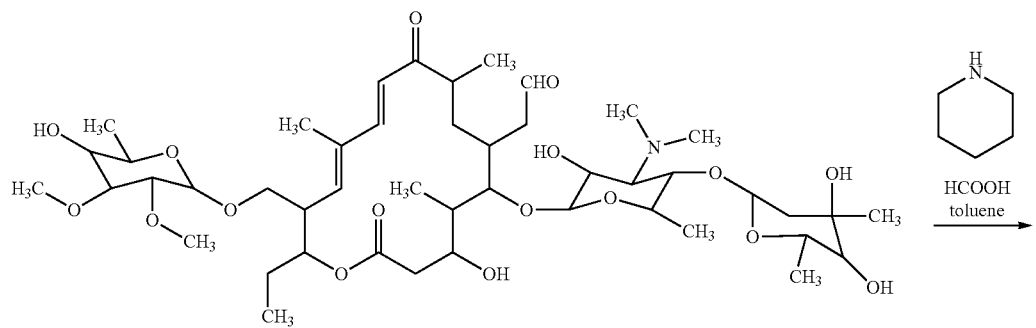

(1)

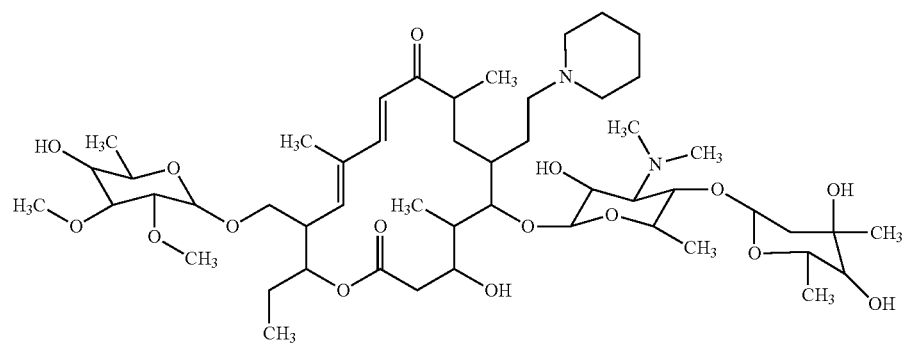

(2)

Toluene (19.2 kg), tylosin A (1) (3.68 kg; ≧80% tylosin A; ≧95% tylosin A, B, C, & D), piperidine (0.40 kg), and formic acid (0.55 kg) were charged to a reactor. The mixture was heated to 70-80° C., while being stirred. Stirring was then continued at that temperature for 1-2 more hours. The formation of the 20-piperidinyl-tylosin compound (2) was monitored by HPLC. After reaction completion (≦2% tylosin A (1)), the product mixture was cooled to ambient temperature.

Part B. Acid hydrolysis of mycarosyloxy substituent. Preparation of 23-O-mycinosyl-20-piperidinyl-5-O-mycaminosyl-tylonolide compound (3).

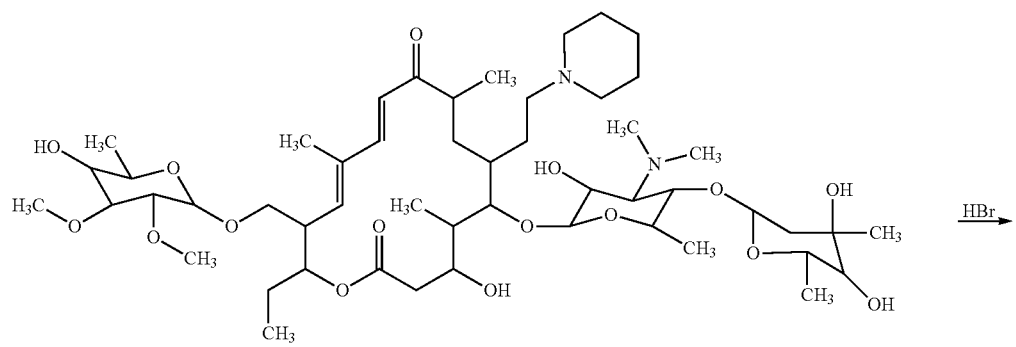

(2)

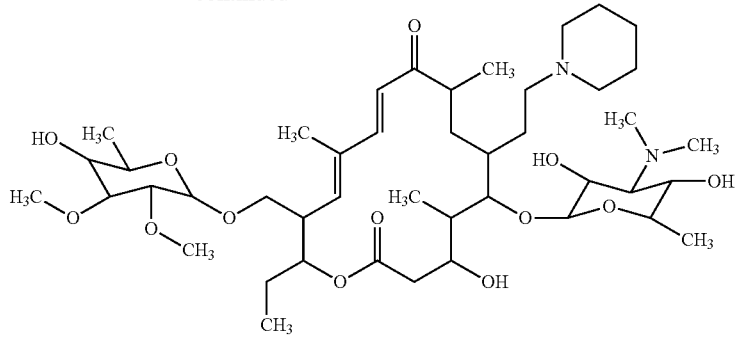

(3)

HBr (48% HBr diluted to 24%) was added to the product mixture of Part A while stirring and maintaining the mixture at less than 40° C. Afterward, the phases in the product mixture were separated using a 20-minute phase separation period. The product mixture was at 20-25° C. during this phase separation. HPLC of the lower phase was used to confirm reaction completion (≦2% 20-piperidinyl-tylosin compound (2)).

Part C. Acid hydrolysis of mycinosyloxy substituent. Preparation of 23-Hydroxyl-20-Piperidinyl-5-O-Mycaminosyl-Tylonolide (4).

Twenty-four percent HBr (18.4 L) was added at ambient temperature to the aqueous phase obtained from Part B, followed by heating to 54±3° C. within about 1 hour while stirring. Stirring was continued at this temperature for 2-4 more hours, while the reaction was monitored using HPLC. After completion of the reaction (≦2% 23-O-mycinosyl-20-piperidinyl-5-O-mycaminosyl-tylonolide compound (3)), the mixture was cooled to ambient temperature using a −10° C. cooling jacket. After cooling, the mixture was extracted with dichloromethane three times (9.8 kg each time). The aqueous product was cooled to 4-8° C., and then 6 N NaOH

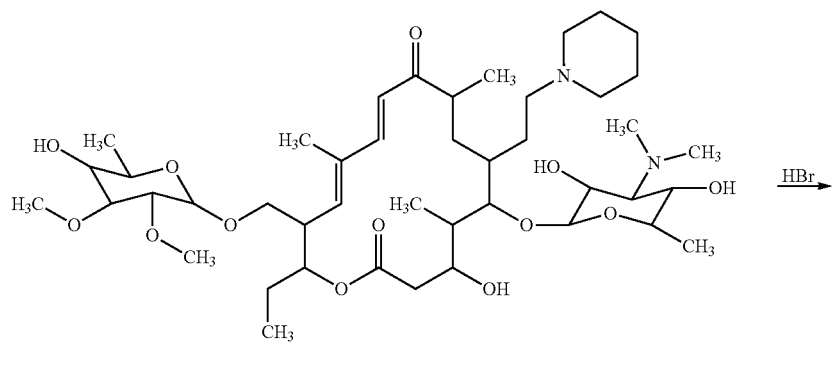

(3) →HBr

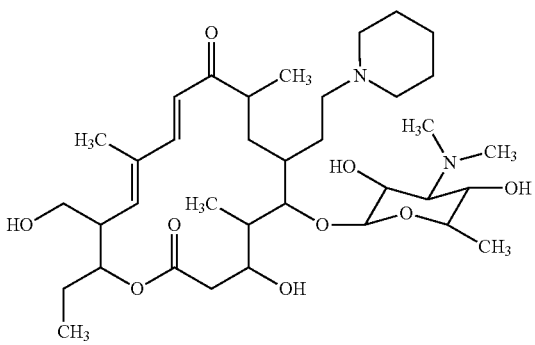

(4)

(33.6 kg) was slowly added to adjust the pH to ≧10. The resulting mixture was extracted with dichloromethane three times (with 32.6 kg, 29.3 kg, and 24.5 kg) at ambient temperature. The combined organic phases were charged to a separate reactor. Sodium sulfate (2.9 kg; $Na_2SO_4$) was added and filtered off. Dichloromethane (4.9 kg) was then added and removed via distillation. The resulting crude product was dissolved and re-crystallized twice in tert-butyl methyl ether (6.1 kg each time) at ambient temperature. Afterward, the product was isolated on a Nutsch filter, washed twice with tert-butyl methyl ether (1.0 kg each time), and dried in a tray dryer under vacuum overnight at 40° C. The final product was analyzed using HPLC.

Part D. Iodination. Preparation of activated compound (5).

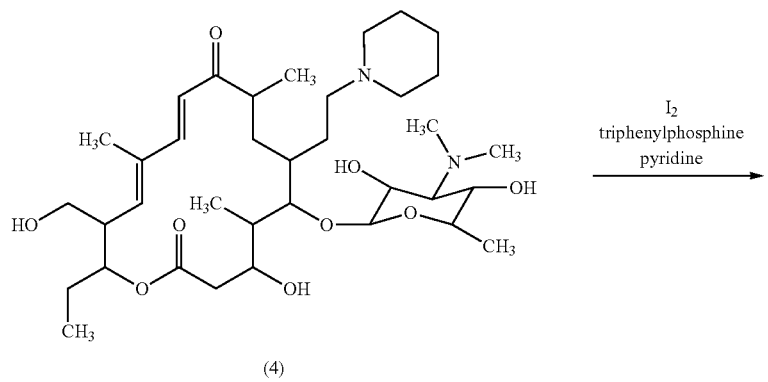

(4)

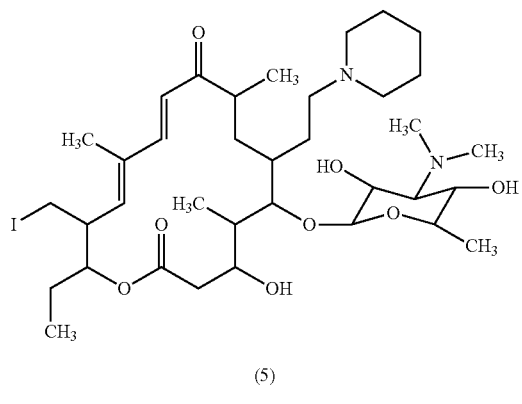

(5)

Triphenylphosphine (0.9 kg) and pyridine (0.3 kg; free of water) were dissolved into dichloromethane (11.7 kg) at ambient temperature. Iodine (0.8 kg) was then added. The resulting mixture was then stirred until all the iodine dissolved. The mixture was then cooled to 13° C. The cooled mixture was added to the product from Part C in dichloromethane (11.7 kg) while stirring at 15±3° C. The reaction was monitored by HPLC, and was determined to be completed in 2-2.5 hours (≦2% 23-hydroxyl-20-piperidinyl-5-O-mycaminosyl-tylonolide compound).

Part E. Amination. Preparation of 20,23-dipiperidinyl-5-O-mycaminosyl-tylonolide (6)

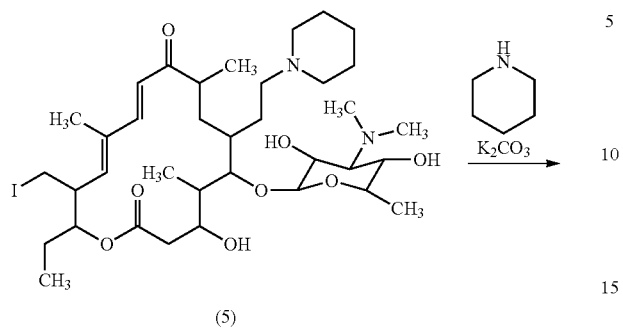

(5)

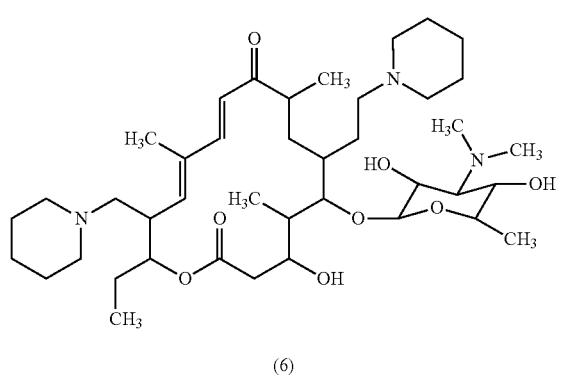

(6)

Potassium carbonate (1.8 kg), acetonitrile (16.7 kg), and piperidine (1.1 kg) were added to the product of Part D. The resulting mixture was then heated to 78° C. while distilling off dichloromethane. After solvent exchange to acetonitrile, the mixture was stirred at 2-2.5 hours at reflux, and then cooled to ambient temperature. Afterward, the residual potassium carbonate was filtered off, the filter cake was washed with acetonitrile (2.8 kg), and the solvent was distilled off under vacuum at a 50° C. jacket temperature. The resulting residue was dissolved in ethyl acetate (15.8 kg), and mixed with 0.5 N HCl (35.6 kg). The phases were separated at ambient temperature, and the lower aqueous phase was extracted three times with ethyl acetate (15.8 kg were used each time). The resulting aqueous phase was set to a pH of 11 by addition of 6 N NaOH (6.4 kg) and extracted three times with dichloromethane (18.7 kg each time) at ambient temperature. The combined lower organic phases were recharged to the reactor with sodium sulfate (5.3 kg). The mixture was then filtered to form a cake, which, in turn, was washed with dichloromethane (4.9 kg) and dried under vacuum at a jacket temperature of 50° C. to form a macrolide product. This product, in turn, was mixed with acetonitrile (21.7 L) and re-crystallized. The resulting crystals were isolated on a Nutsch filter, washed twice with cold acetonitrile (3.5 L each time), and dried under vacuum at 40° C. overnight to form macrolide (5) product. The composition of the product was confirmed using HPLC.

Example 2

Alternative Amination. Preparation of 20,23-Dipiperidinyl-5-O-Mycaminosyl-Tylonolide (2)

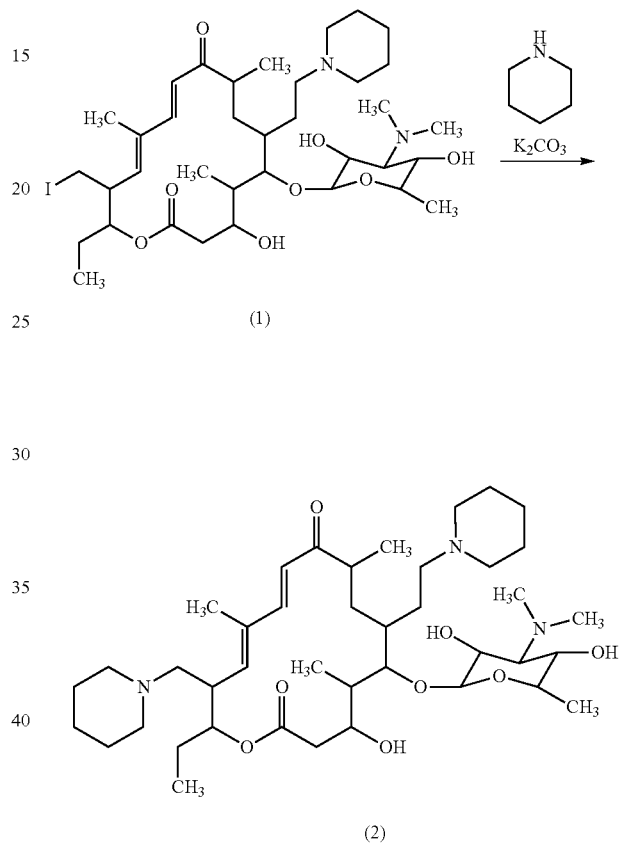

Potassium carbonate (0.94 kg), xylene (5 L), and piperidine (0.55 kg) are added to 1.0 kg of activated compound (1) made in accordance with the procedure in Part D. The resulting mixture is then heated to 95-105° C. for 15 hours. Work-up includes dissolving the K$_2$CO$_3$ in water; removing excess piperidine; extracting into diluted HCl; extracting into tert-butyl methyl ether at a pH of 11; conducting a solvent switch to ethanol; and precipitating, isolating, and drying of the crude product. The product is then re-crystallized from methyl acetate or ethyl acetate. The composition of the product is confirmed using HPLC.

Example 3

Preparing the Form I polymorph of 20,23-dipiperidinyl-5-O-mycaminosyl-tylonolide Part A. Reductive amination. Preparation of 23-O-mycinosyl-20-piperidinyl-5-O-mycaminosyl-tylonolide compound (2).

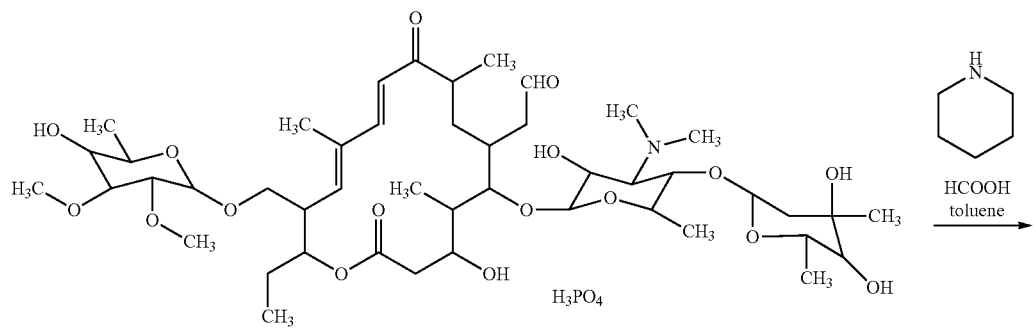

(1)

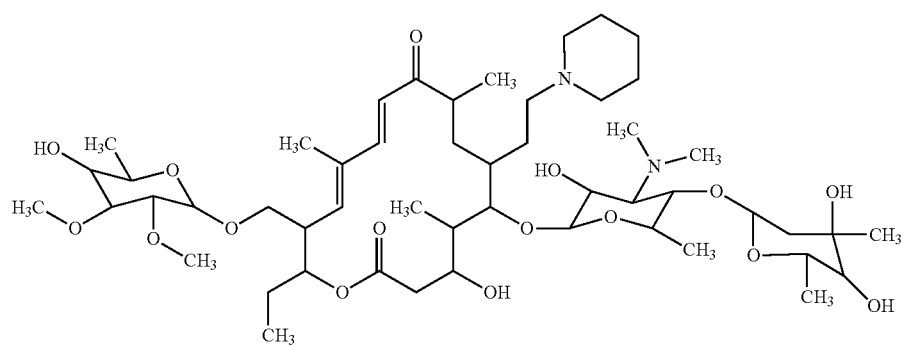

(2)

Tylosin phosphate (1) and dichloromethane (1.3 L per kg tylosin phosphate) were charged to a reactor. The resulting mixture was stirred to produce a clear solution. Next, piperidine (1.2 eq, based on the tylosin phosphate), formic acid (4.5 eq, based on the tylosin phosphate), and toluene (6.7 L per kg tylosin phosphate) were sequentially charged to the reactor. The resulting mixture was heated to 76° C. while being stirred. Stirring was then continued at that temperature for 2.5 hours. Additional piperidine (0.1 eq, based on the tylosin phosphate) was then charged, and the resulting mixture was stirred at 76° C. for an additional hour. The product mixture was cooled to 50° C.

Part B. Acid hydrolysis of mycarosyloxy substituent. Preparation of 23-hydroxyl-20-piperidinyl-5-O-mycaminosyl-tylonolide (4).

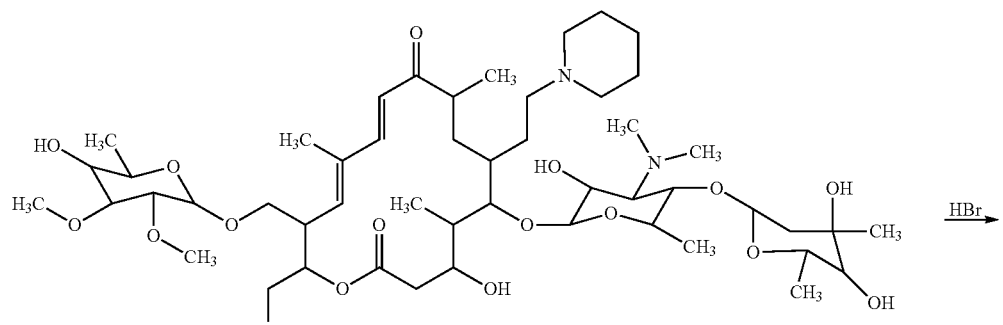

(2)

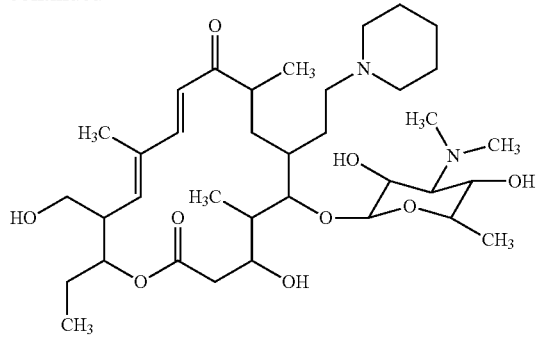

(4)

Aqueous HBr (23.3 eq, based on the tylosin phosphate used in Part A) was added to the product mixture of Part A at 50° C. The resulting mixture was stirred at 56° C. for 5 hours. HPLC was used to monitor the reaction.

Once the desired conversion was obtained, the product mixture was cooled. The aqueous phase was extracted twice with dichloromethane at 25-30° C. The aqueous phase was then cooled to 0° C., and the pH was adjusted to 10-10.5 with NaOH at ≦5° C. Afterward, the aqueous phase was extracted twice with dichloromethane at 20° C. The resulting combined organic phases were extracted twice with aqueous NaHCO$_3$. The dichloromethane was then removed from the combined organic phases via distillation, and replaced with isopropyl alcohol. Afterward, heptane at 45° C. was added to initiate precipitation. The mixture was then stirred at 0° C. Afterward, the crystalline product was isolated by filtration. The isolated crystals were washed with heptane and isopropyl alcohol, dried, and analyzed using HPLC.

The above procedure made 0.23 kg of product per kilogram of tylosin phosphate used in Part A. This product may contain isopropyl alcohol. To remove the isopropyl alcohol, the product may be dissolved in toluene and dichloromethane, followed by distillation.

Part C. Iodination. Preparation of activated compound (5).

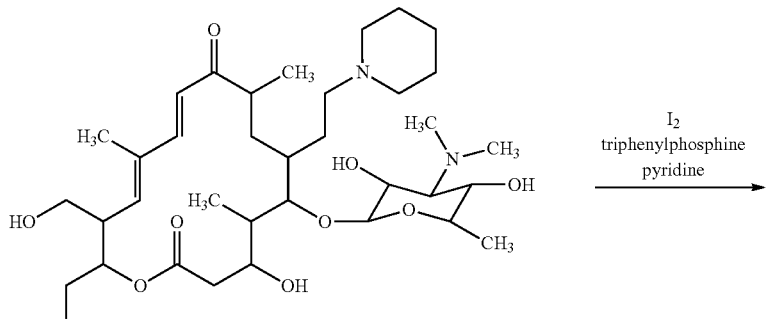

(4)

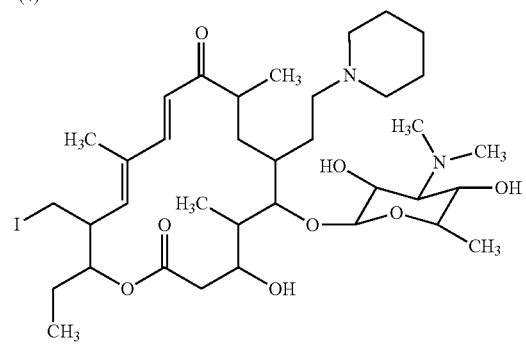

(5)

Triphenylphosphine (0.41 kg per kg of product of Part B) was dissolved in dichloromethane (12 L per kg of triphenylphosphine, ≦100 ppm H$_2$O) at 25° C. Pyridine (0.3 kg per kg triphenylphosphine) was then added. Next, iodine (0.9 kg per kg of triphenylphosphine) was added in 5 portions at 25° C. The resulting mixture was stirred for 40 minutes at 25° C., and then cooled to −6° C. The mixture was then added to the product from Part B over 50 minutes while stirring at −6°

C. Afterward, stirring was continued for 7 hours while maintaining the mixture at −5° C. The reaction was monitored by HPLC (if sufficient conversion is not reached, the mixture may be stirred at −5° C. for an additional amount of time, e.g., 1.5 hours).

When the desired conversion was reached, the product mixture was washed with aqueous $Na_2SO_3$ solution at −5° C. Dichloromethane was then removed from the organic phase by distillation, and replaced with tetrahydrofuran.

Part D. Amination. Preparation of 20,23-dipiperidinyl-5-O-mycaminosyl-tylonolide (6).

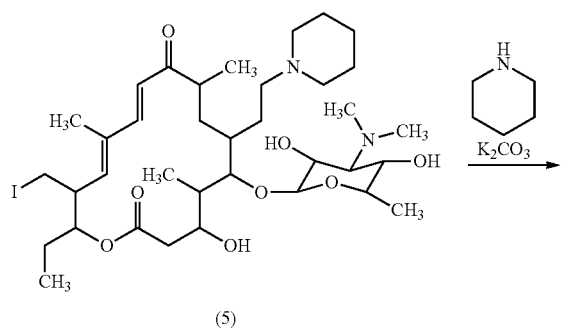

(5)

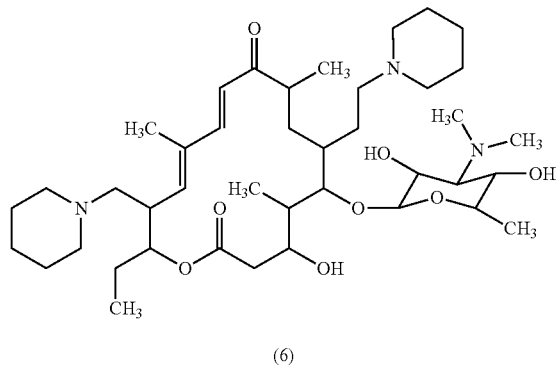

(6)

Piperidine (0.55 kg per kg of product from Part B) was added to the product from Part C, followed by potassium carbonate (0.94 kg per kg of product from Part B). The resulting mixture was heated to 55° C., and then maintained at that temperature for 3 hours while stirring. Afterward, the mixture was heated to 72° C. over 1 hour, and then stirred at that temperature for 6 hours. The composition of the product was analyzed using HPLC.

Once the desired conversion was obtained, the product mixture was cooled to 20° C., and toluene was added. The resulting mixture was washed twice with water, and the organic phase was extracted twice with aqueous HCl, resulting in an aqueous phase having a pH of ≦3. This mixture was cooled to 0-5° C.

Part E. Preparation of ethyl acetate S1 crystalline solvate of 20,23-dipiperidinyl-5-O-mycaminosyl-tylonolide. The acidic aqueous product solution prepared in accordance with Part D was combined with ethyl acetate (6.7 L per kg of product from Part B) at 3° C. The pH of the resulting emulsion was adjusted to 10.5-11.0 at 3° C. with caustic soda. The phases were separated at 3° C. The organic phase was washed once with water. After phase separation, the organic phase was concentrated by distillation, resulting in an ethyl acetate solution. Upon seeding, crystallization began. The resulting product was filtered off to obtain a filter cake of the ethyl acetate crystalline solvate. The filter cake was washed with heptane at 0° C. This yielded approximately 0.78 kg of crude wet crystalline solvate per kg of product from Part B used.

Part F. Preparing the Form I polymorph of 20,23-dipiperidinyl-5-O-mycaminosyl-tylonolide. A washed crystalline solvate wet cake formed in accordance with Part E was combined with heptane (6.1 L per kg wet cake). The resulting suspension was heated to 72° C. and seeded. Afterward, the suspension was stirred at 72° C., and then at 20° C. The suspension was then filtered, and the resulting solids were washed with heptane and dried. This yielded approximately 0.53 kg of Form I crystals per kg of product from Part B used (or 0.68 kg of Form I crystals per kg of crude wet crystalline solvate product from Part E used).

Example 4

Preparing the Form II Polymorph of 20,23-dipiperidinyl-5-O-mycaminosyl-tylonolide Part A. Preparation of activated compound. 23-Hydroxyl-20-piperidinyl-5-O-mycaminosyl-tylonolide (50 g) was prepared in accordance with the process described in Example 1, Parts A-C, except the acid used in the acid hydrolysis reactions (i.e., Parts B and C) was HCl instead of HBr. The 23-hydroxyl-20-piperidinyl-5-O-mycaminosyl-tylonolide at 13° C. was charged to a stirred reactor containing dichloromethane (250 ml at 13° C.). The resulting mixture was stirred for about 5 minutes at 13° C. In parallel, dichloromethane (250 ml at ambient temperature) was charged to a separate reactor, and stirring was initiated. Triphenylphosphine (24.6 g at ambient temperature) was then charged to the reactor, followed by pyridine (7.8 ml at ambient temperature) and then iodine (22.83 g at ambient temperature). Afterward, the mixture was stirred for 2 minutes at ambient temperature, and then combined with the dichloromethane mixture containing 23-hydroxyl-20-piperidinyl-5-O-mycaminosyl-tylonolide at 13° C. using dropping funnel. The resulting mixture was stirred for 130 minutes at 13° C. to form an activated product Part B. Preparing the Form II polymorph 20,23-dipiperidinyl-5-O-mycaminosyl-tylonolide.

Potassium carbonate (51.81 g), then acetonitrile (600 ml), and finally piperidine (37.1 ml) were added to the activated product of Part A at 13° C. The resulting mixture was then heated to 78° C. over 90 minutes, and then stirred at that temperature (reflux) for 130 additional minutes. The mixture was then cooled to 15-25° C. over 60 minutes, and stirring was ceased. Afterward, the residual potassium carbonate was filtered off, the filter cake was washed with acetonitrile (100 ml), and the solvent was distilled off under vacuum at 50° C. over 60 minutes. The resulting residue was dissolved in ethyl acetate (500 ml), and mixed with 0.5 N HCl (1000 ml). After stirring for 5 minutes, stirring was ceased, and the phases were separated. The lower aqueous phase was extracted three times with ethyl acetate (500 ml were used each time). Stirring of the resulting aqueous phase was initiated, and the temperature was reduced to 5-8° C. The pH was then adjusted to a pH of 11 by addition of 6 N NaOH (150 ml). The pH-adjusted mixture was then extracted three times with dichloromethane (400 ml each time) at ambient temperature. The combined lower organic phases were recharged to the reactor with sodium sulfate (150 g) at ambient temperature. The resulting mixture was stirred for 15 minutes, and then filtered to form a cake, which, in turn, was washed with dichloromethane (100 ml). The solvent was removed by distillation, and the resulting product was dried under vacuum at 50° C. for 60 minutes. This yielded 57.5 g of crude macrolide product.

The crude product was crystallized from acetonitrile (90 ml) at 50° C. To avoid oil formation, seeding crystals of 20,23-dipiperidinyl-5-O-mycaminosyl-tylonolide were added at ambient temperature (the seeding crystals were obtained earlier by dissolving 3 g of crude 20,23-dipiperidinyl-5-O-mycaminosyl-tylonolide in 12 ml acetonitrile, and collecting via filtration the crystals that formed after 24 hours at ambient temperature). The product precipitated as an off-white solid over 5 h at ambient temperature and overnight (15 h) at 5° C. The solid was separated by filtration, and washed twice with cold acetonitrile (2×25 ml). The remaining solid was dried under reduced pressure (8 mbar) at 40° C. overnight, resulting in 18.2 g of 20,23-dipiperidinyl-5-O-mycaminosyl-tylonolide (content: 90% (w/w) as determined by HPLC). The product (15 g) was further purified by re-crystallization in acetonitrile. This resulted in 10.7 g of product (HPLC purity at 254 nm: 100%; content: 94% (w/w) as determined by HPLC).

Example 5

Re-Crystallization of the Form II Polymorph of 20,23-dipiperidinyl-5-O-mycaminosyl-tylonolide in Acetonitrile The Form II polymorph of 20,23-dipiperidinyl-5-O-mycaminosyl-tylonolide (80 mg) prepared in accordance with Example 4 was dissolved in acetonitrile (2 ml). The resulting solution was filtered, and the acetonitrile was allowed to evaporate at ambient temperature to form crystals. The FT-Raman spectrum of the product crystals was approximately identical to the spectrum of the product crystals in Example 4.

Example 6

Preparing the ethyl acetate S1 crystalline solvate of 20,23-dipiperidinyl-5-O-mycaminosyl-tylonolide. The Form II polymorph of 20,23-dipiperidinyl-5-O-mycaminosyl-tylonolide (312 mg) prepared in accordance with Example 4 was dissolved in ethyl acetate (0.5 ml). A few minutes after complete dissolution, new crystals formed and, after a few additional minutes, filled the solution. Additional ethyl acetate (1 ml) was added, and the crystals were filtered off and dried at ambient temperature and atmospheric pressure.

Example 7

Preparing the Form III polymorph of 20,23-dipiperidinyl-5-O-mycaminosyl-tylonolide. The Form III polymorph of 20,23-dipiperidinyl-5-O-mycaminosyl-tylonolide was prepared by drying, under vacuum at ambient temperature for 20 hours, the ethyl acetate S1 crystalline solvate of 20,23-dipiperidinyl-5-O-mycaminosyl-tylonolide (50 mg) prepared in accordance with Example 6.

Example 8

Preparing the ethyl acetate S1 crystalline solvate of 20,23-dipiperidinyl-5-O-mycaminosyl-tylonolide. The Form II polymorph of 20,23-dipiperidinyl-5-O-mycaminosyl-tylonolide (146.1 mg) prepared in accordance with Example 4 was dissolved in ethyl acetate (0.5 ml) with stirring. After crystallization began, heptane (5 ml) was added while stirring was continued. The resulting solid was filtered off after 3 days. All these steps were conducted at ambient temperature. The resulting crystals were in the form of very fine needles. The FT-Raman spectrum of the crystals coincided with the FT-Raman spectrum of the crystals from Example 6.

Example 9

Preparing the ethyl acetate S1 crystalline solvate of 20,23-dipiperidinyl-5-O-mycaminosyl-tylonolide. The Form II polymorph of 20,23-dipiperidinyl-5-O-mycaminosyl-tylonolide (99.6 mg) prepared in accordance with Example 4 was dissolved in ethyl acetate (2 ml). The resulting solution was filtered, and the solvent was allowed to evaporate. After evaporation of almost all the solvent, an amorphous reside remained. Ethyl acetate was added again, and allowed to evaporate. A few seed crystals prepared in Example 6 were added at different stages of the evaporation. This yielded crystals in the form of needles. The FT-Raman spectrum of these crystals coincided to the FT-Raman of the crystals from Example 6.

Example 10

Preparing the Form III polymorph of 20,23-dipiperidinyl-5-O-mycaminosyl-tylonolide. The Form III polymorph of 20,23-dipiperidinyl-5-O-mycaminosyl-tylonolide was prepared by drying, under vacuum at from about 40 to about 70° C. for 3 days, the ethyl acetate S1 crystalline solvate of 20,23-dipiperidinyl-5-O-mycaminosyl-tylonolide prepared in accordance with Example 9. The FT-Raman spectrum for these crystals coincided to the FT-Raman spectrum of the crystals from Example 7.

Example 11

Preparing the Form III polymorph of 20,23-dipiperidinyl-5-O-mycaminosyl-tylonolide. The Form II polymorph of 20,23-dipiperidinyl-5-O-mycaminosyl-tylonolide (150.5 mg) prepared in accordance with Example 4 and acetonitrile (1 ml) were combined and subjected to temperature cycling between 20 and 40° C. with time intervals of 1 hour for each heating/cooling step and temperature hold. This cycling was stopped after 5 days. The resulting crystals (in the form of fine needles) were filtered off and allowed to dry at ambient temperature. The PXRD spectrum for these crystals coincided to the PXRD spectrum of the crystals in Example 7.

Example 12

Preparing the Form I polymorph of 20,23-dipiperidinyl-5-O-mycaminosyl-tylonolide. The Form II polymorph of 20,23-dipiperidinyl-5-O-mycaminosyl-tylonolide (170.5 mg) prepared in accordance with Example 4 was stirred at ambient temperature for 4 days with a solvent (1 ml) consisting of heptane and tert-butyl methyl ether ("tBME") at a heptane/tBME ratio of 95:5 (vol/vol). Afterward, the resulting crystals were filtered off, washed with additional heptane/tBME (95:5 vol/vol) solvent, and vacuum dried.

Example 13

Preparing the Form I polymorph of 20,23-dipiperidinyl-5-O-mycaminosyl-tylonolide. The Form II polymorph of 20,23-dipiperidinyl-5-O-mycaminosyl-tylonolide (147.4 mg) prepared in accordance with Example 4 was dissolved in tBME (0.5 ml) with stirring to form a clear solution. Heptane was then added, leading to slight precipitation. The crystals were then isolated after 3 days. All these steps were conducted at ambient temperature. The FT-Raman spectrum of the resulting crystals coincided to the FT-Raman spectrum of the crystals in Example 12.

Example 14

Preparing the Form I polymorph of 20,23-dipiperidinyl-5-O-mycaminosyl-tylonolide. The Form II polymorph of 20,23-dipiperidinyl-5-O-mycaminosyl-tylonolide (164.5 mg) prepared in accordance with Example 4 was stirred with heptane (1 ml) at ambient temperature for 4 days. The resulting solid was filtered off, washed with heptane, and vacuum dried. The washed and dried product (90 mg) and Form III polymorph crystals of 20,23-dipiperidinyl-5-O-mycaminosyl-tylonolide (98 mg) were suspended in heptane and stirred. The temperature was maintained at 25° C. for 10 days, except for an accidental brief temperature increase to 60° C. during the fifth night. The FT-Raman spectrum of the resulting crystals coincided with the FT-Raman spectrum of the crystals of Example 12.

Example 15

Preparing the Form I polymorph of 20,23-dipiperidinyl-5-O-mycaminosyl-tylonolide. Form III polymorph crystals of 20,23-dipiperidinyl-5-O-mycaminosyl-tylonolide (171.8 mg) were suspended in a solvent (1 ml) of heptane and tBME at a heptane/tBME ratio of 95:5 (vol/vol). The resulting solution was stirred at for 9 days. The solid was filtered off and washed with heptane (1 ml). All these steps were conducted at ambient temperature. The FT-Raman spectrum of the resulting crystals coincided with the FT-Raman spectrum of the crystals of Example 12.

Example 16

Preparing the Form I polymorph of 20,23-dipiperidinyl-5-O-mycaminosyl-tylonolide. Form II polymorph crystals of 20,23-dipiperidinyl-5-O-mycaminosyl-tylonolide (173.4 mg) were suspended in a solvent (1 ml) of heptane and tBME at a heptane/tBME ratio of 95:5 (vol/vol). The resulting solution was stirred for 9 days. The solid was filtered off and washed with heptane (1 ml). All these steps were conducted at ambient temperature. FT-Raman spectra of the crystals at 5 days and at the end of the 9 days coincided with the FT-Raman spectrum of the crystals of Example 12.

Example 17

Preparing the ethanol S1 crystalline solvate of 20,23-dipiperidinyl-5-O-mycaminosyl-tylonolide. The Form II polymorph of 20,23-dipiperidinyl-5-O-mycaminosyl-tylonolide (150 mg) prepared in accordance with Example 4 was dissolved in ethanol (1 ml). After filtering, the ethanol was allowed to evaporate at ambient temperature. A solid formed, which was once again dissolved in ethanol (1 ml). After filtering, the ethanol was allowed to evaporate at ambient temperature. The PXRD and FT-Raman spectra for the resulting crystals coincided with the corresponding spectra for the crystal product of Example 6.

Example 18

Preparing the diethyl ketone S1 crystalline solvate of 20,23-dipiperidinyl-5-O-mycaminosyl-tylonolide. The Form II polymorph of 20,23-dipiperidinyl-5-O-mycaminosyl-tylonolide (206.6 mg) prepared in accordance with Example 4 was dissolved in diethyl ketone (0.5 ml), and then allowed to sit overnight. The next morning, the crystals were obtained using filtration. The PXRD spectrum for the resulting crystals coincided with the PXRD spectrum for the crystal product of Example 6.

Example 19

Preparing the tBME S2 Crystalline Solvate of 20,23-dipiperidinyl-5-O-mycaminosyl-tylonolide The Form II polymorph of 20,23-dipiperidinyl-5-O-mycaminosyl-tylonolide (304 mg) prepared in accordance with Example 4 was dissolved in tert-butyl methyl ether (0.5 ml). Overnight, a large crystal formed at the bottom of the vessel. Upon scratching, the entire solution volume filled with crystals within 15 minutes. Additional tert-butyl methyl ether (1 ml) was added. The crystals were then filtered off and dried at ambient temperature.

Although this procedure was successfully repeated for forming S2 solvate crystals, additional batches of S2 solvate crystals were formed by dissolving an additional amount of the Form II polymorph of 20,23-dipiperidinyl-5-O-mycaminosyl-tylonolide in tert-butyl methyl ether, seeding S2 solvate crystals from the first batch, and removing the tert-butyl methyl ether. In one experiment, the S2 crystalline solvate was prepared by dissolving the Form II polymorph of 20,23-dipiperidinyl-5-O-mycaminosyl-tylonolide (245.7 mg) in tert-butyl methyl ether (0.5 ml), and slowly evaporating a portion of the solvent at ambient temperature. After no crystals formed, additional tert-butyl methyl ether was added, followed by seeding S2 solvate crystals from the first batch. The solvent was then allowed to evaporate completely. The FT-Raman spectrum for these crystals was approximately identical to the FT-Raman spectrum for the crystals from the first batch. In further testing, the crystals were vacuum-dried at ambient temperature for 20 hours, and then dried again under vacuum for 24 hours at about 70° C. The FT-Raman spectra of the crystals after each drying step coincided to the FT-Raman spectrum from the first batch.

Example 20

Preparing the tetrahydrofuran S3 crystalline solvate of 20,23-dipiperidinyl-5-O-mycaminosyl-tylonolide. The Form II polymorph of 20,23-dipiperidinyl-5-O-mycaminosyl-tylonolide (150 mg) prepared in accordance with Example 4 was dissolved in tetrahydrofuran (1.0 ml). The resulting mixture was filtered, and then the solvent was allowed to evaporate at ambient temperature. Crystallization occurred after a relatively large proportion of the solvent evaporated.

Example 21

Preparing the methyl acetate S4 crystalline solvate of 20,23-dipiperidinyl-5-O-mycaminosyl-tylonolide. The Form II polymorph of 20,23-dipiperidinyl-5-O-mycaminosyl-tylonolide (204.0 mg) prepared in accordance with Example 4 was dissolved in methyl acetate (0.5 ml). Re-crystallization initiated during dissolution. After 15 minutes, the whole volume was filled with needles. The solid was filtered off. The final crystals were prismatic in shape.

Example 22

Preparing the ethyl formate S4 crystalline solvate of 20,23-dipiperidinyl-5-O-mycaminosyl-tylonolide. The Form II polymorph of 20,23-dipiperidinyl-5-O-mycaminosyl-tylonolide (208.3 mg) prepared in accordance with Example 4 was dissolved in ethyl formate (0.5 ml). The flask was left open for a few minutes, whereupon the material slowly crystallized to form large needles. The solid was filtered off. The final crystals were prismatic in shape. The PXRD spectrum for the resulting crystals coincided with the PXRD spectrum for the crystal product of Example 21.

Example 23

Preparing the Form IV polymorph of 20,23-dipiperidinyl-5-O-mycaminosyl-tylonolide. Solvent-wet ethyl acetate S1 crystalline solvate of 20,23-dipiperidinyl-5-O-mycaminosyl-tylonolide (3.4 g, corresponding to 2.0 g dry product) was mixed with 27.7 g heptane (which corresponds to a ratio of 14 g solvent to 1 g product). The mixture was distilled at 73-95° C. to remove 8.4 g of solvent (ethyl acetate and heptane combined), which also resulted in a product dissolution. The solution was cooled to 45° C. within 2 hours, which lead to precipitation of some sticky solid at 45° C. The solution was heated to 60° C., and seeding crystals were added (these seeding crystals were prepared earlier by mixing crude 20,23-dipiperidinyl-5-O-mycaminosyl-tylonolide (0.9 g) with heptane (4.5 g), stirring the mixture at 80° C. for 8 hours, stirring the mixture at 23° C. for 21 hours, and filtering off the resulting crystals). The solution was cooled to 45° C., whereupon some solid formed. The mixture was heated to 80° C., and then maintained at that temperature while being stirred for 8 hours. Afterward, the mixture was cooled to 22° C., causing product to form at the wall of the reaction flask. This product was separated.

The words "comprise," "comprises," and "comprising" in this disclosure (including the claims) are to be interpreted inclusively rather than exclusively.

The term "pharmaceutically acceptable" is used adjectivally in this disclosure to mean that the modified noun is appropriate for use in a pharmaceutical product. When it is used, e.g., to describe an excipient or a salt, it characterizes the excipient or salt as having a benefit(s) that outweighs any deleterious effect(s) that the excipient or salt may have to the intended recipient animal.

Unless otherwise characterized by this disclosure, the term "ambient temperature" means a temperature of from about 20 to about 25° C.

The term "amorphous" as applied to 20,23-dipiperidinyl-5-O-mycaminosyl-tylonolide in this disclosure refers to a solid-state wherein the 20,23-dipiperidinyl-5-O-mycaminosyl-tylonolide molecules are present in a disordered arrangement, and do not form a distinguishable crystal lattice or unit cell. When subjected to powder X-ray diffraction, amorphous 20,23-dipiperidinyl-5-O-mycaminosyl-tylonolide does not produce any characteristic crystalline peaks.

The term "crystalline form" as applied to 20,23-dipiperidinyl-5-O-mycaminosyl-tylonolide in this disclosure refers to a solid-state form wherein the 20,23-dipiperidinyl-5-O-mycaminosyl-tylonolide molecules are arranged to form a distinguishable crystal lattice that: (i) comprises distinguishable unit cells, and (ii) yields diffraction peaks when subjected to powder X-ray radiation.

The term "crystallization" can refer to crystallization and/or re-crystallization, depending on the applicable circumstances relating to preparation of the 20,23-dipiperidinyl-5-O-mycaminosyl-tylonolide starting material.

The term "direct crystallization" refers to crystallization of 20,23-dipiperidinyl-5-O-mycaminosyl-tylonolide directly from a suitable solvent without formation and desolvation of an intermediate solvated crystalline solid-state form of 20,23-dipiperidinyl-5-O-mycaminosyl-tylonolide.

The term "particle size" refers to particle size, as measured by conventional particle size measuring techniques well known in the art, such as laser light scattering, sedimentation field flow fractionation, photon correlation spectroscopy, or disk centrifugation. A non-limiting example of a technique that can be used to measure particle size is a liquid dispersion technique employing a Sympatec Particle Size Analyzer.

The term "HPLC" means high pressure liquid chromatography.

Unless otherwise characterized by this disclosure, the term "purity" means the chemical purity of 20,23-dipiperidinyl-5-O-mycaminosyl-tylonolide according to conventional HPLC assay.

The term "phase purity" as used in this disclosure means the solid-state purity of 20,23-dipiperidinyl-5-O-mycaminosyl-tylonolide with regard to a particular crystalline or amorphous form of the 20,23-dipiperidinyl-5-O-mycaminosyl-tylonolide as determined by X-ray powder diffraction analytical methods described in this disclosure. The term "phase-pure" refers to purity with respect to other solid-state forms of 20,23-dipiperidinyl-5-O-mycaminosyl-tylonolide, and does not necessarily imply a high degree of chemical purity with respect to other compounds. The term "substantially phase-pure" refers to at least about 90% purity (e.g., at least about 95% purity) with respect to other solid-state forms of 20,23-dipiperidinyl-5-O-mycaminosyl-tylonolide.

All references cited in this disclosure are incorporated by reference herein.

What is claimed is:

1. A method for treating a disease, wherein the disease is selected from the group consisting of pasteurellosis, swine respiratory disease, and bovine respiratory disease, the method comprising:
    administering a pharmaceutical composition to an animal in need of such treatment, the pharmaceutical composition comprising a therapeutically effective amount of a solid crystalline 20,23-dipiperidinyl-5-O-mycaminosyl-tylonolide form having the following characteristics:
        an FT-Raman spectrum comprising an absorption band at a frequency of each of about 2935, about 1633, about 1596, about 1712, about 1683, and about 781 cm$^{-1}$;
        a powder X-ray diffraction spectrum comprising a peak at each of 5.0 (±0.2) and 5.6 (±0.2) degrees 2Θ;
        an attenuated total reflection infrared spectrum comprising an absorption band at a frequency of each of about 2932, about 1711, about 1682, about 1635, about 1599, about 1442, about 1404, about 1182, about 1079, about 1053, about 1008, about 985, about 842, and about 783 cm$^{-1}$; and
        a melting point of from about 192° C. to about 195° C.

2. The method according to claim 1, the method further comprising:
    combining the therapeutically effective amount of the solid crystalline 20,23-dipiperidinyl-5-O-mycaminosyl-tylonolide form with at least one solid excipient to form the pharmaceutical composition.

3. The method according to claim 1, wherein the bovine respiratory disease is associated with at least one of *Mannheimia haemolytica*, *Pasteurella multocida*, and *Histophilus somni* and the swine respiratory disease is associated with at least one of *Actinobacillus pleuropneumoniae*, *Pasteurella multocida*, and *Bordetella bronchiseptica*.

4. The method according to claim 2, wherein the solid excipient comprises a member selected from the group consisting of saccharides, starches, and cellulose derivatives.

5. A method for treating a disease, wherein the disease is selected from the group consisting of pasteurellosis, swine respiratory disease, and bovine respiratory disease, the method comprising:
an administering a pharmaceutical composition to an animal in need of such treatment, the pharmaceutical composition comprising a therapeutically effective amount of a solid crystalline 20,23-dipiperidinyl-5-O-mycaminosyl-tylonolide form having the following characteristics:
an FT-Raman spectrum comprising an absorption band at a frequency of each of about 2929, about 1625, about 1595, about 1685, and about 783 cm$^{-1}$;
a powder X-ray diffraction spectrum comprising a peak at 6.5 (±0.2) degrees 2Θ; and
an attenuated total reflection infrared spectrum comprising an absorption band at a frequency of each of about 2935, about 1736, about 1668, about 1587, about 1451, about 1165, about 1080, about 1057, about 1042, about 1005, about 981, about 838, and about 755 cm$^{-1}$.

6. A method for treating a disease, wherein the disease is selected from the group consisting of pasteurellosis, swine respiratory disease, and bovine respiratory disease, the method comprising:
administering a pharmaceutical composition to an animal in need of such treatment, the pharmaceutical composition comprising a therapeutically effective amount of a solid crystalline 20,23-dipiperidinyl-5-O-mycaminosyl-tylonolide form having the following characteristics:
an FT-Raman spectrum comprising an absorption band at a frequency of each of about 2943, about 2917, about 1627, about 1590, about 1733, about 1669, about 1193, about 1094, and about 981 cm$^{-1}$;
a powder X-ray diffraction spectrum comprising a peak at each of 5.6 (±0.2) and 6.1 (±0.2) degrees 2Θ; and
an attenuated total reflection infrared spectrum comprising an absorption band at a frequency of each of about 2931, about 1732, about 1667, about 1590, about 1453, about 1165, about 1081, about 1057, about 1046, about 1005, about 981, about 834, and about 756 cm$^{-1}$.

7. A method for treating a disease selected from the group consisting of pasteurellosis, swine respiratory disease, and bovine respiratory disease, the method comprising:
administering a pharmaceutical composition to an animal in need of such treatment, the pharmaceutical composition comprising a therapeutically effective amount of a solid crystalline 20,23-dipiperidinyl-5-O-mycaminosyl-tylonolide form having the following characteristics:
an attenuated total reflection infrared spectrum comprising an absorption band at a frequency of each of about 3559, about 2933, about 1743, about 1668, about 1584, about 1448, about 1165, about 1075, about 1060, about 1045, about 1010, about 985, about 839, and about 757 cm$^{-1}$; and a melting point of from about 149° C. to about 155° C.

8. A method for treating a disease selected from the group consisting of pasteurellosis, swine respiratory disease, and bovine respiratory disease, the method comprising:
administering a pharmaceutical composition to an animal in need of such treatment, the pharmaceutical composition comprising a therapeutically effective amount of a solid solvated crystalline form of 20,23-dipiperidinyl-5-O-mycaminosyl-tylonolide, wherein the solid solvated crystalline form comprises at least one of the following:
an ethyl acetate solvated crystalline form of 20,23-dipiperidinyl-5-O-mycaminosyl-tylonolide;
an ethanol solvated crystalline form of 20,23-dipiperidinyl-5-O-mycaminosyl-tylonolide;
a diethyl ketone solvated crystalline form of 20,23-dipiperidinyl-5-O-mycaminosyl-tylonolide;
a tert-butyl methyl ether solvated crystalline form of 20,23-dipiperidinyl-5-O-mycaminosyl-tylonolide;
a tetrahydrofuran solvated crystalline form of 20,23-dipiperidinyl-5-O-mycaminosyl-tylonolide;
a methyl acetate solvated crystalline form of 20,23-dipiperidinyl-5-O-mycaminosyl-tylonolide; or
an ethyl formate solvated crystalline form of 20,23-dipiperidinyl-5-O-mycaminosyl-tylonolide.

9. A pharmaceutical composition prepared by a process comprising combining at least one solid excipient with a therapeutically effective amount of a solid crystalline 20,23-dipiperidinyl-5-O-mycaminosyl-tylonolide form having the following characteristics:
an FT-Raman spectrum comprising an absorption band at a frequency of each of about 2935, about 1633, about 1596, about 1712, about 1683, and about 781 cm$^{-1}$;
a powder X-ray diffraction spectrum comprising a peak at each of 5.0 (±0.2) and 5.6 (±0.2) degrees 2Θ;
an attenuated total reflection infrared spectrum comprising an absorption band at a frequency of each of about 2932, about 1711, about 1682, about 1635, about 1599, about 1442, about 1404, about 1182, about 1079, about 1053, about 1008, about 985, about 842, and about 783 cm$^{-1}$; and
a melting point of from about 192° C. to about 195° C.

10. A pharmaceutical composition prepared by a process comprising combining at least one solid excipient with a therapeutically effective amount of a solid crystalline 20,23-dipiperidinyl-5-O-mycaminosyl-tylonolide form having the following characteristics:
an FT-Raman spectrum comprising an absorption band at a frequency of each of about 2929, about 1625, about 1595, about 1685, and about 783 cm$^{-1}$;
a powder X-ray diffraction spectrum comprising a peak at 6.5 (±0.2) degrees 2Θ; and
an attenuated total reflection infrared spectrum comprising an absorption band at a frequency of each of about 2935, about 1736, about 1668, about 1587, about 1451, about 1165, about 1080, about 1057, about 1042, about 1005, about 981, about 838, and about 755 cm$^{-1}$.

11. A pharmaceutical composition prepared by a process comprising combining at least one solid excipient with a therapeutically effective amount of a solid crystalline 20,23-dipiperidinyl-5-O-mycaminosyl-tylonolide form having the following characteristics:
an FT-Raman spectrum comprising an absorption band at a frequency of each of about 2943, about 2917, about 1627, about 1590, about 1733, about 1669, about 1193, about 1094, and about 981 cm$^{-1}$;
a powder X-ray diffraction spectrum comprising a peak at each of 5.6 (±0.2) and 6.1 (±0.2) degrees 2Θ; and
an attenuated total reflection infrared spectrum comprising an absorption band at a frequency of each of about 2931, about 1732, about 1667, about 1590, about 1453, about 1165, about 1081, about 1057, about 1046, about 1005, about 981, about 834, and about 756 cm$^{-1}$.

12. A pharmaceutical composition prepared by a process comprising combining at least one solid excipient with a therapeutically effective amount of a solid crystalline 20,23-dipiperidinyl-5-O-mycaminosyl-tylonolide form having the following characteristics:
- an attenuated total reflection infrared spectrum comprising an absorption band at a frequency of each of about 3559, about 2933, about 1743, about 1668, about 1584, about 1448, about 1165, about 1075, about 1060, about 1045, about 1010, about 985, about 839, and about 757 $cm^{-1}$; and
- a melting point of from about 149° C. to about 155° C.

13. A pharmaceutical composition prepared by a process comprising combining at least one solid excipient with a therapeutically effective amount of a solid solvated crystalline form of 20,23-dipiperidinyl-5-O-mycaminosyl-tylonolide, wherein the solid solvated crystalline form comprises at least one of the following:
- an ethyl acetate solvated crystalline form of 20,23-dipiperidinyl-5-O-mycaminosyl-tylonolide;
- an ethanol solvated crystalline form of 20,23-dipiperidinyl-5-O-mycaminosyl-tylonolide;
- a diethyl ketone solvated crystalline form of 20,23-dipiperidinyl-5-O-mycaminosyl-tylonolide;
- a tert-butyl methyl ether solvated crystalline form of 20,23-dipiperidinyl-5-O-mycaminosyl-tylonolide;
- a tetrahydrofuran solvated crystalline form of 20,23-dipiperidinyl-5-O-mycaminosyl-tylonolide;
- a methyl acetate solvated crystalline form of 20,23-dipiperidinyl-5-O-mycaminosyl-tylonolide; or
- an ethyl formate solvated crystalline form of 20,23-dipiperidinyl-5-O-mycaminosyl-tylonolide.

* * * * *